US00RE48024E

(19) United States
(12) Reissued Patent
Bolea et al.

(10) Patent Number: US RE48,024 E
(45) Date of Reissued Patent: Jun. 2, 2020

(54) OBSTRUCTIVE SLEEP APNEA TREATMENT DEVICES, SYSTEMS AND METHODS

(71) Applicant: LivaNova USA, Inc., Houston, TX (US)

(72) Inventors: Stephen L. Bolea, Watertown, MN (US); Thomas B. Hoegh, Edina, MN (US); Bruce J. Persson, Dresser, WI (US); Robert E. Atkinson, Elmo, MN (US); Sidney F. Hauschild, St. Paul, MN (US); Paula M. Kaplan, St. Paul, MN (US); Brian D. Kuhnley, Maple Grove, MN (US); Keith E. Jasperson, Andover, MN (US); Wondimeneh Tesfayesus, St. Paul, MN (US); Christopher K. Thorp, Chanhassen, MN (US)

(73) Assignee: LivaNova USA, Inc., Houston, TX (US)

(21) Appl. No.: 14/681,764

(22) Filed: Apr. 8, 2015

Related U.S. Patent Documents

Reissue of:
(64) Patent No.: 8,417,343
Issued: Apr. 9, 2013
Appl. No.: 11/907,533
Filed: Oct. 12, 2007

U.S. Applications:
(60) Provisional application No. 60/851,386, filed on Oct. 13, 2006, provisional application No. 60/918,257, filed on Mar. 14, 2007.

(51) Int. Cl.
*A61N 1/36* (2006.01)
*A61N 1/05* (2006.01)
(Continued)

(52) U.S. Cl.
CPC ..... *A61N 1/3606* (2013.01); *A61N 1/0556* (2013.01); *A61N 1/0558* (2013.01);
(Continued)

(58) Field of Classification Search
CPC ..... A61N 1/36; A61N 1/3601; A61N 1/3611; A61N 1/36128; A61N 1/36135;
(Continued)

(56) References Cited

U.S. PATENT DOCUMENTS 758,030 A 4/1904 Carence
1,520,930 A 12/1924 Calhoun
(Continued)

FOREIGN PATENT DOCUMENTS

EP 0 892 926 B1 6/2002
EP 0 900 102 B1 7/2004
(Continued)

OTHER PUBLICATIONS

European Search Report issued in corresponding European Application No. 121 637 91 dated Jun. 25, 2012, (3 page)s.
(Continued)

*Primary Examiner* — Catherine S Williams
(74) *Attorney, Agent, or Firm* — Foley & Lardner LLP

(57) ABSTRACT

Devices, systems and methods for nerve stimulation for OSA therapy.

51 Claims, 85 Drawing Sheets

(51) Int. Cl.
*A61N 1/372* (2006.01)
*A61B 5/08* (2006.01)
*A61B 5/00* (2006.01)

(52) U.S. Cl.
CPC ..... *A61N 1/3601* (2013.01); *A61N 1/37229* (2013.01); *A61B 5/0809* (2013.01); *A61B 5/4818* (2013.01); *A61B 5/7239* (2013.01)

(58) Field of Classification Search
CPC ..... A61N 1/36139; A61N 1/36146; A61N 1/36167; A61N 1/0556; A61N 1/3605; A61N 1/3606; A61N 1/36175; A61N 1/38; A61B 5/0809; A61B 5/7239
See application file for complete search history.

(56) References Cited

U.S. PATENT DOCUMENTS 1,701,277 A 2/1929 Shindel
1,914,418 A 6/1933 Goyena
2,046,664 A 7/1936 Weaver
2,151,227 A 3/1939 Pawelek
2,237,954 A 4/1941 Wilson
2,243,360 A 5/1941 Slatis
2,274,886 A 3/1942 Carroll
2,526,586 A 10/1950 Shuff
2,693,799 A 11/1954 Herman
2,777,442 A 1/1957 Zelano
2,928,388 A 3/1960 Jaroslaw
3,457,917 A 7/1969 Mercurio
3,513,839 A 5/1970 Vacante
3,680,555 A 8/1972 Warncke
3,722,509 A 3/1973 Nebel
3,774,618 A 11/1973 Avery
3,865,106 A 2/1975 Palush
3,884,223 A 5/1975 Keindl
3,893,463 A 7/1975 Williams
3,906,936 A 9/1975 Habal
4,160,252 A 7/1979 Lucas et al.
4,160,255 A 7/1979 Kobayashi
4,178,524 A 12/1979 Ritter
4,200,440 A 4/1980 Renko
4,220,150 A 9/1980 King
4,221,217 A 9/1980 Amezcua
4,225,034 A 9/1980 Sarovich
4,239,918 A 12/1980 Keeley
4,242,987 A 1/1981 Viessmann
4,267,831 A 5/1981 Aguilar
4,283,867 A 8/1981 Brown
4,302,951 A 12/1981 Fall et al.
4,313,442 A 2/1982 Knudson et al.
4,346,398 A 8/1982 Lai
4,374,527 A 2/1983 Iversen
4,414,986 A 11/1983 Dickhudt et al.
4,506,666 A 3/1985 Durkan
4,567,892 A 2/1986 Plicchi et al.
4,573,481 A 3/1986 Bullara
4,602,624 A 7/1986 Kauer
4,612,934 A 9/1986 Borkan
4,777,963 A 10/1988 McKenna
4,830,008 A 5/1989 Meer
4,899,750 A 2/1990 Ekwall
4,915,105 A 4/1990 Lee
4,919,136 A 4/1990 Alt
4,934,368 A * 6/1990 Lynch ..... 607/2
4,940,065 A 7/1990 Tanagho et al.
4,960,133 A 10/1990 Hewson
4,979,511 A 12/1990 Reese
4,996,983 A 3/1991 AmRhein
5,016,808 A 5/1991 Heil, Jr. et al.
5,036,862 A 8/1991 Pohndorf
5,095,905 A 3/1992 Klepinski
5,105,826 A 4/1992 Smits et al.
5,121,754 A 6/1992 Mullett
5,133,354 A 7/1992 Kallok
5,146,918 A 9/1992 Kallok et al.
5,158,080 A 10/1992 Kallok
5,174,287 A 12/1992 Kallok et al.
5,178,156 A 1/1993 Takishima et al.
5,190,053 A 3/1993 Meer
5,211,173 A 5/1993 Kallok et al.
5,215,082 A 6/1993 Kallok et al.
5,277,193 A 1/1994 Takishima et al.
5,281,219 A 1/1994 Kallok et al.
5,282,468 A 2/1994 Klepinski
5,300,094 A 4/1994 Kallok et al.
5,324,321 A 6/1994 Pohndorf et al.
5,335,657 A 8/1994 Terry, Jr. et al.
5,344,438 A 9/1994 Testerman et al.
5,388,578 A 2/1995 Yomtov et al.
5,392,773 A 2/1995 Bertrand
5,417,205 A 5/1995 Wang
5,425,359 A 6/1995 Liou
5,458,629 A 10/1995 Baudino et al.
5,483,969 A 1/1996 Testerman et al.
5,485,836 A 1/1996 Lincoln
5,485,851 A 1/1996 Erickson ..... A61N 1/3601 600/529
5,487,756 A 1/1996 Kallesoe et al.
5,511,543 A 4/1996 Shirley
5,522,382 A 6/1996 Sullivan et al.
5,522,862 A 6/1996 Testerman et al. .. A61N 1/3601 600/529
5,531,778 A 7/1996 Maschino et al.
5,540,731 A 7/1996 Testerman
5,540,732 A 7/1996 Testerman
5,540,733 A 7/1996 Testerman et al.
5,540,734 A 7/1996 Zabara
5,546,938 A 8/1996 McKenzie
5,549,655 A 8/1996 Erickson
5,568,808 A 10/1996 Rimkus
5,591,216 A 1/1997 Testerman et al.
5,630,411 A 5/1997 Holscher
5,682,881 A 11/1997 Winthrop et al.
5,697,105 A 12/1997 White
5,697,363 A 12/1997 Hart
5,730,122 A 3/1998 Lurie
5,740,798 A 4/1998 McKinney
5,752,511 A 5/1998 Simmons et al.
5,787,884 A 8/1998 Tovey
5,848,589 A 12/1998 Welnetz
5,855,552 A 1/1999 Houser et al.
5,871,531 A 2/1999 Struble
5,890,491 A 4/1999 Rimkus
5,895,360 A 4/1999 Christopherson et al.
5,919,220 A 7/1999 Stieglitz et al.
5,922,014 A 7/1999 Warman et al.
5,938,596 A 8/1999 Woloszko et al.
5,944,680 A 8/1999 Christopherson et al.
5,947,119 A 9/1999 Reznick
6,010,459 A 1/2000 Silkoff et al.
6,015,389 A 1/2000 Brown
6,021,352 A 2/2000 Christopherson et al.
6,021,354 A 2/2000 Warman et al.
6,029,667 A 2/2000 Lurie
6,041,780 A 3/2000 Richard
6,066,165 A 5/2000 Racz
6,098,624 A 8/2000 Utamaru
6,109,262 A 8/2000 Tovey
6,119,690 A 9/2000 Pantaleo
6,126,611 A 10/2000 Bourgeois et al.
6,132,384 A 10/2000 Christopherson et al.
6,198,970 B1 3/2001 Freed et al.
6,201,994 B1 3/2001 Warman et al.
6,205,360 B1 3/2001 Carter et al.
6,217,527 B1 4/2001 Selmon et al.
6,221,049 B1 4/2001 Selmon et al.
6,231,546 B1 5/2001 Milo et al.
6,240,316 B1 5/2001 Richmond et al.
6,244,267 B1 6/2001 Eifrig
6,251,126 B1 6/2001 Ottenhoff et al.
6,269,269 B1 7/2001 Ottenhoff et al.
6,292,703 B1 9/2001 Meier et al.
6,345,202 B2 2/2002 Richmond et al.

(56) References Cited

U.S. PATENT DOCUMENTS 6,366,815 B1 4/2002 Haugland et al.
6,460,539 B1 10/2002 Japuntich et al.
6,484,725 B1 11/2002 Chi
6,511,458 B2 1/2003 Milo et al.
6,514,217 B1 2/2003 Selmon et al.
6,542,776 B1 4/2003 Gordon et al.
6,561,188 B1 5/2003 Ellis
6,587,725 B1 * 7/2003 Durand et al. ..... 607/42
6,600,956 B2 7/2003 Maschino et al.
6,606,521 B2 8/2003 Paspa et al.
6,609,031 B1 8/2003 Law et al.
6,626,179 B1 9/2003 Pedley
6,636,767 B1 10/2003 Knudson et al.
6,641,542 B2 11/2003 Cho et al.
6,647,289 B2 11/2003 Prutchi
6,651,652 B1 11/2003 Ward
6,718,982 B2 4/2004 Smith et al.
6,719,725 B2 4/2004 Milo et al.
6,721,603 B2 4/2004 Zabara et al.
6,772,015 B2 8/2004 Dahl et al.
6,776,162 B2 8/2004 Wood
6,799,575 B1 10/2004 Carter
6,819,958 B2 11/2004 Weiner et al.
6,829,503 B2 12/2004 Alt
6,829,508 B2 12/2004 Schulman et al.
RE38,705 E 2/2005 Hill et al.
6,876,885 B2 4/2005 Swoyer et al.
6,881,192 B1 4/2005 Park
6,883,518 B2 4/2005 Mittelstadt et al.
6,890,306 B2 5/2005 Poezevera
6,904,320 B2 6/2005 Park et al.
6,907,295 B2 6/2005 Gross et al.
6,928,324 B2 8/2005 Park et al.
6,978,171 B2 12/2005 Goetz et al.
6,997,177 B2 2/2006 Wood
7,027,869 B2 4/2006 Danek et al.
7,054,692 B1 5/2006 Whitehurst et al.
7,065,410 B2 6/2006 Bardy et al.
7,082,331 B1 7/2006 Park et al.
7,087,053 B2 8/2006 Vanney
7,089,932 B2 8/2006 Dodds
7,094,206 B2 8/2006 Hoffman
7,117,036 B2 10/2006 Florio
7,128,717 B1 10/2006 Thach et al.
7,142,919 B2 11/2006 Hine et al.
7,149,573 B2 12/2006 Wang
7,152,604 B2 12/2006 Hickle et al.
7,155,278 B2 12/2006 King et al.
7,156,098 B2 1/2007 Dolezal et al.
7,160,252 B2 1/2007 Cho
7,160,255 B2 1/2007 Saadat
7,178,524 B2 2/2007 Noble
7,200,440 B2 4/2007 Kim et al.
7,225,034 B2 5/2007 Ries et al.
7,239,918 B2 7/2007 Strother et al.
7,239,920 B1 7/2007 Thacker et al.
7,242,987 B2 7/2007 Holleman et al.
7,263,996 B2 9/2007 Seoul
7,277,749 B2 10/2007 Gordon et al.
7,283,867 B2 10/2007 Strother et al.
7,302,951 B2 12/2007 Mittelstadt et al.
7,313,442 B2 12/2007 Velasco et al.
7,343,202 B2 3/2008 Mrva et al.
7,346,398 B2 3/2008 Gross et al.
7,366,572 B2 4/2008 Heruth et al.
7,396,333 B2 7/2008 Stahmann et al.
7,438,686 B2 10/2008 Cho et al.
7,463,928 B2 12/2008 Lee et al.
7,473,227 B2 1/2009 Hsu et al.
7,515,968 B2 4/2009 Metzler et al.
7,524,292 B2 4/2009 Cho et al.
7,561,922 B2 7/2009 Cohen et al.
7,591,265 B2 9/2009 Lee et al.
7,596,413 B2 9/2009 Libbus et al.
7,596,414 B2 9/2009 Whitehurst et al.
7,627,375 B2 12/2009 Bardy et al.
7,630,771 B2 12/2009 Cauller
7,634,315 B2 12/2009 Cholette
7,636,602 B2 12/2009 Baru Fassio et al.
7,657,311 B2 2/2010 Bardy et al.
7,660,632 B2 2/2010 Kirby et al.
7,662,105 B2 2/2010 Hatlestad
7,672,728 B2 3/2010 Libbus et al.
7,672,729 B2 3/2010 Koh et al.
7,680,537 B2 3/2010 Stahmann et al.
7,680,538 B2 3/2010 Durand et al.
7,684,869 B2 3/2010 Bradley et al.
7,697,968 B2 4/2010 Moore
7,697,984 B2 4/2010 Hill et al.
7,697,990 B2 4/2010 Ujhazy et al.
7,717,848 B2 5/2010 Heruth et al.
7,720,534 B2 5/2010 Bardy et al.
7,725,195 B2 5/2010 Lima et al.
7,725,198 B2 5/2010 Cross, Jr. et al.
7,734,340 B2 6/2010 De Ridder
7,734,348 B2 6/2010 Zhang et al.
7,738,952 B2 6/2010 Yun et al.
7,747,323 B2 6/2010 Libbus et al.
7,751,880 B1 7/2010 Cholette
7,751,885 B2 7/2010 Bardy et al.
7,758,384 B2 7/2010 Alexander et al.
7,765,000 B2 7/2010 Zhang et al.
7,769,461 B2 8/2010 Whitehurst et al.
7,783,353 B2 8/2010 Libbus et al.
7,785,262 B2 8/2010 Melker et al.
7,787,959 B1 8/2010 Morgan
7,792,590 B1 9/2010 Pianca et al.
7,797,050 B2 9/2010 Libbus et al.
7,797,057 B2 9/2010 Harris
7,797,058 B2 9/2010 Mrva et al.
7,805,195 B2 9/2010 Zealear
7,809,442 B2 10/2010 Bolea et al.
7,813,797 B2 10/2010 Bardy et al.
7,813,802 B2 10/2010 Tcheng et al.
7,813,809 B2 10/2010 Strother et al.
7,818,063 B2 10/2010 Wallace et al.
7,822,486 B2 10/2010 Foster et al.
7,860,570 B2 12/2010 Whitehurst et al.
7,979,128 B2 7/2011 Tehrani et al.
8,249,723 B2 8/2012 McCreery
8,255,056 B2 8/2012 Tehrani
8,311,645 B2 11/2012 Bolea et al.
8,386,046 B2 2/2013 Tesfayesus et al.
8,428,727 B2 4/2013 Bolea et al.
8,498,712 B2 7/2013 Bolea et al.
8,626,304 B2 1/2014 Bolea et al.
8,639,354 B2 1/2014 Bolea et al.
8,718,783 B2 5/2014 Bolea et al.
8,744,589 B2 6/2014 Bolea et al.
8,855,771 B2 10/2014 Tesfayesus et al.
9,186,511 B2 11/2015 Bolea
2001/0010010 A1 7/2001 Richmond et al.
2001/0031929 A1 10/2001 O'Toole
2002/0010495 A1 1/2002 Freed et al.
2002/0049479 A1 4/2002 Pitts
2002/0092527 A1 7/2002 Wood
2002/0128700 A1 9/2002 Cross
2002/0156507 A1 10/2002 Lindenthaler
2002/0165462 A1 11/2002 Westbrook et al.
2002/0166556 A1 11/2002 Jacob
2002/0195108 A1 12/2002 Mittelstadt et al.
2002/0195109 A1 12/2002 Mittelstadt et al.
2003/0034031 A1 2/2003 Lev et al.
2003/0040785 A1 2/2003 Maschino et al.
2003/0078643 A1 4/2003 Schulman et al.
2003/0083696 A1 5/2003 Avital
2003/0093128 A1 5/2003 Freed et al.
2003/0106555 A1 6/2003 Tovey
2003/0106556 A1 6/2003 Alperovich et al.
2003/0114895 A1 6/2003 Gordon et al.
2003/0114905 A1 6/2003 Kuzma
2003/0153953 A1 * 8/2003 Park et al. ..... A61N 1/36585 607/17
2003/0167018 A1 9/2003 Wyckoff

(56) References Cited

U.S. PATENT DOCUMENTS

2003/0195571 A1 10/2003 Burnes et al.
2003/0209145 A1 11/2003 Soper
2003/0216789 A1 11/2003 Deem et al.
2004/0015204 A1 1/2004 Whitehurst et al.
2004/0020489 A1 2/2004 Gillespie et al.
2004/0049241 A1 3/2004 Campos
2004/0055603 A1 3/2004 Bruce
2004/0073272 A1 4/2004 Knudson et al.
2004/0089303 A1 5/2004 Chien
2004/0111139 A1* 6/2004 McCreery ..... 607/117
2004/0116819 A1 6/2004 Alt
2004/0116978 A1 6/2004 Bradley
2004/0122497 A1 6/2004 Zhang et al.
2004/0138581 A1 7/2004 Frei et al.
2004/0153127 A1 8/2004 Gordon et al.
2004/0162499 A1 8/2004 Nagai et al.
2004/0194784 A1 10/2004 Bertrand
2004/0215288 A1 10/2004 Lee et al.
2004/0215290 A1 10/2004 Zealer
2004/0230278 A1 11/2004 Dahl et al.
2004/0233058 A1 11/2004 Dodds
2004/0260310 A1 12/2004 Harris
2004/0261791 A1 12/2004 Horian
2005/0004610 A1 1/2005 Kim et al.
2005/0010265 A1 1/2005 Fassio et al.
2005/0038490 A1 2/2005 Gross et al.
2005/0039757 A1 2/2005 Wood
2005/0043644 A1 2/2005 Stahmann et al.
2005/0043772 A1 2/2005 Stahmann et al.
2005/0076908 A1 4/2005 Lee et al.
2005/0085865 A1 4/2005 Tehrani
2005/0085866 A1 4/2005 Tehrani
2005/0085868 A1 4/2005 Tehrani et al. .... A61N 1/36132 607/42
2005/0085869 A1 4/2005 Tehrani et al.
2005/0085874 A1 4/2005 Davis et al.
2005/0098176 A1 5/2005 Hoffrichter
2005/0101833 A1 5/2005 Hsu et al.
2005/0119711 A1 6/2005 Cho et al.
2005/0139216 A1 6/2005 Mittelstadt et al.
2005/0165457 A1 7/2005 Benser et al.
2005/0209513 A1 9/2005 Heruth et al.
2005/0209643 A1 9/2005 Heruth et al.
2005/0234523 A1* 10/2005 Levin et al. ..... 607/42
2005/0235992 A1 10/2005 Djupesland
2005/0240241 A1 10/2005 Yun et al.
2005/0251216 A1 11/2005 Hill et al.
2005/0261747 A1 11/2005 Schuler et al.
2005/0267380 A1 12/2005 Poezevara
2005/0267547 A1 12/2005 Knudson et al.
2005/0277844 A1 12/2005 Strother et al.
2005/0277999 A1 12/2005 Strother et al.
2005/0278000 A1 12/2005 Strother et al.
2006/0004429 A1 1/2006 Mrva et al.
2006/0005842 A1 1/2006 Rashad et al.
2006/0025828 A1 2/2006 Armstrong et al.
2006/0030919 A1* 2/2006 Mrva et al. ..... 607/118
2006/0032497 A1 2/2006 Doshi
2006/0041295 A1* 2/2006 Osypka ..... 607/117
2006/0052836 A1 3/2006 Kim et al.
2006/0058588 A1 3/2006 Zdeblick
2006/0058852 A1 3/2006 Koh et al.
2006/0064029 A1 3/2006 Arad
2006/0064138 A1 3/2006 Velasco et al.
2006/0079802 A1 4/2006 Jensen et al.
2006/0095088 A1 5/2006 De Ridder
2006/0111755 A1 5/2006 Stone et al.
2006/0116739 A1 6/2006 Betser et al.
2006/0129189 A1 6/2006 George et al.
2006/0135886 A1 6/2006 Lippert et al.
2006/0136024 A1 6/2006 Cohen et al.
2006/0142815 A1 6/2006 Tehrani et al.
2006/0144398 A1 7/2006 Doshi et al.
2006/0149334 A1* 7/2006 Tehrani et al. ..... A61N 1/3601 607/42
2006/0149345 A1 7/2006 Boggs et al.
2006/0150978 A1 7/2006 Doshi et al.
2006/0150979 A1 7/2006 Doshi et al.
2006/0150980 A1 7/2006 Kim
2006/0155341 A1 7/2006 Tehrani et al.
2006/0167497 A1 7/2006 Armstrong et al.
2006/0184204 A1 8/2006 He
2006/0195170 A1 8/2006 Cohen et al.
2006/0211951 A1 9/2006 Milijasevic et al.
2006/0224209 A1 10/2006 Meyer
2006/0224211 A1 10/2006 Durand
2006/0241506 A1 10/2006 Melker et al.
2006/0241708 A1 10/2006 Boute
2006/0247729 A1 11/2006 Tehrani et al.
2006/0259079 A1 11/2006 King
2006/0264777 A1 11/2006 Drew
2006/0266369 A1 11/2006 Atkinson et al.
2006/0271118 A1 11/2006 Libbus et al.
2006/0271137 A1 11/2006 Stanton-Hicks
2006/0282127 A1 12/2006 Zealear
2006/0293720 A1 12/2006 DiLorenzo
2006/0293723 A1 12/2006 Whitehurst et al.
2007/0021785 A1 1/2007 Inman et al.
2007/0027482 A1 2/2007 Parnis et al.
2007/0038265 A1 2/2007 Tcheng et al.
2007/0043411 A1 2/2007 Foster et al.
2007/0095347 A1 5/2007 Lampotang et al.
2007/0125379 A1 6/2007 Pierro et al.
2007/0150006 A1 6/2007 Libbus
2007/0175478 A1 8/2007 Brunst
2007/0227542 A1 10/2007 Kashmakov et al.
2007/0239243 A1 10/2007 Moffitt et al.
2007/0277832 A1 12/2007 Doshi et al.
2007/0282410 A1 12/2007 Cross et al.
2007/0283692 A1 12/2007 Tetsuka et al.
2007/0283962 A1 12/2007 Doshi et al.
2007/0295338 A1 12/2007 Loomas et al.
2008/0023007 A1 1/2008 Dolezal et al.
2008/0027480 A1 1/2008 van der Burg et al.
2008/0027502 A1 1/2008 Ransom
2008/0041373 A1 2/2008 Doshi et al.
2008/0099029 A1 5/2008 Lamberg
2008/0103407 A1 5/2008 Bolea et al.
2008/0103545 A1 5/2008 Bolea et al.
2008/0147142 A1 6/2008 Testerman et al.
2008/0163875 A1 7/2008 Aarestad et al.
2008/0183254 A1 7/2008 Bly et al.
2009/0044814 A1 2/2009 Iancea et al.
2009/0270707 A1 10/2009 Alfoqaha et al.
2009/0276024 A1 11/2009 Bonde et al.
2009/0308395 A1 12/2009 Lee et al.
2009/0318986 A1 12/2009 Alo et al.
2009/0326408 A1 12/2009 Moon et al.
2010/0016749 A1 1/2010 Atsma et al.
2010/0036285 A1 2/2010 Govari et al.
2010/0047376 A1 2/2010 Imbeau et al.
2010/0076536 A1 3/2010 Merz et al.
2010/0094379 A1 4/2010 Meadows et al.
2010/0100150 A1 4/2010 Kirby et al.
2010/0125310 A1 5/2010 Wilson et al.
2010/0131029 A1 5/2010 Durand et al.
2010/0137931 A1 6/2010 Hopper et al.
2010/0137949 A1 6/2010 Mazgalev et al.
2010/0137956 A1 6/2010 Osypka et al.
2010/0152553 A1 6/2010 Ujhazy et al.
2010/0174341 A1 7/2010 Bolea et al.
2010/0228133 A1 9/2010 Averina et al.
2010/0228317 A1 9/2010 Libbus et al.
2010/0241207 A1 9/2010 Bluger
2010/0257729 A1 10/2010 Alexander et al.
2010/0262209 A1 10/2010 King et al.
2011/0071591 A1 3/2011 Bolea et al.
2011/0093032 A1 4/2011 Boggs et al.
2012/0017920 A1 1/2012 Sanders
2012/0022389 A1 1/2012 Sanders

(56) References Cited

U.S. PATENT DOCUMENTS

| | | | |
|---|---|---|---|
| 2012/0192874 | A1 | 8/2012 | Bolea et al. |
| 2013/0085546 | A1 | 4/2013 | Bolea et al. |

FOREIGN PATENT DOCUMENTS

| | | | |
|---|---|---|---|
| EP | 1 404 221 | | 2/2007 |
| EP | 1 404 221 | B1 | 2/2007 |
| EP | 1 854 494 | A1 | 11/2007 |
| EP | 1 322 384 | B1 | 12/2007 |
| JP | 53118893 | | 10/1978 |
| JP | 9-294819 | | 11/1997 |
| JP | 2000-506601 | | 5/2000 |
| JP | 2000-508562 | | 7/2000 |
| JP | 2003-305135 | | 10/2003 |
| JP | 2004-508908 | | 3/2004 |
| JP | 2004-532707 | | 10/2004 |
| JP | 3688301 | | 5/2005 |
| JP | 3688301 | | 6/2005 |
| JP | 2005-521485 | | 7/2005 |
| JP | 2007-21156 | | 2/2007 |
| WO | WO 98/20938 | | 5/1998 |
| WO | WO 02/024279 | | 3/2002 |
| WO | WO 03/000133 | | 1/2003 |
| WO | WO 03/000347 | A1 | 1/2003 |
| WO | WO 03/082393 | A1 | 10/2003 |
| WO | WO 2005/004993 | A1 | 1/2005 |
| WO | WO 2006/045251 | A1 | 5/2006 |
| WO | WO 2006/063339 | A2 | 6/2006 |
| WO | WO 2007/134458 | A1 | 11/2007 |
| WO | WO 2008/046190 | | 4/2008 |
| WO | WO 2008/046190 | A1 | 4/2008 |

OTHER PUBLICATIONS

Schwartz et al. "Therapeutic Electrical Stimulation of the Hypoglossal Nerve in Obstructive Sleep Apnea." Arch Otolaryngol Head Neck Surg/vol. 127, Oct. 2001 (8 pages).

Aziz, L. and Ejnell, H. "Obstructive Sleep Apnea Caused by Bilateral Vocal Fold Paralysis." Ear Nose Throat J. Apr. 2003; 82(4): 326-7.

Extended Search Report on European application No. 19151866 dated May 22, 2019. 7 pages.

Ferguson et al., "Effect of Mandibular and Tongue Protrusion on Upper Airway Size During Wakefulness," American Journal of Respiratory and Critical Care Medicine, 1997, pp. 1748-1754, vol. 155.

Huang et al. "Dilation of the oropharynx via selective stimulation of the hypoglossal nerve." J. Neural Eng. 2005; 2:73-80.

Isono et al., "Interaction of cross-sectional area, driving pressure, and airflow of passive velopharynx," American Physiological Society, 1997, pp. 851-859, vol. 83.

Oliven et al., "Effect of genioglossus contraction on pharyngeal lumen and airflow in sleep apnoea patients," European Respiratory Journal, 2007, pp. 748-758, vol. 30, No. 4.

Response to the Notice of Opposition for Opposition against patent EP 2 116 274 (Application No. 09 161 958.5) dated Dec. 2, 2013 (30 pages).

Statement of Grounds filed in Opposition of EP Patent No. 2116274 dated Jul. 25, 2012 (32 pages).

Stern et al. "Obstructive sleep apnea following treatment of head and neck cancer", Ear, Nose, and Throat Journal, Feb. 2007, vol. 86, No. 2, pp. 101-103.

European Search Report for Patent Application No. 16162666, dated Jul. 8, 2016, 7 pages.

Extended European Search Report for EP Application No. 15192695.3 dated Mar. 2, 2016, 7 pages.

Spence et al., "High-flow nasal cannula as a device to provide continuous positive airway pressure in infants," *Journal of Perinatology*, Dec. 2007, pp. 772-775, vol. 27 (12), Nature Publishing Group.

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

De Almeida et al., "Nasal pressure recordings to detect obstructive sleep apnea" *Sleep and Breathing*, Feb. 25, 2006, pp. 62-69, vol. 10 (2), Springer Heidelberg.

Saslow et al., "Work of breathing using high-flow nasal cannula in preterm infants" *Journal of Perinatology*, May 11, 2006, pp. 476-480, vol. 26 (8), Nature Publishing Group.

Campbell et al., "Nasal Continuous positive airway pressure from high flow cannula versus Infant Flow for preterm infants," *Journal of Perinatology*, Jul. 2006, pp. 546-549, vol. 26 (9), Nature Publishing Group.

Trevisanuto et al., "A new device for administration of continuous positive airway pressure in preterm infants: comparison with a standard nasal CPAP continuous positive airway pressure system," *Intensive Care Medicine*, Apr. 2005, pp. 859-864, vol. 31 (6), Springer-Verlag.

Verse et al., "New developments in the therapy of obstructive sleep apnea," *European Archives of Oto-Rhino-Laryngology*, Jan. 2001, pp. 31-37, vol. 258 (1), Springer-Verlag.

Paquereau et al., "Positive pressure titration in the treatment of obstructive sleep apnea syndrome using continuous airway positive pressure," *Revue Des Maladies Respiratoires*, Apr. 2000, pp. 459-465, vol. 17 (2), Masson Editeur.

Mahadevia et al., "Effects of expiratory positive airway pressure on sleep-induced respiratory abnormalities in patients with hypersomnia-sleep apnea syndrome," *Am. Rev. Respir. Dis.*, Feb. 1983, vol. 128, pp. 708-711.

Tiran et al., "An Improved Device for Posterior Rhinomanometry to Measure Nasal Resistance" *Journal of Biomechnical Engineering*, Nov. 2005, vol. 127, pp. 994-997.

Noseda et al., "Compliance with nasal continuous positive airway pressure assessed with a pressure monitor: pattern of use and influence of sleep habits," Chest Clinics and Sleep Laboratories, Hôpitaux Erasme et Brugmann, Université Libre de Bruxelles, Brussels, Belgium, 2000, vol. 94, pp. 76-81.

Sahin et al., "Chronic recordings of hypoglossal nerve activity in a dog model of upper airway obstruction," *Journal of Applied Physiology* 87(6), 1999, The American Physiological Society, pp. 2197-2206.

Goding Jr. et al., "Relief of Upper Airway Obstruction With Hypoglossal Nerve Stimulation in the Canine," *The Laryngoscope*, Feb. 1998, pp. 162-169, vol. 108, Lippincott-Raven Publishers, U.S.A.

Partial European Search Report dated Aug. 19, 2009, issued in corresponding European Patent Application No. 09161958.5 (4 pages).

European Search Report issued in corresponding European Application No. 121 637 91 on Jun. 25, 2012, 3 pages.

* cited by examiner

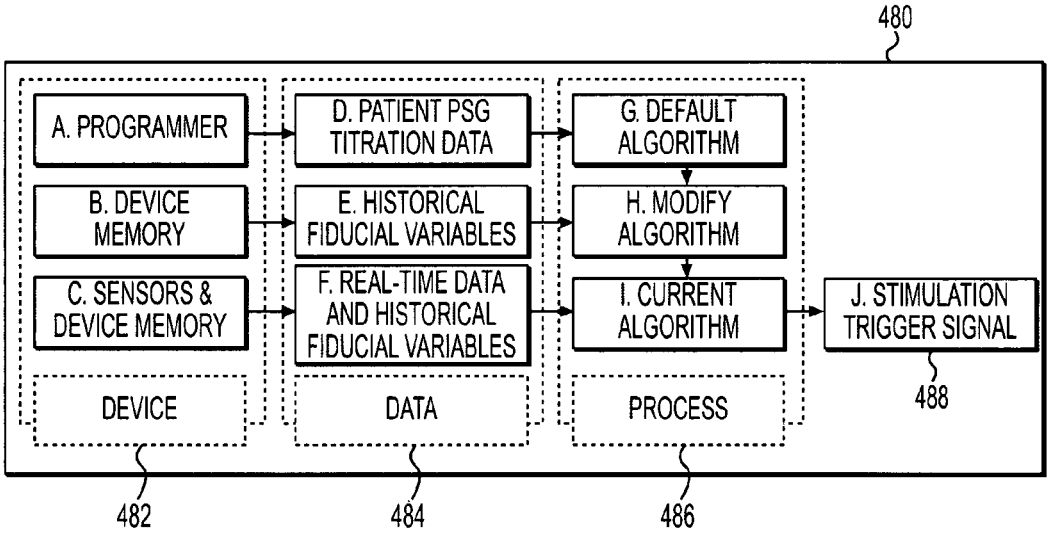

FIG. 48

| REFERENCE MARKER ON GRAPH | VARIABLE NAME | VALUE & TIME OF EVENT |
|---|---|---|
| T | T | TIME OF ONSET OF INSPIRATION AS INDICATED BY PRESSURE SENSOR IN-LINE WITH AIRFLOW. |
| | T.est | ESTIMATED ONSET AS CALCULATED FROM HISTORICAL FIDUCIAL VARIABLES. |
| | T. pred | PREDICTED ONSET AS CALCULATED FROM REAL-TIME DATA AND HISTORICAL FIDUCIAL VARIABLES. |
| A | Vmax t.Vmax | POSITIVE PEAK OF PRIMARY SIGNAL |
| B | Vmin t.Vmin | MINIMUM OF PRIMARY SIGNAL BETWEEN SUCCESSIVE POSITIVE PEAKS |
| C | dV.in t.dV.in | MOST POSITIVE 1ST DERIVATIVE DURING EXPIRATION |
| D | dV.ex t.dV.ex | MOST NEGATIVE 1ST DERIVATIVE DURING EXPIRATION |
| E | D2V.in t.d2V.in | MOST POSITIVE 2ND DERIVATIVE DURING INSPIRATION. THIS TYPICALLY OCCURS SOON AFTER ONSET OF INSPIRATION. |
| F | d2V.pk t.d2V.pk | MOST NEGATIVE 2ND DERIVATIVE SLOPE. THIS OCCURS AT OR NEAR THE POSITIVE PEAK OF PRIMARY SIGNAL. |
| G | d2V.ex t.d2V.ex | MOST POSITIVE 2ND DERIVATIVE FOLLOWING INSPIRATION. THIS TYPICALLY OCCURS NEAR THE OFFSET OF EXPIRATION. |
| C2 | V.in50 t.V.in50 | THE POINT AT WHICH THE PRIMARY SIGNAL'S MAGNITUDE IS 50% BETWEEN POSITIVE PEAK AND PRECEEDING MINIMUM. |
| D2 | V.ex50 t.V.ex50 | THE POINT AT WHICH THE PRIMARY SIGNAL'S MAGNITUDE IS 50% BETWEEEN POSITIVE PEAK AND FOLLOWING MINIMUM. |

FIG. 49

OBSTRUCTIVE SLEEP APNEA TREATMENT DEVICES, SYSTEMS AND METHODS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This [patent] application *is a reissue application of U.S. Pat. No. 8,417,343 B2, which issued on Apr. 9, 2013, from U.S. patent application Ser. No. 11/907,533, filed on Oct. 12, 2007, which* claims the benefits of priority under 35 U.S.C. §§119 and 120 to U.S. Provisional Patent Application Nos. 60/851,386 and 60/918,257, filed on Oct. 13, 2006, and Mar. 14, 2007, respectively, *the disclosures of which are expressly incorporated by reference herein.* [The entire contents of these provisional applications are incorporated herein by reference.] *This application is related to reissue application Ser. No. 14/693,836, filed on Apr. 22, 2015.*

FIELD OF THE INVENTION

The inventions described herein relate to devices, systems and associated methods for treating sleeping disorders. More particularly, the inventions described herein relate to devices, systems and methods for treating obstructive sleep apnea.

BACKGROUND OF THE INVENTION

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc.

Continuous positive airway pressure (CPAP) is a standard treatment for OSA. While CPAP is non-invasive and highly effective, it is not well tolerated by patients. Patient compliance for CPAP is often reported to be between 40% and 60%.

Surgical treatment options for OSA are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibulary advancement), and/or they may be socially stigmatic (e.g., tracheostomy).

U.S. Pat. No. 4,830,008 to Meer proposes hypoglossal nerve stimulation as an alternative treatment for OSA. An example of an implanted hypoglossal nerve stimulator for OSA treatment is the Inspire™ technology developed by Medtronic, Inc. (Fridely, Minn.). The Inspire device is not FDA approved and is not for commercial sale. The Inspire device includes an implanted neurostimulator, an implanted nerve cuff electrode connected to the neurostimulator by a lead, and an implanted intra-thoracic pressure sensor for respiratory feedback and stimulus trigger. The Inspire device was shown to be efficacious (approximately 75% response rate as defined by a 50% or more reduction in RDI and a post RDI of ≤20) in an eight patient human clinical study, the results of which were published by Schwartz et al. and Eisele et al. However, both authors reported that only three of eight patients remained free from device malfunction, thus demonstrating the need for improvements.

SUMMARY OF THE INVENTION

To address this and other unmet needs, the present invention provides, in exemplary non-limiting embodiments, devices, systems and methods for nerve stimulation for OSA therapy as described in the following detailed description.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIGS. 48-50 schematically illustrate alternative stimulation trigger algorithms;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Description of Fully Implanted Neurostimulator System

Figure 1:
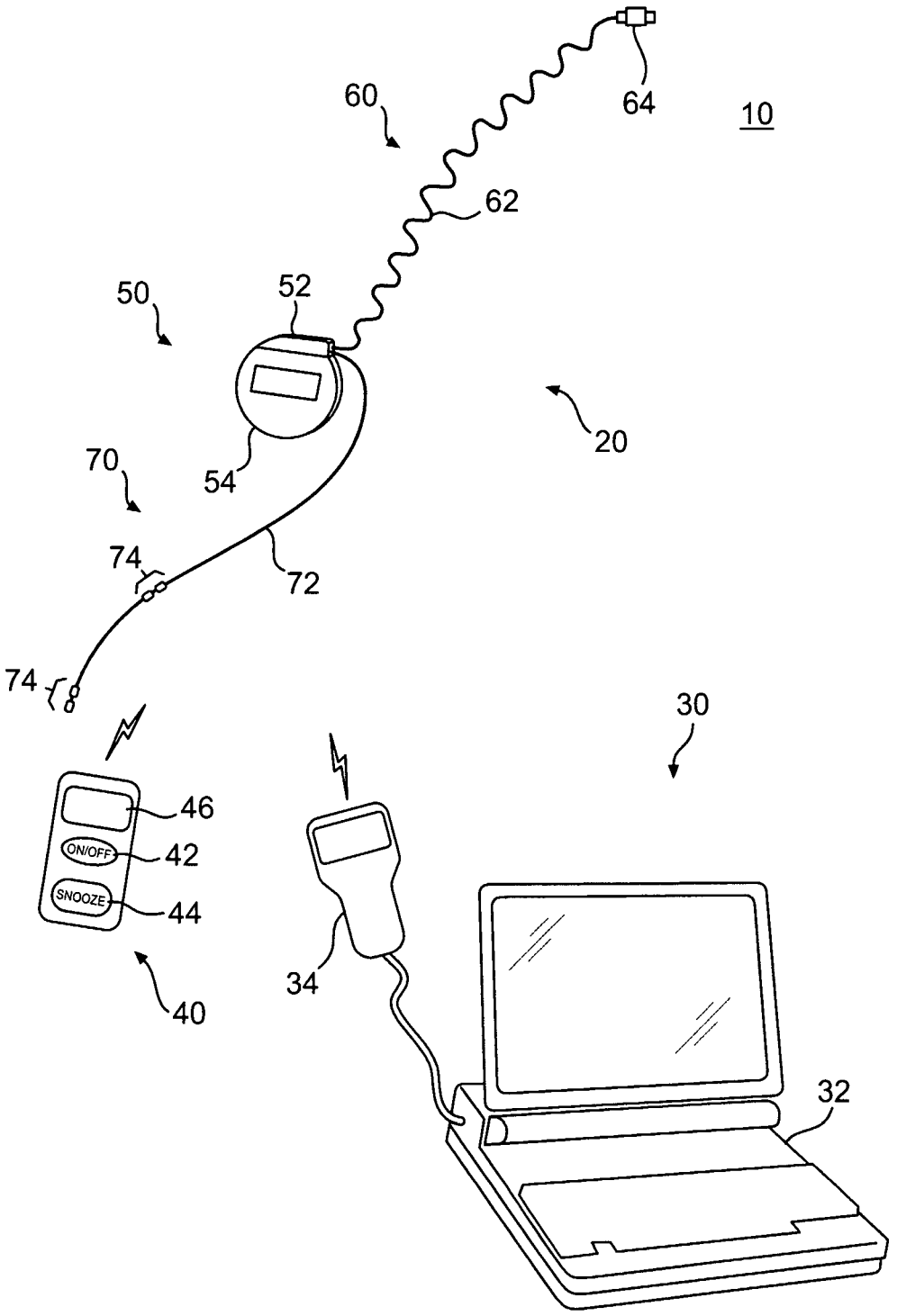
FIG. 1 is a schematic diagram showing a fully implanted neurostimulator system with associated physician programmer and patient controller for treating obstructive sleep apnea.

With reference to FIG. 1, a neurostimulator system 10 including implanted components 20, physician programmer 30 and patient controller 40 is shown schematically. The implanted components of the system 10 may generally include an implanted neurostimulator (INS) 50 (a.k.a., implanted pulse generator (IPG)), an implanted stimulation lead (or leads) 60, and an implanted respiration sensing lead (or leads) 70. The INS 50 generally includes a header 52 for connection of the leads 60/70, and a hermetically sealed housing 54 for the associated electronics and long-life or rechargeable battery (not visible). The stimulation lead 60 generally includes a lead body 62 with a proximal connector and a distal nerve electrode cuff 64. The respiration sensing lead 70 generally includes a lead body 72 with a proximal connector and one or more sensors 74 disposed on or along a distal portion thereof. Suitable designs of the INS 50, stimulation lead 60 and respiration sensing lead 70 are described in more detail hereinafter.

Figure 2:
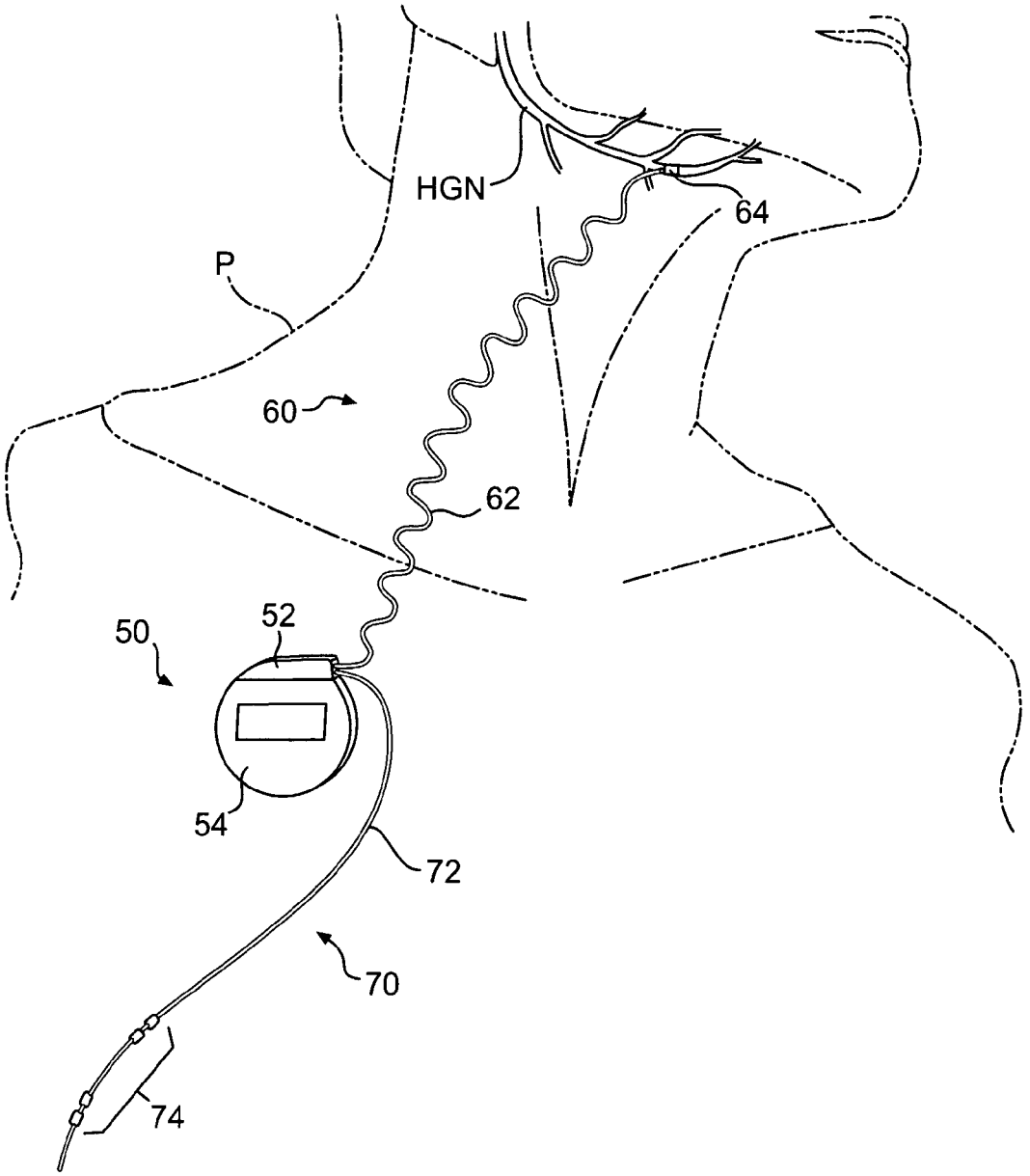
FIG. 2 is a schematic diagram showing the implantable components of FIG. 1 implanted in a patient.

As shown in FIG. 2, and by way of example, not limitation, the implanted components 20 (shown faded) of the neurostimulator system 10 are implanted in a patient P with the INS 50 disposed in a subcutaneous pocket, the stimulation lead body 62 disposed in a subcutaneous tunnel, the nerve cuff electrode 64 disposed on a nerve (e.g., hypoglossal nerve (HGN)) innervating a muscle (e.g., genioglossus muscle, not shown) controlling the upper airway, the respiration sensing lead body 72 disposed in a subcutaneous tunnel, and the respiration sensors 74 disposed adjacent lung tissue and/or intercostal muscles outside the pleural space.

Generally, electrical stimulus is delivered by the INS 50 via the stimulation lead 60 to a nerve innervating a muscle controlling upper airway patency to mitigate obstruction thereof. To reduce nerve and muscle fatigue, the stimulus may be delivered for only a portion of the respiratory cycle, such as during inspiration which corresponds to negative pressure in the upper airway. Stimulation may be thus triggered as a function of respiration as detected by respiration sensing lead 70 in a closed-loop feedback system. By way of example, the stimulus may be triggered to turn on at the end of expiration (or at the beginning of inspiration), and triggered to turn off at the beginning of expiration (or at the end of inspiration). Triggering the stimulus as a function of expiration improves capture of the entire inspiratory phase, including a brief pre-inspiratory phase of about 300 milliseconds, thus more closely mimicking normal activation of upper airway dilator muscles. Over-stimulation may cause nerve and/or muscle fatigue, but a 40% to 50% duty cycle may be safely tolerated, thus enabling limited over-stimulation. As an alternative, stimulus may be delivered independent of actual respiration wherein the stimulus duty cycle is set for an average inspiratory duration at a frequency approximately equal to an average respiratory cycle.

Stimulus may be delivered to one or more of a variety of nerve sites to activate one muscle or muscle groups controlling patency of the upper airway. For example, stimulation of the genioglossus muscle via the hypoglossal nerve moves or otherwise stiffens the anterior portion of the upper airway, thereby decreasing the critical pressure at which the upper airway collapses during inspiration and reducing the likelihood of an apnea or hypopnea event occurring during sleep. Because the systems described herein work at the level of the tongue, it may be desirable to combine this therapy with a therapy (e.g., UPPP or palatal implant) that work at the level of the soft palate, thus increasing efficacy for a broader range of patients.

With reference back to FIG. 1, the physician programmer 30 may comprise a computer 32 configured to control and program the INS 50 via a wireless link to a programming wand 34. The physician programmer 30 may be resident in a sleep lab where the patient undergoes a polysomnographic (PSG) study during which the patient sleeps while the INS 50 is programmed to optimize therapy.

The patient controller 40 may comprise control circuitry and associated user interface to allow the patient to control the system via a wireless telemetry link while at home, for example. The patient controller 40 may include a power switch 42 to turn the system on and slowly ramp up when the patient goes to sleep at night, and turn it off when the patient wakes in the morning. A snooze switch 44 may be used to temporarily put the INS 50 in standby mode during which electrical stimulus is paused for a preprogrammed period of time to allow the patient to temporarily wake, after which the INS 50 turns back on and ramps up to the desired stimulus level. A display 46 may be provided to indicate the status of the INS 50 (e.g., on, off or standby), to indicate satisfactory wireless telemetry link to the INS 50, to indicate remaining battery life of the INS 50, to indicate normal operation of the INS 50, and/or to indicate the need for patient action etc. Display 46 may be configured to be a dash-board-like display, and may be any suitable display available to those of ordinary skill in the art, such as, for example, an LED or LCD display. Furthermore, information may be communicated to the patient controller 40 for display purposes by any suitable means known to those of ordinary skill in the art. For example, communication of information may be achieved through inductively coupled or radio frequency telemetry. The patient controller 40 may also have programmability to adjust stimulus parameters (e.g., amplitude) within a pre-set range determined by the physician in order to improve efficacy and/or to reduce sensory perception, for example. Optionally, the patient controller 40 may be configured to function as the programming wand 34 of the physician programmer 30.

Furthermore, the patient controller 40 may be provided with one or more mechanisms for improving patient compliance. For example, patient controller 40 may be provided with a time-keeping mechanism having the capabilities of a conventional alarm clock. In certain embodiments, controller 40 may be programmed by the user and/or the physician to alert the user when action, such as, for example, turning the system 10 on or off, is required by the user. Controller 40 may be configured to alert the user by any suitable means known in the art. For example, controller 40 may emit an audible alarm at programmed time intervals. In other embodiments, the patient controller 40 may be used to monitor a patient. For example, the patient controller 40 may be programmed to periodically send reports of patient actions, patient compliance, system status, etc., to a clinician or caregiver via a telephone or computer network.

Figure 3:
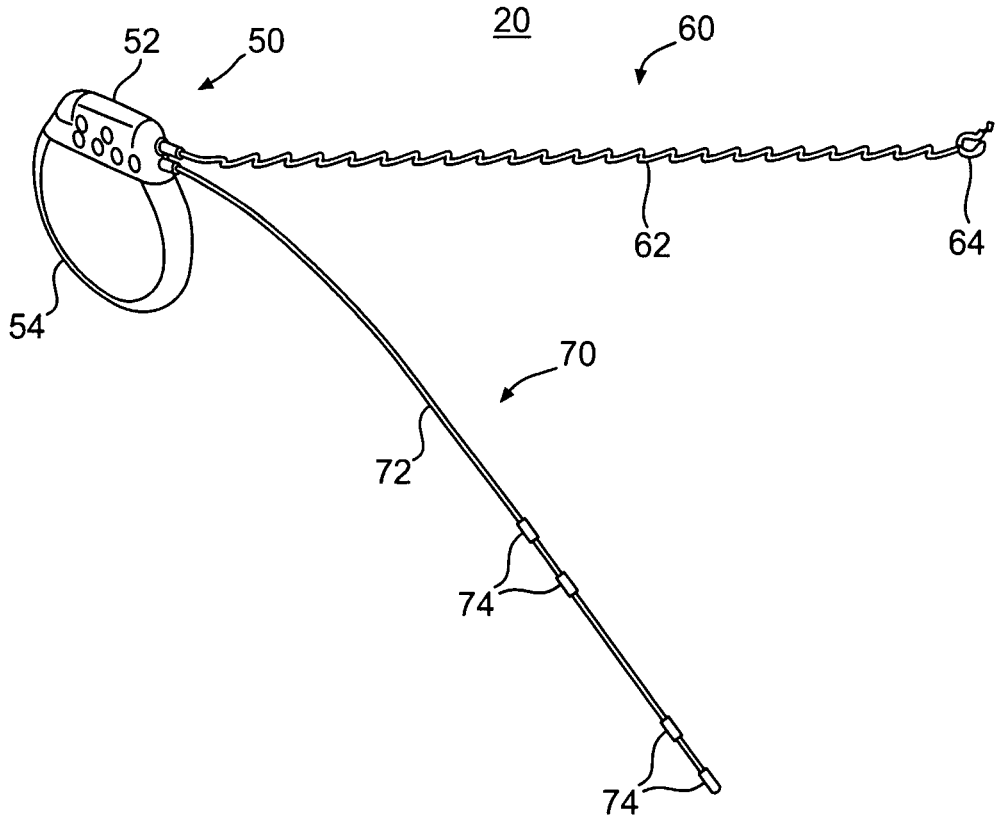
FIG. 3 is a perspective view of the implantable components shown in FIG. 1.

With reference to FIG. 3, the implanted components 20 are shown schematically with more detail. The implanted components include INS 50, stimulation lead 60, and respiration sensing lead 70. The INS 50 includes header 52 and housing 54. The stimulation lead 60 includes lead body 62 and nerve cuff electrode 64. The respiration sensing lead 70 includes lead body 72 and respiration sensors 74 (e.g., impedance sensing electrodes).

Figure 4:
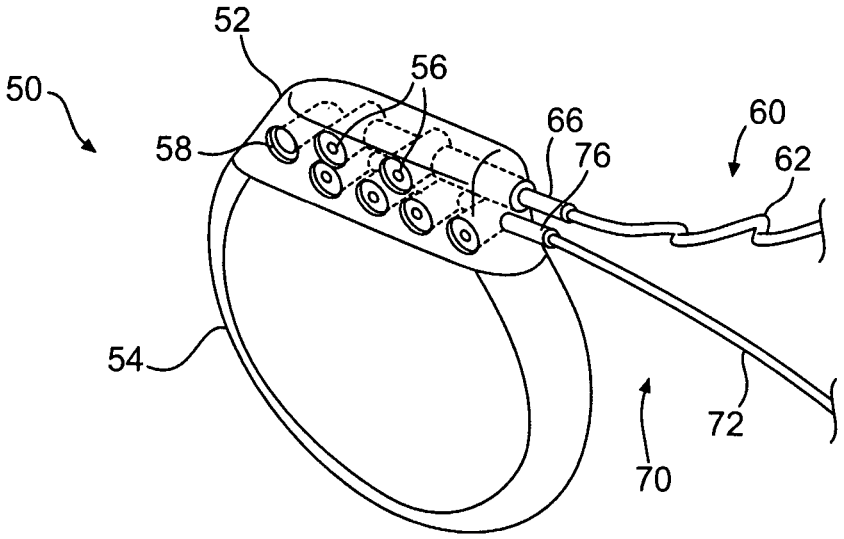
FIG. 4 is a detailed perspective view of the implantable neurostimulator (INS) shown in FIG. 3.

With reference to FIG. 4, the INS 50 is shown schematically in more detail. The INS 50 includes header 52 that may be formed using conventional molding or casting techniques and may comprise conventional materials such as epoxy or polyurethane (e.g., Tecothane brand polyurethane). The housing 54 may be formed using conventional stamping or forming techniques and may comprise conventional materials such as titanium or ceramic. The housing 54 may include one or more isolated electrodes, and/or if a conductive material is used for the housing 54, the housing 54 may comprise an electrode, which may be used for respiratory sensing, for example. The housing 54 may be hermetically sealed to the header 52 using conventional techniques. The header 52 may include two or more receptacles for receiving the proximal connectors 66/76 of the stimulation lead body 62 and respiration sensing lead body 72. The connectors 66/76 may comprise a conventional design such as IS1 or other in-line designs. The header 52 may also include set screw seals and blocks 56 for receiving set screws (not shown) that establish electrical contact between the INS 50 and the conductors of the leads 60/70 via connectors 66/76, and that establish mechanical fixation thereto. Some electrical contact may be achieved through spring type or cam-locked mechanisms. As shown, two set screw arrangements 56 are shown for the stimulation lead 60 and four set screw arrangements 56 are shown for the respiration sensing lead 70, but the number may be adjusted for the number of conductors in each lead. A hole 58 may be provided in the header 52 for securing the INS 50 to subcutaneous tissue using a suture at the time of implantation.

The INS 50 may comprise a conventional implanted neurostimulator design used in neurostimulation applications, such as those available from Texcel (US), CCC (Uruguay) and NeuroTECH (Belgium), but modified for the present clinical application in terms of stimulation signal parameters, respiratory signal processing, trigger algorithm, patient control, physician programming, etc. The INS may contain a microprocessor and memory for storing and processing data and algorithms. Algorithms may be in the form of software and/or firmware, for example. One of several different embodiments of the neurostimulator may be implemented. For example, the neurostimulator may be an internal/implanted neurostimulator (INS) powered by a long-life primary battery or rechargeable battery, or an external neurostimulator (ENS) wirelessly linked (e.g., inductive) to an implanted receiver unit connected to the leads. The INS (or the receiver, unit of the ENS) may be implanted and optionally anchored in a number of different locations including a subcutaneous pocket in the pectoral region, the dorsal neck region, or cranial region behind the ear, for example.

The INS 50 may include any suitable circuitry and programming in accordance with the principles of the present disclosure. In one embodiment, INS 50 may include an activity sensor (not shown) for sensing the activity of a patient, including the amount of activity of the patient. The activity sensor may detect motion of a patient by any suitable means available to those of ordinary skill in the art. For example, a patient's motion may be detected by, for example, using an internal accelerometer and/or measuring the impedance of the patient's torso with, for example, the built-in respiration sensor discussed below, and/or measuring a tissue pressure on the surface of the implanted INS 50.

The data corresponding to a patient's detected motion may be stored, evaluated, and utilized in any of a number of various ways. In one embodiment, data corresponding to a patient's motion may be used to determine whether a patient is sleeping or awake. For example, when a patient's activity level falls below a predetermined threshold, it may be assumed that the patient is sleeping. Conversely, when the patient's activity level rises above the pre-determined threshold, it may be assumed that the patient is awake. The activity sensor therefore may be used to facilitate selectively applying treatment when the patient is detected to be sleeping and/or inhibiting treatment when the patient is detected to be awake. Alternatively, data corresponding to a patient's motion may be evaluated over a long period of time, such as, for example, the first few months of treatment, for indications of improvement in a patient's quality of life. It is contemplated that increases in a patient's average level of daily activity will correspond to successful treatment of OSA. This, in turn, may correspond to improvements in the patient's quality of life.

Moreover, the INS 50 may include a long-life battery (not shown) which requires periodic replacement after years of service. Alternatively, the INS may include a rechargeable power source such as a rechargeable battery or super capacitor that is used instead of the long-life battery. To facilitate recharging, the INS may include a receiver coil inductively linked to a transmitter coil that is connected to a recharging unit powered by a larger battery or line power. Because the patient is stationary while sleeping, recharging may be scheduled to occur sometime during sleep to eliminate the need to carry the recharging unit during daily activities. The transmitter coil and the receiver coil may be arranged coaxially in parallel planes to maximize energy transfer efficiency, and may be held in proximity to each other by a patch, garment, or other means as described with reference to the external neurostimulator embodiments. Other examples of neurostimulator designs will be described in more detail hereinafter.

Figure 5:
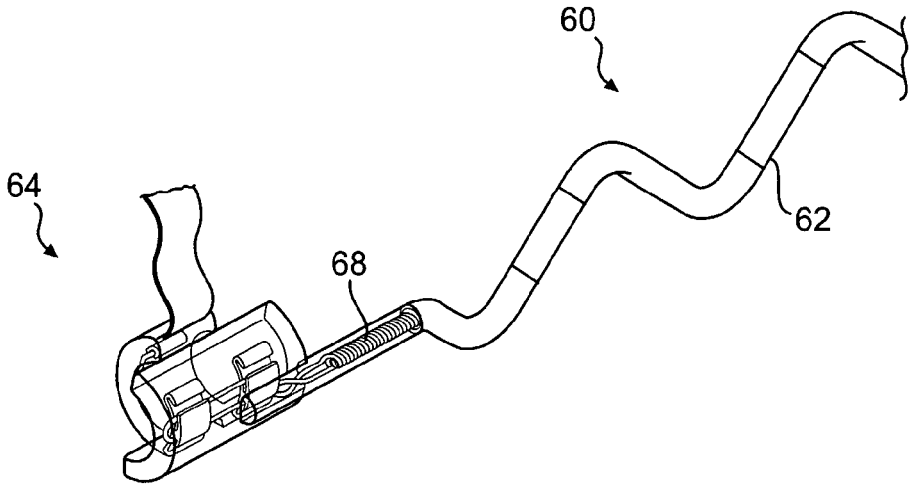
FIG. 5 is a detailed perspective view of the nerve cuff electrode and lead body shown in FIG. 3.

With reference to FIG. 5, the stimulation lead 60 may comprise a variety of different design embodiments and may be positioned at different anatomical sites. For example, a nerve cuff electrode(s) 64 may be attached to a nerve(s) innervating musculature affecting patency of the upper airway. As an alternative or in addition, the nerve cuff electrode 64 may be replaced with an intramuscular electrode and placed directly in the musculature affecting patency of the upper airway. The nerve electrode 64 may be attached to a specific branch of a nerve innervating the desired muscle(s), or may be attached to a proximal trunk of the nerve in which a specific fascicle innervating the desired muscle(s) is targeted by steering the stimulus with multiple electrodes. One or more electrodes may be used for attachment to one or more portions of nerves on one side (unilateral) of the body, or one or more electrodes may be used for attachment to one or more portions of nerves on both sides (bilateral) of the body. Variations in lead body 62 and electrode 64 design as well as variations in the target stimulation site or sites will be described in more detail hereinafter.

With continued reference to FIG. 5, the lead body 62 may be sigmoid shaped, for example, to reduce strain applied to the cuff electrode 64 when the lead body 62 is subject to movement. The sigmoid shape, which may alternatively comprise a variety of other waveform shapes, may have a wavelength of approximately 1.0 to 1.5 cm, and an amplitude of approximately 0.75 to 1.5 cm, for example. The lead body 62 may comprise a tubular jacket with electrical conductors 68 extending therein. The tubular jacket may comprise extruded silicone having an outside diameter of approximately 0.047 inches and an inside diameter of approximately 0.023 inches, for example. The tubular jacket may optionally have a covering of co-extruded polyurethane, for example, to improve durability. The conductors 68, shown in a transparent window in the jacket for purposes of illustration only, may comprise a bifilar coil of insulated (e.g., ETFE) braided stranded wire (BSW) of MP35NLT material. The number of conductors 68 is shown as two, but may be adjusted depending on the desired number of independent electrodes used.

The various embodiments of stimulation leads, for example, stimulation lead 60, disclosed herein may be fabricated by any suitable means known to those having ordinary skill in the art, and may be made from any suitable material. For example, the discussed sigmoid shape of the tubular jacket of lead body 62 may be formed by first extruding silicone in a semi-cured or semi cross-linked state. Next, the semi cross-linked extruded tubular jacket may be placed in a sigmoid mold and then allowed to become fully cross-linked. In particular, the semi cross-linked extruded tubular jacket may be placed in an oven and heated to convert the semi cross-linked silicone of the extruded tubular jacket to fully cross-linked silicone. Additionally, a lumen within the tubular jacket may be created along a longitudinal axis of the tubular jacket by any suitable means.

Furthermore, in accordance with the principles of the present disclosure, it is contemplated that one or more of the various embodiments of stimulation leads disclosed herein may be implanted in or near highly mobile portions of the body. For example, embodiments of the disclosed stimulation leads may be implanted in the ventral neck, for example, along a path between the clavicle and mandible of a patient. Additionally, although mastication, deglutition, and speech may result in mechanical loading on an implanted stimulation lead, it has been found that gross movement of the head and neck may create high mechanical stresses in the conductors of the lead body, lead jacket, and the junction between the conductor wires and the anchor points, such as, for example, the electrodes. Accordingly, it may be desirable to configure the various embodiments of stimulation leads to withstand certain predetermined amounts of fatigue and/or stresses, which may result from mechanical loading on a lead body due to gross movements of a patient's neck and head.

In particular, research has revealed that approximately 98% of the population may experience a 38.5% elongation or less in the distance between the clavicle and angle of the mandible (e.g., adjacent a contemplated area of implantation for a stimulation lead in accordance with the principles of this disclosure). It has also been found that the angular range of motion of the cervical spine between adjacent vertebrae may be approximately 12 degrees, thereby flexing the lead through this angle with a bend radius assumed to be approximately 1.0 centimeter. See Augustus A. White III et al., Clinical Biomechanics of the Spine, pp. 84, 356, and 373 (1978). Furthermore, the frequency of gross head movement through the range of motion in the contemplated area of implantation has been estimated to be approximately 300,000 cycles per year, or on the average approximately 50 times per waking hour.

Figure 5A:
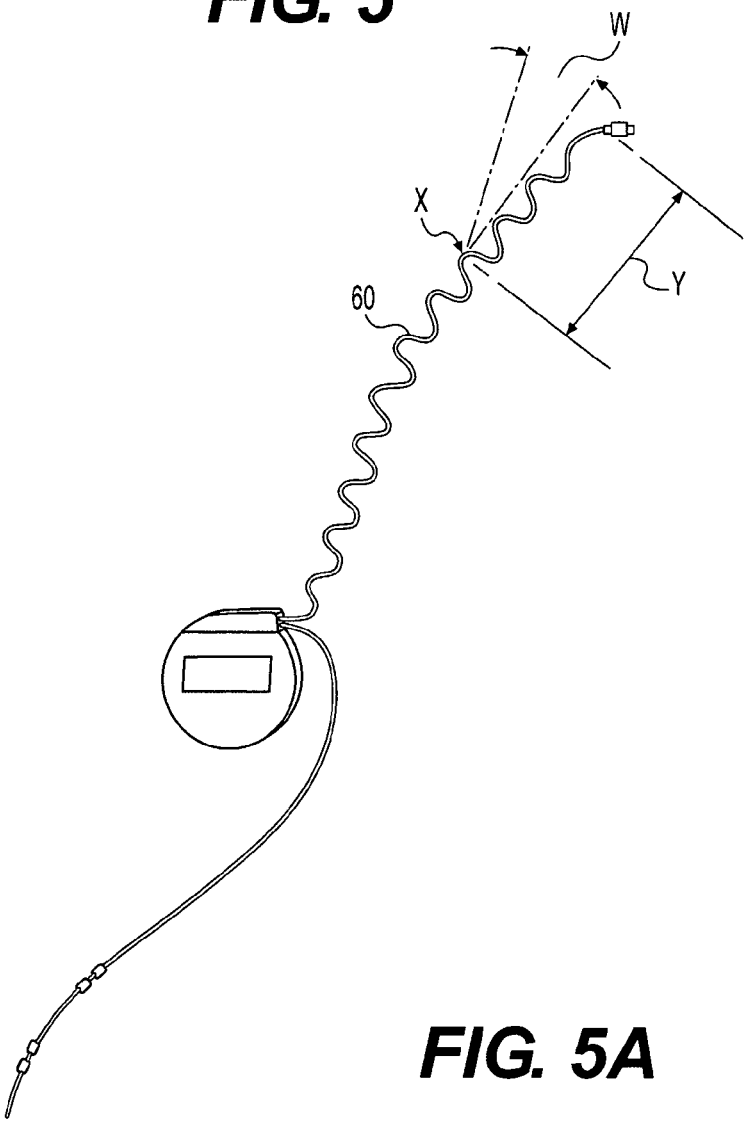
FIG. 5a is an illustration of exemplary movements a lead body may be configured to withstand.

Thus, it may be desirable to design a lead body that is capable of withstanding, among other things, the stresses imparted by the above-noted head and neck movements for an extended amount of time, such as, for example, ten years. In particular, in order to design a lead body that may remain functional for the exemplary ten year implanted life, it may be desirable to configure the lead bodies disclosed herein to withstand at least the above noted elongation and ranges of motion. For example, since implanted lead bodies are likely to be elongated by at least 38.5%, it may be desirable to design lead bodies to withstand being elongated by a predetermined distance Y, such as, for example, approximately 40% (+/−2%) from an initial unstressed state, for a minimum of 3.0 million cycles without failure, as depicted in FIG. 5A. In addition, since it is likely that an implanted lead body may experience an angular range of motion of at least 12 degrees, with a bend radius of approximately 1.0 centimeter, it may be desirable to configure the lead bodies to withstand being flexed around a predetermined radius X, such as, for example, 1.0 centimeter (+/−0.05 centimeters), for a predetermined amount of rotation W, such as, for example, from approximately 0 degrees to approximately 15 degrees (+/−3 degrees), such that the 15 degree maximum deflection occurs coincidentally with the maximum elongation of the lead body.

Figure 6:
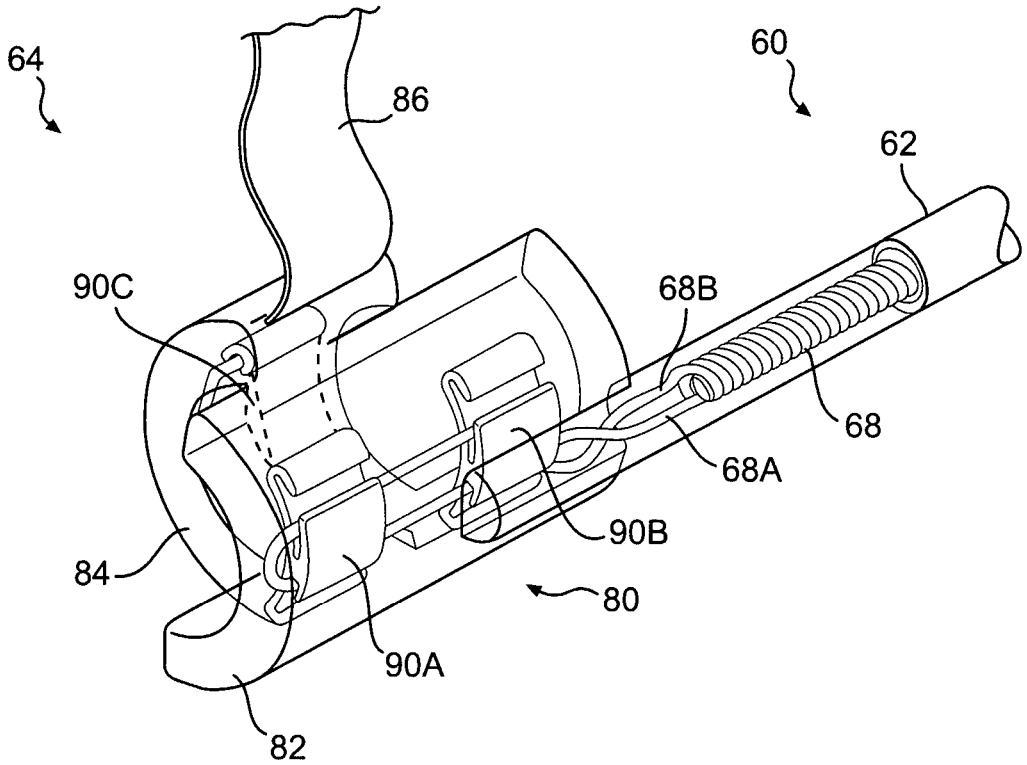
FIG. 6 is a close-up detailed perspective view of the nerve cuff electrode shown in FIG. 3.

With reference to FIG. 6, the nerve cuff electrode 64 may comprise a cuff body 80 having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. This configuration reduces the dissection of nerve branches and vascular supply required to get the cuff around a nerve. For the nerve cuff implant sites discussed herein, the medial side 84 may have a length of less than 6 mm, and preferably in the range of approximately 3 to 5 mm, for example. The lateral side 82 may have a length of more than 6 mm, and preferably in the range of approximately 7 to 8 mm, for example. The cuff body 80 may be compliant and may be available in different sizes with an inside diameter of approximately 2.5 to 3.0 mm or 3.0 to 3.5 mm, for example. The cuff size may also be adjusted depending on the nominal diameter of the nerve at the site of implantation. The cuff body 80 may have a wall thickness of approximately 1.0 mm and may be formed of molded silicone, for example, and may be reinforced with imbedded fibers or fabrics. An integral tow strap 86 may be used to facilitate wrapping the cuff around a nerve by first inserting the strap 86 under and around the deep side of the nerve and subsequently pulling the strap to bring the medial side 84 in position on the deep side of the nerve and the lateral side 82 on the superficial side of the nerve.

With continued reference to FIG. 6, the nerve cuff electrode 64 includes electrode contacts 90A, 90B, and 90C imbedded in the body 80 of the cuff, with their inside surface facing exposed to establish electrical contact with a nerve disposed therein. A transverse guarded tri-polar electrode arrangement is shown by way of example, not limitation, wherein electrode contacts 90A and 90B comprise anodes transversely guarding electrode contact 90C which comprises a cathode.

With this arrangement, the anode electrodes 90A and 90B are connected to a common conductor 68A imbedded in the body 80, and the cathode electrode 90C is connected to an independent conductor 68B extending from the lateral side 82 to the medial side 84 and imbedded in the body 80. By using the conductors 68 to make connections within the body 80 of the cuff 64, fatigue stresses are imposed on the conductors rather than the electrode contacts 90A, 90B and 90C.

Figure 7:
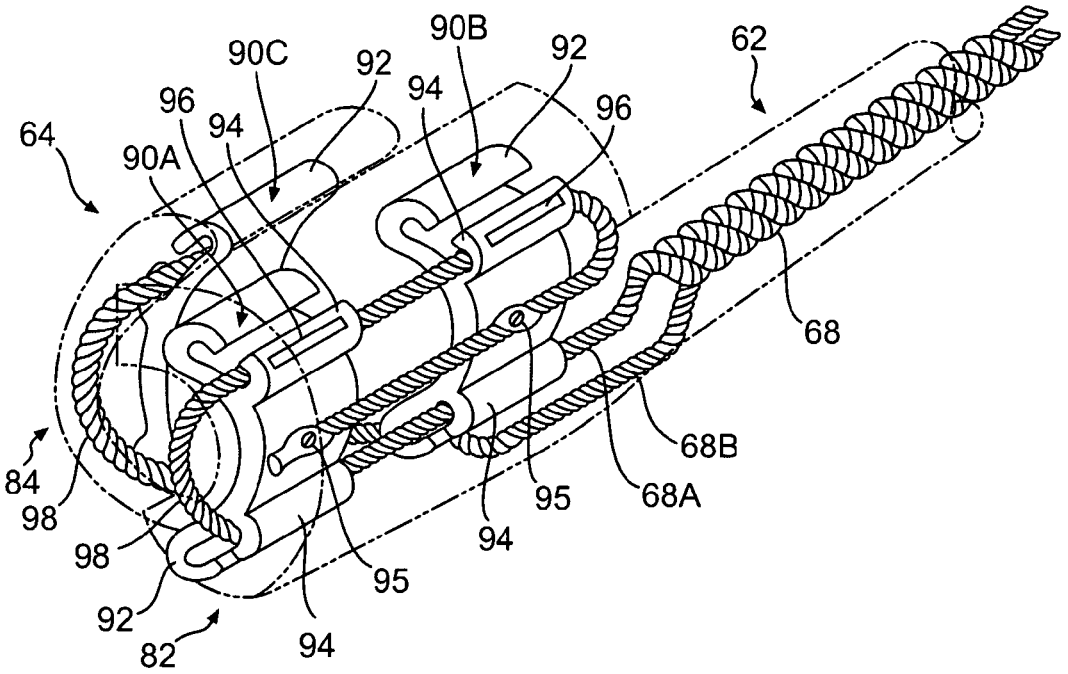
FIG. 7 is a detailed perspective view of the internal components of the nerve cuff electrode shown in FIG. 6.
Figure 8:
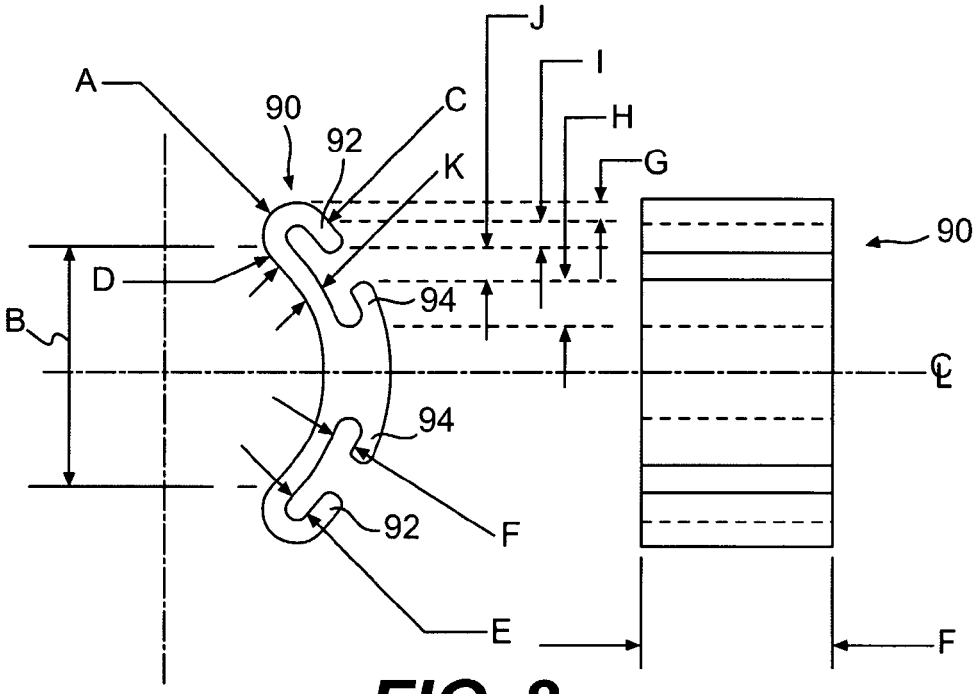
FIG. 8 shows side and end views of an electrode contact of the nerve cuff electrode shown in FIG. 7.

With additional reference to FIGS. 7 and 8, the electrode contacts 90A, 90B and 90C may thus be semi-circular shaped having an arc length of less than 180 degrees, and preferably an arc length of approximately 120 degrees, for example. Each electrode 90 may have two reverse bends (e.g., hooked or curled) portions 92 to provide mechanical fixation to the body 80 when imbedded therein. Each electrode 90 may also have two crimp tabs 94 defining grooves thereunder for crimping to the conductors 68 or for providing a pass-through. As shown in FIG. 7, conductor 68A passes through the grooves under the lower crimp tabs 94 of electrodes 90B and 90A, loops 98 around through the grooves under the upper crimp tabs 94 of electrodes 90A and 90B, is crimped 96 by the upper tabs 94 of electrodes 90A and 90B to provide mechanical and electrical connection, is looped again back between the crimp tabs 94 on the outside of the electrode contact 90, and is resistance spot welded 95 to provide redundancy in mechanical and electrical connection. Also as shown in FIG. 7, conductor 68B passes through the groove under the lower crimp tab 94 of electrode 90C, loops around through the groove under the upper crimp tab 94 of electrode 90C, and is crimped by the upper tab 94 of electrode 90C to provide mechanical and electrical connection. This arrangement avoids off-axis tensile loading at the crimp sites 96 which may otherwise fail due to stress concentration, and the looped portion 98 provides additional strain relief.

FIG. 8 provides example dimensions (inches) of an electrode contact 90 for a 2.5 mm inside diameter cuff, wherein the electrode is formed of 90/10 or 80/20 platinum iridium alloy formed by wire EDM, for example. As illustrated, and as exemplary and approximate dimensions, electrode contact 90 may include a surface A having a full radius, a dimension B of 0.079 inches from tangent to tangent, a dimension C of 0.020 inches (3×), a radius of curvature D of 0.049 R with a 16 micro-inch RMS, a dimension E of 0.008 inches (2×), a dimension F of 0.0065 inches (+/−0.001 inches) (2×), a dimension G of 0.006 inches (+0.002 inches, −0.001 inches) (2×), a dimension H of 0.014 inches (2×), a dimension I of 0.010 inches (2×), a dimension J of 0.010 inches (2×), and a dimension K of 0.006 inches (+/−0.001 inches).

Figure 9B:
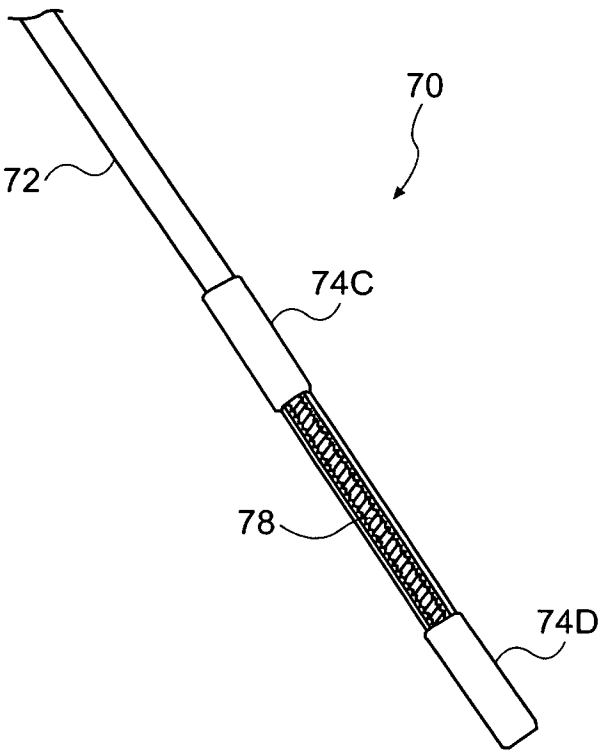
FIGS. 9A and 9B are perspective views of the respiration sensing lead shown in FIG. 3.
Figure 9A:
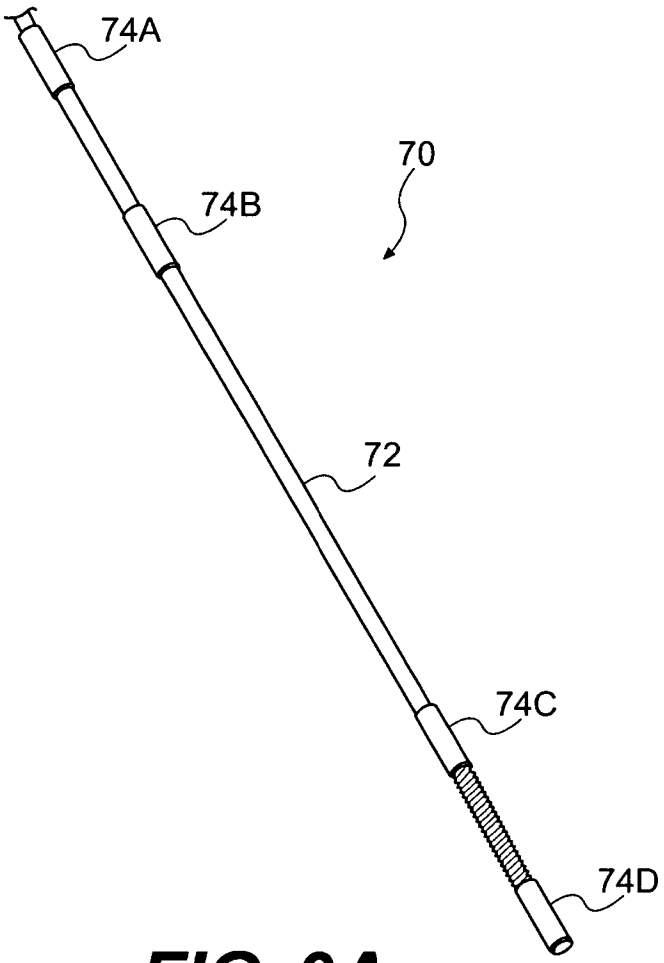

With reference to FIGS. 9A and 9B, a distal portion of the respiration sensing lead 70 and a distal detail of the sensing lead 70, respectively, are shown schematically. In the illustrated embodiment, the respiration sensing lead 70 and associated sensors 74 are implanted as shown in FIG. 2. However, the respiration sensor(s) may comprise a variety of different design embodiments, both implanted and external, and may be positioned at different anatomical sites. Generally, the respiratory sensor(s) may be internal/implanted or external, and may be connected to the neurostimulator via a wired or wireless link. The respiratory sensor(s) may detect respiration directly or a surrogate thereof. The respiratory sensor(s) may measure, for example, respiratory airflow, respiratory effort (e.g., diaphragmatic or thoracic movement), intra-pleural pressure, lung impedance, respiratory drive, upper airway EMG, changes in tissue impedance in and around the lung(s) including the lungs, diaphragm and/or liver, acoustic airflow or any of a number other parameters indicative of respiration. Detailed examples of suitable respiration sensing leads and sensors will be described in more detail hereinafter.

With continued reference to FIGS. 9A and 9B, the respiration sensing lead 70 includes a lead body 72 and a plurality of respiration sensors 74A-74D comprising ring electrodes for sensing bio-impedance. The lead body 72 of the respiration sensing lead 70 may include a jacket cover comprising an extruded silicone tube optionally including a polyurethane cover (80A durometer), or may comprise an extruded polyurethane tube (55D durometer). The ring electrodes 74A-74D may comprise 90/10 or 80/20 platinum iridium alloy tubes having an outside diameter of 0.050 inches and a length of 5 mm, and secured to the jacket cover by laser welding and/or adhesive bonding, for example. The lead body 72 may include a plurality of conductors 78 as seen in the transparent window in the jacket cover, which is shown for purposes of illustration only. The conductors 78 may comprise insulated and coiled BSW or solid wire (optionally DFT silver core wire) disposed in the tubular jacket, with one conductor provided for each ring electrode 74A-74D requiring independent control. Generally, the impedance electrodes 74A-74D may comprise current emitting electrodes and voltage sensing electrodes for detecting respiration by changes in bio-impedance. The number, spacing, anatomical location and function of the impedance electrodes will be described in more detail hereinafter.

System 10 may also include a plurality of diagnostic mechanisms (e.g., circuitry and/or programming) for monitoring and/or determining the functionality of certain components, such as, for example, stimulation lead 60. In particular, system 10 may include one or more switching circuits (not shown) that facilitate connection of the respiratory/trans-thoracic impedance sensing circuits of the present disclosure (discussed in greater detail below) to stimulation lead 60 for measuring the impedance of lead 60. In some embodiments, the impedance sensing circuit may be connected to each electrode pair. In other embodiments, the impedance sensing circuit may be connected between the case of the implanted INS 50 and each conductor 68 within the lead 60. While those having ordinary skill in the art will readily recognize that any suitable impedance sensing method may be utilized to monitor and/or determine the functionality of lead 60, the respiratory/trans-thoracic impedance sensing circuit of the present disclosure may be preferred, since this circuit may be capable of identifying small changes in impedance rather than the large changes detectable by standard methods.

As alluded to above, sensing the impedance of lead 60 may provide for monitoring and/or determining the functionality of lead 60. Specifically, sensing the impedance of lead 60 may facilitate diagnosing and distinguishing between differing types of failures of lead 60. In particular, research has revealed that changes in the impedance of lead 60 may be indicative of certain types of failures, including, but not limited to, corrosion, high contact resistance, breakage, and/or shorting. For example, a broken wire inside the lead could be identified by an excessively high lead impedance value. Corrosion of an electrode with its resultant decrease in effective electrode surface area could be identified by a smaller increase in impedance of that electrode. Similarly, an abnormally low value could correspond with a short between conductors in the lead, or an abrasion of the lead body that exposed a conductor to the tissue. Measuring from the case of the INS to each electrode allows independent identification of the integrity of each wire/electrode in the lead. In addition, sensing the impedance of lead 60 may facilitate periodic, automated adjustment of stimulation pulse amplitude so as to maintain constant current, energy, and/or charge delivery using a simpler voltage mode delivery circuit. Such automated adjustment may facilitate ensuring safety and effectiveness by consistently delivering the prescribed current, energy, or charge in the presence of tissue/electrode impedance variations. By consistently controlling the delivery of only the minimally required energy necessary for stimulation of the nerve, the stimulation amplitude may be programmed closer to the actual stimulation threshold rather than programming a wide margin to ensure continued effectiveness. This enhances safety and reduces power consumption. Moreover, sensing the impedance of lead 60 may allow monitoring of certain system dynamics, such as, for example, doses actually delivered to a patient.

Description of Implant Procedure

Figure 10:
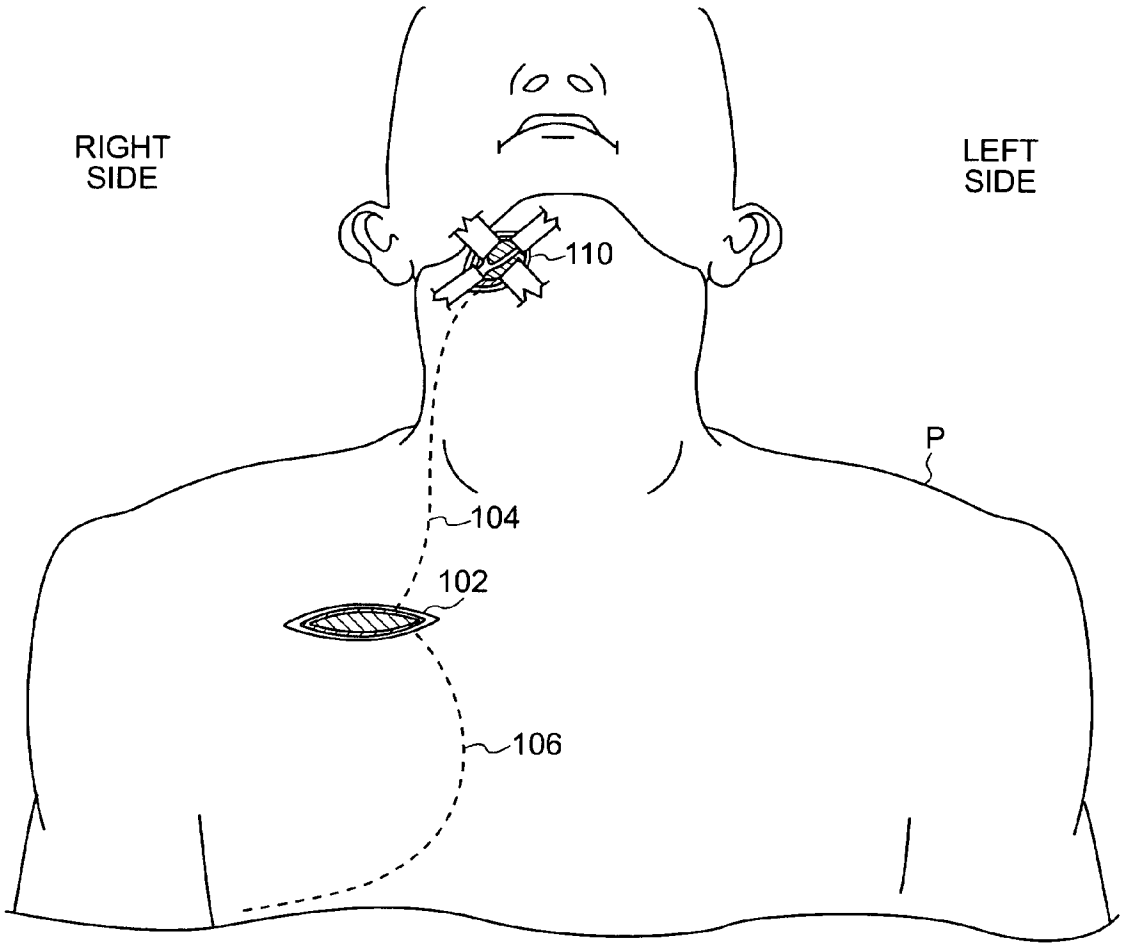
FIG. 10 schematically illustrates surgical access and tunneling sites for implanting the system illustrated in FIG. 2.

With reference to FIG. 10, surgical access sites are schematically shown for implanting the internal neurostimulator components 20 shown in FIG. 1. The internal neurostimulator components 20 may be surgically implanted in a patient on the right or left side. The right side may be preferred because it leaves the left side available for implantation of a pacemaker, defibrillator, etc., which are traditionally implanted on the left side. The right side may also be preferred because it lends itself to a clean respiratory signal less susceptible to cardiac artifact and also offers placement of respiratory sensors across the interface between the lung, diaphragm and liver for better detection of impedance changes during respiration.

With continued reference to FIG. 10, the INS (not shown) may be implanted in a subcutaneous pocket 102 in the pectoral region, for example. The stimulation lead (not shown) may be implanted in a subcutaneous tunnel 104 along (e.g., over or under) the platysma muscle in the neck region. The respiration sensing lead (not shown) may be implanted in a subcutaneous tunnel 106 extending adjacent the ribcage to an area adjacent lung tissue and/or intercostal muscles outside the pleural space. The nerve cuff electrode (not shown) may be attached to a nerve by surgical dissection at a surgical access site 110 proximate the targeted stimulation site. In the illustrated example, the target nerve is the right hypoglossal nerve and the surgical access site is in the submandibular region.

Figure 11A:
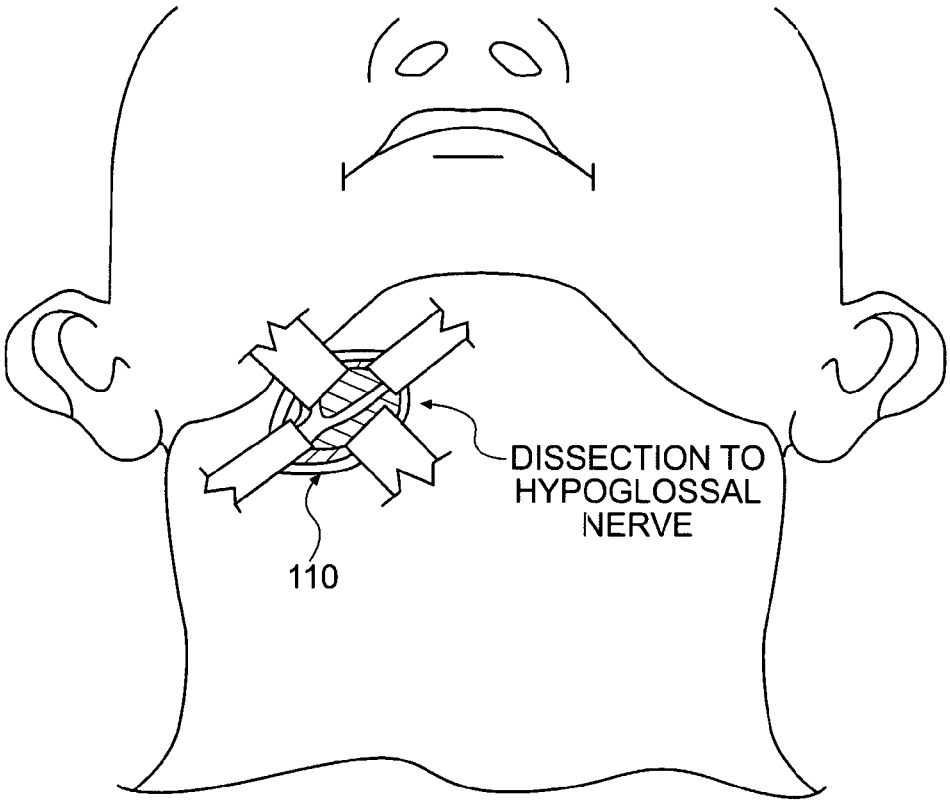
FIGS. 11A and 11B schematically illustrate dissection to a hypoglossal nerve.
Figure 11B:
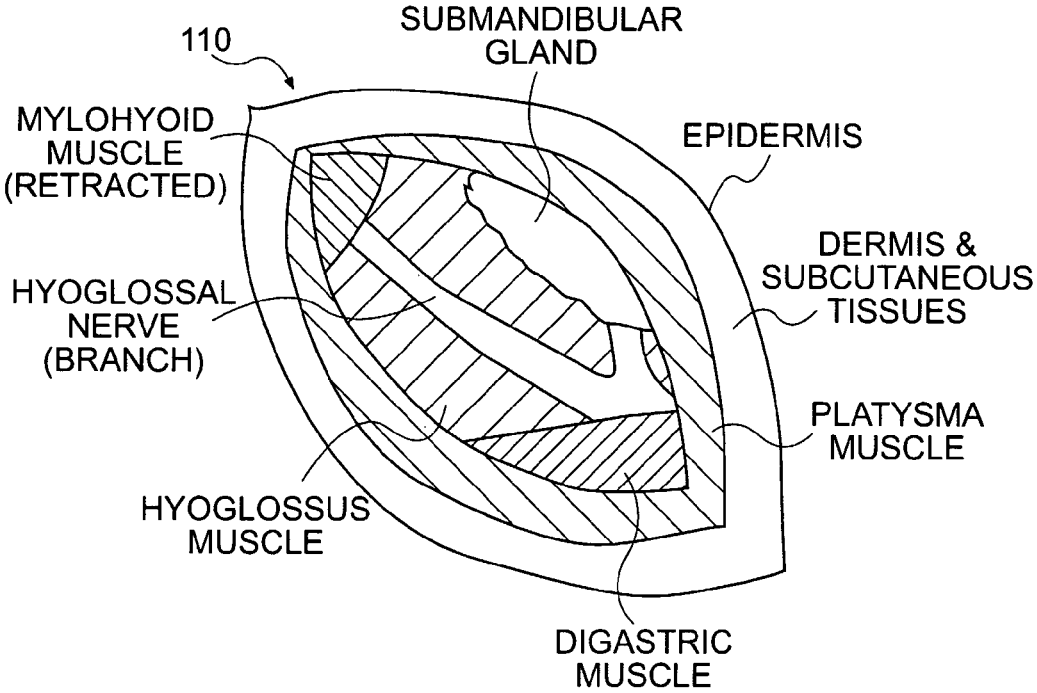

With reference to FIGS. 11A and 11B, a surgical dissection 110 to the hypoglossal nerve is shown schematically. A uni-lateral dissection is shown, but a bilateral approach for bilateral stimulation may also be employed. Conventional surgical dissection techniques may be employed. The branch of the hypoglossal nerve (usually a medial or distal branch) leading to the genioglossus muscle may be identified by stimulating the hypoglossal nerve at different locations and observing the tongue for protrusion. Because elongation and/or flexion may be mistaken for protrusion, it may be desirable to observe the upper airway using a flexible fiber optic scope (e.g., nasopharyngoscope) inserted into the patient's nose, through the nasal passages, past the nasopharynx and velopharynx to view of the oropharynx and hypopharynx and visually confirm an increase in airway caliber by anterior displacement (protrusion) of the tongue base when the nerve branch is stimulated.

The implant procedure may be performed with the patient under general anesthesia in a hospital setting on an outpatient basis. Alternatively, local anesthesia (at the surgical access sites and along the subcutaneous tunnels) may be used together with a sedative in a surgical center or physician office setting. As a further alternative, a facial nerve block may be employed. After a post-surgical healing period of about several weeks, the patient may return for a polysomnographic (PSG) test or sleep study at a sleep center for programming the system and titrating the therapy. A trialing period may be employed prior to full implantation wherein the hypoglossal nerve or the genioglossus muscle is stimulated with fine wire electrodes in a sleep study and the efficacy of delivering stimulus to the hypoglossal nerve or directly to the genioglossus muscle is observed and measured by reduction in apnea hypopnea index, for example.

Other nerve target sites are described elsewhere herein and may be accessed by similar surgical access techniques. As an alternative to surgical dissection, less invasive approaches such as percutaneous or laparoscopic access techniques may be utilized, making use of associated tools such as tubular sheaths, trocars, etc.

Description of Alternative Stimulation Target Sites

Figure 12:
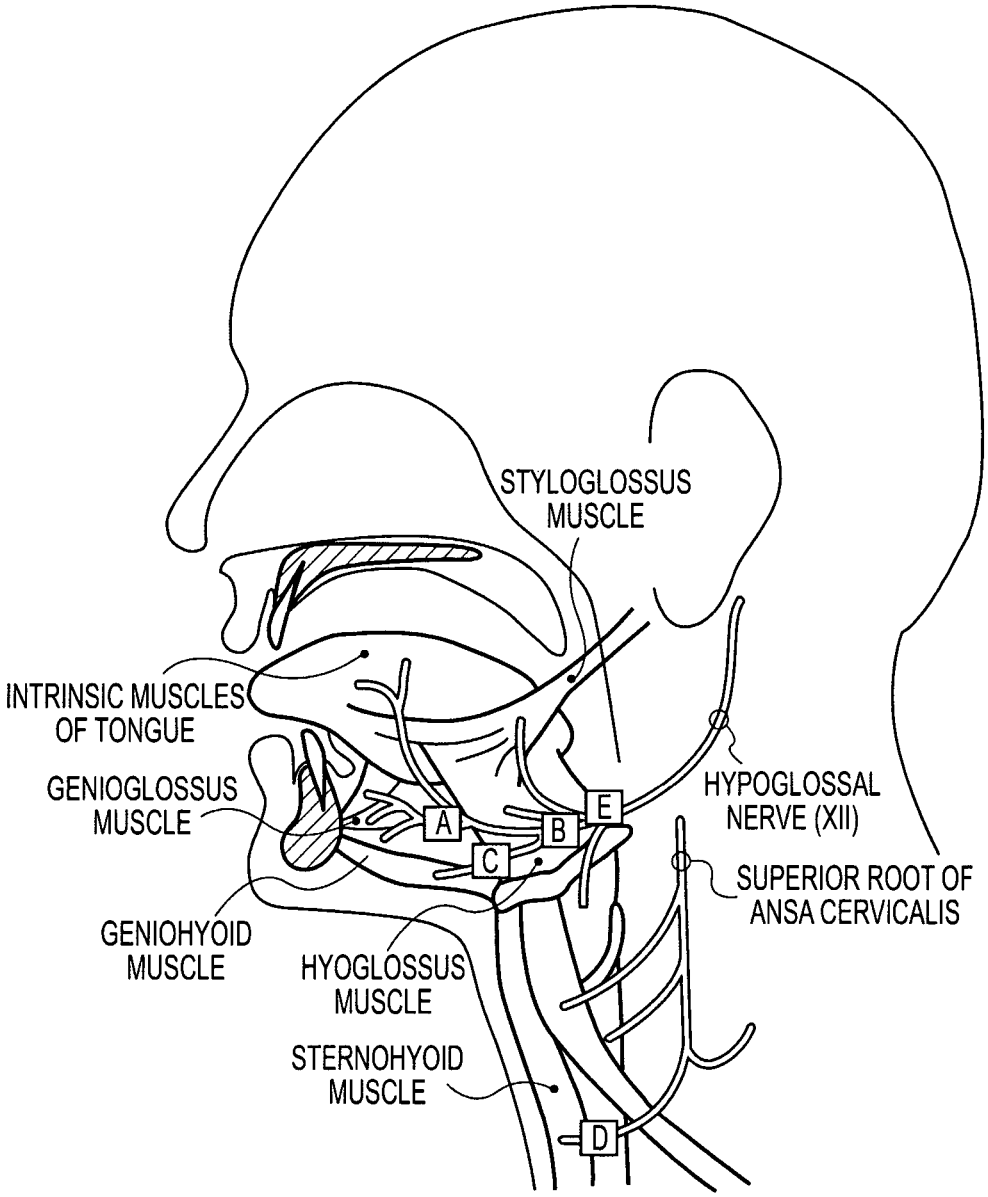
FIGS. 12 and 12A-12D schematically illustrate various possible nerve stimulation sites for activating muscles controlling the upper airway.
Figure 12A:
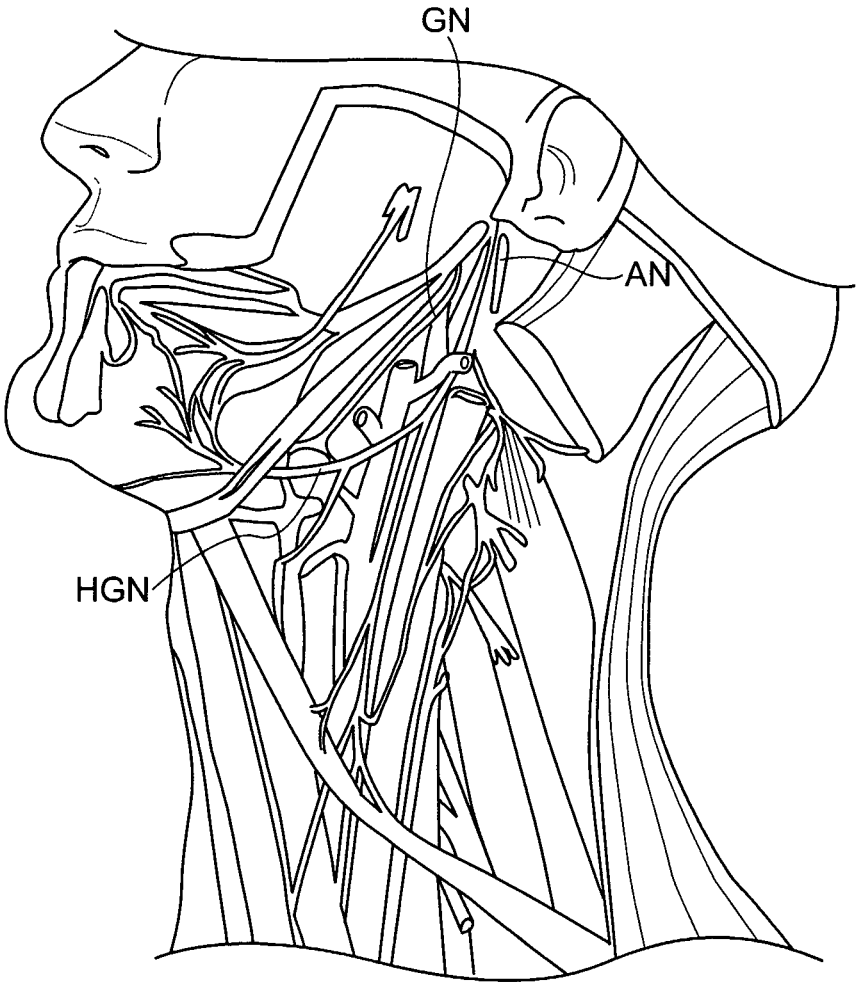
Figure 12B:
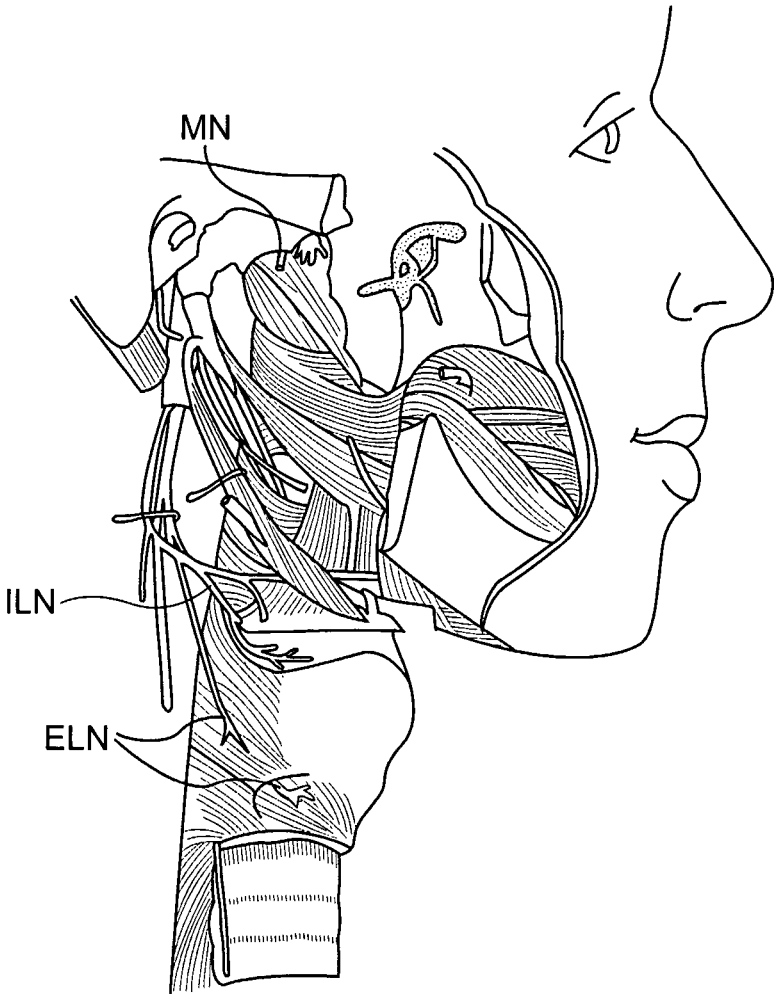
Figure 12C:
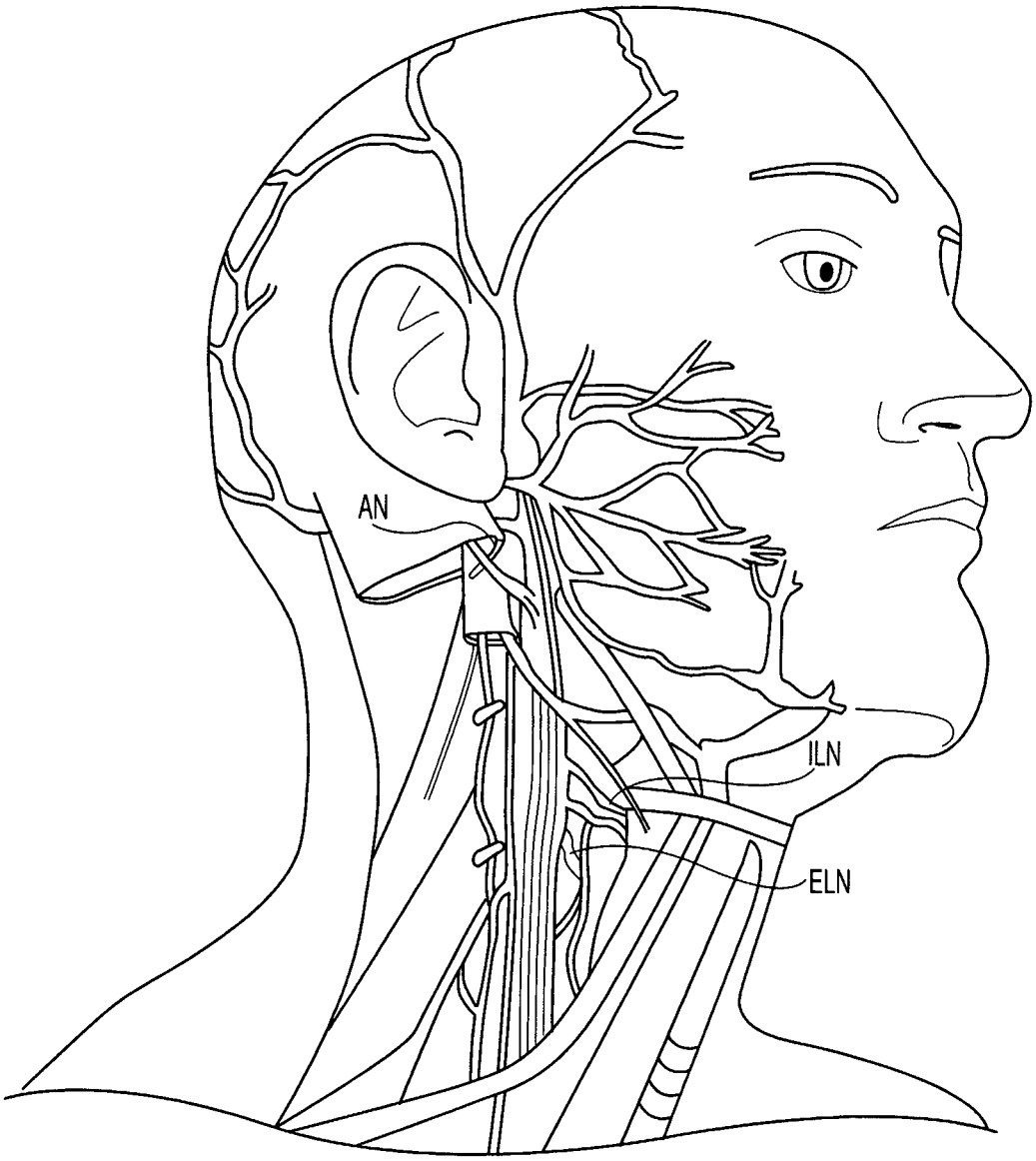
Figure 12D:
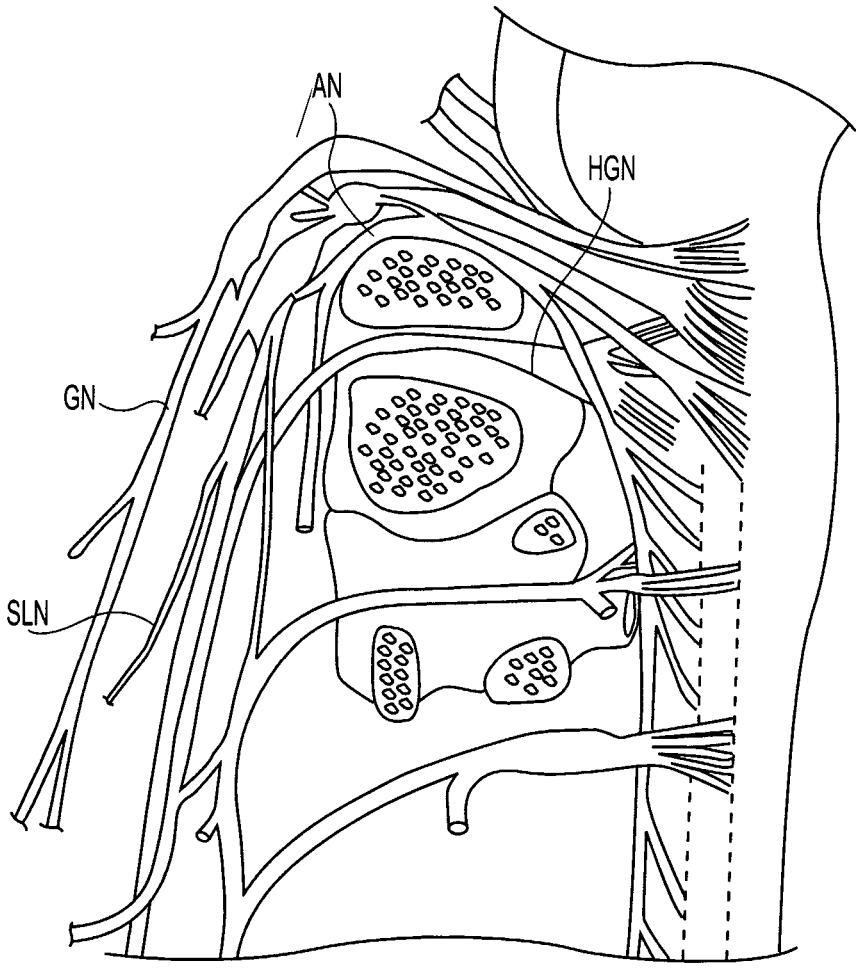

With reference to FIG. 12, various possible nerve and/or direct muscle stimulation sites are shown for stimulating muscles controlling patency of the upper airway. In addition to the upper airway which generally includes the pharyngeal space, other nerves and dilator muscles of the nasal passage and nasopharyngeal space may be selectively targeted for stimulation. A general description of the muscles and nerves suitable for stimulation follows, of which the pharyngeal nerves and muscles are shown in detail in FIG. 12.

Airway dilator muscles and associated nerves suitable for activation include are described in the following text and associated drawings. The dilator naris muscle functions to widen the anterior nasal aperture (i.e., flares nostrils) and is innervated by the buccal branch of the facial nerve (cranial nerve VII). The tensor veli palatine muscle functions to stiffen the soft palate and is innervated by the medial (or internal) pterygoid branch of the mandibular nerve MN. The genioglossus muscle is an extrinsic pharyngeal muscle connecting the base of the tongue to the chin and functions to protrude the tongue. The genioglossus muscle is typically innervated by a distal or medial branch (or braches) of the right and left hypoglossal nerve. The geniohyoid muscle connects the hyoid bone to the chin and the sternohyoid muscle attaches the hyoid bone to the sternum. The geniohyoid muscle functions to pull the hyoid bone anterosuperiorly, the sternohyoid muscle functions to pull hyoid bone inferiorly, and collectively (i.e., co-activation) they function to pull the hyoid bone anteriorly. The geniohyoid muscle is innervated by the hypoglossal nerve, and the sternohyoid muscle is innervated by the ansa cervicalis nerve.

By way of example, a nerve electrode may be attached to a specific branch of the hypoglossal nerve innervating the genioglossus muscle (tongue protruder), or may be attached to a more proximal portion (e.g., trunk) of the hypoglossal nerve in which a specific fascicle innervating the genioglossus muscle is targeted by steering the stimulus using an electrode array. Activating the genioglossus muscle causes the tongue to protrude thus increasing the size of anterior aspect of the upper airway or otherwise resisting collapse during inspiration.

As an alternative to activation of any or a combination of the airway dilator muscles, co-activation of airway dilator and airway restrictor or retruder muscles may be used to stiffen the airway and maintain patency. By way of example, a nerve electrode may be attached to specific branches of the hypoglossal nerve innervating the genioglossus muscle (tongue protruder), in addition to the hyoglossus and styloglossus muscles (tongue retruders), or may be attached to a more proximal portion (e.g., trunk) of the hypoglossal nerve in which specific fascicles innervating the genioglossus, hyoglossus and styloglossus muscles are targeted by steering the stimulus using an electrode array. Activating the hyoglossus and styloglossus muscles causes the tongue to retract, and when co-activated with the genioglossus, causes the tongue to stiffen thus supporting the anterior aspect of the upper airway and resisting collapse during inspiration. Because the tongue retruder muscles may overbear the tongue protruder muscle under equal co-activation, unbalanced co-activation may be desired. Thus, a greater stimulus (e.g., longer stimulation period, larger stimulation amplitude, higher stimulation frequency, etc.) or an earlier initiated stimulus may be delivered to the portion(s) of the hypoglossal nerve innervating the genioglossus muscle than to the portion(s) of the hypoglossal nerve innervating the hyoglossus and styloglossus muscles.

With continued reference to FIG. 12, examples of suitable nerve stimulation sites include B; A+C; A+C+D; B+D; C+D; and E. Sites B and E may benefit from selective activation by field steering using an electrode array. As mentioned before, nerve electrodes may be placed at these target nerve(s) and/or intramuscular electrodes may be placed directly in the muscle(s) innervated by the target nerve(s).

Site A is a distal or medial branch of the hypoglossal nerve proximal of a branch innervating the genioglossus muscle and distal of a branch innervating the geniohyoid muscle. Site B is a more proximal portion of the hypoglossal nerve proximal of the branches innervating the genioglossus muscle and the geniohyoid muscle, and distal of the branches innervating the hyoglossus muscle and the styloglossus muscle. Site C is a medial branch of the hypoglossal nerve proximal of a branch innervating the geniohyoid muscle and distal of branches innervating the hyoglossus muscle and the styloglossus muscle. Site D is a branch of the ansa cervicalis nerve distal of the nerve root and innervating the sternohyoid. Site E is a very proximal portion (trunk) of the hypoglossal nerve proximal of the branches innervating the genioglossus, hyoglossus and styloglossus muscles.

Activating site B involves implanting an electrode on a hypoglossal nerve proximal of the branches innervating the genioglossus muscle and the geniohyoid muscle, and distal of the branches innervating the hyoglossus muscle and the styloglossus muscle.

Co-activating sites A+C involves implanting a first electrode on a hypoglossal nerve proximal of a branch innervating the genioglossus muscle and distal of a branch innervating the geniohyoid muscle, and implanting a second electrode on the hypoglossal nerve proximal of a branch innervating the geniohyoid muscle and distal of branches innervating the hyoglossus muscle and the styloglossus muscle.

Co-activating sites A+C+D involves implanting a first electrode on a hypoglossal nerve proximal of a branch innervating the genioglossus muscle and distal of a branch innervating the geniohyoid muscle; implanting a second electrode on the hypoglossal nerve proximal of a branch innervating the geniohyoid muscle and distal of branches innervating the hyoglossus muscle and the styloglossus muscle; and implanting a third electrode on a branch of an ansa cervicalis nerve distal of the nerve root and innervating the sternohyoid.

Co-activating sites B+D involves implanting a first electrode on a hypoglossal nerve proximal of branches innervating the genioglossus muscle and the geniohyoid muscle, and distal of branches innervating the hyoglossus muscle and the styloglossus muscle; and implanting a second electrode on a branch of an ansa cervicalis nerve distal of the nerve root and innervating the sternohyoid.

Co-activating sites C+D involves implanting a first electrode on a hypoglossal nerve proximal of a branch innervating the geniohyoid muscle, and distal of branches innervating the hyoglossus muscle and the styloglossus muscle and implanting a second electrode on a branch of an ansa cervicalis nerve distal of the nerve root and innervating the sternohyoid.

Activating site E involves implanting an electrode on a hypoglossal nerve proximal of the branches innervating the genioglossus, hyoglossus and styloglossus muscles; and selectively activating (e.g., by field steering) the genioglossus muscle before or more than the hyoglossus and styloglossus muscles.

With reference now to FIGS. 12A-12D, additional possible nerve stimulation sites are shown for effecting muscles controlling patency of the upper airway. For example, the cranial root of the accessory nerve AN (cranial nerve XI) innervates the levator veli palatini muscle of the soft palate, which elevates the soft palate. The cranial root of the accessory nerve AN also innervates the palatoglossal muscle, which functions to pull the soft palate inferiorly when the genioglossus is co-activated via the hypoglossal nerve (HGN). Moreover, because the cranial root of the accessory nerve AN also innervates various other muscles including, but not limited to, the palatopharyngeus, specific fibers in the accessory nerve AN may be selectively stimulated with one or more of the fiber selective stimulation means described in greater detail below, in order to only activate desired fibers of the nerve. The glossopharyngeal nerve GN. (cranial nerve IX) innervates the stylopharyngeus, which functions to dilate the lateral walls of the pharynx. However, since the glossopharyngeal nerve GN is a multi-function nerve with both afferent and efferent fibers, one or more of the fiber selective stimulation means described in greater detail below may be used to facilitate targeting the fibers that innervate only the stylopharyngeus. The cranial root of the accessory nerve AN and the glossopharyngeal nerve GN may be singularly activated, or these nerves may be co-activated with other nerve sites, such as, for example, the hypoglossal nerve, for increased efficacy.

Another possible nerve stimulation site may include the superior laryngeal nerve SLN. The superior laryngeal nerve SLN descends posterior and medial from the internal carotid artery and divides into the internal laryngeal nerve ILN and external laryngeal nerve ELN. While the external laryngeal nerve ELN descends behind the sternohyoid with the superior thyroid artery, the internal laryngeal nerve ILN descends near the superior laryngeal artery. The internal laryngeal nerve ILN contains sensory (afferent) fibers that are connected to receptors in the larynx. Some of these receptors include, but are not limited to, mechanoreceptors which detect pressure changes in a patient's upper airway associated with its collapse and institute a physiological response to re-open the patient's upper airway. Therefore, stimulation of specific afferent fibers inside the ILN nerve may result in triggering a reflex response that causes upper airway dilation by activating several muscles groups.

As discussed below, the superior laryngeal nerve SLN, in addition to being a sensory nerve, is also a motor nerve. Therefore, it is contemplated that one or more of the fiber selective stimulation means described in greater detail below may be utilized to facilitate only stimulating the sensory or afferent fibers of the nerve.

Description of Alternative Nerve Electrodes

Any of the alternative nerve electrode designs described hereinafter may be employed in the systems described herein, with modifications to position, orientation, arrangement, integration, etc. made as dictated by the particular embodiment employed. Examples of other nerve electrode designs are described in U.S. Pat. No. 5,531,778, to Maschino et al., U.S. Pat. No. 4,979,511 to Terry, Jr., and U.S. Pat. No. 4,573,481 to Bullara, the entire disclosures of which are incorporated herein by reference.

With reference to the following figures, various alternative electrode designs for use in the systems described above are schematically illustrated. In each of the embodiments, by way of example, not limitation, the lead body and electrode cuff may comprise the same or similar materials formed in the same or similar manner as described previously. For example, the lead body may comprise a polymeric jacket formed of silicone, polyurethane, or a co-extrusion thereof. The jacket may contain insulated wire conductors made from BSW or solid wire comprising MP35N, MP35N with Ag core, stainless steel or Tantalum, among others. The lead body may be sigmoid shaped to accommodate neck and mandibular movement. Also, a guarded cathode tri-polar electrode arrangement (e.g., anode-cathode-anode) may be used, with the electrodes made of 90/10 or 80/20 PtIr alloy with silicone or polyurethane backing.

Figure 13A:
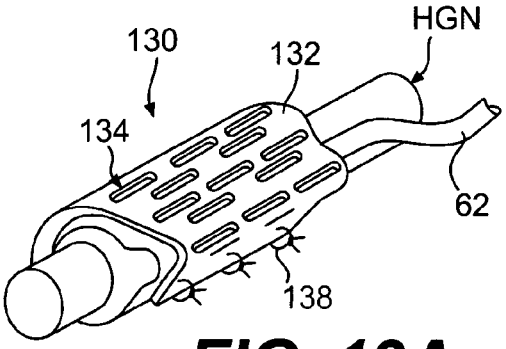
FIGS. 13-22 and 22A-22D are schematic illustrations of various stimulation lead body and electrode designs for use in a neurostimulator system.
Figure 13B:
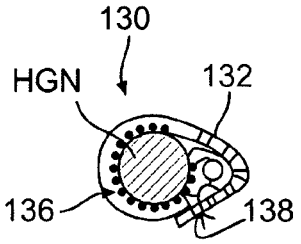

With specific reference to FIGS. 13A and 13B, a self-sizing and expandable design is shown to accommodate nerve swelling and/or over-tightening. FIG. 13A shows a perspective view of a nerve electrode cuff 130 on a nerve such as a hypoglossal nerve, and FIG. 13B shows a cross-sectional view of the nerve cuff electrode 130 on the nerve. In this embodiment, the implantable nerve cuff electrode 130 comprises a compliant sheet wrap 132 configured to be wrapped about a nerve and secured thereto by connecting opposite portions of the sheet by sutures 138, for example. The sheet 132 includes a plurality of radially and longitudinally distributed fenestrations 134 to allow expansion of the sheet 132 to accommodate nerve swelling and/or over tightening. Electrode contacts 136 comprising a coil, foil strip, conductive elastomer or individual solid conductors may be carried by the sheet 132 with an exposed inside surface to establish electrical contact with the nerve.

Figure 14A:
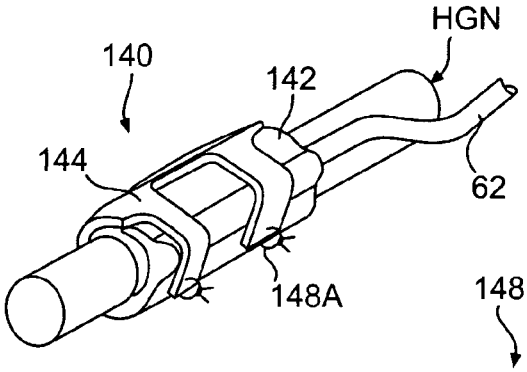
Figure 14B:
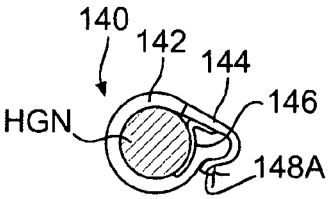
Figure 14C:
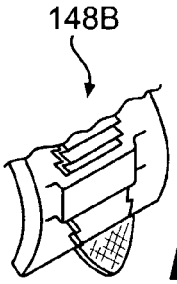

With specific reference to FIGS. 14A-14C, another self-sizing and expandable design is shown to accommodate nerve swelling and/or over-tightening. FIG. 14A shows a perspective view of a nerve electrode cuff 140 on a nerve such as a hypoglossal nerve, and FIG. 14B shows a cross-sectional view of the nerve cuff electrode 140 on the nerve. In this embodiment, the implantable nerve cuff electrode 140 comprises a compliant sheet wrap 142 configured to be wrapped about a nerve and secured thereto by connecting opposite portions of the sheet by sutures 148A, or by a buckle 148B as shown in FIG. 14C, for example. The opposite portions of the sheet 142 comprise one or more narrow strips 144 integral with the sheet 142 to allow expansion and to accommodate nerve swelling and/or over tightening. Electrode contacts 146 comprising a coil, foil strip, conductive elastomer or individual solid conductors may be carried by the sheet 142 with an exposed inside surface to establish electrical contact with the nerve.

Figure 15A:
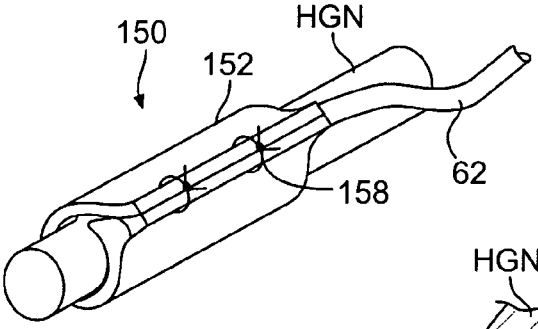
Figure 15B:
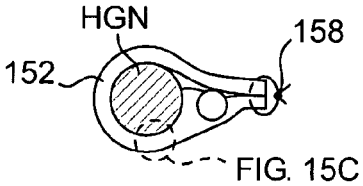
Figure 15C:
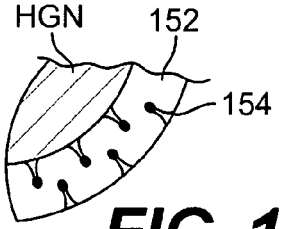

With specific reference to FIGS. 15A-15C, another self-sizing and expandable design is shown to accommodate nerve swelling and/or over-tightening. FIG. 15A shows a perspective view of a nerve electrode cuff 150 on a nerve such as a hypoglossal nerve, and FIG. 15B shows a cross-sectional view of the nerve cuff electrode 150 on the nerve. In this embodiment, the implantable nerve cuff electrode 150 comprises a compliant sheet wrap 152 configured to be wrapped about a nerve and secured thereto by connecting opposite portions of the sheet 152 by sutures 158, for example. The opposite portions of the sheet 152 are offset from the nerve and a thickened portion of the sheet 152 fills the offset space. The offset distance reduces the amount of compressive force that the electrode cuff can exert on the nerve. To further reduce the pressure on the nerve, the sheet 152 includes a plurality of radially distributed slits 154 extending partly through the thickness of the sheet 152 to allow expansion and to accommodate nerve swelling and/or over tightening.

Figure 16A:
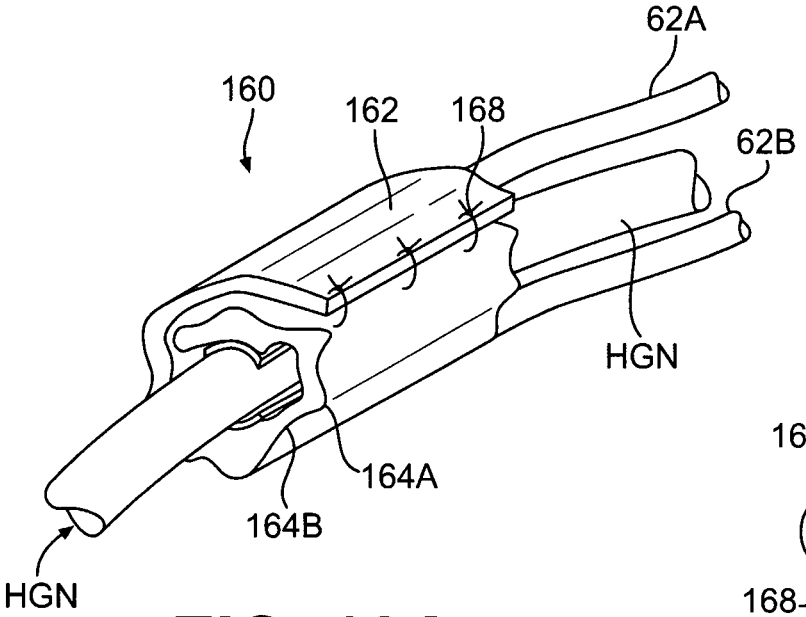
Figure 16B:
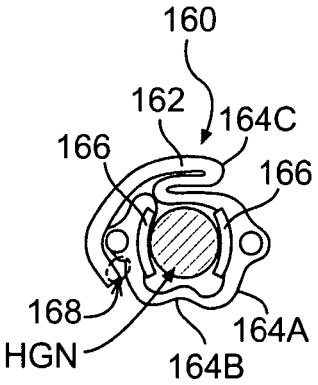

With specific reference to FIGS. 16A and 16B, another self-sizing and expandable design is shown to accommodate nerve swelling and/or over-tightening. FIG. 16A shows a perspective view of a nerve electrode cuff 160 on a nerve such as a hypoglossal nerve, and FIG. 16B shows a cross-sectional view of the nerve cuff electrode 160 on the nerve. In this embodiment, the implantable nerve cuff electrode 160 comprises a compliant sheet wrap 162 configured to be wrapped about a nerve and secured thereto by connecting opposite portions of the sheet 162 by sutures 168, for example. The sheet 162 includes a plurality of radially distributed and longitudinally extending convolutions 164 that may comprise alternative thick 164A and thin 164B portions in the sheet 162 and/or overlapping portions 164C of the sheet 162 to allow expansion and to accommodate nerve swelling and/or over tightening. Electrode contacts 166 comprising a coil, foil strip, conductive elastomer or individual solid conductors may be carried by the sheet 162 with an exposed inside surface to establish electrical contact with the nerve. Nerve cuff electrode 160 may accommodate one or two lead bodies 62A, 62B for connection to the electrode contacts 166 on the same or opposite sides of the nerve.

Figures 16C, 16D:
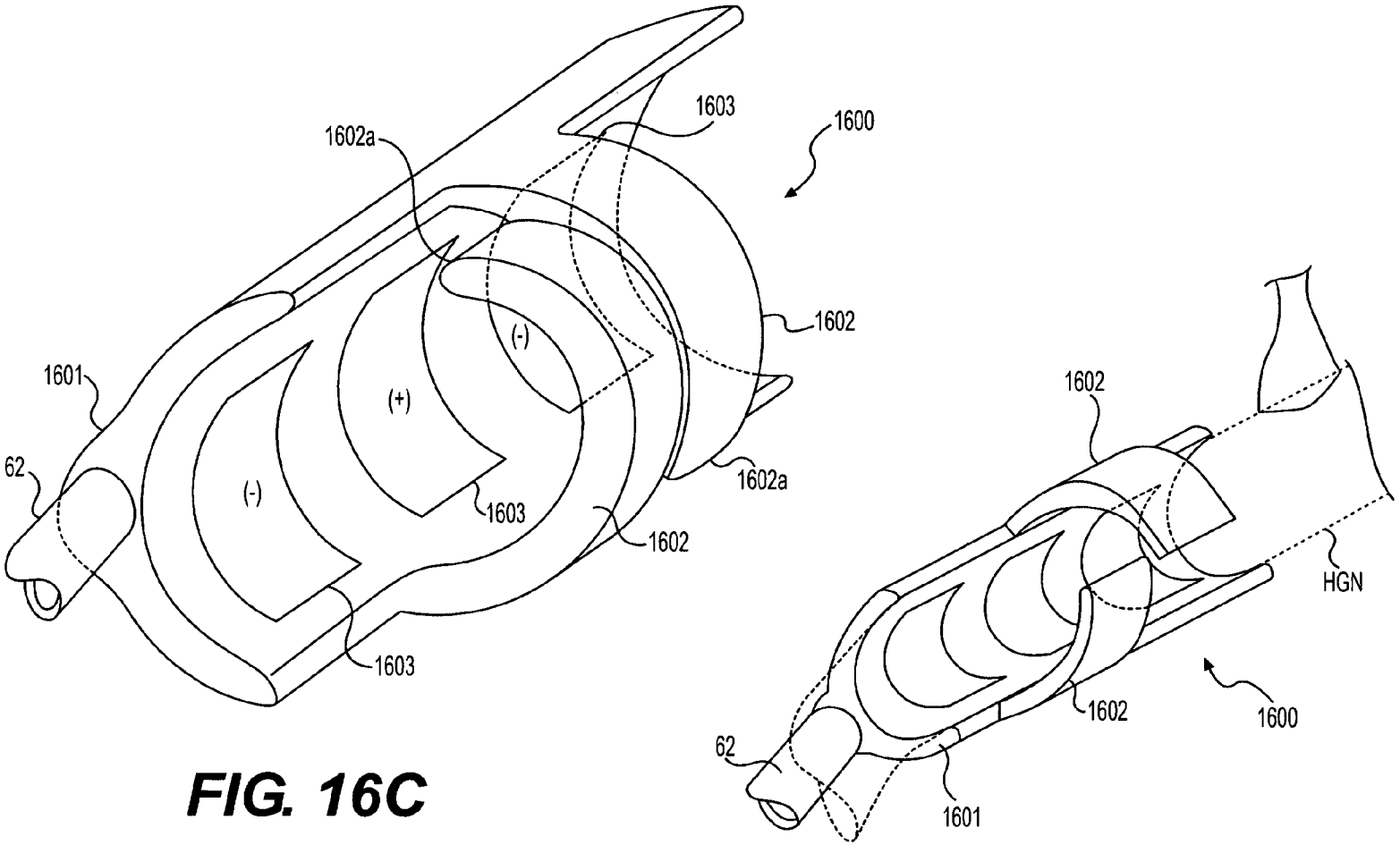

Turning now to FIGS. 16C-16D, additional self-sizing and expandable designs are shown to accommodate nerve swelling and/or over-tightening. With specific reference to FIG. 16C, there is depicted a nerve cuff electrode 1600 having a cuff body with a relatively wide semi-cylindrical lateral side 1601 and a plurality of opposing arms 1602 extending thereform for placement on the deep (contralateral) side of the nerve. Although the embodiment depicted in FIG. 16C includes two such opposing arms 1602, nerve cuff electrode 1600 may include any suitable number of opposing arms 1602. Lateral side 1601 may include an array of electrode contacts 1603. For example, in the depicted embodiment, lateral side may include three electrode contacts 1603. The three electrode contacts 1603 may include one cathode electrode contact 1603 disposed between two anode electrode contacts 1603, as shown.

Arms 1602 may be secured around a nerve (not shown) by any suitable means. For example, it is contemplated that arms 1602 may be elastic in nature, so as to gently grasp the nerve on its deep (contralateral) side. Alternatively, arms 1602 may be actively secured about a nerve by, for example, suturing an end portion of arms 1602 to, e.g., a portion of lateral side 1601. In embodiments where arms 1602 may be actively secured about a nerve, arms 1602 may be provided with a safety mechanism (not shown) that permits nerve cuff electrode 1600 to become disengaged from a nerve it is secured about upon the application of a predetermined amount of force. This predetermined force will be established at a level that is below that which can cause damage to the nerve.

As shown in FIG. 16D, opposing arms 1602 may be configured to expand and/or deform as necessary, in order to accommodate nerve swelling caused by, for example, localized trauma inflicted upon the nerve during cuff implantation. For example, each of opposing arms 1602 may have an unattached terminal end 1602a. In order to facilitate expansion, opposing arms 1602 may be also made from any suitable material known to those having ordinary skill in the art. For example, arms 1602 may be made from an elastomer, such as, for example, silicone or polyurethane. Additionally, one or both of arms 1602 may be provided with one or more limiting mechanisms (not shown) to limit the amount of expansion arms 1602 may undergo as a result of, for example, nerve swelling. Such limiting mechanisms may include any suitable mechanism, including, but not limited to, flanges, barbs, and/or sutures.

Figure 16E:
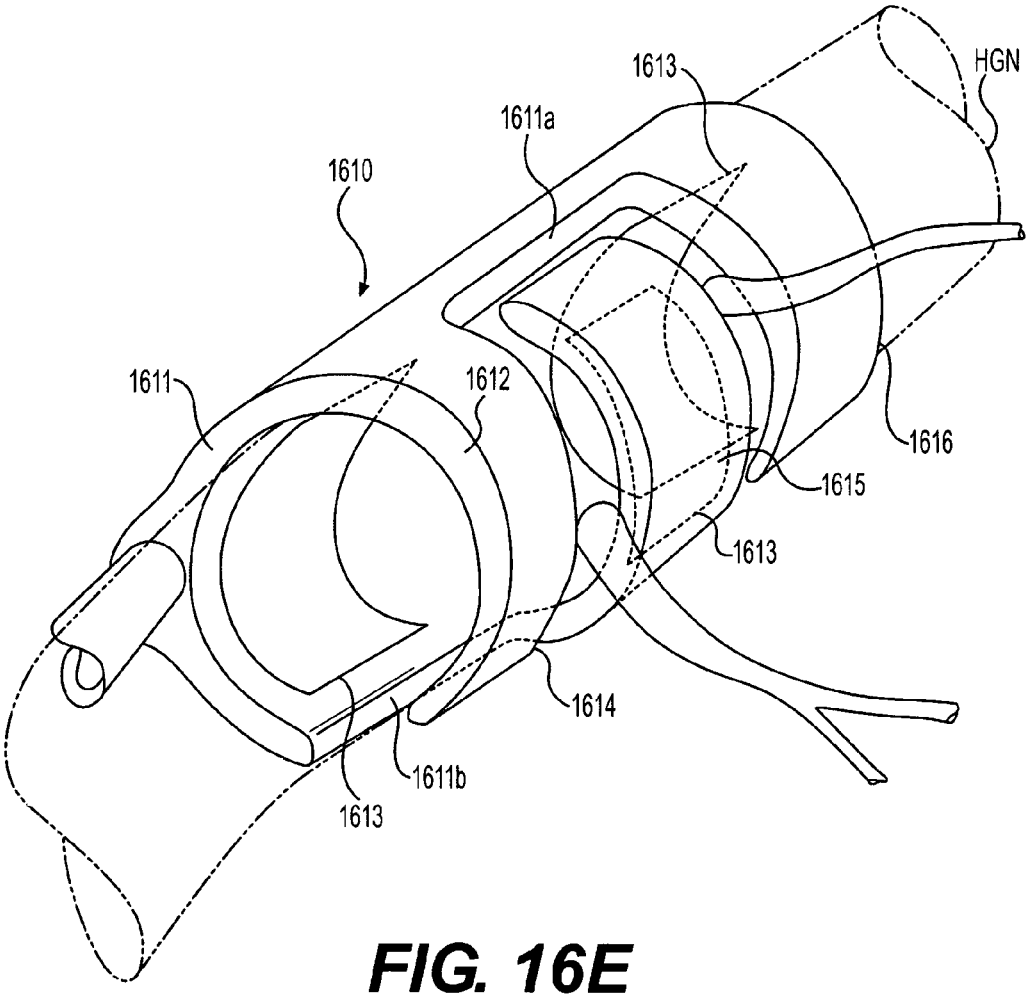

With reference to FIG. 16E, there is depicted another design of a self-sizing and expandable nerve cuff electrode 1610. For the purposes of this disclosure, nerve cuff electrode 1610 may be substantially similar to nerve cuff electrode 1600 depicted in FIGS. 16C-16D. Nerve cuff electrode 1610, however, may differ from nerve cuff electrode 1600 in at least two significant ways. First, for example, lateral side 1611 of nerve cuff electrode 1610 may carry two anode electrode contacts 1613 and the medial side 1612 may carry one cathode electrode contact 1613 in an arrangement that may be referred to as transverse guarded tri-polar. Second, for example, nerve cuff electrode 1610 may include three arms 1614-1616 extending from lateral side 1611. In the depicted embodiment, arms 1614 and 1616 may be configured to extend substantially in the same direction from the same edge 1611a of lateral side 1611, while arm 1615 may be configured to extend in substantially the opposing direction from an opposing edge 1611b of lateral side 1611. In the depicted embodiment, arm 1615 may be disposed between arms 1614 and 1616, and may be configured to carry the cathode electrode contact 1613, as mentioned above. However, any suitable arrangement of arms 1614-1616 and/or electrode contacts 1613 may be utilized within the principles of this disclosure.

Figure 16F:
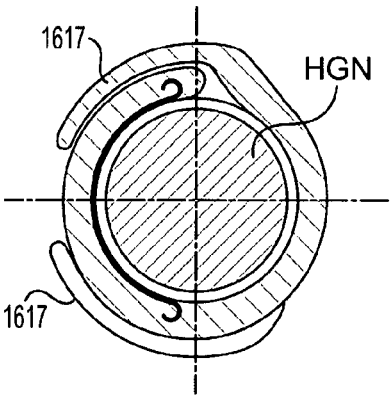

As shown in FIG. 16F, certain embodiments of nerve curve electrode 1600 and/or nerve cuff electrode 1610 may include one or more elongated arms 1617. Arms 1617 may include any suitable length, so as to allow arms 1617 to wrap around a body portion of the cuff electrode one or more times in a spiral-like fashion, when the cuff electrode is mounted about an un-swollen nerve. However, arms 1617 may allow the cuff electrode to remain mounted on the nerve as it accommodates large amounts of nerve swelling by unraveling and/or unwrapping as the nerve swells. For example, each of the arms 1617 may overlap lateral side 1601 or 1611 to accommodate larger amounts of nerve swelling without allowing the cuff to become detached from the nerve. The elongated arms 1617 may extend around the body of the cuff electrode to form a spiral when the nerve is in a substantially un-swollen state, as shown.

Figure 17:
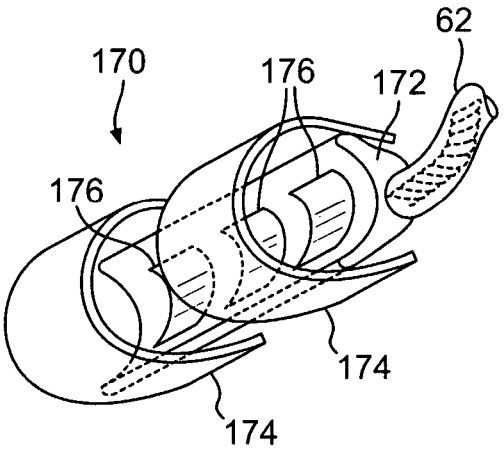

With reference to FIG. 17, a modular nerve electrode cuff 170 is shown that includes a semi-cylindrical body portion 172 with an array of electrode contacts 176 with separate insulative strips 174 for placement on the deep (contralateral side) of the nerve, which typically has more nerve branches and connecting blood vessels. In this embodiment, independent placement of the electrode body 172 on the superficial (lateral) side of the nerve and placement of the insulative strips 174 on the deep (contralateral) side of the nerve minimizes dissection. The strips 174 may be connected to the electrode body 172 by sutures or buckles as described previously. This embodiment is also self-sizing to accommodate nerve swelling and/or over-tightening.

Figure 18:
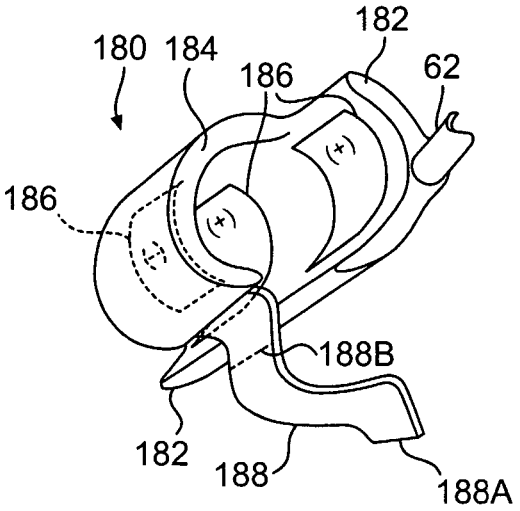

With reference to FIG. 18, a nerve cuff electrode 180 is shown that has a cuff body with a relatively wide semi-cylindrical lateral side 182 and a relatively narrow semi-cylindrical medial side 184 that may extend through a small fenestration around the deep (contralateral) side of a nerve to securely and gently grasp the nerve while minimizing dissection. In the illustrated example, the lateral side 182 carries two anode electrode contacts 186 and the medial side 184 carries one cathode electrode contact 186 in an arrangement that may be referred to as transverse guarded tri-polar. A tow strap 188 is provided for inserting the medial side 184 around the deep side of the nerve. The tow strap 188 may be integrally formed with the medial side 184 of the cuff body, and may include a reinforced tip 188A with a serrated or marked cut line 188B.

Figure 19A:
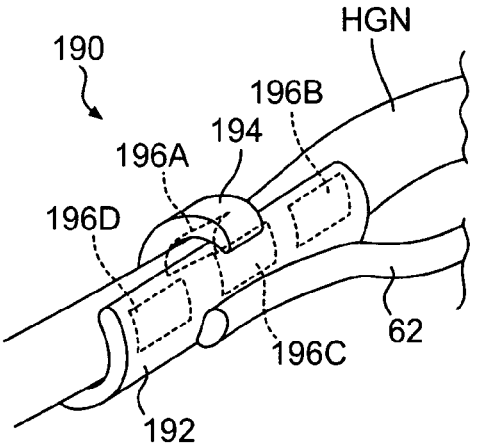
Figure 19B:
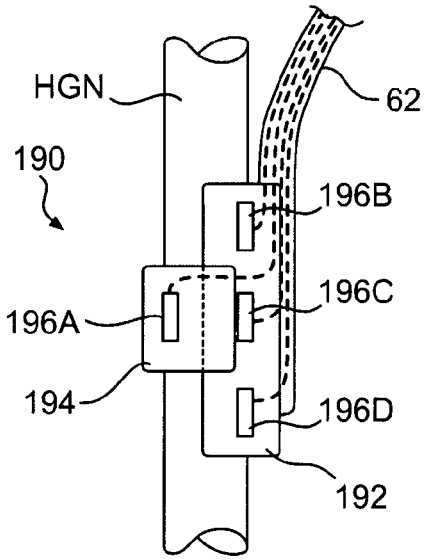

With reference to FIGS. 19A and 19B, a nerve cuff electrode 190 is shown that has a cuff body with a relatively wide semi-cylindrical lateral side 192 and a relatively narrow semi-cylindrical medial side 194 that may extend through a small fenestration around the deep (contralateral) side of a nerve to securely and gently grasp the nerve while minimizing dissection. In the illustrated example, the lateral side 192 carries one cathode electrode contact 196C and two guarding anode electrode contacts 196B and 196D, and the medial side 194 carries one anode electrode contact 196A in an arrangement that may be referred to as transverse and longitudinal guarded quad-polar. The provision of guarding electrode contacts 196B and 196C reduces extrinsic stimulation due to the lack of insulative material on the medial side 194. The embodiments of FIGS. 18, 19A and 19B illustrate two different electrode contact arrangements, but the number and arrangement may be modified to suit the particular application.

Figure 20:
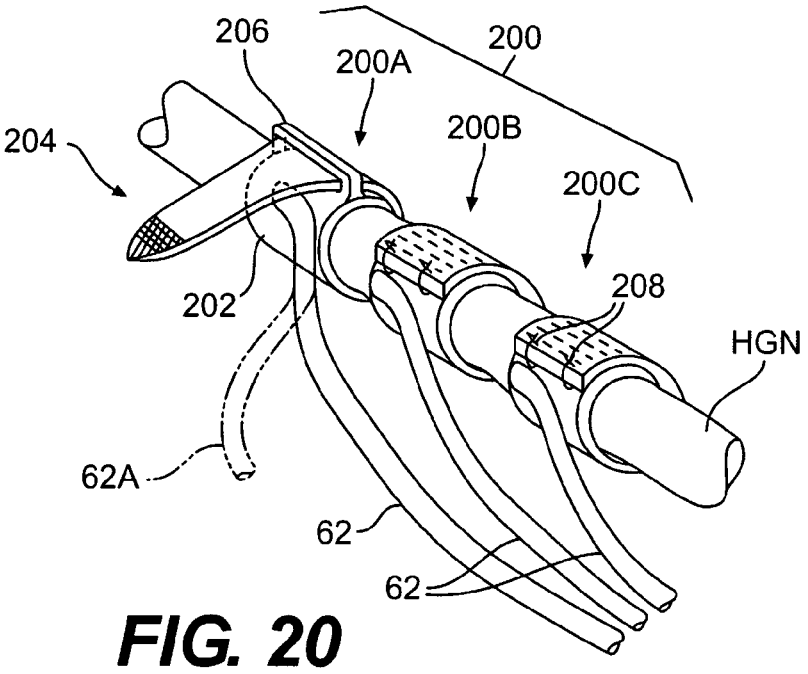

With reference to FIG. 20, a nerve cuff electrode array 200 is shown that utilizes a series of relatively narrow independent cuffs 200A, 200B and 200C with corresponding independent lead bodies 62. Providing a series of relatively narrow independent cuffs 200A, 200B and 200C minimizes the required dissection around the nerve for implantation thereof. Also, the series of independent cuffs 200A, 200B and 200C allows more selectivity in electrode placement to adjust for anatomical variation or multiple target stimulation sites, for example. Providing multiple independent lead bodies 62 allows for more options in routing and placement of the individual lead bodies 62 (e.g., alternate placement of lead body 62A) and also prevents tissue encapsulation around the lead bodies 62 from collectively affecting encapsulation of the nerve cuffs 200. Each of the cuffs 200A, 200B and 200C may include a cuff body 202 with one or more imbedded electrode contacts (not shown) and a tow strap 204 as described before. Also, each of the cuffs 200A, 200B and 200C may include suture 208 or a buckle 206 to lock onto the tow strap 204 for connecting opposite ends of the body 202 around the nerve.

Figure 21A:
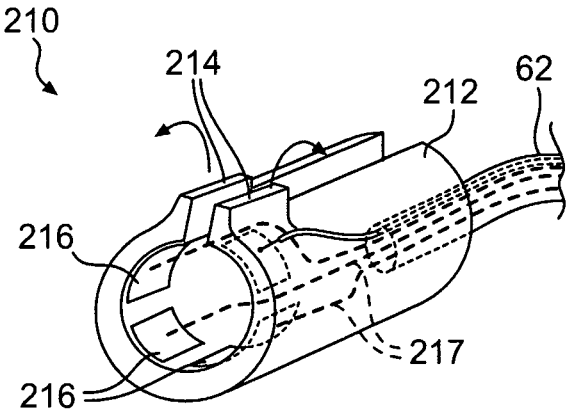
Figure 21B:
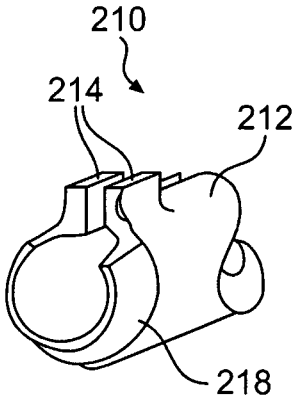

With reference to FIGS. 21A and 21B, a nerve cuff electrode 210 is shown with multiple electrode contacts 216 radially spaced around the inside surface of a compliant split cuff body 212 to establish multiple electrical contact points around the circumference of the nerve. Each of the electrode contacts 216 may be connected to independent conductors in the lead body 62 via axially extending wires 217. This arrangement allows for field steering as discussed herein. The compliant split cuff body 212 together with axially extending wires 217 allows for self-sizing to accommodate nerve swelling and/or over-tightening. One or more pairs of tabs 214 extending from opposite end portions of the cuff body 212 may be connected by a suture (not shown) as described herein. As shown in FIG. 21B, the proximal and distal ends of the cuff body 212 may have tapered thickness extensions 218 to provide strain relief and reduce mechanical irritation of the nerve due to contact with the edge of the cuff.

Figure 22:
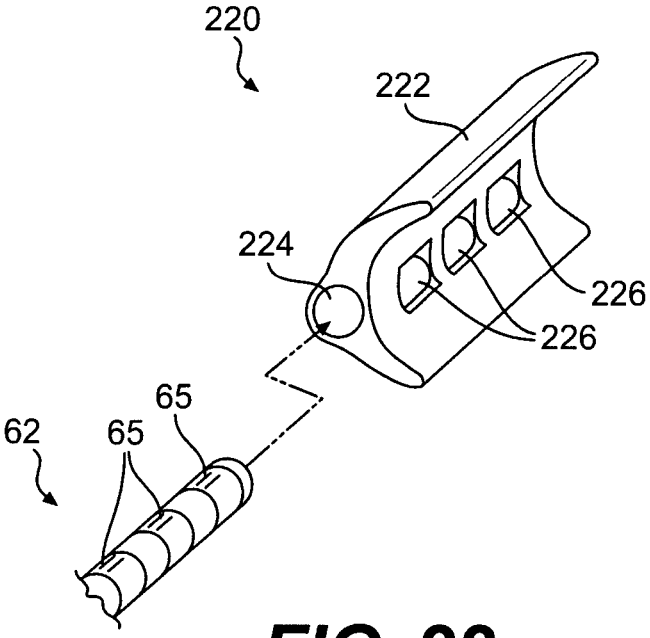

With reference to FIG. 22, a nerve cuff electrode 220 is shown with a separable lead 62 in what may be referred to as a modular design. In this embodiment, the nerve cuff electrode 220 includes a semi-circular flexible cuff body (or housing) 222 with a receptacle 224 configured to accommodate a distal end of a lead body 62 therein. The receptacle 224 may provide a releasable mechanical lock to the lead body 52 as by a press fit, mating detents, etc. The distal end of the lead body 62 carries an array of ring electrodes 65, with windows 226 provided in the cuff body 222 configured to align with the ring electrodes 65 and permit exposure of the ring electrodes 65 to the nerve to establish electrical connection therebetween. The cuff body 222 may be attached to the nerve or simply placed adjacent the nerve. Any of the cuff designs described herein may be provided with a receptacle to accommodate a removable lead body. This embodiment allows postoperative removal of the lead body 62 without removal of the cuff 220, which may be beneficial in revision operations, for example.

Figure 22A:
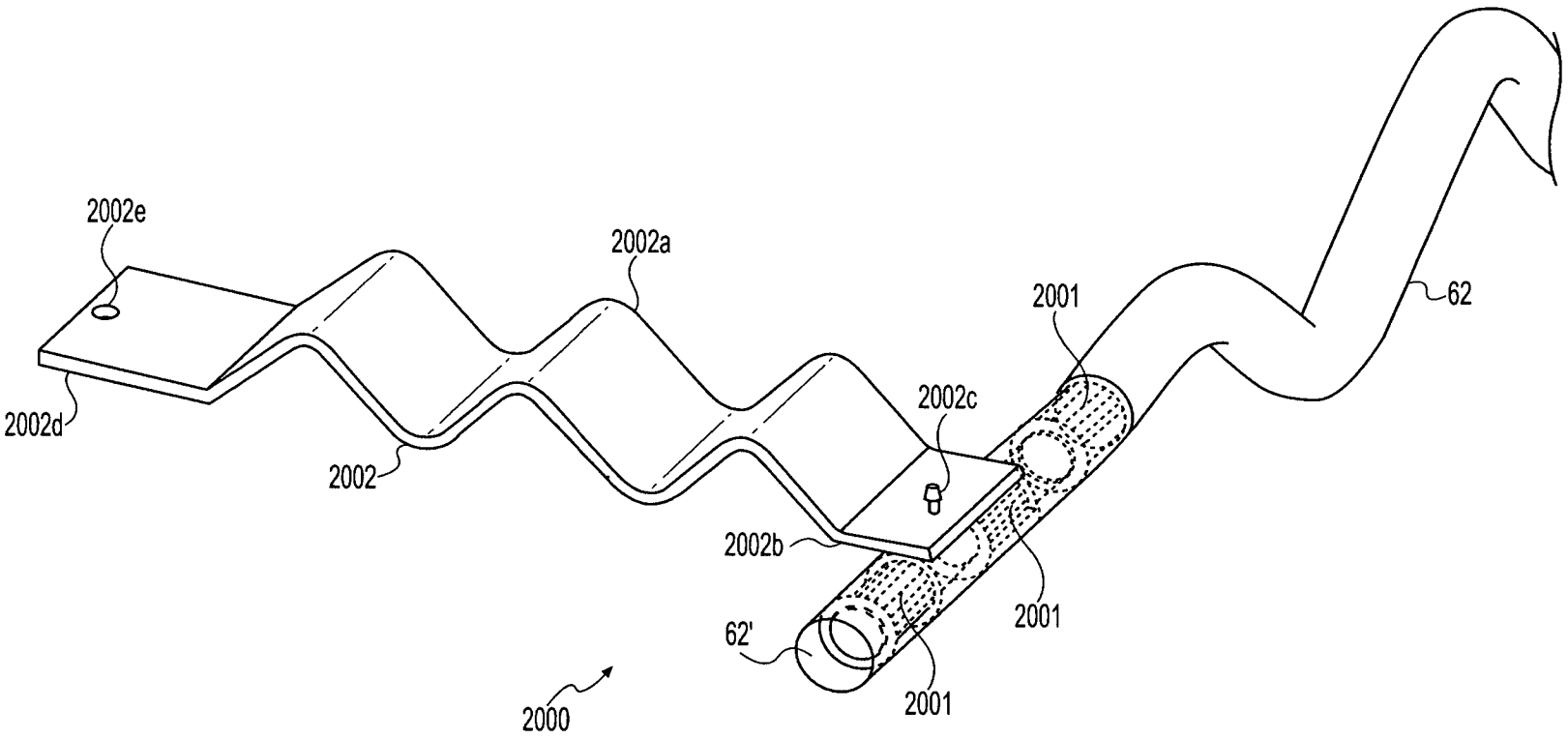

Turning now to FIG. 22A, there is depicted another design for a nerve cuff electrode 2000 where a substantially cylindrical distal portion 62' of lead body 62 carries an array of electrodes 2001. Electrodes 2001 may include ring electrodes that extend completely around the circumference of lead body 62, or, alternatively, may include generally semi-circular electrodes that extend partially around the circumference of lead body 62. The electrode may be selectively insulated on any portion of its surface to allow directional stimulation. Nerve cuff electrode 2000 may further include a nerve securing mechanism for securing lead body 62 to a nerve, such as, for example, a hypoglossal nerve. The nerve securing mechanism may include, for example, a compliant sheet wrap 2002 that is attached on one end to a distal portion of lead body 62, and unattached on the other opposing end. Compliant sheet wrap 2002 may be attached to lead body 62 by any suitable means.

Figure 22B:
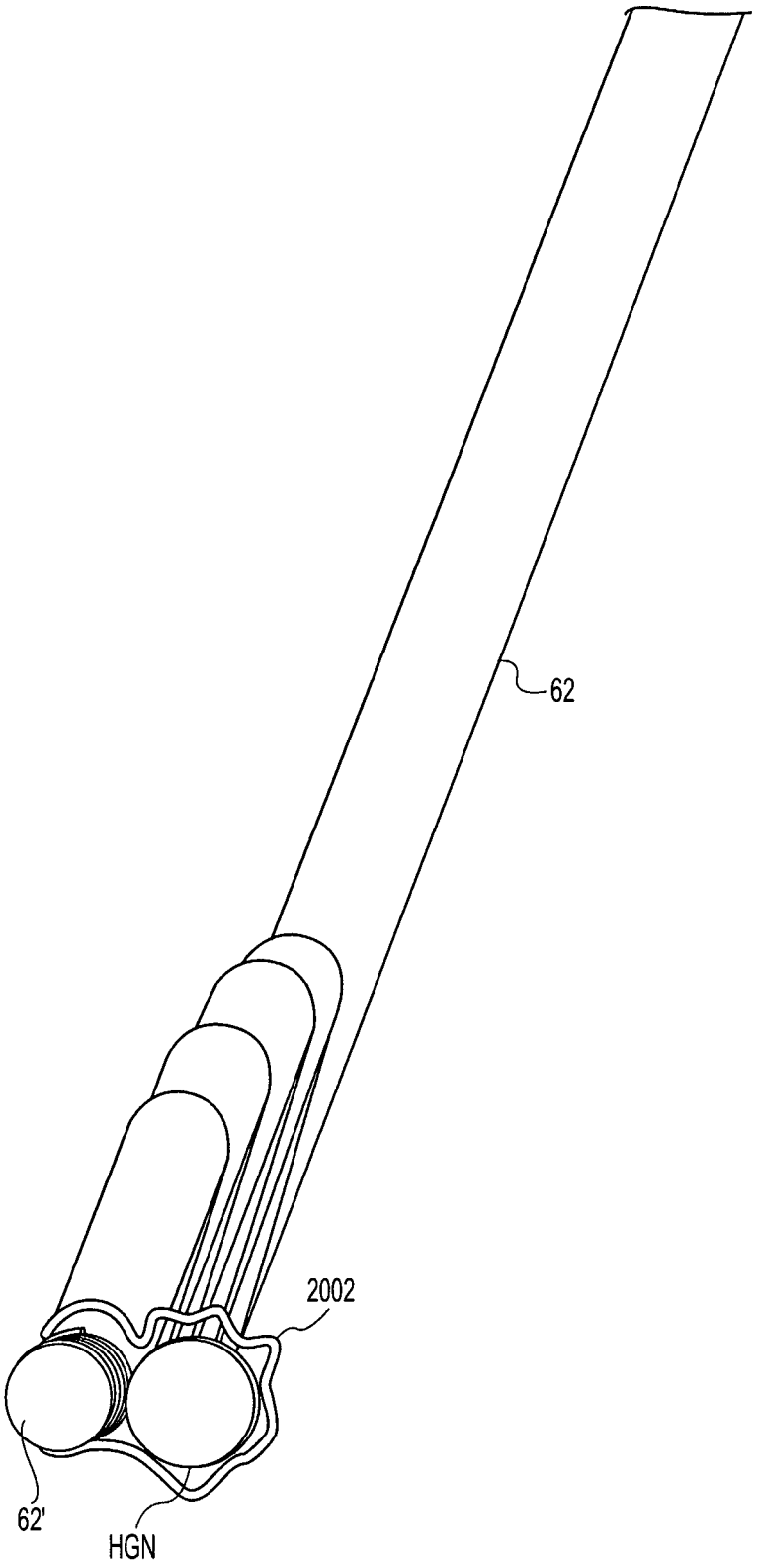
Figure 22C:
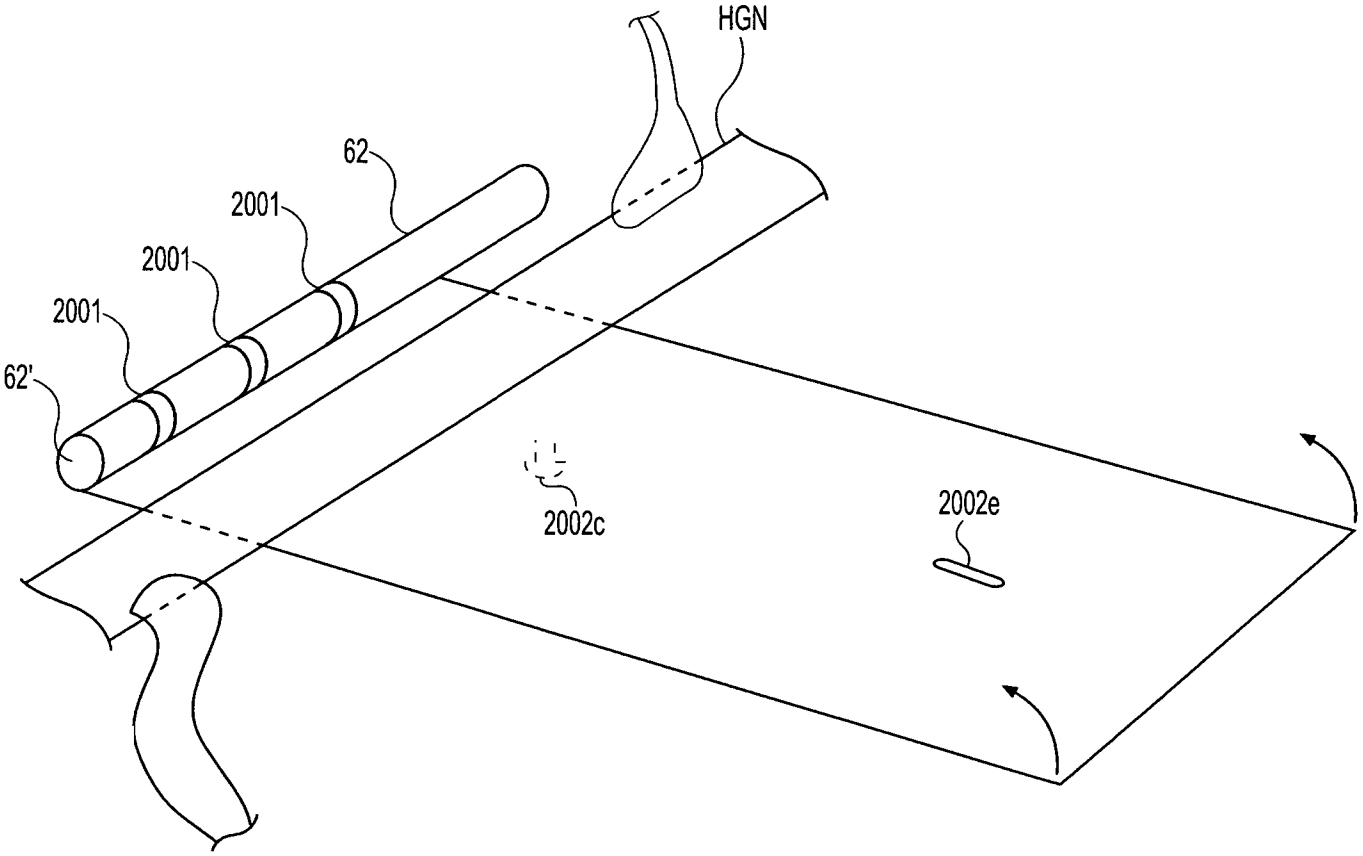

As shown in FIG. 22B, compliant sheet wrap 2002 may be configured to be wrapped around a nerve and secured thereto by, for example, connecting opposite portions of the sheet wrap 2002 together. Sheet wrap 2002 may be provided with one or more features to facilitate such connections. For example, it is contemplated that a portion 2002b of sheet wrap 2002 that is closest to lead body 62 may be provided with a projection 2002c that is configured for insertion into a corresponding opening 2002e provided on a portion 2002d of sheet wrap 2002 that is opposite portion 2002b. Opening 2002e may be configured to retain projection 2002c despite the forces exerted on sheet wrap 2002 during normal nerve swelling. However, opening 2002e may be configured to release projection 2002c when forces greater than a predetermined threshold are exerted on sheet wrap 2002, so as to prevent injury to the nerve. As shown in FIG. 22C, in some embodiments, opening 2002e may be provided as a slot, which, in addition to securing projection 2002c, may allow projection 2002c to slide within the opening 2002e, thereby allowing expansion of the sheet wrap 2002 to accommodate nerve swelling and/or over tightening of the sheet wrap 2002. Additionally, both portions 2002b and 2002d may be provided with suitable openings to facilitate the insertion of sutures (not shown) or other suitable fastening mechanisms. Sheet wrap 2002 may have any desired width. For example, sheet wrap 2002 may have a substantially tapered width, in order to securely wrap the nerve while minimizing dissection.

Compliant sheet wrap 2002 may be provided with any of a number of means that allow sheet wrap 2002 to expand, in order to accommodate nerve swelling and/or over tightening. For example, in one embodiment, sheet wrap 2002 may be provided with a plurality of radially and/or longitudinally distributed fenestrations (not shown). In other embodiments, sheet wrap 2002 may be provided with a plurality of undulations 2002a, such as, for example, sigmoid undulations, which may allow for expansion of sheet wrap 2002.

Figure 22D:
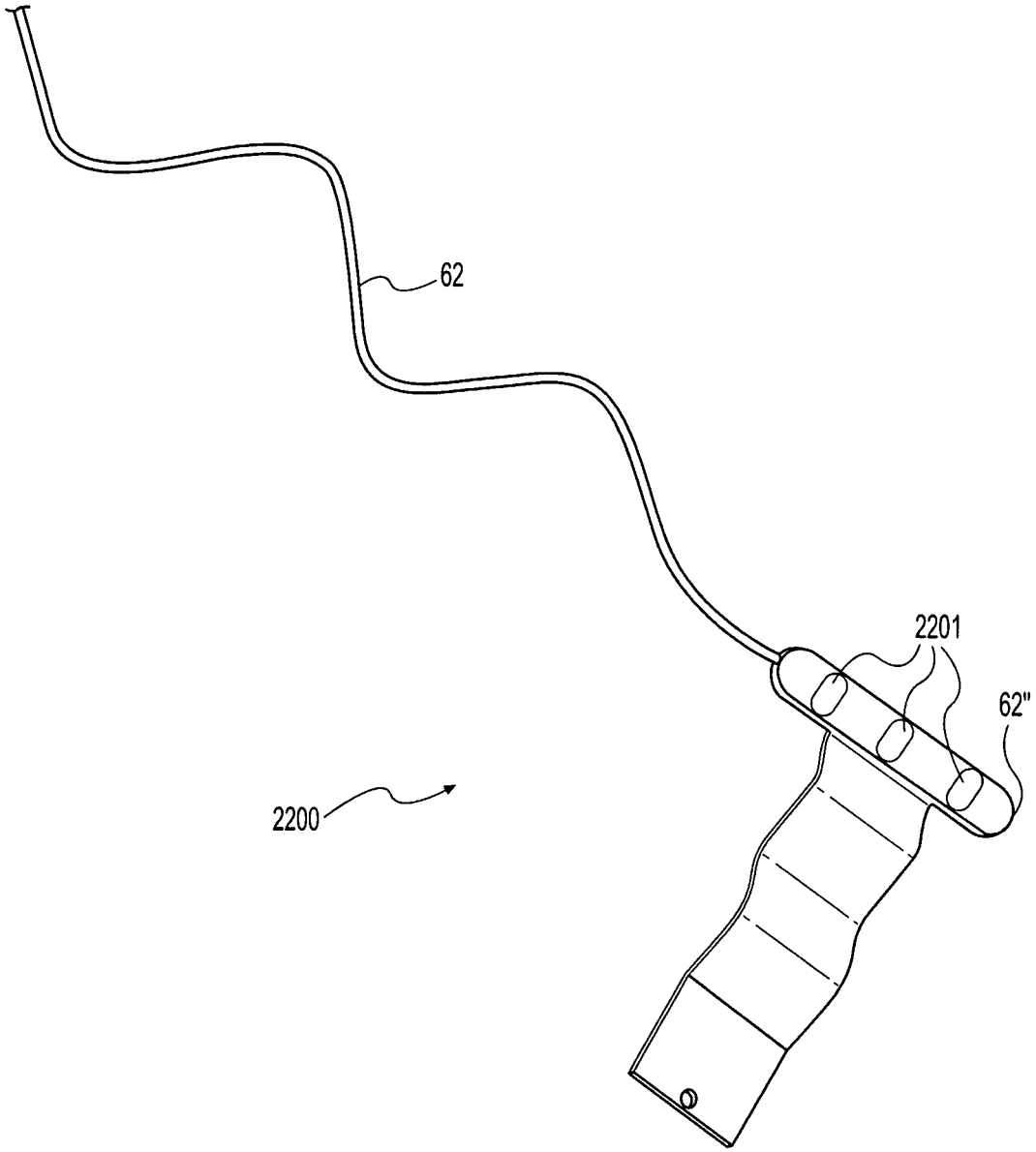

With reference now to FIG. 22D, there is depicted another design for a nerve cuff electrode 2200 where a distal portion 62" of lead body 62 carries an array of electrodes 2201. For the purposes of this disclosure, nerve cuff electrode 2200 may include substantially the same features as nerve cuff electrode 2000 depicted in FIGS. 22A-22C. Nerve cuff electrode 2200, however, may differ from nerve cuff electrode 2000 in that distal portion 62" may be substantially flat or paddle-shaped. Furthermore, electrode contacts 2201, rather than being circular or semi-circular in configuration, may be substantially, flat in configuration. In certain procedures, it is contemplated that the paddle-shaped distal portion 62", along with the substantially flat electrode contacts 2201, may promote greater contact between electrode contacts 2201 and the nerve they are mounted upon.

Description of Alternative Implant Procedure for the Stimulation Lead

Figure 23B:
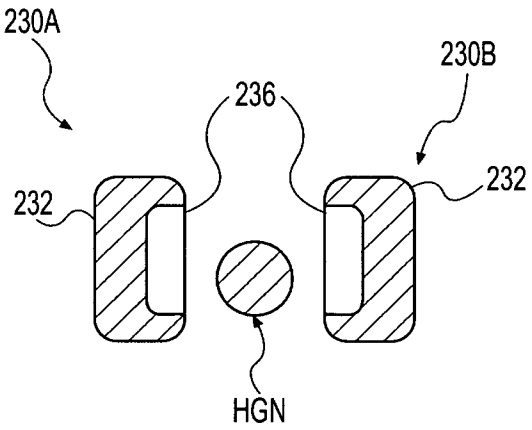
FIGS. 23-24 schematically illustrate alternative implant procedures and associated tools for the stimulation lead.
Figure 23A:
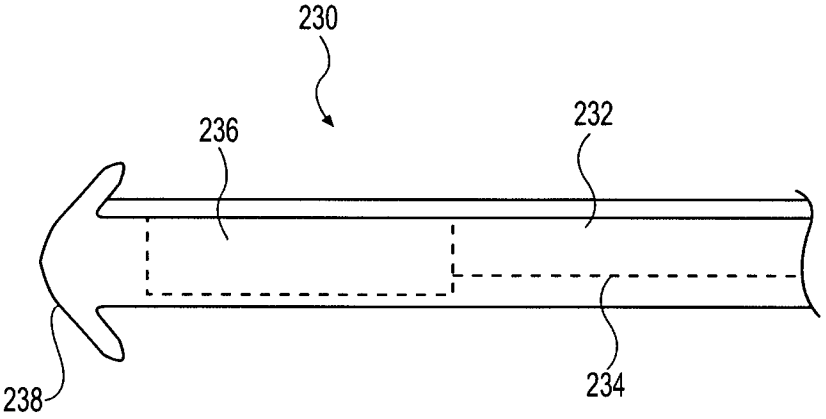
Figure 23C:
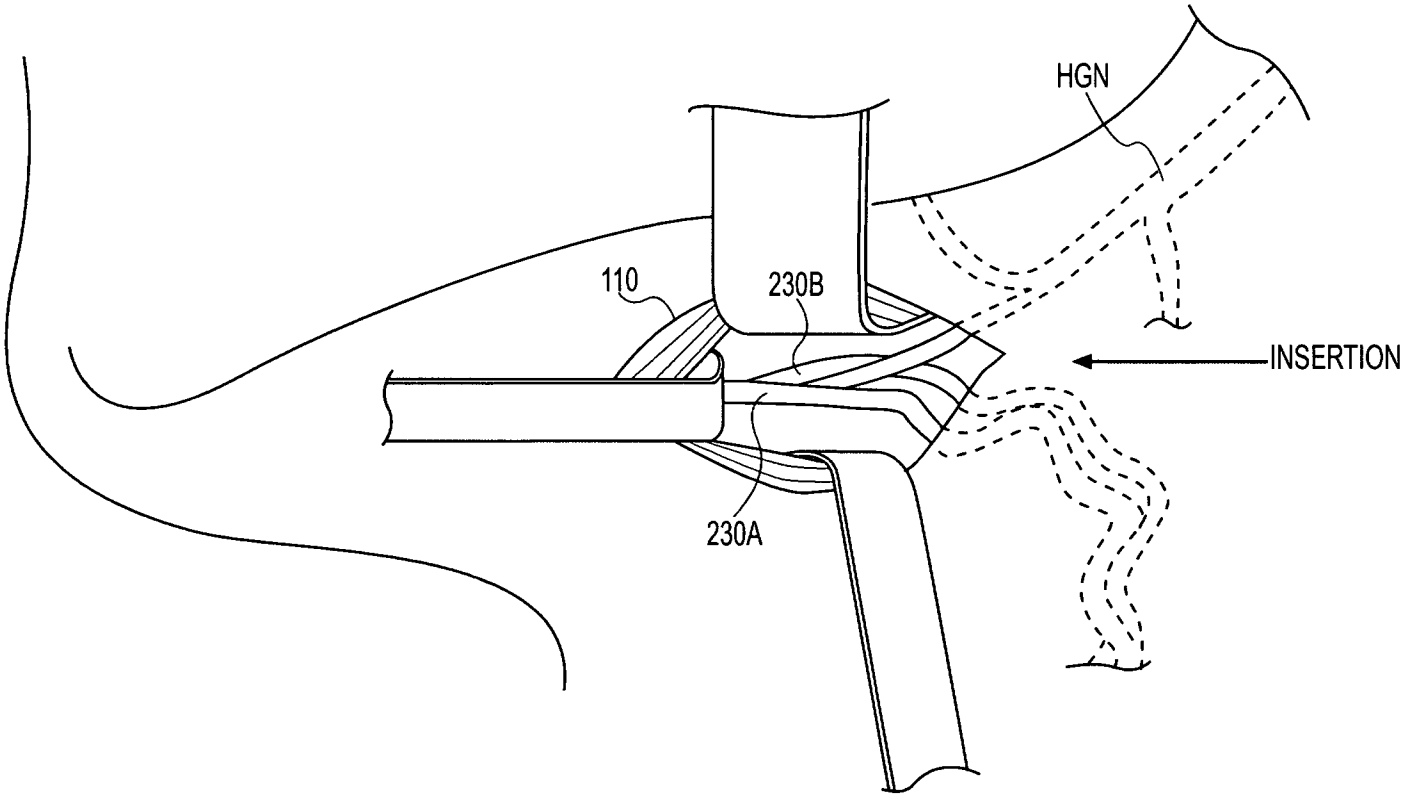

With reference to FIGS. 23A-23C, an insertable paddle-shaped lead 230 design is shown. The insertable lead 230 may have a paddle-shape (rectangular) cross-section with a tubular jacket 232 and one or more conductors 234 extending therethrough to one or more distally placed electrode contact(s) 236. The electrode contact(s) 236 may be imbedded in a molded distal end of the jacket 232 such that the electrode contact 236 has an exposed surface to face the nerve when implanted as shown in FIG. 23B. The space between the nerve and electrode is shown for purposes of illustration only, as the electrodes may be placed in direct contact with the nerve. Soft tines 238 may be integrally formed at the distal end of the tubular jacket 232 for purposes of mild fixation to tissue when implanted. The insertable lead 230 is configured to be placed adjacent to the nerve (thereby negating the need for a cuff) by inserting the lead 230 at the surgical access site 110 and following the nerve distally until the electrode contacts 236 are placed adjacent the target stimulation site. The insertable lead 232 may be used alone or in conjunction with another lead as shown in FIGS. 23B and 23C. In the illustrated example, a first lead 230A is inserted along a superficial side of the nerve and a second lead 230B is inserted along a deep side of the nerve.

A method of implanting lead 230 may generally comprise accessing a proximal extent of the nerve by minimal surgical dissection and retraction of the mylohyoid muscle as shown in FIG. 23C. Special tools may alternatively be employed for percutaneous or laparoscopic access as shown and described with reference to FIGS. 24A-24C. Subsequently, two paddle-shaped leads 230 with distal electrode contacts 236 may be inserted into the surgical access site and advanced beyond the access site along a distal aspect of the nerve to the desired stimulation site on either side of the nerve. These techniques minimize trauma and facilitate rapid recovery.

Figure 24A:
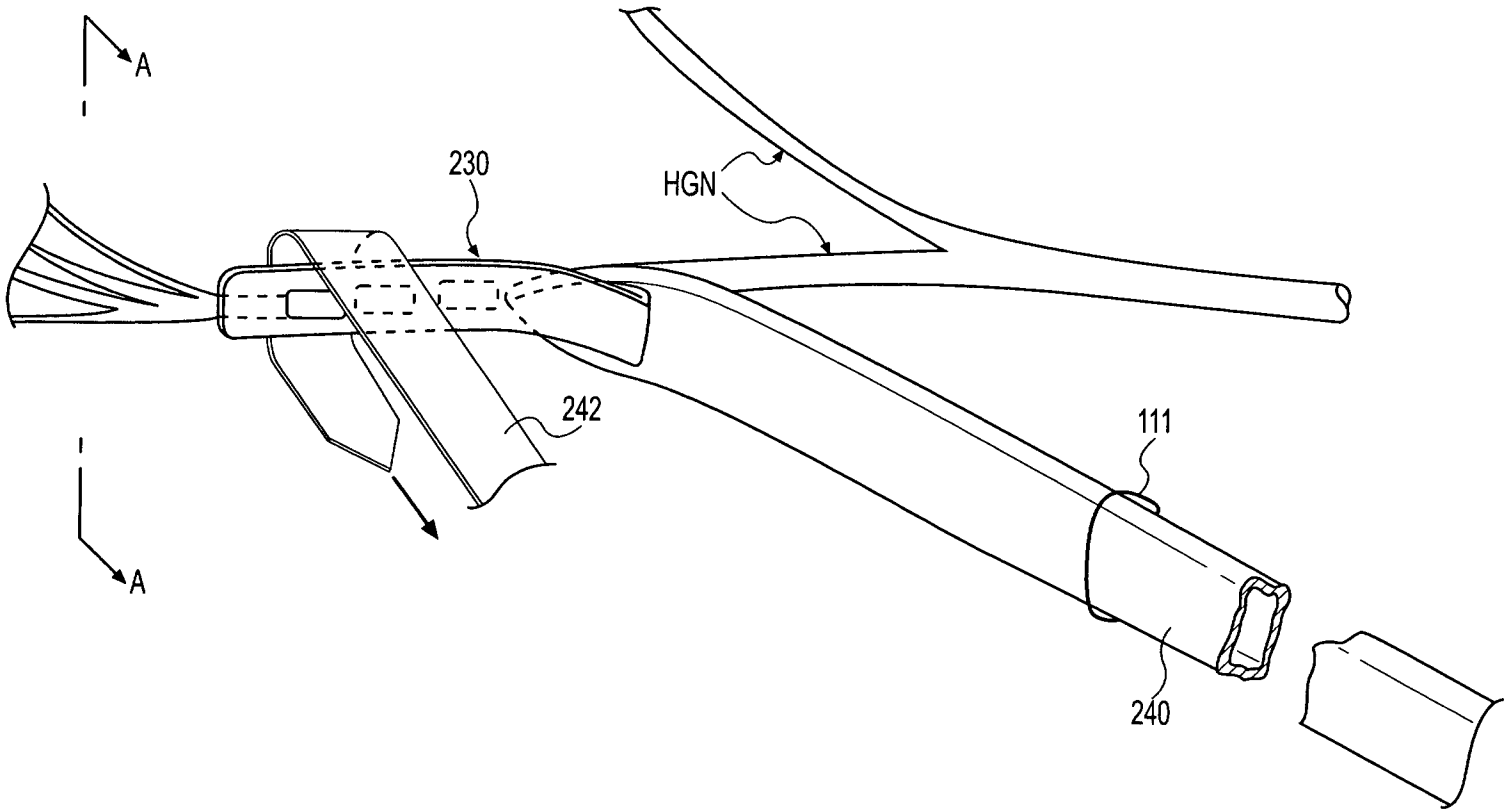
Figure 24C:
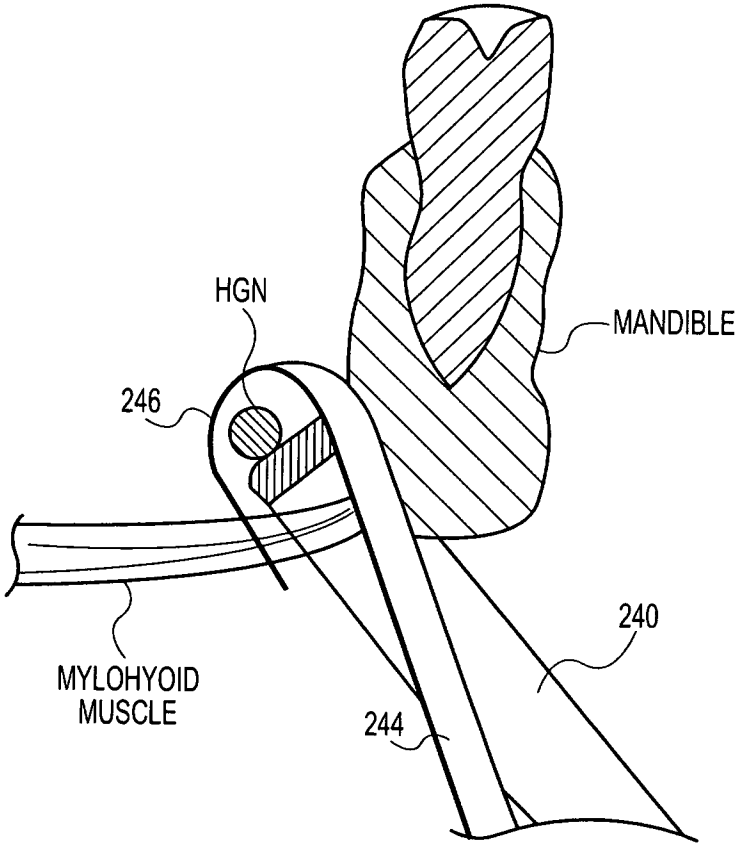
Figure 24B:
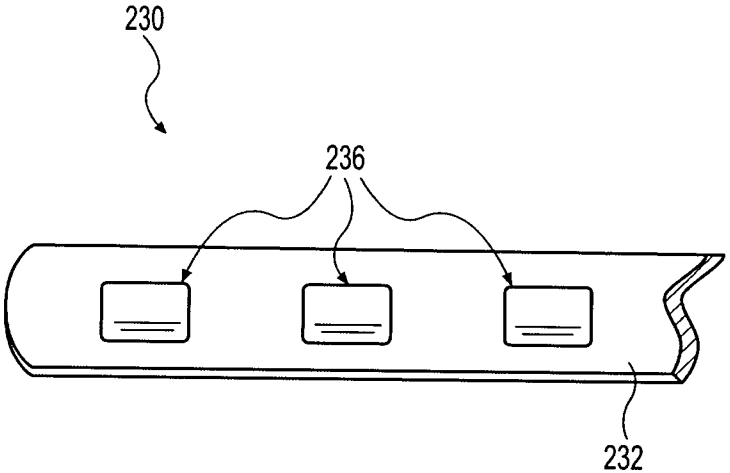

A less invasive method of implanting a paddle-shaped lead 230 is shown in FIGS. 24A-24C. In this embodiment, a rectangular tubular trocar 240 with a sharpened curved tip is placed through a percutaneous access site 111 until a distal end thereof is adjacent the superficial side of the nerve. A paddle-shaped lead 230 is inserted through the lumen of the trocar 240 and advanced distally beyond the distal end of the trocar 240 along the nerve, until the electrode contacts 236 are positioned at the target stimulation site. As shown in FIG. 24B, which is a view taken along line A-A in FIG. 24A, the insertable lead 230 includes multiple electrode contacts 236 in an anode-cathode-anode arrangement, for example, on one side thereof to face the nerve when implanted. In this embodiment, tines are omitted to facilitate smooth passage of the lead 230 through the trocar. To establish fixation around the nerve and to provide electrical insulation, a backer strap 242 of insulative material may be placed around the deep side of the nerve. To facilitate percutaneous insertion of the backer 242, a curved tip needle 244 may be inserted through a percutaneous access site until the tip is adjacent the nerve near the target stimulation site. A guide wire 246 with a J-shaped tip may then be inserted through the needle 244 and around the nerve. The backer 242 may then be towed around using the guide wire 246 as a leader, and secured in place by a buckle (not shown), for example.

Figure 25:
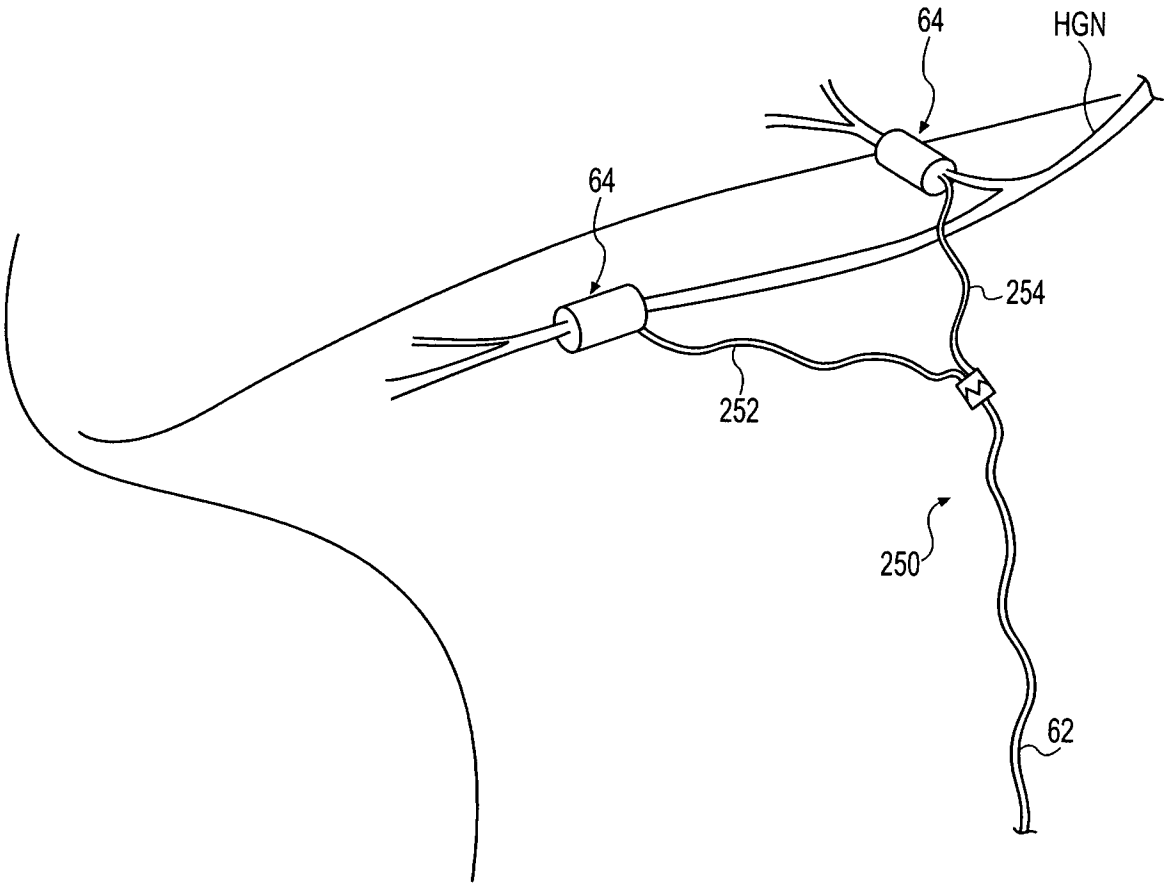
FIG. 25 schematically illustrates an alternative bifurcated lead body design.

With reference to FIG. 25, a bifurcated lead 250 is shown to facilitate separate attachment of electrode cuffs 64 to different branches of the same nerve or different nerves for purposes described previously. Any of the nerve cuff electrode or intramuscular electrode designs described herein may be used with the bifurcated lead 250 as shown. In the illustrated example, a first lead furcation 252 and a second lead furcation 254 are shown merging into a common lead body 62. Each furcation 252 and 254 may be the same or similar construction as the lead body 62, with modification in the number of conductors. More than two electrode cuffs 64 may be utilized with corresponding number of lead furcations.

Description of Stimulation Lead Anchoring Alternatives

Figure 26A:
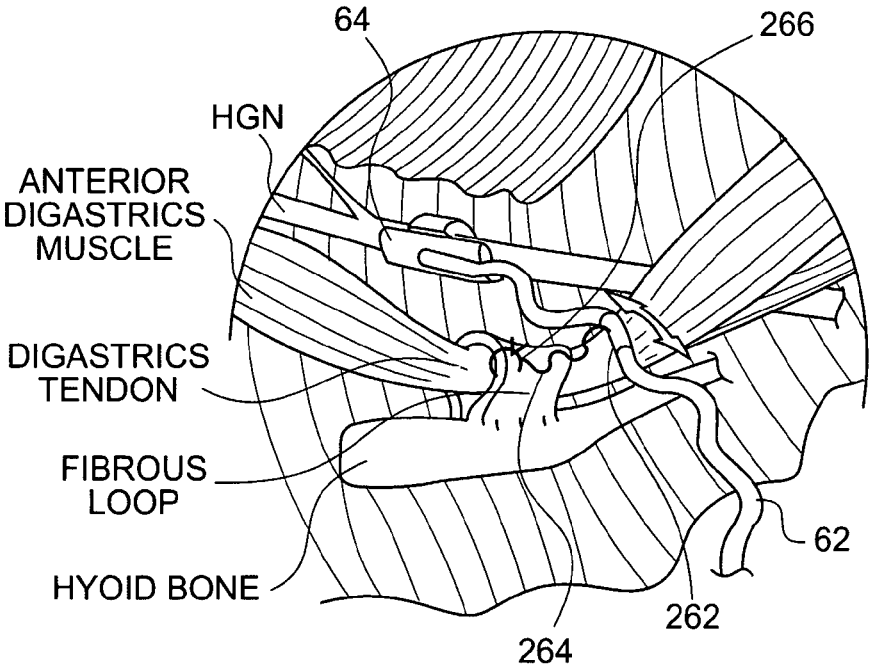
FIGS. 26A-26B schematically illustrate alternative fixation techniques for the stimulation lead and electrode cuff.
Figure 26B:
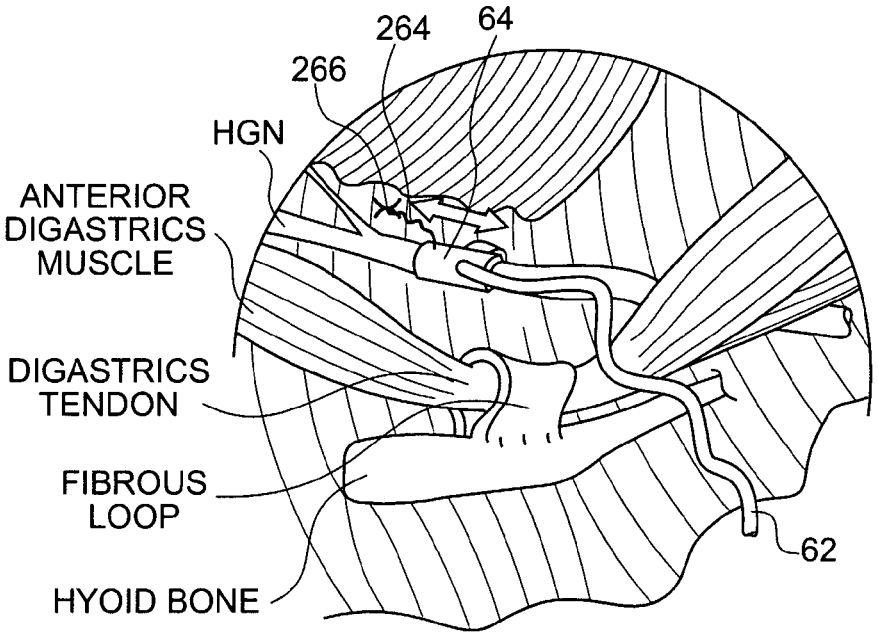

With reference to FIGS. 26A and 26B, an elastic tether 264 with a limited length is utilized to prevent high levels of traction on the electrode cuff 64 around the hypoglossal nerve (or other nerve in the area) resulting from gross head movement. In other words, tether 264 relieves stress applied to the electrode cuff 64 by the lead body 62. FIGS. 26A and 26B are detailed views of the area around the dissection to the hypoglossal nerve, showing alternative embodiments of attachment of the tether 264. The proximal end of the tether 264 may be attached to the lead body 62 as shown in FIG. 26A or attached to the electrode cuff 64 as shown in FIG. 26B. The distal end of the tether 264 may be attached to the fibrous loop carrying the digastrics tendon as shown in FIG. 26A or attached to adjacent musculature as shown in FIG. 26B.

By way of example, not limitation, and as shown in FIG. 26A, a tubular collar 262 is disposed on the lead body 62 to provide connection of the tether 264 to the lead body 62 such that the lead body 62 is effectively attached via suture 266 and tether 264 to the fibrous loop surrounding the digastrics tendon. The tether 264 allows movement of the attachment point to the lead body 62 (i.e., at collar 262) until the tether 264 is straight. At this point, any significant tensile load in the caudal direction will be borne on the fibrous loop and not on the electrode cuff 64 or nerve. This is especially advantageous during healing before a fibrous sheath has formed around the lead body 62 and electrode cuff 64, thus ensuring that the cuff 64 will not be pulled off of the nerve. It should be noted that the length of the tether 262 may be less than the length of the lead body 62 between the attachment point (i.e., at collar 262) and the cuff 64 when the tensile load builds significantly due to elongation of this section of lead body 62.

The tether 264 may be formed from a sigmoid length of braided permanent suture coated with an elastomer (such as silicone or polyurethane) to maintain the sigmoid shape when in the unloaded state. The tether 264 may also be made from a monofilament suture thermoformed or molded into a sigmoid shape. The distal end of the tether 264 may be attached to the fibrous loop using a suture 266 or staple or other secure means. Note that the tether 264 may be made from a biodegradable suture that will remain in place only during healing.

Also by way of example, not limitation, an alternative is shown in FIG. 26B wherein the tether 264 is attached to the electrode cuff 64. The distal end of the tether 264 may be attached to the adjacent musculature by suture 266 such the musculature innervated by branches of the hypoglossal nerve or other musculature in the area where the electrode cuff 64 is attached to the nerve. The tether 264 ensures that the electrode cuff 64 and the hypoglossal nerve are free to move relative to the adjacent musculature (e.g., hyoglossal). As significant tensile load is applied to the lead body 62 due to gross head movement, the tether 264 will straighten, transmitting load to the muscle rather then to the nerve or electrode cuff 64.

Figure 26C:
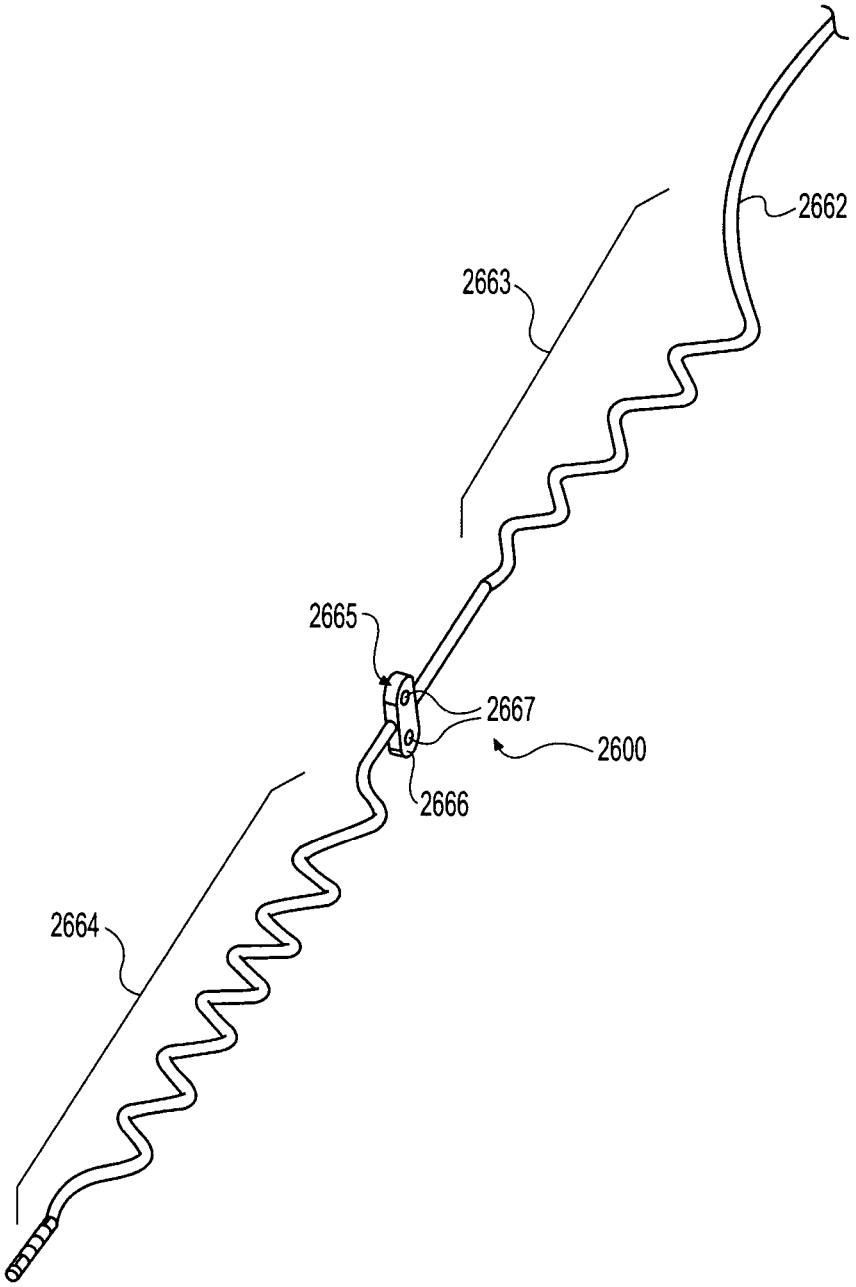
FIG. 26C schematically illustrates an alternative embodiment of a stimulation lead having a fixation mechanism.

As alluded to above, stimulation lead 60 may comprise a number of differing design embodiments. One such embodiment has been discussed above with respect to FIG. 5. Another such embodiment is depicted in FIG. 26C, which illustrates a stimulation lead 2600. Stimulation lead 2600 may be substantially similar to and/or may include one or more of the features described in connection with stimulation lead 60. As shown in FIG. 26C, stimulation lead 2600 may include a lead body 2662 having a first, proximal lead body portion 2663. First lead body portion 2663 may be substantially similar to lead body 62. For example, first lead body portion 2663 may include a similar flexibility as lead body 62. Lead body 2662 may further include a second, distal lead body portion 2664 leading to the distal end of lead body 2662 at the nerve cuff electrode. Second lead body portion 2664 may include a material property that is different than lead body portion 2663, such as, for example, a greater flexibility, in order to accommodate stresses imparted upon lead body 2662 by a nerve cuff electrode and movement of the patient's head, neck, and other neighboring body portions. The highly flexible distal portion 2664 reduces the stress (torque and tension) imparted by lead body 2662 on the electrode cuff, thereby reducing the likelihood that the cuff will be detached from the nerve or damage the nerve.

Lead body portion 2664 may be made more flexible than lead body portion 2663 by any of a variety of ways. For example, lead body portion 2664 may be made from a material having differing flexibility. Alternatively, the diameters of the braided stranded wires (BSW) and/or wire insulation that make up the lead body portion 2664 may be reduced when possible.

With continuing reference to FIG. 26C, stimulation lead 2600 may further include an anchor 2665 operably connected to lead body 2662. Although anchor 2665 in the illustrated embodiment is depicted as being disposed in between lead body portions 2663 and 2664, anchor 2665 may be disposed at any suitable location along the length of lead body 2662. Furthermore, anchor 2665 may be fixedly or movably connected to lead body 2662.

Anchor 2665 may include any suitable configuration known in the art. For example, anchor 2665 may include a substantially flat body portion 2666. Body portion 2666 may be configured to be secured to tissue, such as, for example, tissue proximate a treatment site, by any suitable means available in the art. For example, body portion 2666 may be provided with openings 2667 to facilitate, for example, suturing anchor 2665 to nearby tissue. Anchor 2665 can thereby isolate stress (tension) to one portion of lead body 2662, and particularly portion 2663, caused by gross head and neck movement.

Description of Field Steering Alternatives

Figure 27A:
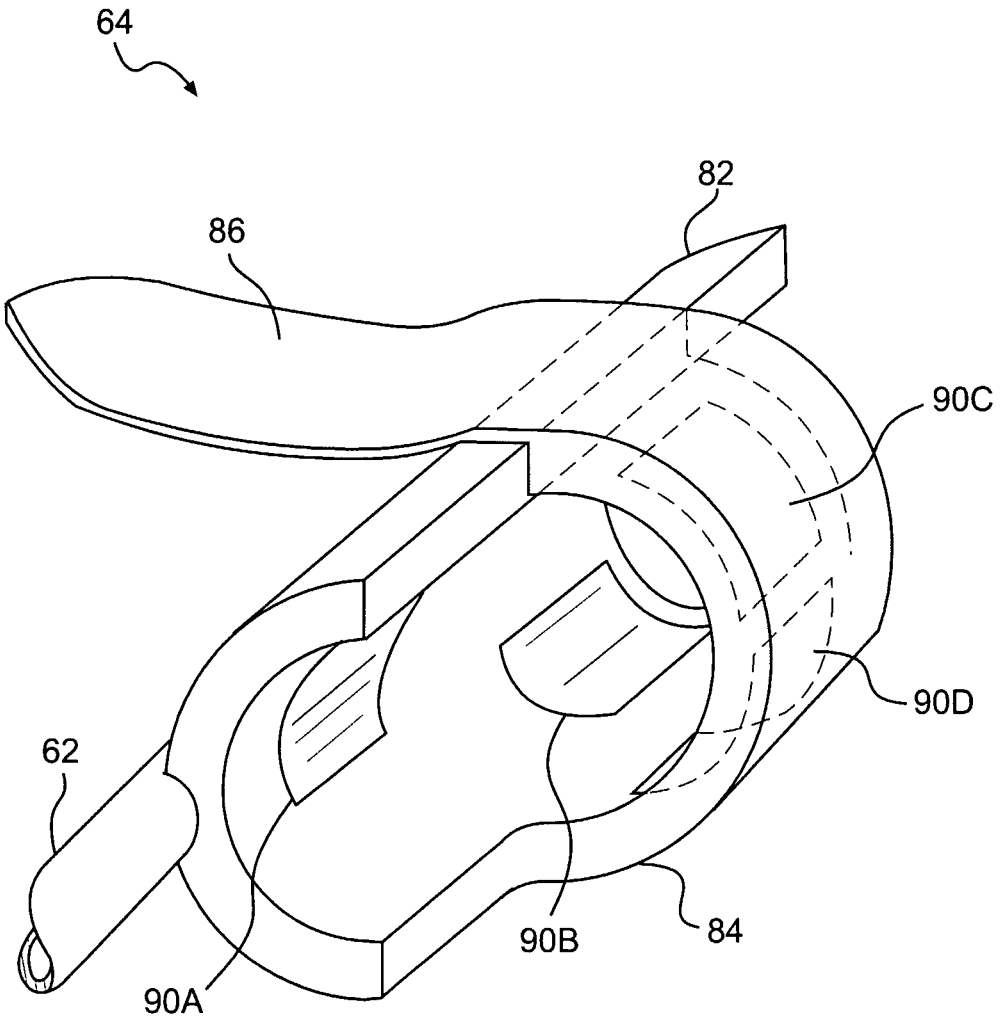
FIGS. 27A-27H schematically illustrate field steering embodiments.

With reference to FIGS. 27A-27G, a field steering nerve cuff electrode 64 is shown schematically. As seen in FIG. 27A, the nerve cuff electrode 64 may include four electrode contacts 90A-90D to enable field steering, and various arrangements of the electrode contacts 90A-90D are shown in FIGS. 27B-27G. Each of FIGS. 27B-27G includes a top view of the cuff 64 to schematically illustrate the electrical field (activating function) and an end view of the cuff 64 to schematically illustrate the area of the nerve effectively stimulated. With this approach, electrical field steering may be used to stimulate a select area or fascicle(s) within a nerve or nerve bundle to activate select muscle groups as described herein.

With specific reference to FIG. 27A, the nerve cuff electrode 64 may comprise a cuff body having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. An integral tow strap 86 may be used to facilitate wrapping the cuff around a nerve. The nerve cuff electrode 64 includes electrode contacts 90A, 90B, 90C and 90D imbedded in the body of the cuff, with their inside surface facing exposed to establish electrical contact with a nerve disposed therein. Electrode contacts 90A and 90B are longitudinally and radially spaced from each other. Electrode contacts 90C and 90D are radially spaced from each other and positioned longitudinally between electrode contacts 90A and 90B. Each of the four electrode contacts may be operated independently via four separate conductors (four filar) in the lead body 62.

With specific reference to FIGS. 27B-27G, each includes a top view (left side) to schematically illustrate the electrical field or activating function (labeled E), and an end view (right side) to schematically illustrate the area of the nerve effectively stimulated (labeled S) and the area of the nerve effectively not stimulated (labeled NS). Electrodes 90A-90D are labeled A-D for sake of simplicity only. The polarity of the electrodes is also indicated, with each of the cathodes designated with a negative sign (−) and each of the anodes designated with a positive sign (+).

Figure 27B:
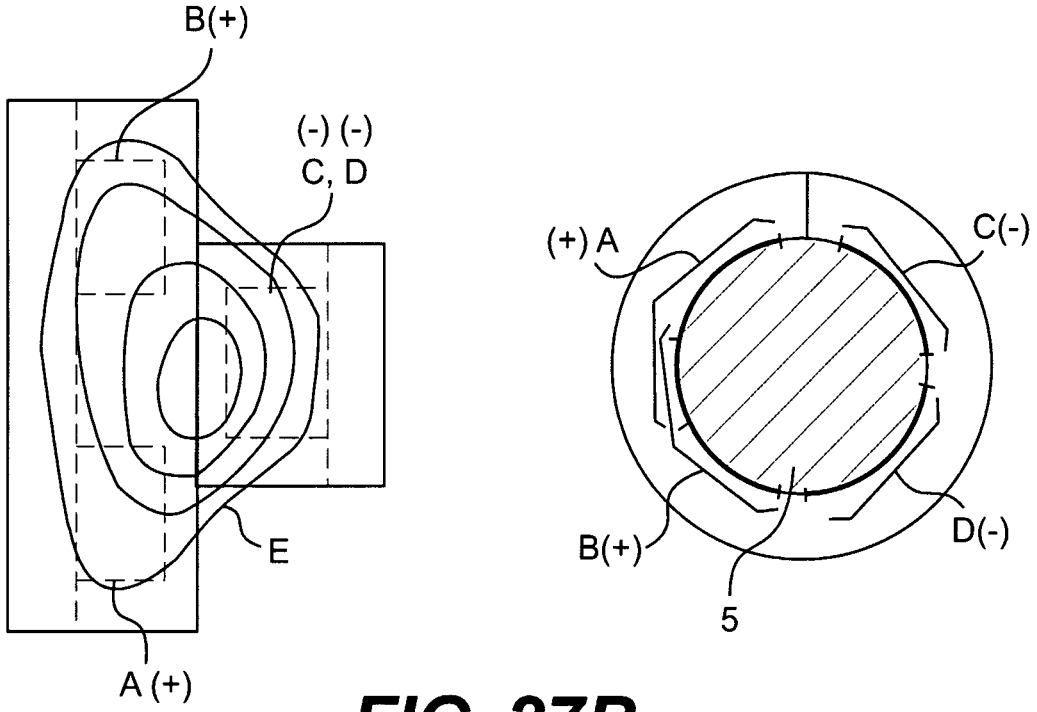

With reference to FIG. 27B, a tripolar transverse guarded cathode arrangement is shown with electrodes C and D comprising cathodes and electrodes A and B comprising anodes, thus stimulating the entire cross-section of the nerve.

Figure 27C:
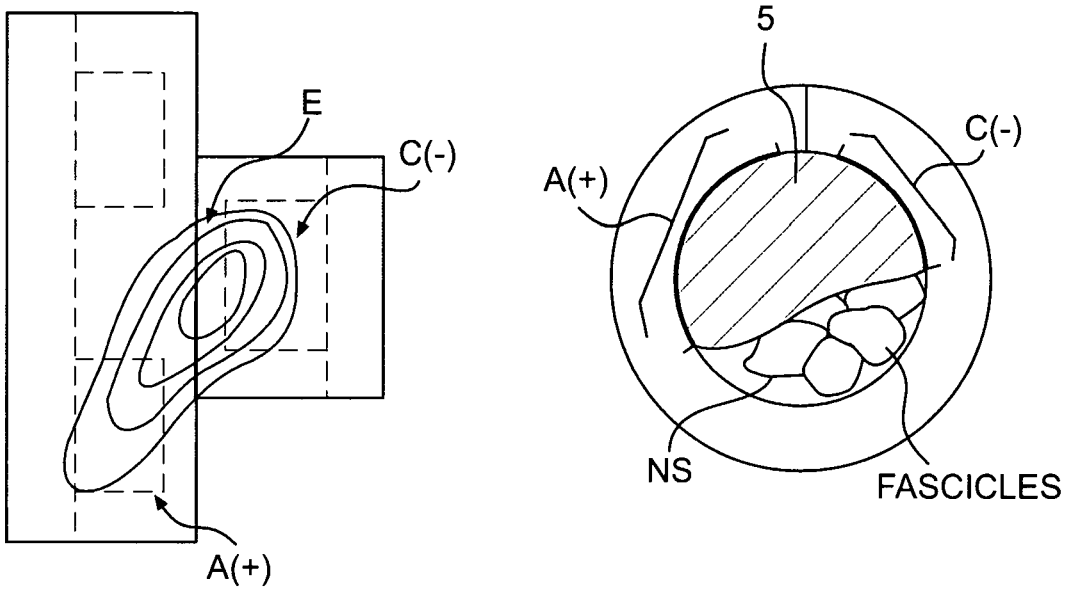

With reference to FIG. 27C, a bipolar diagonal arrangement is shown with electrode C comprising a cathode and electrode A comprising an anode, wherein the fascicles that are stimulated may comprise superior fascicles of the hypoglossal nerve, and the fascicles that are not stimulated may comprise inferior fascicles of the hypoglossal nerve (e.g., fascicles that innervate the intrinsic muscles of the tongue).

Figure 27D:
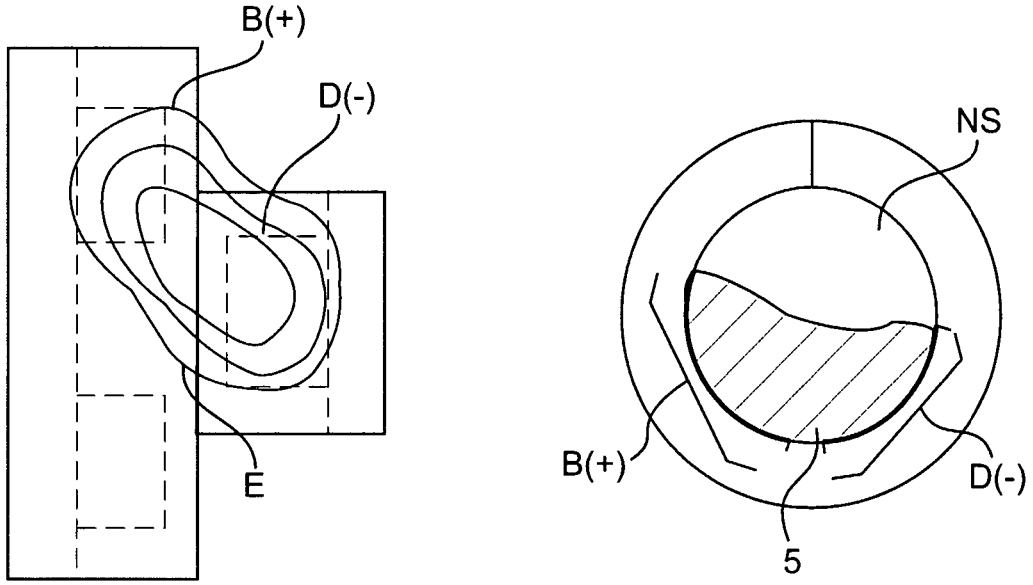

With reference to FIG. 27D, another bipolar diagonal arrangement is shown with electrode D comprising a cathode and electrode B comprising an anode, wherein the fascicles that are stimulated may comprise inferior fascicles of the hypoglossal nerve.

Figure 27E:
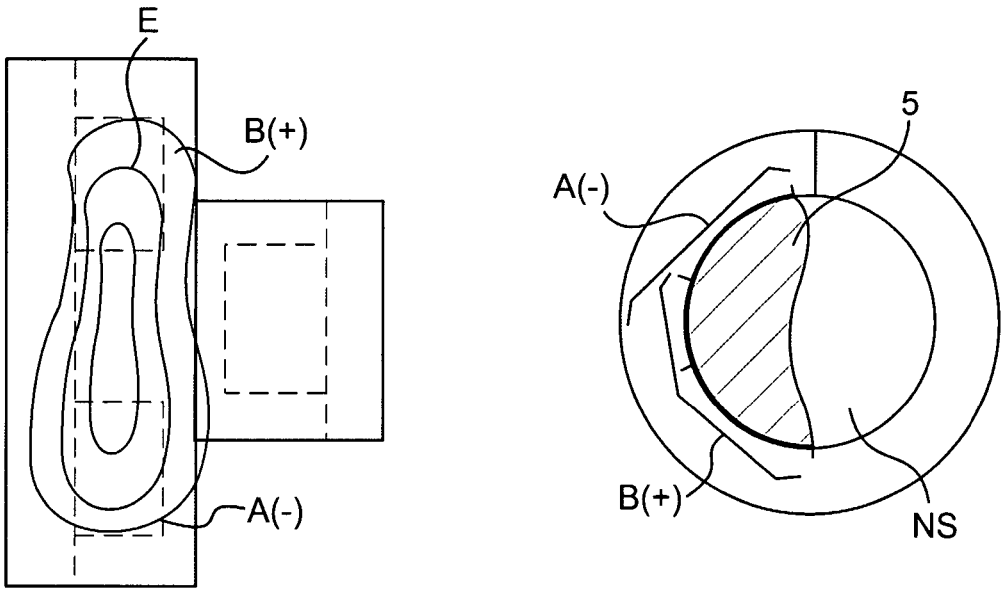

With reference to FIG. 27E, a bipolar axial arrangement is shown with electrode A comprising a cathode and electrode B comprising an anode, wherein the fascicles that are stimulated may comprise lateral fascicles of the hypoglossal nerve.

Figure 27F:
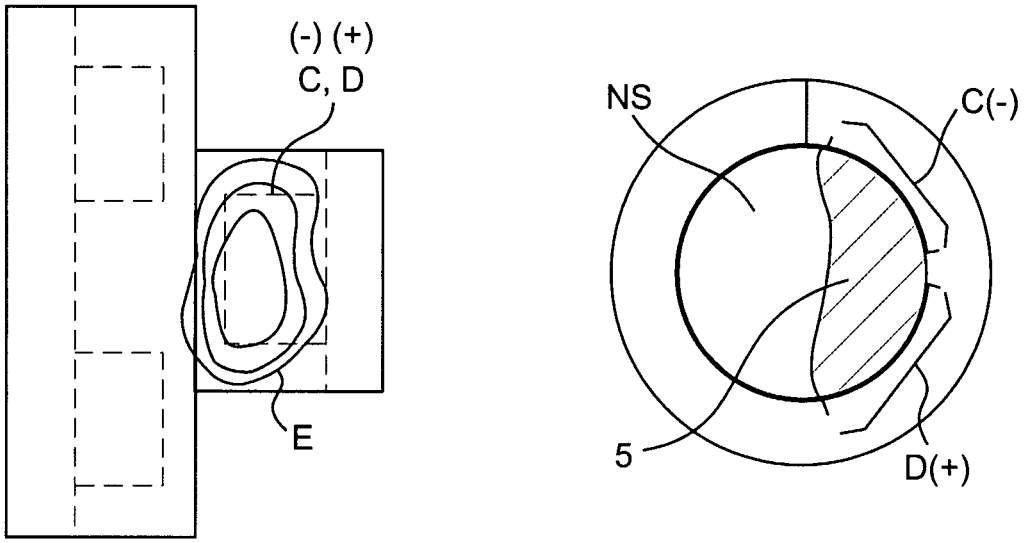

With reference to FIG. 27F, a bipolar transverse arrangement is shown with electrode C comprising a cathode and electrode D comprising an anode, wherein the fascicles that are stimulated may comprise medial fascicles of the hypoglossal nerve.

Figure 27G:
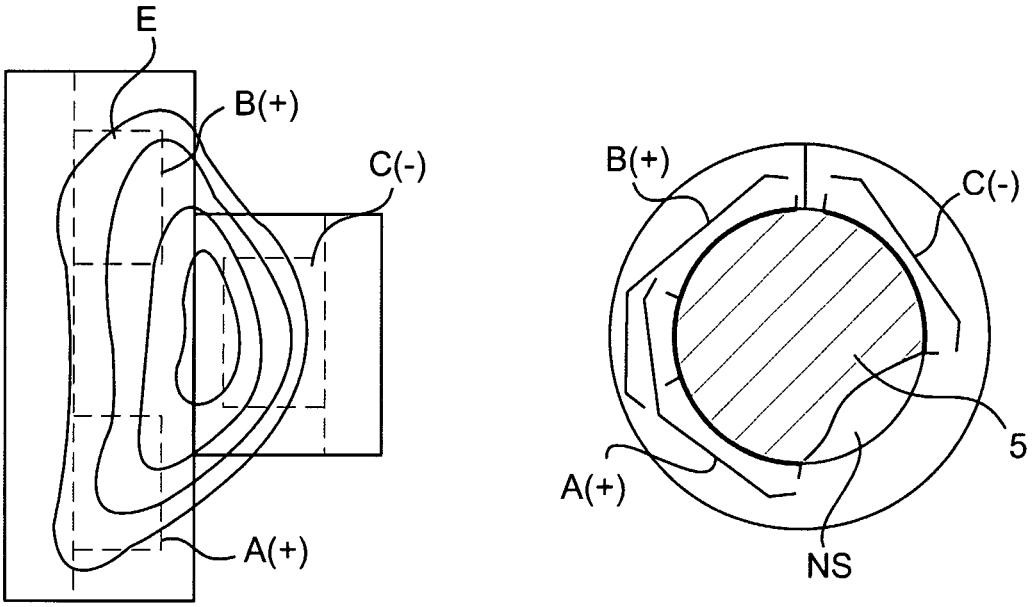

With reference to FIG. 27G, a modified tripolar transverse guarded cathode arrangement is shown with electrode C comprising a cathode and electrodes A and B comprising anodes, thus stimulating the entire cross-section of the nerve with the exception of the inferior medial fascicles.

Nerves like the hypoglossal nerve or superior laryngeal nerve typically include a plurality of fibers having relatively larger diameters and a plurality of fibers having relatively smaller diameters. In the case of single function nerves, such as, for example, the hypoglossal nerve HGN, all of the nerve fibers may either be sensory or motor in function. However, in the case of multi-function nerves, such as, for example, the superior laryngeal nerve SLN, the fibers having relatively larger diameters are typically motor (efferent) fibers, and the fibers having relatively smaller diameters are typically sensory (afferent) fibers. Accordingly, there may be a need to selectively stimulate the differing diameter fibers in a nerve.

Figure 27H:
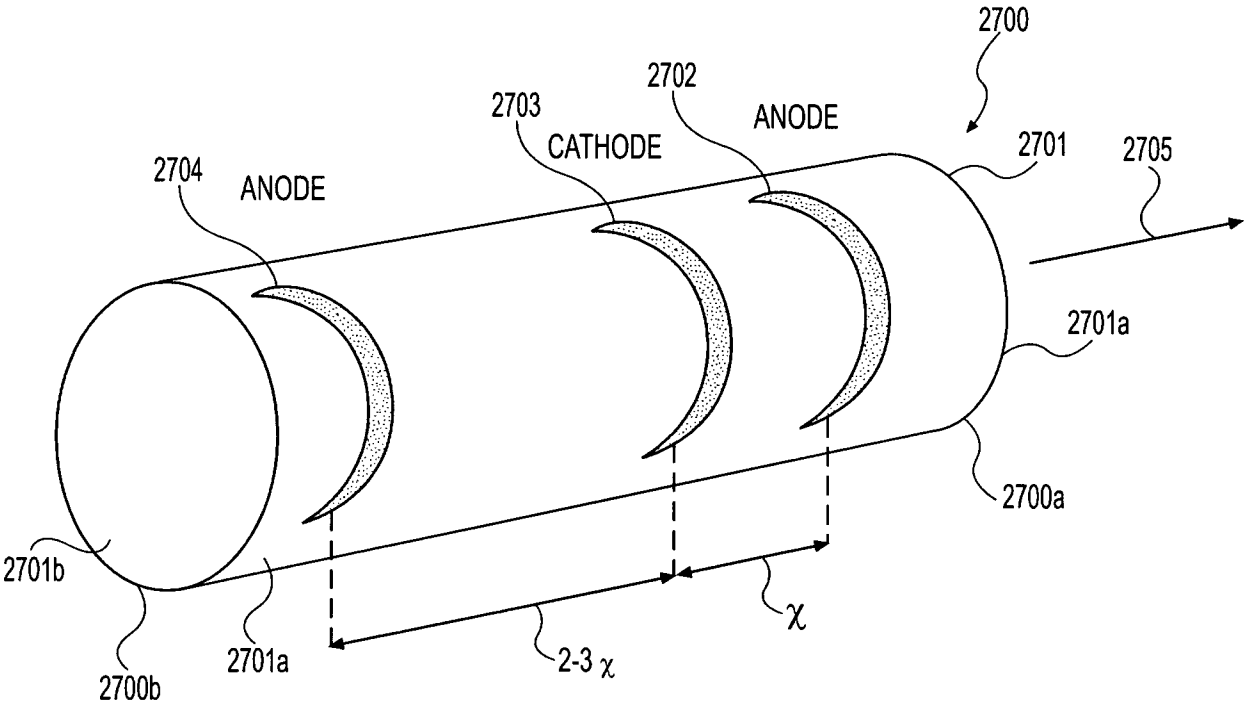

Turning now to FIG. 27H, there is depicted an embodiment of a uni-directional stimulation electrode 2700 having a distal end 2700a and a proximal end 2700b. Electrode 2700 may include a substantially cylindrical nerve cuff 2701 in accordance with the principles of the present disclosure. As illustrated, nerve cuff 2701 may include an outer surface 2701a and an inner surface 2701b. Electrode 2700 may further include a plurality of electrode contacts 2702-2704. Electrode contacts 2702-2704 may be used as any suitable electrode contact known to those of ordinary skill in the art. For example, electrode contact 2702 may be used as an anode, electrode contact 2703 may be used as a cathode, and electrode contact 2704 may be used as a second anode. Electrode contacts 2702-2704 may also include any suitable shape and/or configuration known in the art. For example, electrode contacts 2702-2704 may include a substantially semi-circular configuration.

Electrode contacts 2702-2704 may be disposed on nerve cuff 2701 in any suitable configuration to achieve the desired effect. For example, electrode contacts 2702-2704 may be disposed on inner surface 2701b. As depicted in FIG. 27H, cathode electrode contact 2703 may be disposed approximately equidistant from distal end 2700a and proximal end 2700b, and anode electrode contacts 2702 may be differentially spaced around cathode electrode contact 2703, so as to control the direction of stimulation of electrode 2700. For example, anode electrode contact 2702 may be spaced from cathode electrode contact 2703 by any suitable distance $\chi$, while second anode electrode contact 2704 may be spaced from cathode electrode contact 2703 by a distance that is approximately two or three times greater than distance $\chi$. In this exemplary configuration, the direction of stimulation may be in the direction of arrow 2705.

In use, electrode 2700 may be implanted upon a nerve in accordance with the principles of this disclosure. Electrode 2700 may be oriented on the nerve it is implanted on in any suitable manner, such as, for example, according to the direction of intended stimulation. Thus, in circumstances where it may be desired to stimulate efferent (motor) fibers of a nerve, such as, for example, the superior laryngeal nerve SLN, while avoiding stimulation to afferent (sensory) fibers of the nerve, the electrode 2700 may be oriented on the nerve in a manner such that anode electrode contact 2702 is located distally of cathode electrode contact 2703, with distal and proximal designations based on the relative location of the electrode contact on the nerve. Alternatively, in circumstances where it may be desired to stimulate afferent fibers of a nerve while avoiding stimulation of efferent fibers of the nerve, the electrode 2700 may be oriented on the nerve in a manner such that anode electrode contact 2702 is located proximally of cathode electrode contact 2703.

Figure 27I:
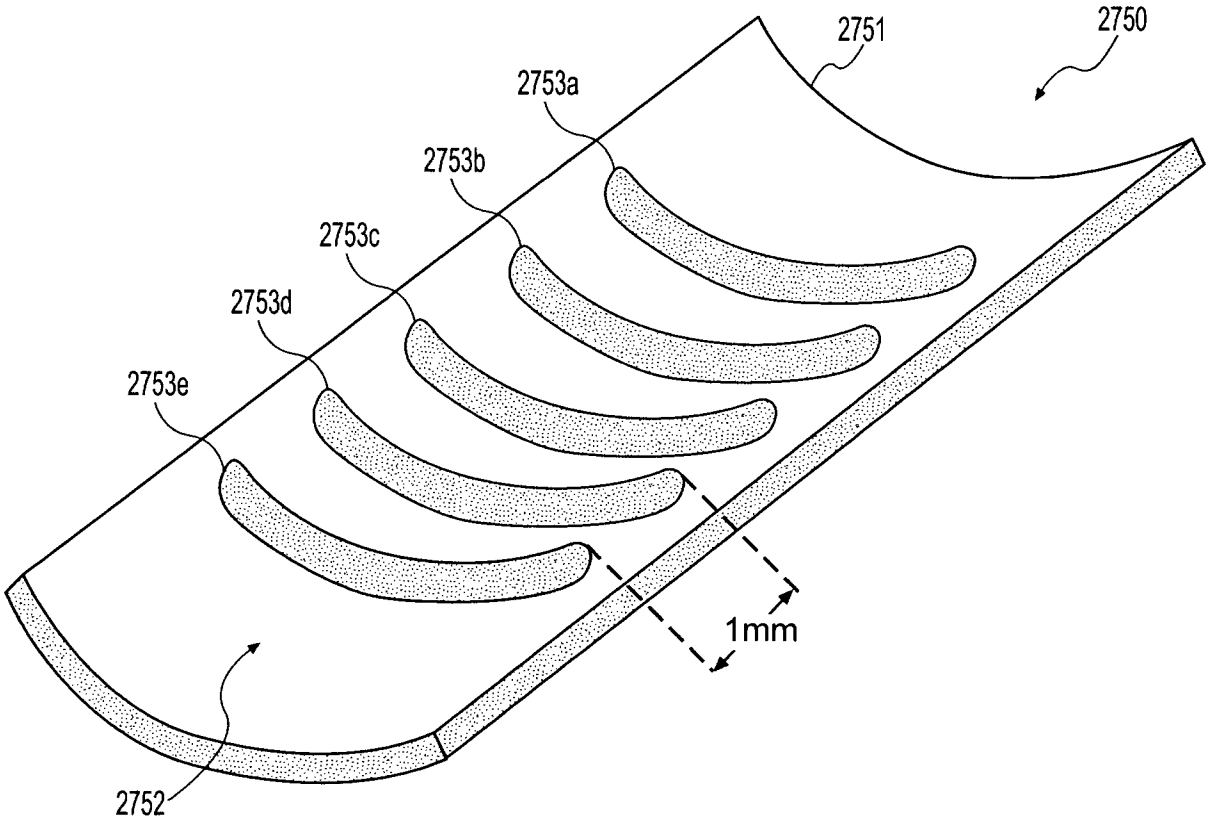
FIGS. 27I-27Q schematically illustrate alternative embodiments of nerve cuff electrodes with selective fiber stimulation mechanisms.

With reference now to FIG. 27I, there is depicted an embodiment of a stimulation electrode 2750 for, among other things, selectively stimulating differing diameter fibers of a nerve, such as, for example, the hypoglossal nerve or superior laryngeal nerve. Electrode 2750 may include a body 2751, and may include any suitable configuration in accordance with the principles of the present disclosure. Additionally, electrode 2750 may include an array 2752 of suitable electrode contacts known to those skilled in the art. Although the depicted embodiment of electrode 2750 includes five electrode contacts 2753a-2753e, array 2752 may include a greater or lesser number of electrode contacts. Electrode contacts 2753a-2753e may be disposed on body 2751 in any suitable configuration to produce the desired effect. For example, as depicted in FIG. 27I, electrode contacts 2753a-2753e may be disposed serially, with approximately a one (1) millimeter spacing in between each electrode contact 2753a-2753e. Electrode contacts 2753a-2753e may be configured to function as either anode electrode contacts or cathode electrode contacts, as desired.

Electrode contacts 2753 may be connected to an implanted neurostimulator (INS), such as, for example, INS 50, in accordance with the present disclosure. The INS may be programmed to select any of electrode contacts 2753a-2753e for nerve stimulation. For example, in circumstances where it may be desired to stimulate the smaller diameter fibers of a nerve, it is contemplated that all electrode contacts 2753a-2753e may be selected for nerve stimulation, since closely spaced electrode contacts typically affect smaller diameter fibers (e.g., afferent or sensory fibers). In these circumstances, electrode contacts 2753a, 2753c, and 2753e may function as anode electrode contacts and electrode contacts 2753b and 2753d may function as cathode electrode contacts. In circumstances where it may be desired to stimulate the larger diameter fibers of a nerve, it is contemplated that only electrode contacts 2753a, 2753c, and 2753e may be selected for nerve stimulation, since loosely spaced electrode contacts typically affect larger diameter fibers (e.g., efferent or motor fibers). In these circumstances, electrode contacts 2753a and 2753e may function as anode electrode contacts, and 2753c may function as a cathode electrode contact.

Alternatively, electrode 2750 may be utilized to reduce muscle fatigue when implanted on single function nerves, such as, for example, the hypoglossal nerve. In such circumstances, muscle fatigue may be reduced by alternatively switching between using loosely spaced electrode contacts 2753a, 2753c, and 2753e, to stimulate large diameter fibers, and closely spaced electrode contacts 2753a-2753e, to stimulate small diameter fibers.

Figure 27K:
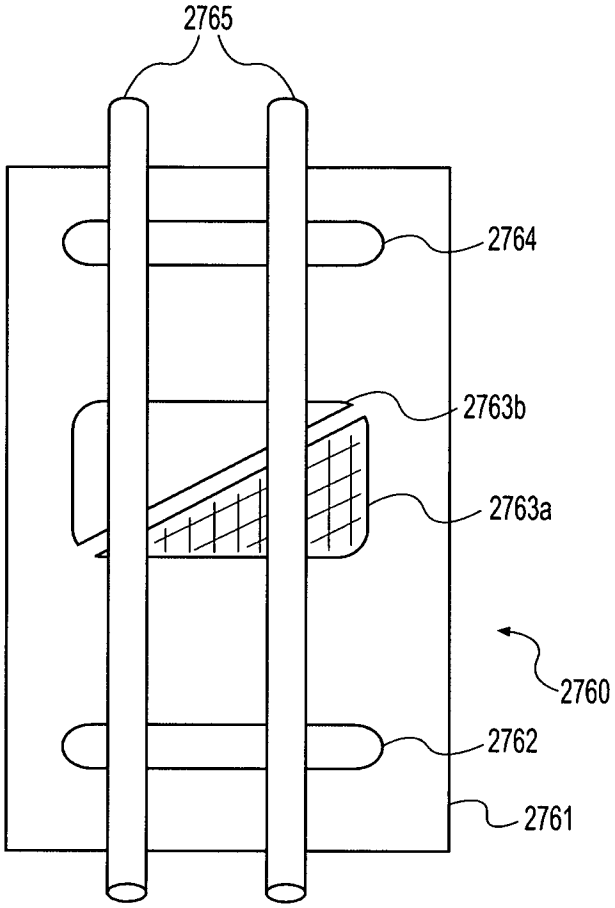
Figure 27J:
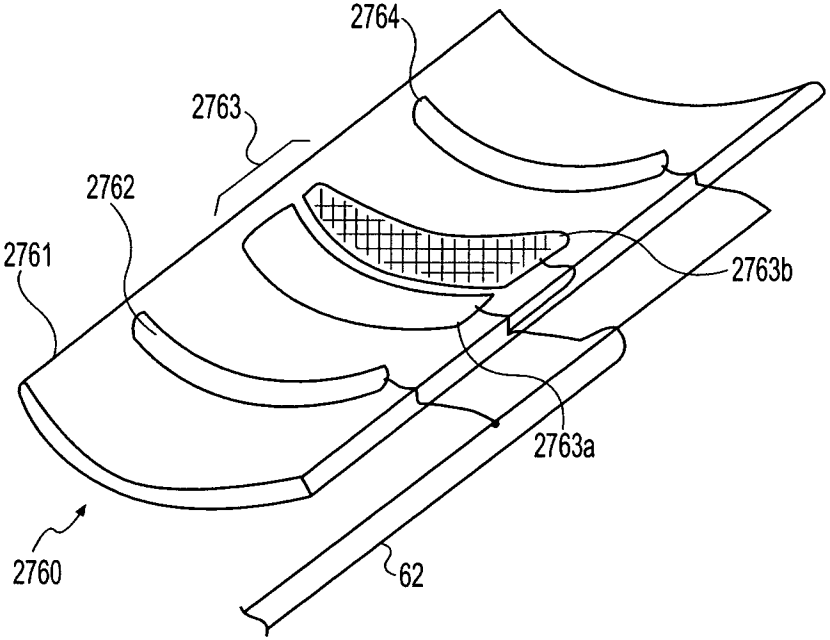

Turning to FIGS. 27J-27K, in accordance with the present disclosure, there is depicted another embodiment of a nerve cuff electrode 2760 for facilitating reduction in muscle fatigue. Nerve cuff electrode 2760 may include a body 2761 having a plurality of electrode contacts 2762, 2763, and 2764. Electrode contacts 2762-2764 may include any suitable electrode contacts in accordance with the present disclosure. Although the depicted embodiment of nerve cuff electrode 2760 includes three electrode contacts 2762-2764, nerve cuff electrode 2760 may include a greater or lesser number of electrode contacts. Furthermore, electrode contacts may be disposed on body 2761 in any suitable configuration to achieve the desired effect, such as, for example, serially, as depicted. In the depicted embodiment, electrode contacts 2762 and 2764 may function as anode electrode contacts, while electrode contact 2763 may function as a cathode electrode contact. Electrode contact 2763 may include two distinct, substantially triangularly shaped portions 2763a and 2763b. However, portions 2763a and 2763b may include any suitable shape. In addition, portions 2763a and 2763b may be configured to be of differing conductive properties, so that, for the same stimulation pulse (e.g., a slow rising, small amplitude pulse having a relatively long duration of approximately 0.2 to 0.35 milliseconds) applied to each of the portions 2763a and 2763b, the resultant charge densities at the surface of each of the portions 2763a and 2763b may be different. For example, portions 2763a and 2763b may be made of electrically differing materials. For discussion purposes only, it is assumed that portion 2763a is configured to deliver a charge density lower than that of portion 2763b. However, portion 2763a may be configured to deliver a charge density that is higher than the charge density of portion 2763b.

Since the small diameter fibers of a nerve are typically stimulated by low charge densities and large diameter fibers of the nerve are typically stimulated by high charge densities, portions 2763a and 2763b may be sequentially utilized to alternate between stimulating the small and large diameter fibers of a nerve. In other words, in use, a stimulation pulse may be first delivered to portion 2763a to stimulate the small diameter fibers of a nerve. A subsequent stimulation pulse may be then delivered to portion 2763b to stimulate the large diameter fibers of a nerve. It is contemplated that alternating between stimulating the small and large diameter fibers of a nerve may facilitate reducing muscle fatigue while also ensuring sufficient muscle mass is stimulated to maintain the necessary contraction and force generation to successfully treat OSA.

Figure 27L:
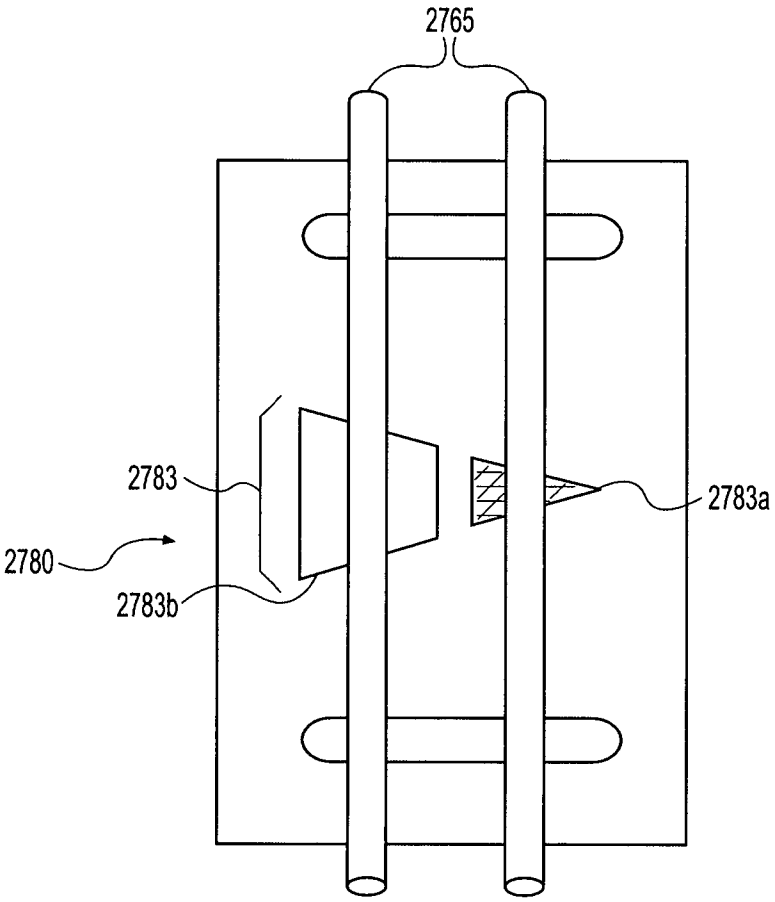
Figure 27M:
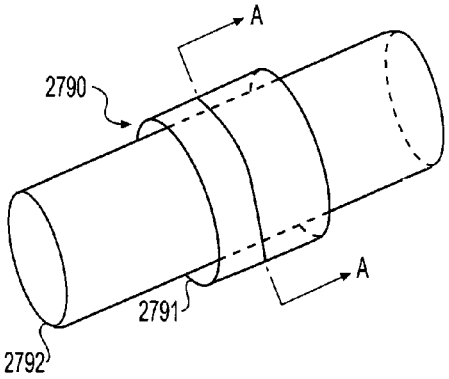
Figure 27N:
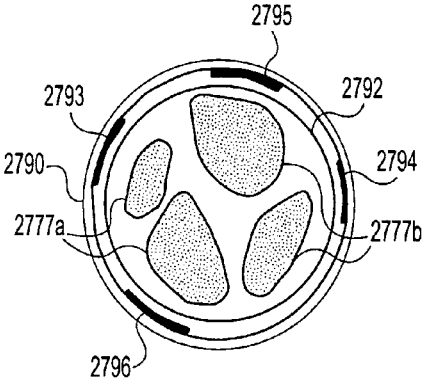
Figure 27O:
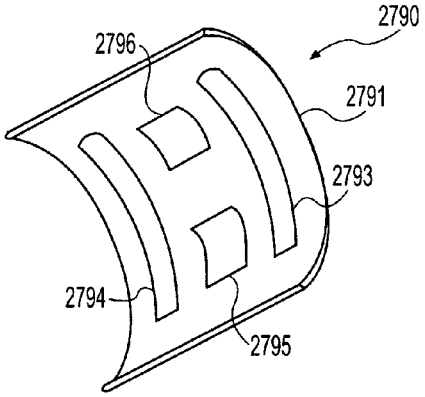

Turning now to FIG. 27L, there is illustrated yet another embodiment of a nerve cuff electrode 2780 for facilitating reduction in muscle fatigue. For the purposes of this disclosure, nerve cuff electrode 2780 may be substantially similar to nerve cuff electrode 2760. Nerve cuff electrode 2780, however, may differ from nerve cuff electrode 2760 in at least one significant way. For example, rather than having two substantially triangular portions, cathode electrode contact 2783 may comprise two substantially different portions 2783a and 2783b. Portions 2783a and 2783b may be spaced apart from one another and may include differing surface areas. For example, as illustrated, portion 2783a may include a smaller surface area than portion 2783b. Furthermore, portions 2783a and 2783b may include any suitable shape known in the art. Although portions 2783a and 2783b in the illustrated embodiment together define a substantially triangular shaped electrode contact 2783, portions 2783a and 2783b together may or may not define any suitable shape known in the art.

Each of portions 2783a and 2783b may be configured to be substantially similar in conductance despite their differing surface areas. For example, portion 2783a may be made of a first material having a relatively lower conductance, while portion 2783b may be made of a second material having a relatively higher conductance. Thus, when subjected to the same stimulation pulse (e.g., a slow rising, small amplitude pulse having a relatively long duration of approximately 0.2 to 0.35 milliseconds), portion 2783a may have a higher charge density than portion 2783b because of its relatively smaller surface area than portion 2783b. Similarly, when subjected to the same stimulation pulse, portion 2783b may have a lower charge density than portion 2783a because of its relatively larger surface area than portion 2783a. Accordingly, because of the differing charge densities, portion 2783a may be adapted to stimulate large diameter fibers of a nerve, and portion 2783b may be adapted to stimulate small diameter fibers of the nerve.

In use, a stimulation pulse may be first delivered to portion 2783a to stimulate the large diameter fibers of a nerve. A subsequent stimulation pulse may be then delivered to portion 2783b to stimulate the small diameter fibers of the nerve. It is contemplated that alternating between stimulating the small and large diameter fibers of a nerve may facilitate muscle fatigue while also ensuring that sufficient muscle mass is stimulated to maintain the necessary contraction and force generation to successfully treat OSA.

In certain embodiments, such as when nerve cuff electrodes 2760 and 2780 are implanted on a multi-function nerve (e.g., the superior laryngeal nerve SLN), it is contemplated that portions 2763a/2763b and portions 2783a/2783b may be utilized to selectively stimulate either the afferent or efferent fibers of the nerve.

With reference now to FIGS. 27M-27Q, there is depicted yet another embodiment of a nerve cuff electrode 2790 for minimizing muscle fatigue. Nerve cuff electrode 2790 may include a cuff body 2791 for mounting about a nerve 2792 in accordance with the present disclosure. Cuff body 2791 may include a plurality of electrode contacts 2793-2796 also in accordance with the present disclosure. Although the depicted embodiment of nerve cuff electrode 2790 includes four electrode contacts 2793-2796, nerve cuff electrode 2790 may include a greater or lesser number of electrode contacts.

Figure 27P:
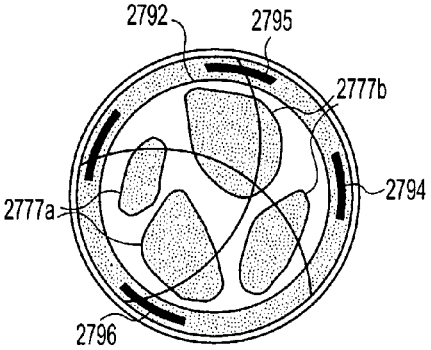
Figure 27Q:
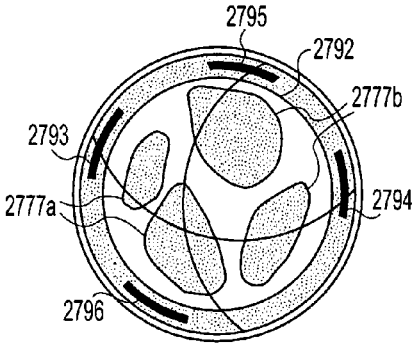
Figure 28:
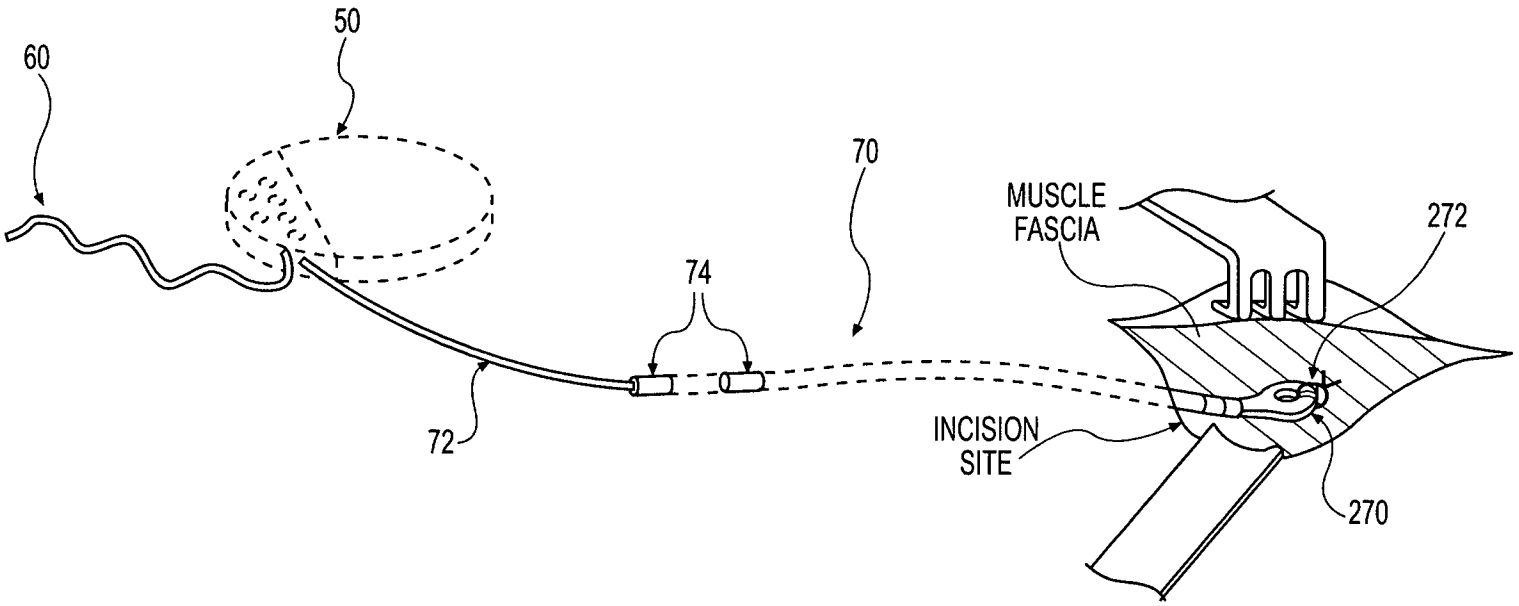
FIGS. 28-33B schematically illustrate alternative fixation techniques for the respiration sensing lead.

Nerve cuff electrode 2790 may be configured to selectively stimulate both small diameter fibers contained in fascicle 2777a and large diameter fibers contained in fascicle 2777b of nerve 2792. For example, as shown in FIG. 27P, by applying an exemplary slow rising, long pulse width waveform to electrode contacts 2796 and 2793, nerve cuff electrode 2790 may stimulate the small diameter fibers contained in fascicle 2777a of nerve 2792. Similarly, as shown in FIG. 27Q, by applying an exemplary fast rising, short pulse width waveform to electrode contacts 2794 and 2795, nerve cuff electrode 2790 may stimulate the large diameter fibers contained in fascicle 2777b of nerve 2792. Fascicles 2777a and 2777b may be stimulated simultaneously or separately. In embodiments, where it is desirable to stimulate fibers contained in fascicles 2777a and 2777b, the pulse generator (e.g., INS 50) may be provided with dual output ports.

Description of Respiration Sensing Lead Anchoring Alternatives

With reference to the following figures, various additional or alternative anchoring features for the respiration sensing lead 70 are schematically illustrated. Anchoring the respiration sensing lead 70 reduces motion artifact in the respiration signal and stabilizes the bio-impedance vector relative to the anatomy.

In each of the embodiments, by way of example, not limitation, the respiration sensing lead 70 includes a lead body 70 with a proximal connector and a plurality of distal respiration sensors 74 comprising ring electrodes for sensing bio-impedance. The lead body 72 of the respiration sensing lead 70 may include a jacket cover containing a plurality of conductors 78, one for each ring electrode 74 requiring independent control. Generally, the impedance electrodes 74 may comprise current emitting electrodes and voltage sensing electrodes for detecting respiration by changes in bio-impedance.

With reference to FIGS. 28-33, various fixation devices and methods are shown to acutely and/or chronically stabilize the respiratory sensing lead 70. With specific reference to FIG. 28, the INS 50 is shown in a subcutaneous pocket and the stimulation lead 60 is shown in a subcutaneous tunnel extending superiorly from the pocket. The respiration sensing lead 70 is shown in a subcutaneous tunnel superficial to muscle fascia around the rib cage. A suture tab or ring 270 may be formed with or otherwise connected to the distal end of the lead body 72. Near the distal end of the lead 70, a small surgical incision may be formed to provide access to the suture tab 270 and the muscle fascia under the lead 70. The suture tab 270 allows the distal end of the lead 70 to be secured to the underlying muscle fascia by suture or staple 272, for example, which may be dissolvable or permanent. Both dissolvable and permanent sutures/staples provide for acute stability and fixation until the lead body 72 is encapsulated. Permanent sutures/staples provide for chronic stability and fixation beyond what tissue encapsulation otherwise provides.

Figure 29A:
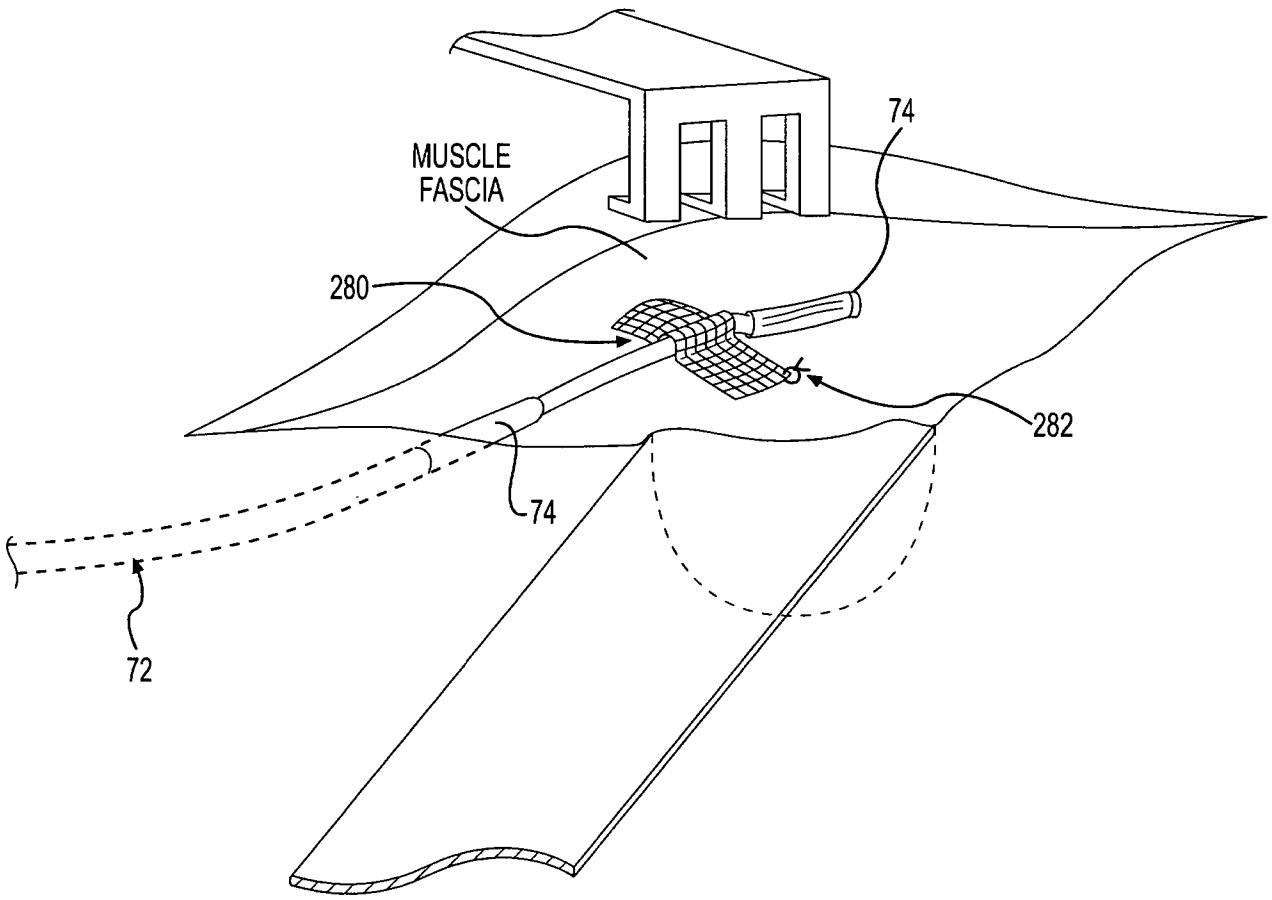
Figure 29B:
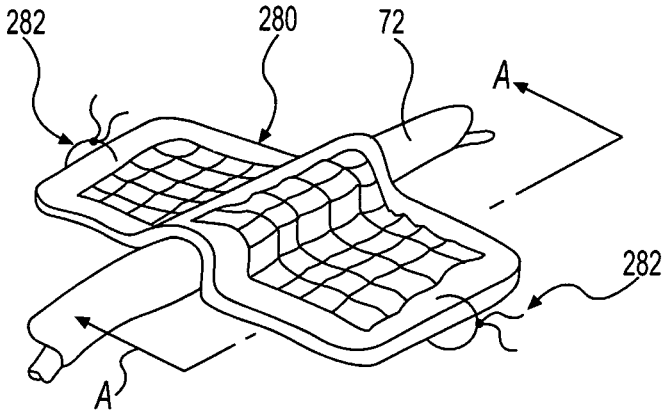
Figure 29C:
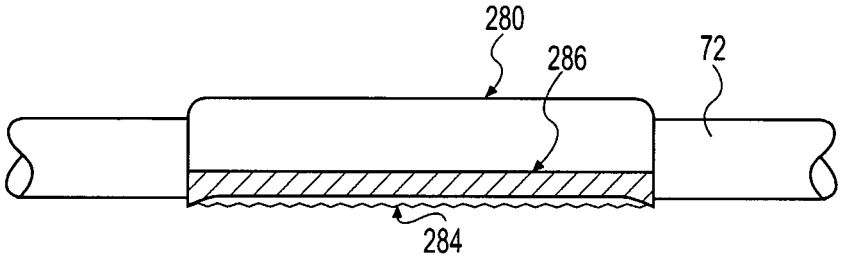

With reference to FIGS. 29A-29C, a fabric tab 280 may be used in place of or in addition to suture tab 270. As seen in FIG. 29A, the fabric tab 280 may be placed over a distal portion of the lead body 72, such as between two distal electrodes 74. A small surgical incision may be formed proximate the distal end of the lead 70 and the fabric tab 280 may be placed over the over the lead body 72 and secured to the underlying muscle fascia by suture or staple 282, for example, which may be dissolvable or permanent, to provide acute and/or chronic stability and fixation. With reference to FIGS. 29B and 29C (cross-sectional view taken along line A-A), the fabric tab 280 may comprise a fabric layer (e.g., polyester) 284 to promote chronic tissue in-growth to the muscle fascia and a smooth flexible outer layer (silicone or polyurethane) 286 for acute connection by suture or staple 282.

Figure 30:
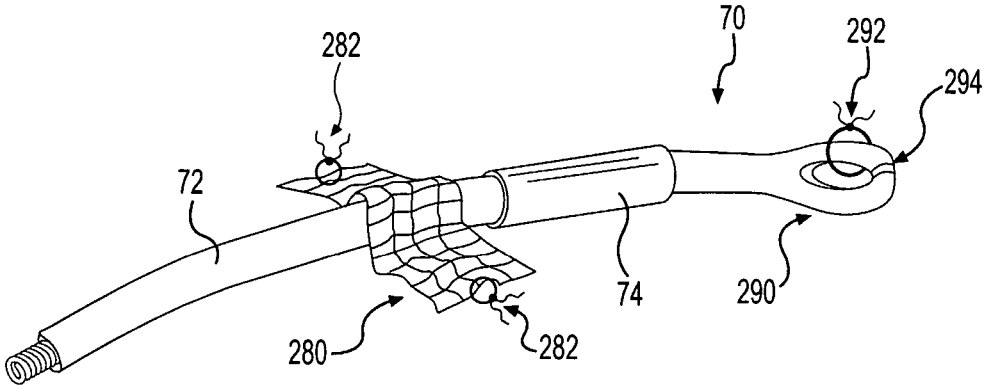

With reference to FIG. 30, lead 70 includes a split ring 290 that may be formed with or otherwise connected to the distal end of the lead body 72. The split ring 290 allows the distal end of the lead 70 to be secured to the underlying muscle fascia by suture or staple 292, for example, which may be dissolvable or permanent. The ring 290 may be formed of compliant material (e.g., silicone or polyurethane) and may include a slit 294 (normally closed) that allows the lead 70 to be explanted by pulling the lead 70 and allowing the suture 292 to slip through the slit 294, or if used without a suture, to allow the ring to deform and slide through the tissue encapsulation. To further facilitate explantation, a dissolvable fabric tab 282 may be used to acutely stabilize the lead 70 but allow chronic removal.

Figure 31A:
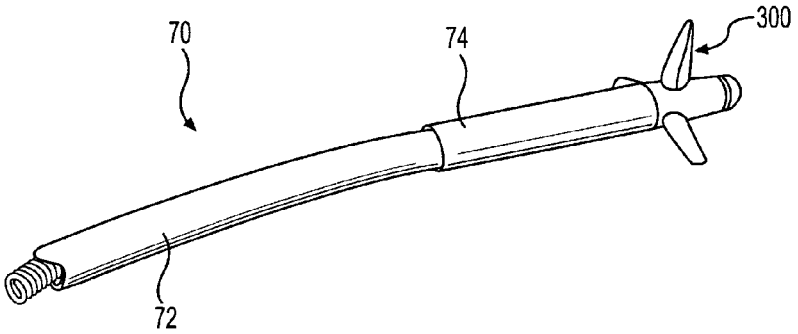
Figure 31B:
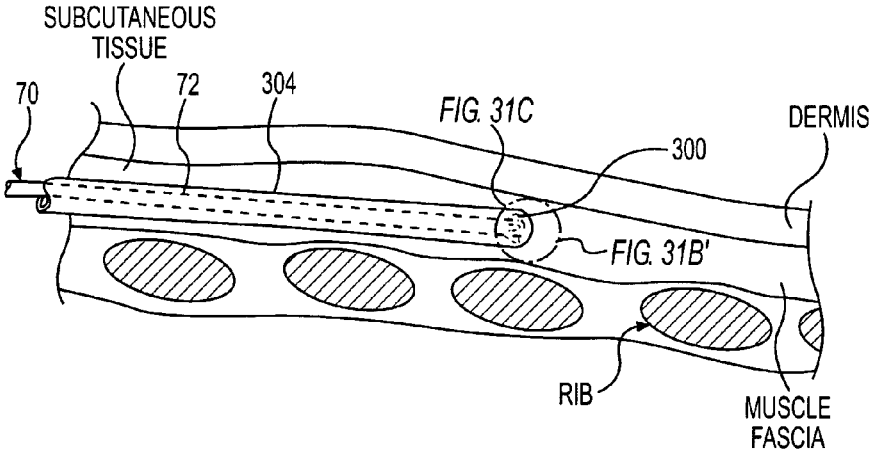
Figure 31B:
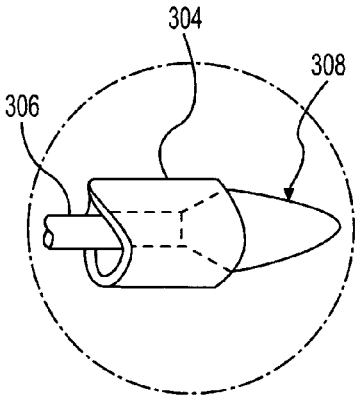
Figure 31C:
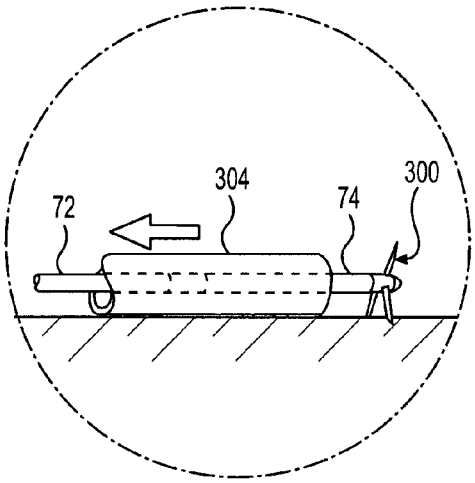

With reference to FIGS. 31A-31C, deployable anchor tines 300 may be used to facilitate fixation of the lead 70. As seen in FIG. 31A, the self-expanding tines 300 may be molded integrally with the lead body 72 or connected thereto by over-molding, for example. The tines 300 may comprise relatively resilient soft material such as silicone or polyurethane. The resilient tines 300 allow the lead 70 to be delivered via a tubular sheath or trocar 304 tunneled to the target sensing site, wherein the tines 300 assume a first collapsed delivery configuration and a second expanded deployed configuration. As seen in FIGS. 31B and 31B, the tubular sheath or trocar 304 may be initially tunneled to the target site using an obtruator 306 with a blunt dissection tip 308. After the distal end of the tubular sheath 304 has been tunneled into position by blunt dissection using the obtruator 306, the obtruator 306 may be removed proximally from the sheath 304 and the lead 70 with collapsible tines 300 may be inserted therein. As seen in FIG. 31C, when the distal end of the lead 70 is in the desired position, the sheath 304 may be proximally retracted to deploy the tines 300 to engage the muscle fascia and adjacent subcutaneous tissue, thus anchoring the lead 70 in place.

Figure 32A:
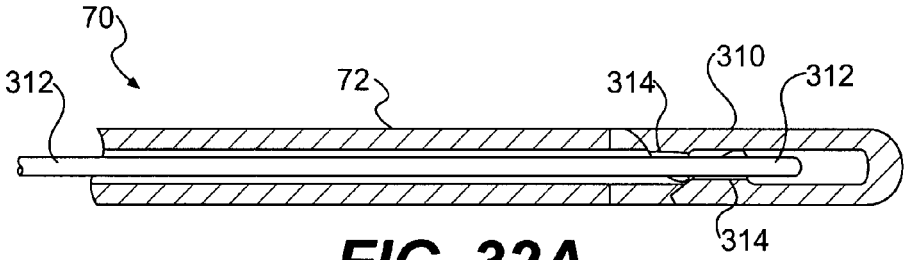
Figure 32B:
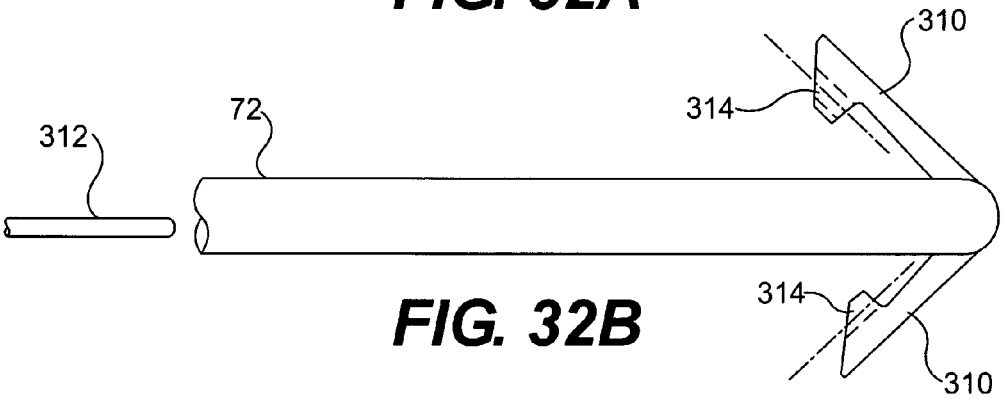

With reference to FIGS. 32A and 32B, an alternative deployable fixation embodiment is shown schematically. In this embodiment, self-expanding tines 310 are held in a collapsed configuration by retention wire 312 disposed in the lumen of the lead body 72 as shown in FIG. 32A. Each of the tines 310 includes a hole 314 through which the retention wire 312 passes to hold the tines 310 in a first collapsed delivery configuration as shown In FIG. 32A, and proximal withdrawal of the retention wire 314 releases the resilient tines 310 to a second expanded deployed configuration as shown in FIG. 32B. The lead 70 may be tunneled to the desired target site with the tines 310 in the collapsed configuration. Once in position, the wire 312 may be pulled proximally to release the tines 310 and secure the lead 70 to the underlying muscle fascia and adjacent subcutaneous tissue to establish fixation thereof.

Figure 33A:
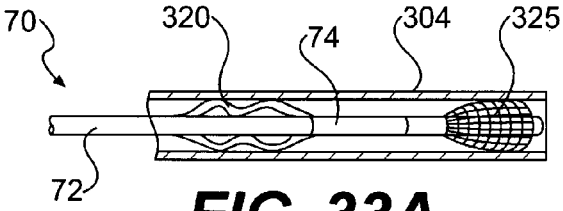
Figure 33B:
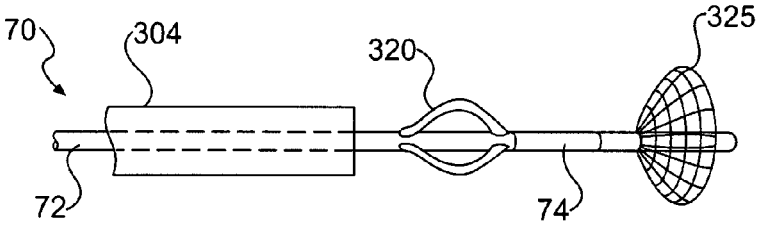

With reference to FIGS. 33A and 33B, another alternative deployable fixation embodiment is shown schematically. In this embodiment, self-expanding structures such as one or more resilient protrusions 320 and/or a resilient mesh 325 may be incorporated (either alone or in combination) into the distal end of the lead 70. By way of example, not limitation, resilient protrusions 320 may comprise silicone or polyurethane loops and resilient mesh 325 may comprise a polyester fabric connected to or formed integrally with the lead body 72. Both the resilient protrusions 320 and the resilient mesh 325 may be delivered in a collapsed delivery configuration inside tubular sheath 304 as shown in FIG. 33A, and deployed at the desired target site by proximal retraction of the sheath 304 to release the self-expanding structures 320/325 to an expanded deployed configuration as shown in FIG. 33B. Both the resilient protrusions 320 and the resilient mesh 325 engage the underlying muscle fascia through tissue encapsulation and adjacent subcutaneous tissues to provide fixation of the lead 70 thereto.

Other fixation embodiments may be used as well. For example, the fixation element may engage the muscle fascia and adjacent subcutaneous tissues or may be embedded therein. To this end, the electrodes may alternatively comprise intramuscular electrodes such as barbs or helical screws.

Description of Respiration Sensing Electrode Alternatives

A description of the various alternatives in number, spacing, anatomical location and function of the impedance electrodes follows. Generally, in each of the following embodiments, the respiration sensing lead includes a lead body and a plurality of respiration sensors comprising ring electrodes for sensing bio-impedance. The lead body may include a plurality of insulated conductors disposed therein, with one conductor provided for each ring electrode requiring independent connection and/or control. The impedance electrodes may comprise current emitting electrodes and voltage sensing electrodes for detecting respiration by changes in bio-impedance.

Figure 34:
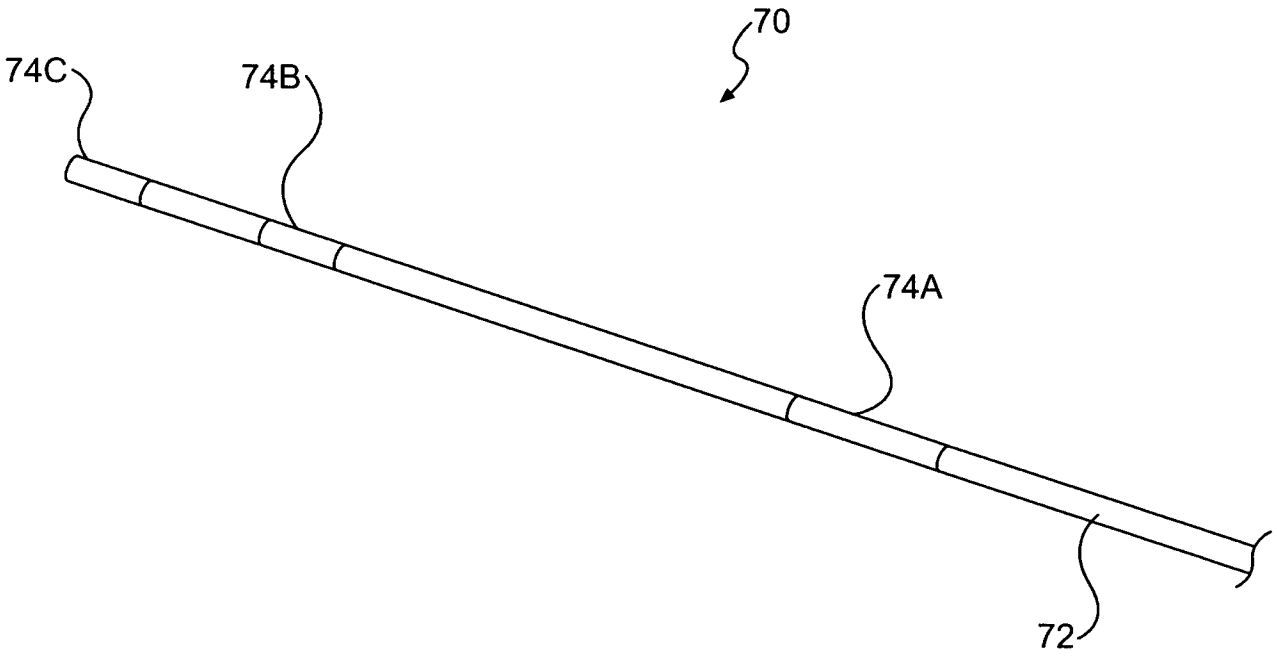
FIG. 34 schematically illustrates the distal portion of an exemplary respiration sensing lead FIGS. 35A-35E and 36 schematically illustrate alternative electrode arrangements on the respiration sensing lead.

With reference to FIG. 34, the distal portion of a respiration sensing lead 70 is shown by way of example, not limitation. The respiration sensing lead 70 includes a lead body 72 with a proximal connector and a plurality of distal impedance electrodes 74. In this example, the lead body 72 and electrodes 74 are cylindrical with a diameter of 0.050 inches. The distal current-carrying electrode 74A may be 5 mm long and may be separated from the voltage-sensing electrode 74B by 15 mm. The distal voltage sensing electrode may be 5 mm long and may be separated from the proximal combination current-carrying voltage-sensing electrode 74C by 100 mm. The proximal electrode 74C may be 10 mm long. The proximal portion of the lead 70 is not shown, but would be connected to the INS (not shown) as described previously. The lead body incorporates a plurality of insulated electrical conductors (not shown), each of which correspond to an electrode 74A-74C. The electrodes and conductors may be made of an alloy of platinum-iridium. The lead body 72 may comprise a tubular extrusion of polyurethane, silicone, or a co-extrusion of polyurethane over silicone. The conductors may be formed of multi-filar wire coiled to provide extensibility for comfort and durability under high-cycle fatigue.

Figure 35A:
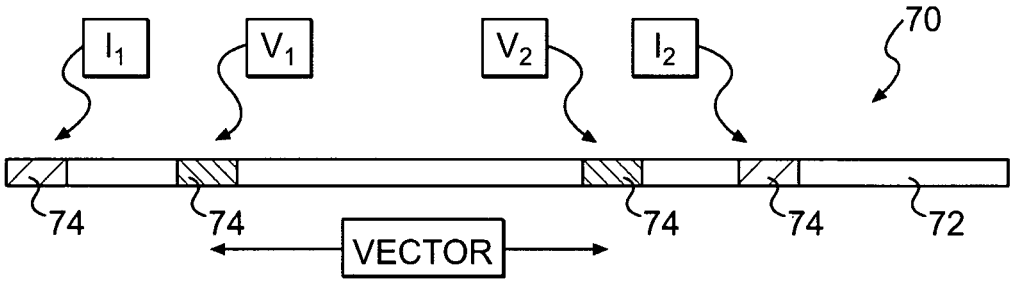
Figure 35B:
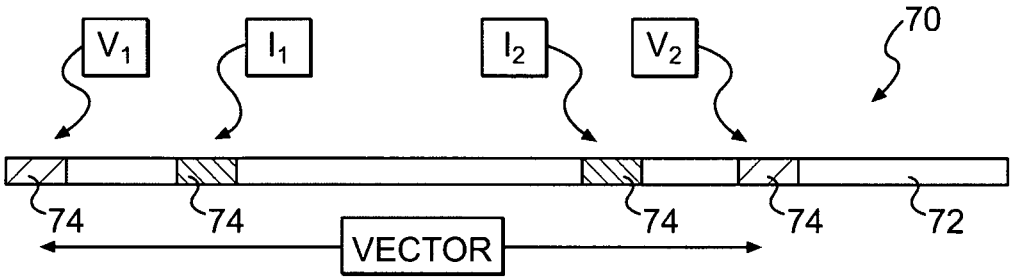
Figure 35C:
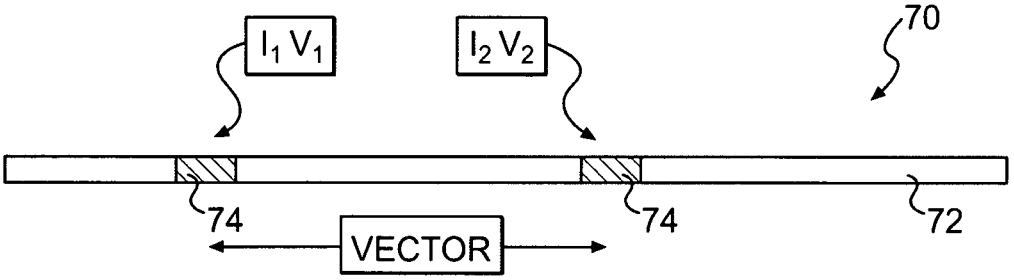
Figure 35D:
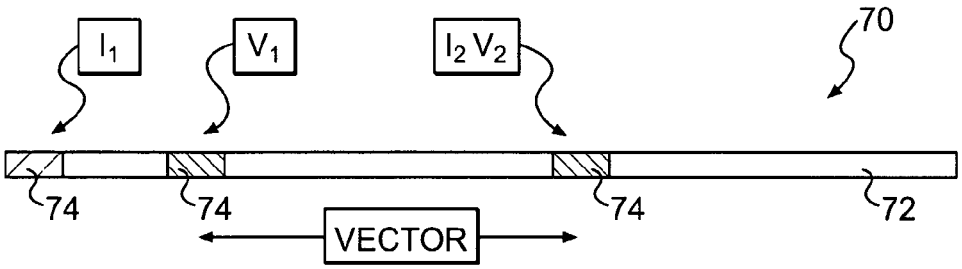
Figure 35E:
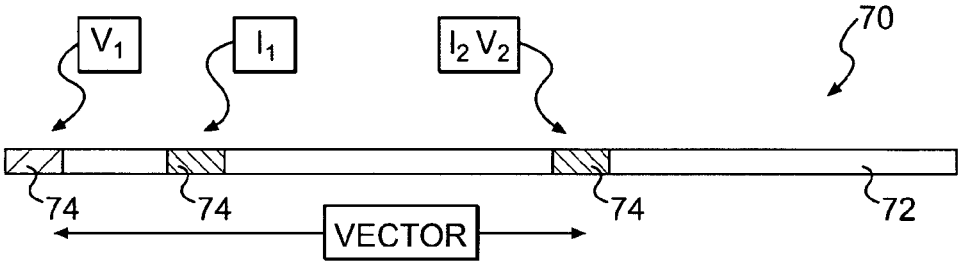

With reference to FIGS. 35A-35E, the position of the electrodes 74 may be characterized in terms of bio-impedance or bio-Z vectors. The bio-Z vector may be defined by the locations of the voltage-sensing electrodes (labeled $V_1$ & $V_2$). The voltage-sensing electrodes may be located on either side of the current-carrying electrodes (labeled $I_1$ & $\mathbf{1}_2$). For example, it is possible to locate either one or both of the voltage-sensing electrodes between the current-carrying electrodes as shown in FIG. 35A (4-wire configuration ($I_1$-$V_1$-$V_2$-$I_2$)), and it is possible to locate either one or both of the current-carrying electrodes between the voltage-sensing electrodes as shown in FIG. 35B (inverted 4-wire configuration ($V_1$-$I_1$-$I_2$-$V_2$)). While at least two separate electrodes ($I_1$ & $I_2$) are required to carry current and at least two separate electrodes ($V_1$ & $V_2$) are required to measure voltage, it is possible to combine the current carrying and voltage sensing functions in a common electrode. Examples of combining voltage sensing and current carrying electrodes are shown in FIGS. 35C-35E. FIG. 35C (2-wire configuration ($I_1V_1$--$I_2V_2$)) shows combination electrode $I_1V_1$ and $I_2V_2$ where each of these electrodes is used to carry current and sense voltage. FIGS. 35D (3-wire configuration ($I_1$-$V_1$-$I_2V_2$)) and 35E (inverted 3-wire configuration ($V_1$-$I_1$-$I_2V_2$)) show combination electrode $I_2V_2$ which is used to carry current and sense voltage.

Figure 36:
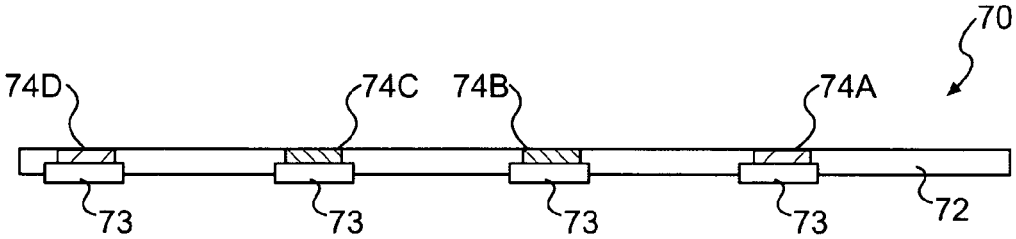

With reference to FIG. 36, insulative material such as strips 73 may cover one side of one or more electrodes 74A-74D to provide directional current-carrying and/or voltage-sensing. The insulative strips may comprise a polymeric coating (e.g., adhesive) and may be arranged to face outward (toward the dermis) such that the exposed conductive side of each electrode 74 faces inward (toward the muscle fascia and thoracic cavity). Other examples of directional electrodes would be substantially two-dimensional electrodes such as discs or paddles which are conductive on only one side. Another example of a directional electrode would be a substantially cylindrical electrode which is held in a particular orientation by sutures or sutured wings. Another example of a directional electrode would be an electrode on the face or header of the implanted pulse generator. It would likely be desirable for the pulse generator to have a non-conductive surface surrounding the location of the electrode.

In addition to the cylindrical electrodes shown, other electrode configurations are possible as well. For example, the electrodes may be bi-directional with one planar electrode surface separated from another planar electrode surface by insulative material. Alternatively or in combination, circular hoop electrodes may be placed concentrically on a planar insulative surface. To mitigate edge effects, each electrode may comprise a center primary electrode with two secondary side electrodes separated by resistive elements and arranged in series. An alternative is to have each primary current-carrying electrode connected by a resistive element to a single secondary side electrode. The conductive housing of the INS 50 may serve as an current-carrying electrode or voltage-sensing electrode. Alternatively or in addition, an electrode may be mounted to the housing of the INS 50.

Because bio-impedance has both a real and imaginary component, it is possible to measure the bio-Z phase as well as magnitude. It may be preferable to extract both magnitude and phase information from the bio-Z measurement because the movement of the lung-diaphragm-liver interface causes a significant change in the phase angle of the measured impedance. This may be valuable because motion artifacts of other tissue have less impact on the bio-Z phase angle than they do on the bio-Z magnitude. This means the bio-Z phase angle is a relatively robust measure of diaphragm movement even during motion artifacts.

An example of a bio-Z signal source is a modulated constant-current pulse train. The modulation may be such that it does not interfere with the stimulation signal. For example, if the stimulation signal is 30 Hz, the bio-Z signal source signal may be modulated at 30 Hz or a sub-multiple of 30 Hz such that bio-Z and stimulation do not occur simultaneously. The pulses in the pulse train may have a pulse width between 1 uS to 1 mS, such as 100 uS. The pulses may be separated by a period of time roughly equal to the pulse width (i.e., on-time of the pulses). The number of pulses in a train may be determined by a trade-off between signal-to-noise and power consumption. For example, no more than 10 pulses may be necessary in any given pulse train. The magnitude of current delivered during the pulse on-time may be between 10 uA and 500 uA, such as 50 uA.

Other wave forms of bio-Z source signal may be used, including, without limitation, pulse, pulse train, bi-phasic pulse, bi-phasic pulse train, sinusoidal, sinusoidal w/ramping, square wave, and square w/ramping. The bio-Z source signal may be constant current or non-constant current, such as a voltage source, for example. If a non-constant current source is used, the delivered current may be monitored to calculate the impedance value. The current-carrying electrodes may have a single current source, a split-current source (one current source split between two or more current-carrying electrodes), or a current mirror source (one current source that maintains set current levels to two or more current-carrying electrodes). Different characteristics of the sensed signal may be measured including, without limitation, magnitude, phase shift of sensed voltage relative to the current source signal, and multi-frequency magnitude and/or phase shift of the sensed signal. Multi-frequency information may be obtained by applying multiple signal sources at different frequencies or a single signal source which contains two or more frequency components. One example of a single multi-frequency source signal is a square wave current pulse. The resultant voltage waveform would contain the same frequency components as the square wave current pulse which would allow extraction of Bio-Z data for more than a single frequency.

Figure 37:
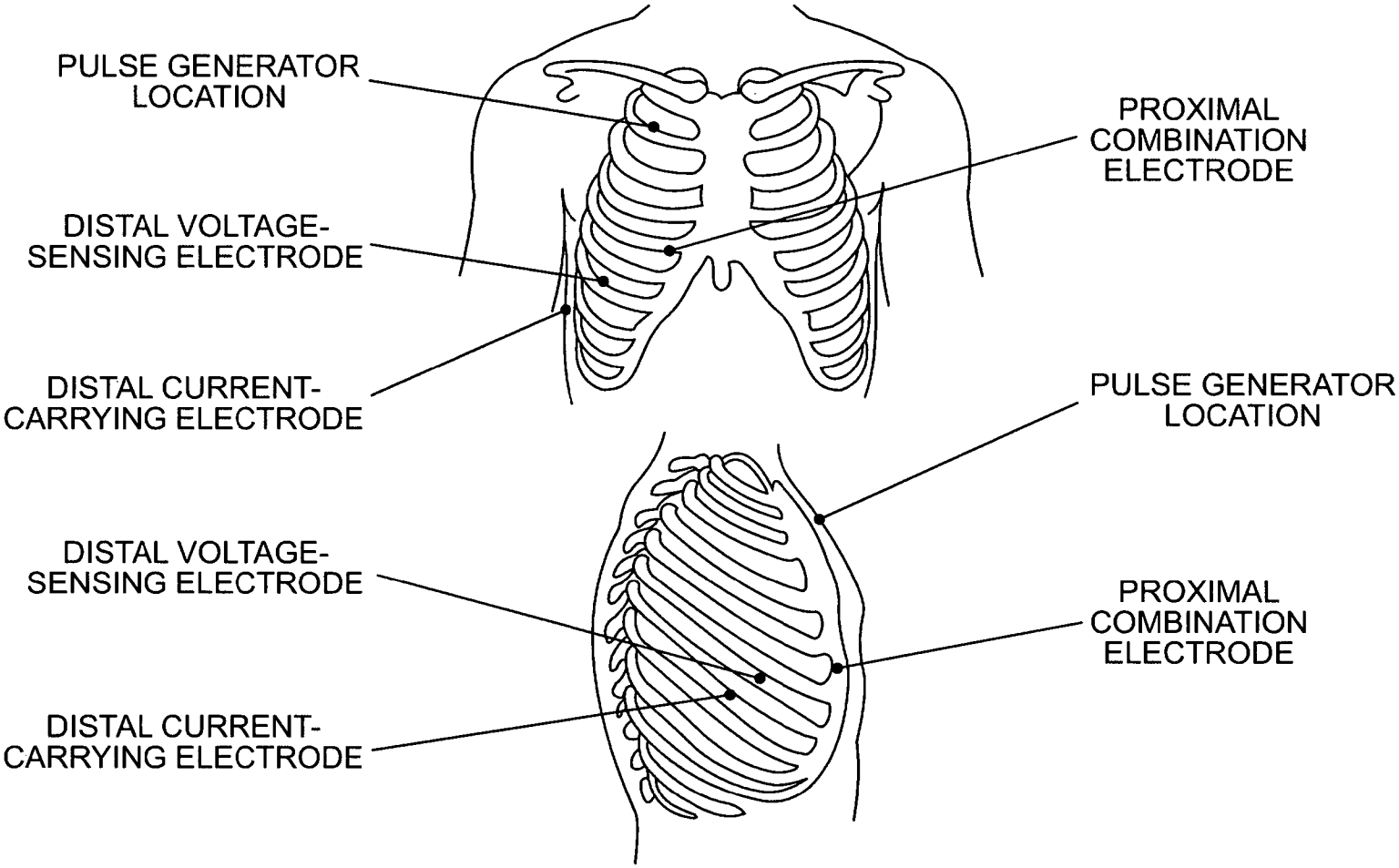
FIGS. 37A-37C schematically illustrate various anatomical positions or bio-Z vectors for the electrodes on the respiration sensing lead.

With reference to FIG. 37, the bio-Z vector may be oriented with regard to the anatomy in a number of different ways. For example, using the electrode arrangement illustrated in FIG. 34 and the anatomical illustration in FIG. 37, the bio-Z vector may be arranged such that the proximal combination electrode is located just to the right of and above the xiphoid below the pectoral muscle between the $5^{th}$ and $6^{th}$ ribs and the distal current-carrying electrode is located mid-lateral between the $7^{th}$ and $8^{th}$ ribs, with the distal voltage-sensing electrode positioned between the $6^{th}$ and $7^{th}$ ribs 10 mm proximal of the distal current-carrying electrode. This arrangement places the electrodes along the interface between the right lung, diaphragm and liver on the right side of the thoracic cavity. The lung-diaphragm-liver interface moves relative to the bio-Z vector with every respiratory cycle. Because the lung has relatively high impedance when inflated and the liver has relatively low impedance due to the conductivity of blood therein, this bio-Z vector arrangement across the lung-diaphragm-liver interface provides for a strong respiratory signal that is indicative of changes between inspiration and expiration. In addition, because the heart is situated more on the left side, positioning the bio-Z vector on the right side reduces cardiac artifact. The net result is a bio-Z vector that provides an excellent signal-to-noise ratio.

A variety of different bio-Z vector orientations relative to the anatomy may be employed. Generally, bio-Z vectors for monitoring respiration may be located on the thorax. However, bio-Z electrodes located in the head and neck may also be used to define respiratory bio-Z vectors. By way of example, not limitation, the bio-Z vector may be arranged transthoracically (e.g., bilaterally across the thorax), anteriorly on the thorax (e.g., bilaterally across the thoracic mid-line), across the lung-diaphragm-liver interface, perpendicular to intercostal muscles, between adjacent ribs, etc. A single bio-Z vector may be used, or multiple independent vectors may be used, potentially necessitating multiple sensing leads. One or more bio-Z sub-vectors within a given bio-Z vector may be used as well.

Figure 37A:
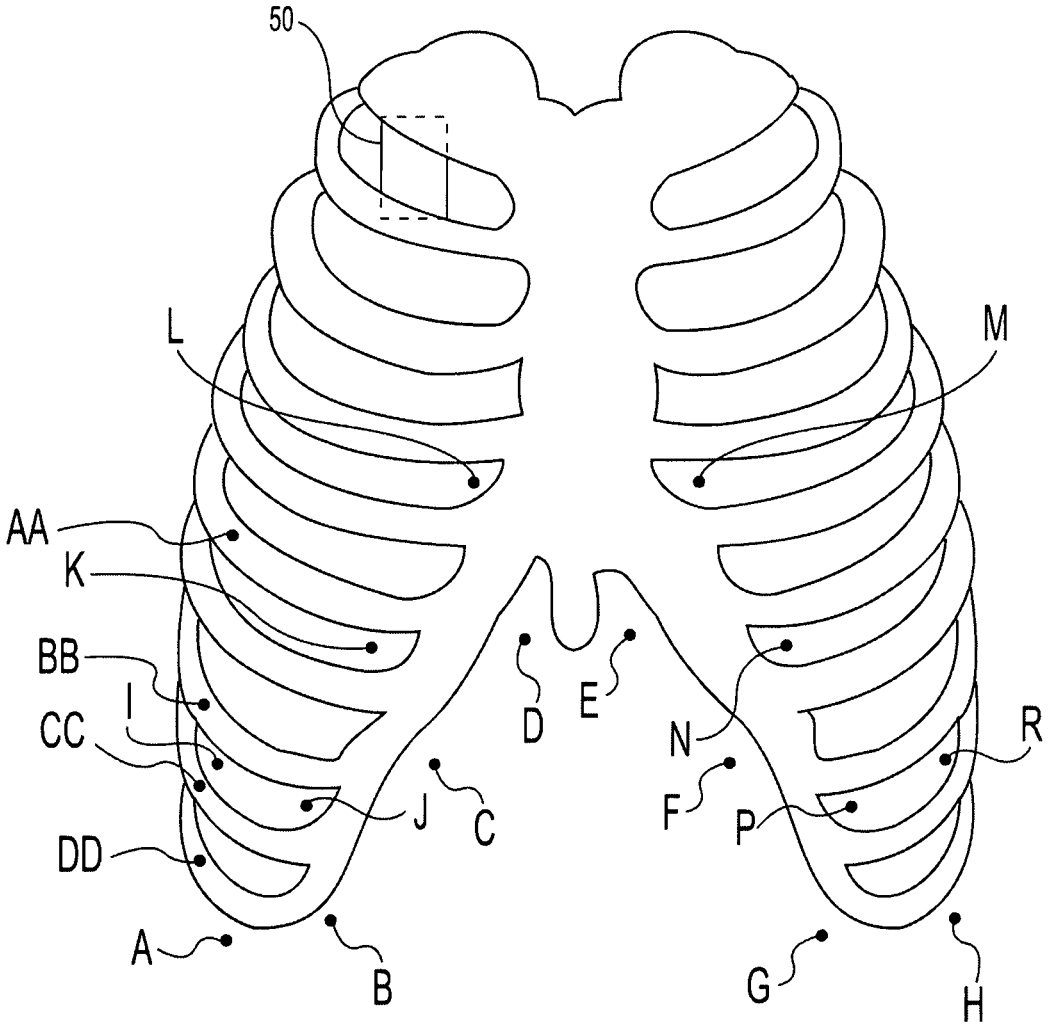
Figure 37B:
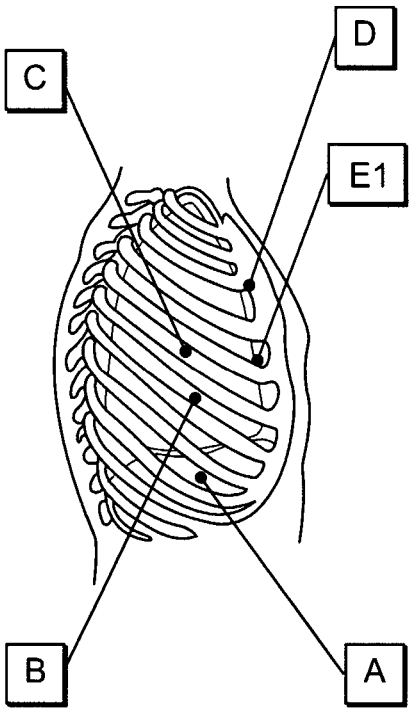
Figure 37C:
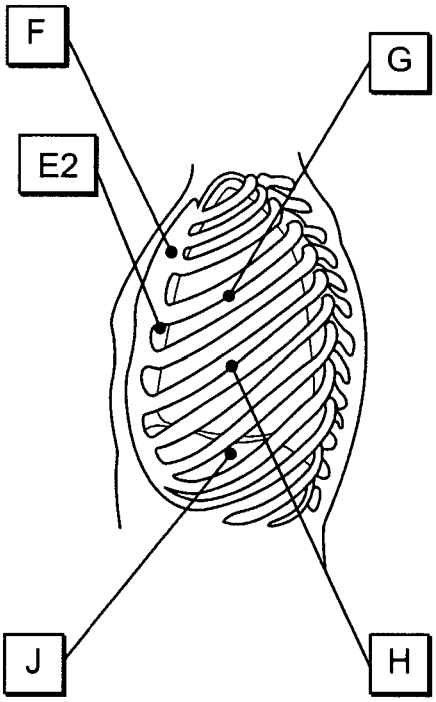

With reference to FIGS. 37A-37C, thoracic locations defining examples of bio-Z vectors are shown schematically. FIG. 37A is a frontal view of the thorax, FIG. 37B is a right-side view of the thorax, and FIG. 37C is a left-side view of the thorax; In each of FIGS. 37A-37C, the outline of the lungs and upper profile of the diaphragm are shown. As mentioned previously, a bio-Z vector may be defined by the locations of the voltage-sensing electrodes. Thus, FIGS. 37A-37C show locations for voltage sensing electrodes which would define the bio-Z vector.

There are several short bio-Z vectors which provide excellent signals correlated to diaphragmatic movement. In general, these vectors have at least one end at or near the lower edge of the ribcage. The short diaphragmatic bio-Z vectors have been successfully used in canines in vector lengths ranging from approximately less than ½ inch to a few inches in length. FIG. 37A shows a variety of locations which are representative of the locations which define such vectors. Locations shown just below the ribcage on the person's right side are designated as A, B, C, and D. Locations shown just below the ribcage on the person's left side are E, F, G, and H. Locations shown just above the lower edge of the ribcage on the person's right side are I, J, K, and L. Locations shown just above the lower edge of the ribcage on the person's left side are M, N, P, and Q. The locations just above the lower edge of the ribcage would fall within a few inches of the lower edge. Short diaphragmatic monitoring vectors would be comprised of location pairs which are relatively closely spaced. For example, vectors D-E, D-C, D-L, and D-K all provide good diaphragmatic signal. The possible vectors fall into three groups. Exemplary vectors which measure primarily diaphragmatic muscle contraction are A-B, B-C, C-D, D-E, E-F, F-G, and G-H. Exemplary vectors which measure a combination of diaphragmatic muscle contraction combined with movement of the lung into the pleural pocket as the diaphragm contracts are I-J, P-R, A-I, A-J, B-I, B-J, G-P, H-R, H-P, and G-R. Exemplary vectors which measure diaphragmatic muscle contraction combined with movement of the diaphragm away from the thoracic wall as that portion of the lung expands are J-K, K-L, M-N, and N-P. It is known that the signal from any given location may be affected by body position and free vs. obstructed respiration. The respiratory signal from short vectors at or near the lower edge of the ribcage may be more robust (e.g., may be not be substantially affected) to body position and obstructed respiration. A further means of obtaining a signal which may be also more robust to body position would be to measure the respiratory impedance from complimentary vectors and sum the resulting bio-Z measurements. Complimentary vectors would be mirror-images or nearly mirror images of one another. Examples of vectors and their mirror images may be C-D and E-F, B-C and G-F, C-K and F-N.

By way of example, not limitation, the following bio-Z vectors may be effective for monitoring respiration and/or for measuring artifacts for subsequent removal of the artifact from the respiration signal. Vector C-G is across the upper left and upper right lobes of the lungs, and provides a good signal of ribcage expansion with moderate cardiac artifact. Vector D-F is a short-path version of C-G that provides a good respiratory signature largely correlated with ribcage expansion, with less cardiac artifact than C-G, but may be sensitive to movement of arms due to location on pectoral muscles. Vector C-D is a short-path ipsilateral vector of the upper right lung that may be sensitive to arm movement but has less cardiac artifact. Vector B-H is a transverse vector of the thoracic cavity that captures the bulk of the lungs and diaphragm movement. Vector B-H, however, may be relatively less susceptible to changes in body position, and may still provide a generally good signal when the patient changes positions. In certain circumstances, the signal produced by vector B-H may have a less than desired signal to noise ratio. However, it is contemplated that generally available methods of signal processing in accordance with the present disclosure may be utilized the improve signal to noise ratio of the signal produced by Vector B-H. Vector A-E is an ipsilateral vector across the lung-diaphragm-liver interface. Because the liver is higher in conductivity and has a different impedance phase angle than the lung, vector A-E1 yields a good signal on both bio-Z magnitude and phase with limited cardiac artifact. Vector B-K is an ipsilateral vector across the lung-diaphragm-liver interface that is substantially between a common set of ribs with a current path that is mostly perpendicular to the intercostal muscles. Because resistivity of muscle is much higher perpendicular to the muscle direction than parallel, vector B-K reduces current-shunting through the muscle which otherwise detracts from the signal of the lung-diaphragm-liver interface. Vector A-K is an ipsilateral vector across the lung-diaphragm-liver interface similar to vector A-E1 but is more sensitive to movement of the lung-diaphragm-liver interface than to changes in resistivity of the lung-diaphragm-liver interface due to inspired air volume and is thus a good indicator of diaphragm movement. Vector B-E1 is a vector across the middle and lower right lung and is good for detecting diaphragm movement with little cardiac artifact. Vector C-E1 is a vector across the upper and middle right lung and is also good for detecting diaphragm movement with little cardiac artifact. Vector D-E1 is a vector across the upper right lung with little cardiac artifact. Vector A-D is an ipsilateral across a substantial portion of the right lung and diaphragm with little cardiac artifact, but may be susceptible to motion artifact due to arm movement. Vector E1-E2 is a vector across the heart and provides a good cardiac signal that may be used for removing cardiac artifact from a respiratory signal. Vector E2-J is a vector across the lung-diaphragm-stomach interface that provides a good measure of diaphragm movement using bio-Z phase vs. magnitude because the stomach has almost no capacitive component and generally low conductivity. Vector L-M is a trans-diaphragm vector that is generally across the lung-diaphragm-liver interface with little cardiac artifact. Vector L-M may be relatively less susceptible to body position and movement and may yield a good signal even if the patient is laying on the side of the sensing lead. In embodiments where the signal produced by vector L-M has a less than desired signal to noise ratio, it is contemplated that generally available methods of signal processing may be utilized to improve the signal to noise ratio of the signal produced by vector L-M.

Electrodes placed at any of the above-noted locations may include, but are not limited to, combination electrodes, such as, for example, electrodes capable of both providing a current charge and sensing a voltage.

With reference to FIGS. 37A and 38D, an exemplary vector selection method 3800 for detecting and utilizing a signal from the vector that produces the most desirable signal of all vectors is dicussed. The disclosed vector selection method 3800 may be performed continuously, periodically, singularly, and/or may be repeated as desired. For example, method 3800 may be performed once in a 24 hour period. In addition, one or more steps associated with method 3800 may be selectively omitted and/or the steps associated with method 3800 may be performed in any order. The steps associated with method 3800 are described in a particular sequence for exemplary purposes only.

With specific reference to FIG. 38D, method 3800 may include a plurality of steps 3801-3803 for detecting and utilizing the signal with the best characteristics of all signals produced by a plurality of vectors. Specifically, method 3800 may include sampling short distance vectors first to determine if any of these vectors are producing a desirable signal, step 3801. Method 3800 may also include sampling intermediate distance vectors if the short distance vectors are not producing a desirable signal, step 3802. Method 3800 may further include sampling long distance vectors if the intermediate distance vectors are not producing a desirable signal, step 3803.

Turning to FIG. 37A, there is depicted an exemplary embodiment of a neurostimulator in accordance with the principles of the present disclosure. The exemplary neurostimulator may include an implanted INS 50 and implanted electrode contacts AA-DD. While the depicted embodiment includes electrode contacts AA-DD disposed between a patient's $5^{th}$ and lowest ribs, electrode contacts AA-DD may be disposed at any suitable location. Furthermore, electrode contacts AA-DD may include, but are not limited to, the combination electrodes discussed above. In the depicted embodiment, exemplary short distance vectors may include the vectors between, for example, adjacent electrode contacts AA, BB, CC, and DD; exemplary intermediate distance vectors may include the vectors AA-CC, AA-DD, and BB-DD, and exemplary long distance vectors may include the vectors between the INS 50 and each of electrode contacts AA-DD.

Figure 38A:
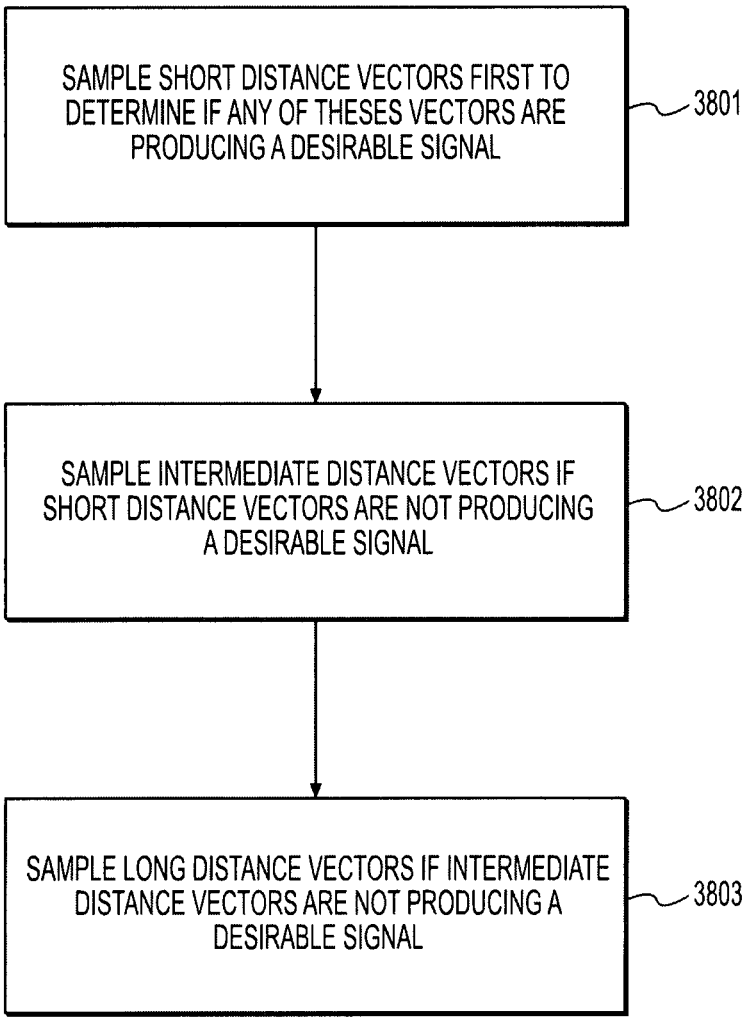
FIG. 38A illustrates an exemplary method of sampling a plurality of vector signals.

With reference to FIG. 37A and FIG. 38A, step 3801 may include, for example, sampling short distance vectors AA-BB, BB-CC, and CC-DD first to determine whether any of these vectors may be producing a sufficient signal in accordance with the principles of this disclosure, since these vectors generally produce signals with desirable signal to noise ratios. Next, step 3802 of method 3800 may include sampling the intermediate distance vectors AA-CC, AA-DD, and BB-DD if the short distance vectors are producing a less than desirable signal. Lastly, step 3803 of method 3800 may include sampling the long distance vectors INS-AA, INS-BB, INS-CC, and INS-DD if the intermediate distance vectors are producing a less than desirable signal.

Figure 38B:
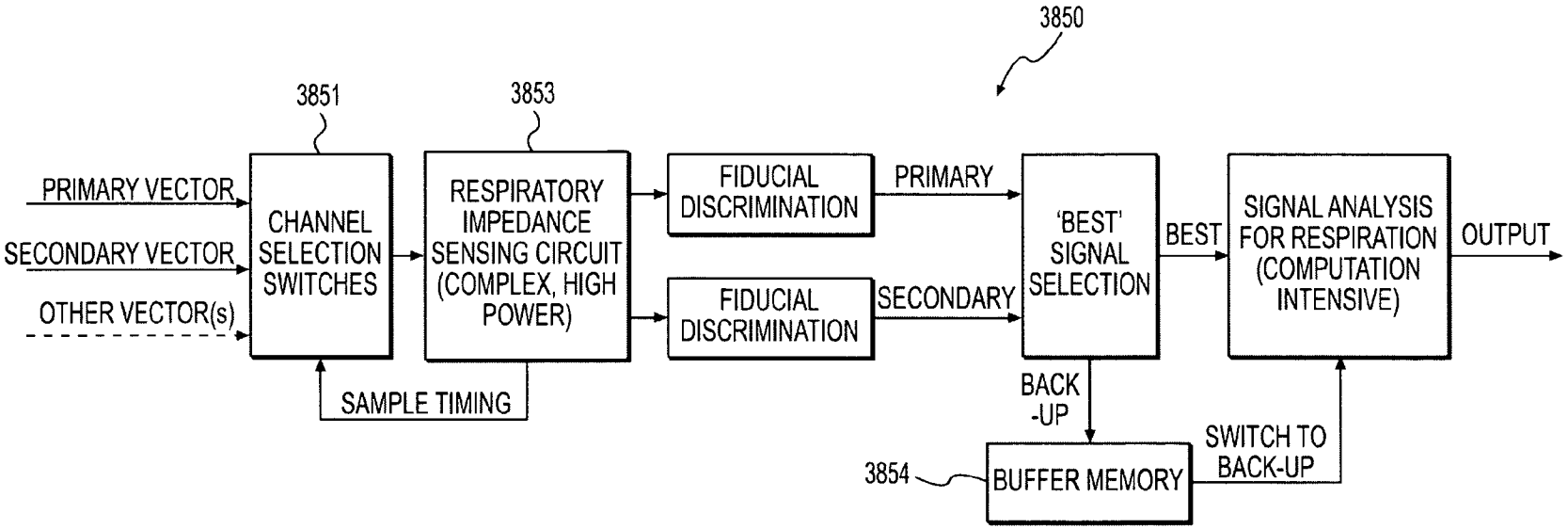
FIGS. 38B-46 schematically illustrate alternative respiration signal processing techniques.

In some embodiments, it is contemplated that several short, intermediate, and long distance vectors may be continually sampled, even if a desirable signal is being received from a short distance vector, in order to identify secondary vector signals that may be utilized if the currently utilized vector signal fails for any reason. However, fully processing the data from signals generated by all of the vectors may require complex sensing circuitry and processing of detection algorithms that may utilize undesirable amounts of battery power. Therefore, it may be desirable to only monitor selected characteristics of the secondary vector signals. With specific reference to FIG. 38B, there is depicted an embodiment of a method 3850 for utilizing multiple sensing channels to optimize respiratory sensing with minimal additional hardware and power consumption. It uses a single sensing circuit which is time multiplexed (interleaved) to sample each of the vectors. Since, as noted above, fully processing the data from all vector signals may require higher computational power, method 3850 may be used to identify the best vector signal for respiration detection, while simultaneously monitoring the remaining vectors signals for only relevant fiducial points. These fiducial points may include, but are not limited to, significant "landmarks" within a signal, such as, for example, peak amplitude and time, point of highest slew rate, and zero crossing. The detected fiducial points for the secondary vector signals may be then stored in a circular buffer memory 3854 for analysis if the primary signal fails for any reason, thereby, allowing immediate switching to an alternate vector signal and eliminating the need for a long signal acquisition period after a need to switch vector signals has been determined.

In particular, method 3850 may include feeding the signals from all available vectors into a plurality of channel selection switches 3851. The signals may be then analyzed for relevant fiducials by the respiratory impedance sensing circuit 3853. Once relevant fiducials have been discriminated, it may be possible to identify the best vector signal for respiration signal analysis. The fiducials of the remaining vectors may be then stored in circular buffer memory 3854 (as noted above) to facilitate switching to a secondary vector signal if the primary signal is no longer suitable for respiration detection.

The periodic monitoring (or interleaving) of secondary vector signals may facilitate faster switching to those vector signals when necessary. In particular, it is contemplated that when a decision to switch to a secondary vector signal is made (i.e., when the primary signals degrades to a point where it is no loner desirable for detecting respiration), the saved data (e.g., relevant fiducials) may be used to "seed" a signal analysis algorithm with recently collected data, so as to promote faster vector switching by eliminating the need to wait for collection of sufficient data for the secondary vector signal. In other words, because select information of a secondary signal is available before the signal is actually used for respiration detection, analysis of the secondary signal for, among other things, respiration detection may begin slightly faster than it would have if no data was available.

Furthermore, in certain embodiments, additional impedance sensors may be used as backup sensors to the sensor generating the primary vector signal. In these embodiments, data from the secondary sensors may be also analyzed to identify and save relevant fiducials in the memory. This stored information may be used to provide supplemental or alternate information to facilitate identifying appropriate respiratory timing, when switching vector signals becomes necessary as a result of primary signal degradation.

The respiratory bio-Z signal is partly due to the resistivity change which occurs when air infuses lung tissue, partly due to the relative movement of electrodes as the rib cage expands, and partly due to the displacement of other body fluids, tissue and organs as the lungs move along with the ribcage and diaphragm. As described above, each vector measures certain of these changes to different extents. It may be desirable, therefore, to combine vectors which have complementary information or even redundant information to improve the respiratory information of the bio-Z signal. To this end, multiple vectors may be used. For example, one vector may be used to sense changes in the lung-diaphragm-liver interface and a second vector may be used to detect changes (e.g., expansion, contraction) of the lung(s). Examples of the former include A-K, B-K, A-E1, B-E1, and A-B. Examples of the later include D-F, B-D, C-G, D-E1, and C-E1. Note that some vector combinations which share a common vector endpoint such as A-E1, D-E1 and B-E1, B-D may use a common electrode which would simplify the respiratory sensing lead or leads.

An advantage of using the lung-diaphragm-liver interface vector is that it provides a robust signal indicative of the movement of the diaphragm throughout the respiratory cycle. The liver is almost two times more electrically conductive than lung tissue so a relatively large bio-Z signal can be obtained by monitoring the movement of the lung-diaphragm-liver interface. Because the liver functions to filter all the blood in the body, the liver is nearly completely infused with blood. This helps to dampen out the cardiac artifact associated with the pulsatile flow of the circulatory system. Another advantage of this location is that vectors can be selected which avoid significant current path through the heart or major arteries which will help reduce cardiac artifact.

It is worth noting that diaphragm movement is not necessarily synchronous with inspiration or expiration. Diaphragm movement typically causes and therefore precedes inspiration and expiration. Respiratory mechanics do allow for paradoxical motion of the ribcage and diaphragm, so diaphragm movement is not necessarily coincident with inspiration. During REM sleep, the diaphragm is the dominant respiratory driver and paradoxical motion of the ribs and diaphragm can be problematic, especially if movement of the ribcage is being relied upon as an inspiratory indicator. Monitoring the diaphragm for pre-inspiratory movement becomes especially valuable under these circumstances. Bio-Z monitoring of the diaphragm can be used as a more sophisticated indicator of impending inspiration rather than the antiquated approach of desperately trying to identify and respond to inspiration in pseudo-real time based on sensors which are responding to characteristics of inspiration.

For purposes of monitoring respiration, it is desirable to minimize shunting of the electrical current through tissues which are not of interest. Shunting may result in at least two problems: reduced signal from the lungs; and increased chance of artifacts from the shunted current path. Skeletal muscle has non-isotropic conductivity. The muscle's transverse resistivity (1600 ohm-cm) is more than 5 times its longitudinal resistivity (300 ohm-cm). In order to minimize the adverse effect of shunting current, it is desirable to select bio-Z sensing vectors which are perpendicular to muscle structure if possible. One such example is to locate two or more electrodes of a bio-Z sensing array substantially aligned with the ribs because the intercostal muscles are substantially perpendicular to the ribs.

Description of Respiration Signal Processing

Figure 39:
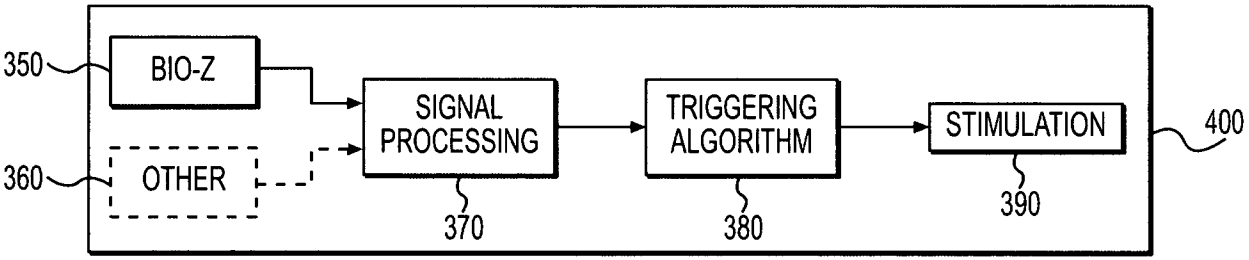

With reference to FIG. 39, the neurostimulation system described herein may operate in a closed-loop process 400 wherein stimulation of the targeted nerve may be delivered as a function of a sensed feedback parameter (e.g., respiration). For example, stimulation of the hypoglossal nerve may be triggered to occur during the inspiratory phase of respiration. Alternatively, the neurostimulation system described herein may operate in an open-loop process wherein stimulation is delivered as a function of preset conditions (e.g., historical average of sleeping respiratory rate).

With continued reference to FIG. 39, the closed-loop process 400 may involve a number of generalized steps to condition the sensed feedback parameter (e.g., bio-Z) into a useable trigger signal for stimulation. For example, the closed-loop process 400 may include the initial step of sensing respiration 350 using bio-Z, for example, and optionally sensing other parameters 360 indicative of respiration or other physiologic process. The sensed signal indicative of respiration (or other parameter) may be signal processed 370 to derive a usable signal and desired fiducials. A trigger algorithm 380, which will be discussed in greater detail below, may then be applied to the processed signal to control delivery of the stimulation signal 390.

Figure 38C:
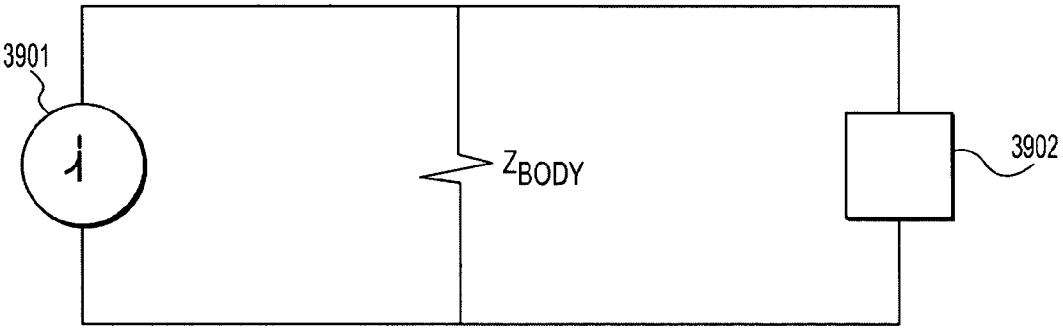

As noted above, the present disclosure contemplates conditioning sensed bio-impedance into a useable trigger signal for stimulation. However, one exemplary limitation to using sensed bio-impedance may be the body's nominal impedance. In practice, a sensed bio-impedance signal may be obtained by applying a suitable, known current through one portion of a tissue of interest and measuring the voltage potential across the same tissue. This measurement technique is illustrated in FIG. 38C and may be referred to herein as the "direct measurement" technique. The applied current and measured voltage potentials may be used to calculate the impedance of the tissue. It is this measured impedance that may constitute the sensed bio-impedance signal. However, sense bio-impedance signals of the present disclosure have been found to typically include two components, a relatively large nominal body impedance component and a relatively small respiratory impedance component. Thus, since the body's impedance constitutes a large portion of the sensed signal, it may be difficult to detect that relatively small impedance changes associated with respiration on top of a body's nominal impedance. Therefore, in accordance with the principles of the present disclosure, it may be desirable to "filter" the sensed impedance signal in a manner so as to remove most or all of the body's nominal impedance, in order to improve resolution of the respiratory signal. In some embodiments, this may be achieved with the aid of a conventional Wheatstone bridge at or near the front-end of an impedance measuring circuit. In particular, the Wheatstone bridge may facilitate precise measurements of the relatively small impedance changes associated with respiration by removing most, if not all, of the body's nominal impedance.

Figure 39A:
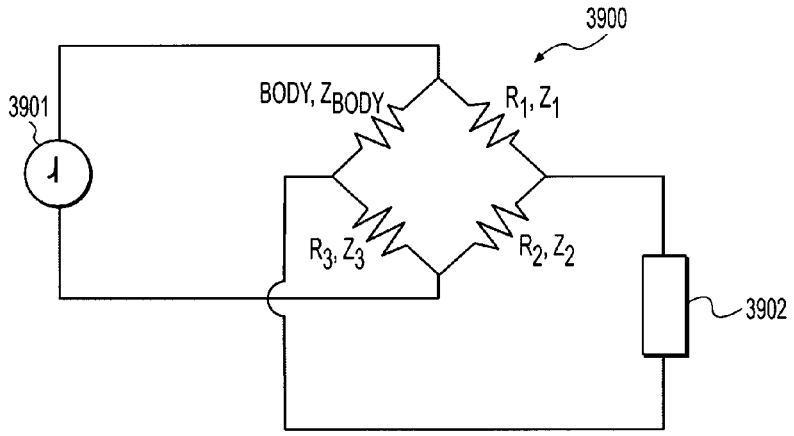

Turning now to FIG. 39A, there is depicted an exemplary Wheatstone bridge 3900. The Wheatstone bridge 3900 may include an electrical current source 3901. Wheatstone bridge 3900 may also include a first resistor $R_1$ having an impedance $Z_1$ connected in series to a second resistor $R_2$ having an impedance $Z_2$. Resistors $R_1$ and $R_2$ may be connected in parallel to resistor $R_3$ having an impedance $Z_3$, which may be connected serially to the patient's body having an impedance $Z_{body}$. As discussed below, impedances $Z_2$ and $Z_3$ may be substantially similar to each other. Wheatstone bridge 3900 may further include any suitable voltage measuring device, such as, for example, those used in conjunction the direct measurement technique described above.

In use, the impedance $Z_1$ of exemplary bridge 3900 may be closely matched to the expected impedance of a patient's body $Z_{body}$, the impedance $Z_2$ matched to impedance $Z_3$, and the voltage potential across voltage measuring device 3902 may be measured. It is contemplated that if impedances $Z_1$-$Z_3$ are closely matched to $Z_{body}$, the measured voltage potential across voltage measuring device 3902 will be predominantly due to respiratory impedance changes and the voltage signal due to the body's nominal impedance will be largely removed. Further, it is contemplated that the voltage changes measured at 3902 due to respiratory impedance changes will have an amplitude that is approximately ½ of the amplitude of the voltage changes, measured with the above-noted direct-measurement technique, assuming the same currently flow through the body. The removal of the voltage signal due to the body's nominal impedance while retaining ½ of the voltage signal amplitude due to changes in respiratory impedance, may facilitate detecting the small impedance changes associated with respiration by improving the resolution of those changes.

Figure 39B:
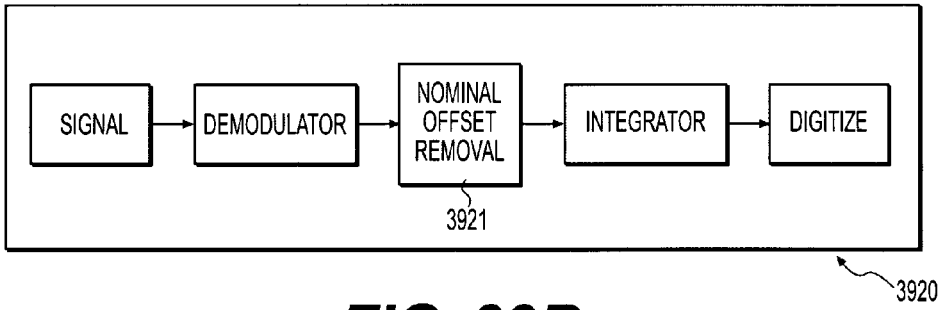

In other embodiments, the body's nominal impedance may be removed or reduced from a sensed signal by, for example, introducing a nominal offset removal module 3921 into an impedance measuring circuit 3920 of the present disclosure, as depicted in FIG. 39B. An exemplary impedance-measuring circuit may generally include feeding a sensed respiratory signal into a demodulator. The signal exiting the demodulator may be then fed into an integrator, and the integrated signal exiting the integrator may then be digitized for analysis. It is therefore contemplated that introducing nominal offset removal module 3921 to act upon the upon the signal exiting the demodulator may achieve the desired effect of removing or reducing the body's nominal impedance from a sensed impedance signal.

Figure 39C:
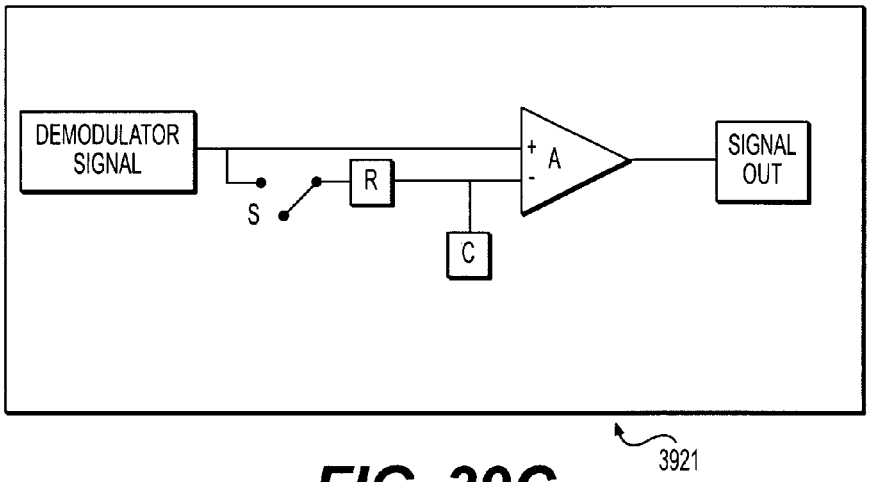

Turning now to FIG. 39C, module 3921 may include a switch S, a resistor R, a capacitor C, and a non-inverting amplifier A. The switch S, resistor R, and capacitor C create a sample and hold reference voltage to the difference amplifier A. The amplifier subtracts this reference voltage from the input signal. The result is to remove or reduce the nominal body impedance component of the signal leaving mainly the respiratory component of the measured impedance. The Resistor-Capacitor (R-C) combination is selected such that it will track with changes in nominal impedance levels but does not significantly distort the respiratory signal. Respiratory signal frequency components of interest are typically between 0.05 Hz and 3 Hz. There are several options for how the Nominal Offset Removal may be operated. An implanted bio -impedance circuit would typically use a modulated excitation signal for measuring impedance. In that case, the switch, S may be open when there is no signal present and may be closed whenever a signal is present. For example, if a Demodulator Signal is present for 1 ms every 100 ms, switch S would be closed during all or a part of the time that Signal In is present. Switch S may also be operated such that it does not close on every instance when Demodulator Signal is present. The switch S, may be closed on every $10^{th}$ or $100^{th}$ instance when Demodulator Signal is present. A third possibility is to close switch S only when Signal Out causes the Integrator to reach an unacceptable threshold. The integrator reaching an unacceptable threshold may be indicative that the reference voltage provided by the R-C combination is no longer providing a sufficiently good estimate of the nominal signal component and so needs to be updated with new information.

Figure 39D:
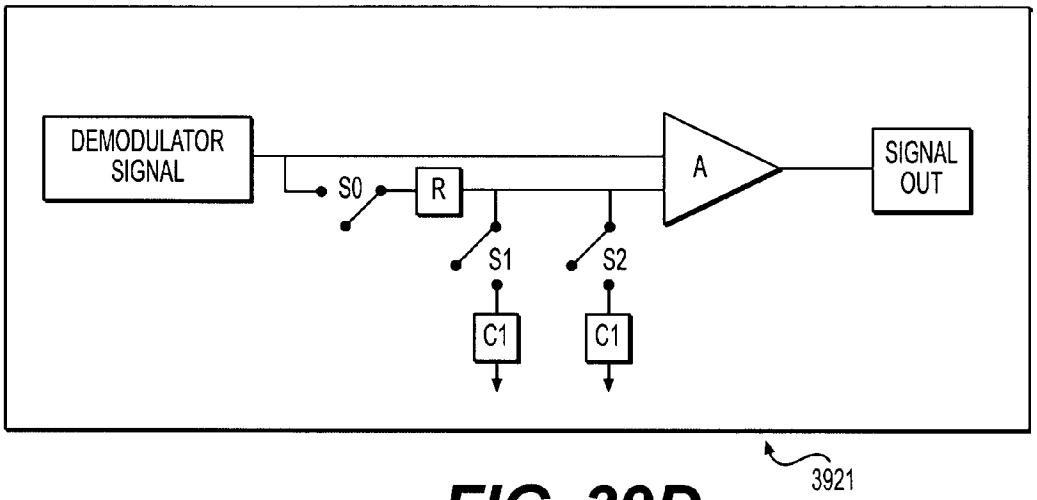

Turning now to FIG. 39D, there is depicted an alternative embodiment of nominal offset removal module. A further improvement on the Nominal Offset Removal module is shown in FIG. 39D. If it is desired to measure two or more different impedance signals it will be necessary to have a different nominal offset reference voltage provided to amplifier A for each signal. It is also desirable to keep the component count as low as possible. In the diagram below, S0 and S1 may be closed and S2 may be open to provide an offset reference for a first signal with the appropriate combination of R-C1. S0 and S2 may be closed and S1 may be open to provide an offset reference for a second signal with the appropriate combination of R-C2. This strategy allows rapid sequential measurement of two or more impedance signals.

Figure 40:
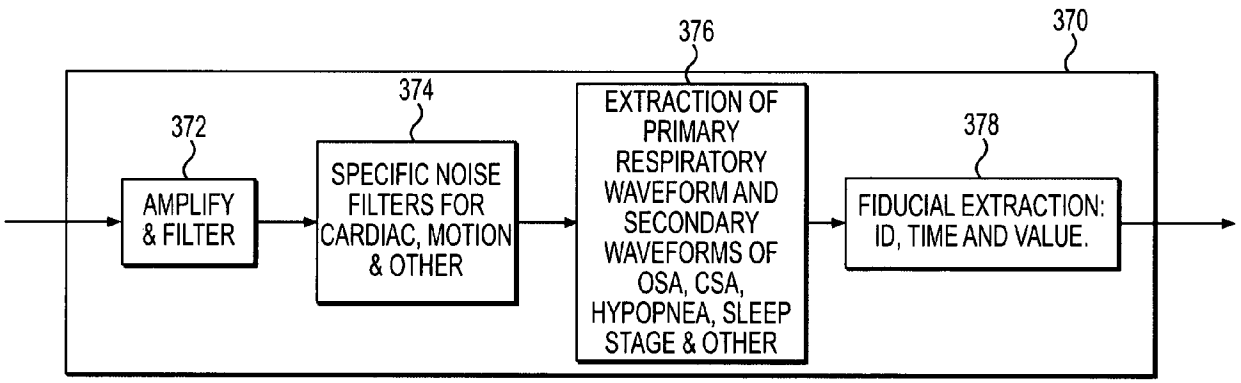

With reference to FIG. 40, the signal processing step 370 may include general signal amplification and noise filtering 372. The step of amplification and filtering 372 may include band pass filtering to remove DC offset, for example. The respiratory waveform may then be processed to remove specific noise artifacts 374 such as cardiac noise, motion noise, etc. A clean respiratory waveform may then be extracted 376 along with other waveforms indicative of specific events such as obstructive sleep apnea (OSA), central sleep apnea (CSA), hypopnea, sleep stage, etc. Specific fiducial points may then be extracted and identified (e.g., type, time, and value).

The step of removing specific noise artifacts 374 may be performed in a number of different ways. However, before signal processing 374, both cardiac and motion noise artifact may be mitigated. For example, both cardiac and motion noise artifact may be mitigated prior to signal processing 374 by selection of bio-Z vectors that are less susceptible to noise (motion and/or cardiac) as described previously. In addition, motion artifact may be mitigated before signal processing 374 by minimizing movement of the sensing lead and electrodes relative to the body using anchoring techniques described elsewhere herein. Furthermore, motion artifact may be mitigated prior to signal processing 374 by minimizing relative movement between the current-carrying electrodes and the voltage-sensing electrodes, such as by using combined current-carrying and voltage-sensing electrodes.

After cardiac and motion artifact has been mitigated using the pre-signal processing techniques described above, both cardiac and motion artifact may be removed by signal processing 374.

For example, the signal processing step 374 may involve the use of a low pass filter (e.g., less than 1 Hz) to remove cardiac frequency noise components which typically occur at 0.5 to 2.0 Hz, whereas resting respiration frequency typically occurs below 1.0 Hz.

Figure 41:
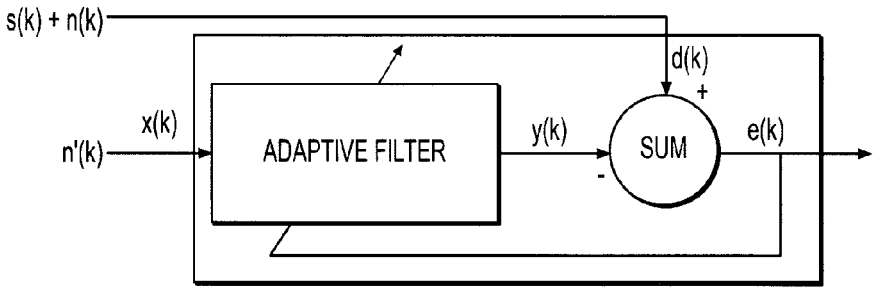

Alternatively, the signal processing step 374 may involve the use of a band pass or high pass filter (e.g., greater than 1 Hz) to obtain a cardiac sync signal to enable removal of the cardiac noise from the bio-Z signal in real time using an adaptive filter, for example. Adaptive filters enable removal of noise from a signal in real time, and an example of an adaptive filter is illustrated in FIG. 41. To remove cardiac artifact from the bio-Z signal which contains both cardiac noise n(k) and respiratory information s(k), a signal n'(k) that represents cardiac noise is input to the adaptive filter and the adaptive filter adjusts its coefficients to reduce the value of the difference between y(k) and d(k), removing the noise and resulting in a clean signal in e(k). Notice that in this application, the error signal actually converges to the input data signal, rather than converging to zero.

Another signal processing technique to remove cardiac noise is to combine signals from two or more bio-Z vectors wherein respiration is the predominate signal with some cardiac noise. This may also be used to reduce motion artifact and other asynchronous noise. Each of the two or more signals from different bio-Z vectors may be weighted prior to combining them into a resultant signal Vw(i). If it is assumed that (a) the respiratory bio-impedance is the largest component in each measured vector, (b) the non-respiratory signal components in one vector are substantially independent of the non-respiratory components in the other vector, and (c) the ratio of the non-respiratory component to the respiratory components in one vector is substantially equal to the same ratio in the other vector, then a simple weighting scheme may be used wherein each signal is divided by it's historic peak-to-peak magnitude and the results are added. For example, if $M_A$=historical average peak-to-peak magnitude of signal from vector A, $M_B$=historical average peak-to-peak magnitude of signal from vector B, $V_A(i)$=data point (i) from vector A, $V_B(i)$=data point (i) from vector B, then the resultant signal $V_W(i)$ (i.e., weighted average of A & B for data point (i)) may be expressed as $V_W(i)=V_A(i)/M_A+V_B(i)/M_B$.

Yet another signal processing technique for removing cardiac noise is to subtract a first signal that is predominantly respiration from a second signal that is predominantly cardiac. For example, the first signal may be from a predominantly respiratory bio-Z vector (e.g., vector B-H) with some cardiac noise, and the second signal may be from a predominantly cardiac bio-Z vector (e.g., vector E1-E2) with some respiration signal. Each of the two signals from the different bio-Z vectors may be weighted prior to subtracting them. The appropriate weighting may be determined, for example, by calculating the power density spectra in the range of 2-4 Hz for a range of weighted differences across at least several respiratory cycles A minimum will occur in the power density spectra for the weighted averages which are sufficiently optimal.

Motion artifact may be removed by signal processing 374 as well. Motion artifact may be identified and rejected using signal processing techniques such as monitoring voltage magnitude, testing the correlation of magnitude and phase, and/or testing correlation at two or more frequencies. Motion artifacts may cause a large change in measured bio-impedance. A typical feature of motion artifacts is that the voltage swings are much larger than respiration. Another feature is that the voltage changes are highly erratic. Using these characteristics, which will be described in more detail below, motion artifact may be removed from the respiration signal.

Figure 42:
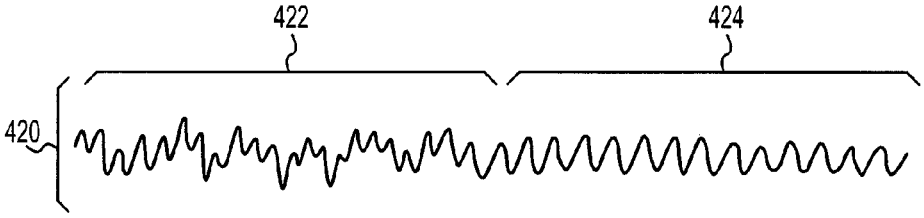
Figure 43:
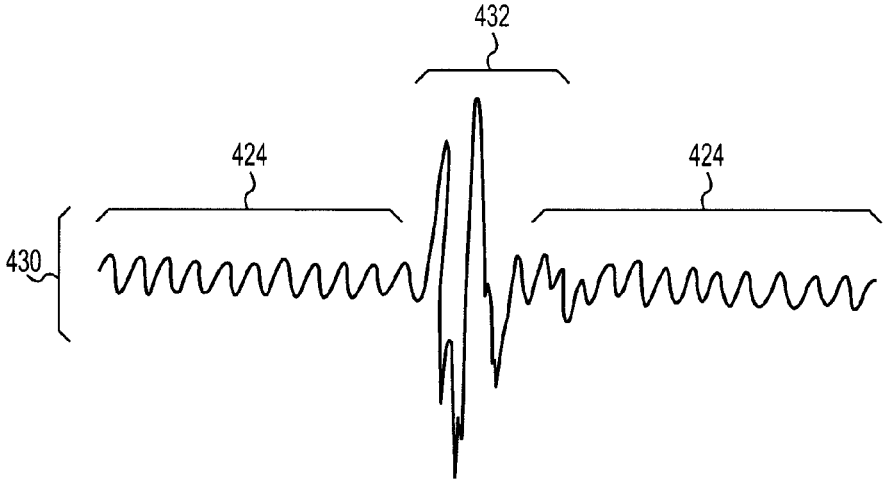
Figure 44:
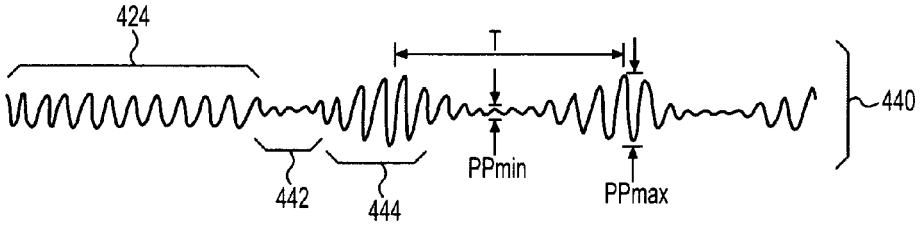
Figure 45:
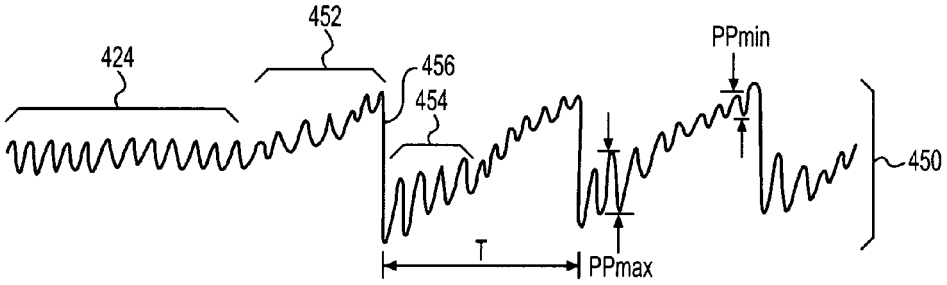
Figure 46:
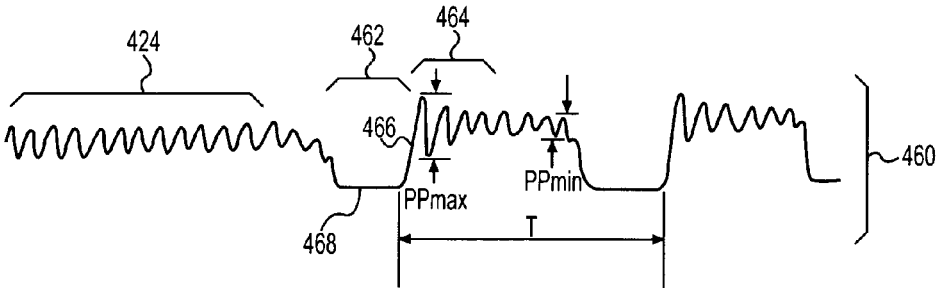

The step of extracting waveforms indicative of respiration and other events 374 may be better explained with reference to FIGS. 42-46 which schematically illustrate various representative unfiltered bio-Z signals. FIG. 42 schematically illustrates a bio-Z signal 420 with representative signatures indicative normal respiration (i.e., event free) during an awake period 422 and a sleeping period 424. FIG. 43 schematically illustrates a bio-Z signal 430 with representative signatures indicative of normal respiration during sleeping periods 424 interrupted by a period of motion 432 (i.e., motion artifact). FIG. 44 schematically illustrates a bio-Z signal 440 with representative signatures indicative of normal respiration during a sleeping period 424 followed by periods of hypopnea (HYP) 442 and recovery 444. FIG. 45 schematically illustrates a bio-Z signal 450 with representative signatures indicative of normal respiration during a sleeping period 424 followed by periods of obstructive sleep apnea (OSA) 452 and recovery 454 (which typically includes an initial gasp 456). FIG. 46 schematically illustrates a bio-Z signal 460 with representative signatures indicative of normal respiration during a sleeping period 424 followed by periods of central sleep apnea (CSA) 462 (which typically includes a cessation in breathing 468) and recovery 464.

The step of extracting 374 waveform data indicative of an awake period 422 vs. a sleep period 424 from a bio-Z signal 420 may be explained in more detail with reference to FIG. 42. In addition, the step of filtering 372 waveform data indicative of motion 432 from a bio-Z signal 430 may be explained in more detail with reference to FIG. 43. One way to determine if a person is awake or moving is to monitor the coefficient of variation (CV) of sequential peak-to-peak (PP) magnitudes over a given period of time. CV is calculated by taking the standard deviation (or a similar measure of variation) of the difference between sequential PP magnitudes and dividing it by the average (or a similar statistic) of the PP magnitudes. N is the number of respiratory cycles which occur in the selected period of time.

The CV may be calculated as follows:

$$CV = \frac{sd(dPP)}{\overline{PP}}$$

Where:

$$sd(dPP) = \sqrt{\frac{\sum_{i=1}^{N}(dPP_i - \overline{dPP})}{(N-1)}}$$

$$\overline{dPP} = \frac{\sum_{i=1}^{N}(dPP_i)}{(N)}$$

$$dPP_i = PP_{i+1} - PP_i$$

$$\overline{PP} = \frac{\sum_{i=1}^{N}(PP_i)}{(N)}$$

Generally, if the CV is greater than 0.20 over a one minute period then person is awake. Also generally, if the CV is less than 0.20 over a one-minute period then person is asleep. These events may be flagged for the step of fiducial extraction 378 wherein data (e.g., event duration, CV, PP range, PPmin, PPmax, etc.) may be time stamped and stored with an event identifier. If CV is greater than 1.00 over a 20 second period then body movement is affecting the bio-Z signal. By way of example, not limitation, if body movement is detected, then (a) stimulation may be delivered in an open loop fashion (e.g., based on historical respiratory data); (b) stimulation may be delivered constantly the same or lower level; or (c) stimulation may be turned off during the period of movement. The selected stimulation response to detected movement may be preset by the physician programmer or by the patient control device. Other stimulation responses may be employed as will be described hereinafter.

In each of FIGS. 44-46, maximum and minimum peak-to-peak magnitudes (PPmax and PPmin) may be compared to distinguish hypopnea (HYP), obstructive sleep apnea (OSA), and central sleep apnea (CSA) events. Generally, PP values may be compared within a window defined by the event (HYP, OSA, CSA) and the recovery period thereafter. Also generally, the window in which PP values are taken excludes transitional events (e.g., gasp 456, 466). As a general alternative, peak-to-peak phases may be used instead of peak-to-peak magnitude. The hypopnea and apnea events may be flagged for the step of fiducial extraction 378 wherein data (e.g., event duration, CV, PP range, PPmin, PPmax, etc.) may be time stamped and stored with an event identifier.

A typical indication of hypopnea (HYP) and apnea (OSA, CSA) events is a recurrent event followed by a recovery. The period (T) of each event (where PP oscillates between PPmax and PPmin and back to PPmax) may be about 15 to 120 seconds, depending on the individual. The largest PP values observed during hypopneas and apneas are usually between 2 and 5 times larger than those observed during regular breathing 424 during sleep. The ratio of the PPmax to PPmin during recurrent hypopnea and apnea events is about 2 or more. During the event and recovery periods (excluding transitional events), PP values of adjacent respiratory cycles do not typically change abruptly and it is rare for the change in PP amplitude to be more than 50% of PPmax. One exception to this observation is that some people gasp 456, 466 (i.e., transitional event) as they recover from a CSA or OSA event.

The ratio of successive PP magnitudes during normal (non-event) sleep 424 is mostly random. The ratio of successive PP magnitudes during apnea and hypopnea events will tend to be a non-random sequence due to the oscillatory pattern of the PP values. Recurrent apneas and hypopneas may be diagnosed by applying a statistical test to the sequence of successive PP ratios.

The step of extracting 374 waveform data indicative of an hypopnea event 442 from a bio-Z signal 440 may be explained in more detail with reference to FIG. 44. The ratio of PPmax to PPmin during recurrent hypopneas is typically between 2 and 5. This is in contrast to CSA's which have very small PPmin due to the complete cessation of breathing. This results in CSA's having PPmax to PPmin ratios larger than 5. Accordingly, hypopnea events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of an OSA event 452 from a bio-Z signal 450 may be explained in more detail with reference to FIG. 45. The sharp change 456 in the bio-Z respiratory magnitude due to OSA is typically in the range of 1 to 4 times the magnitude of the peak-to-peak respiratory cycle magnitude. The sharp change 456 typically takes less than 5 seconds to occur. OSA tends to occur in a recurring sequence where the period (T) between sequential events is between 15 and 120 seconds. A one-minute period is commonly observed. According to these characteristics, OSA events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of a CSA event 462 from a bio-Z signal 460 may be explained in more detail with reference to FIG. 46. The behavior of the Bio-Z signal throughout recurrent CSA events differ from other hypopnea and OSA in three ways. First, during CSA there is complete cessation of respiratory activity which results in a flat Bio-Z signal. This means the ratio of PPmax to PPmin is typically greater than 5 during recurrent CSA events. The duration of the estimated respiratory cycle may also be used to distinguish between CSA from OSA and hypopnea. The lack of respiratory activity during CSA results in an inflated estimate for the respiratory cycle period. The PP typically does not vary by more than 50% for successive cycles. The respiratory cycle duration during a CSA event is more than twice as long as the duration of the respiratory cycles preceding the CSA event. Second, during CSA the Bio-Z magnitude will drift outside the PP magnitude range observed during respiration. It has been observed that with the onset of central sleep apnea (CSA) the magnitude and phase of the Bio-Z signal settle to a steady-state value outside the peak-to-peak range observed during the normal respiratory cycle during sleep. Third, upon arousal from CSA a person will typically gasp. This gasp results in a large PP. The PP of the first respiratory cycle following the CSA event and the PP observed during the CSA (which is essentially noise) will exceed 50% of PPmax.

With continued reference to FIG. 46, the flat portions 468 of the data traces are periods of respiratory cessation. Upon arousal the subject gasps 466 and the raw bio-Z signal resumes cyclic oscillation above the static impedance level observed during CSA. According to these characteristics, CSA events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of sleep stage (e.g., rapid eye movement (REM) sleep vs. no-rapid eye movement (NREM) sleep) may be performed by comparing the phase difference between a first vector and a second vector wherein the first bio-Z vector is along the lung-diaphragm-liver interface (e.g., vector A-K or vector B-K) and the second bio-Z vector is about the lung(s). Examples of the first bio-Z vector include A-K, B-K, A-E1, B-E1, and A-B. Examples of the second bio-Z vector include D-F, B-D, C-G, D-E1, and C-E1. Note that some vector combinations which share a common vector endpoint such as A-E1, D-E1 and B-E1, B-D may use a common electrode and to simplify the respiratory sensing lead or leads. Typically, during NREM sleep, the two vectors are substantially in phase. During REM sleep, the diaphragm is the primary respiratory driver and a common consequence is paradoxical motion of the ribcage and diaphragm (i.e., the two vectors are substantially out of phase). This characteristic would allow for an effective monitor of a person's ability to reach REM sleep. Accordingly, REM and NREM sleep stages may be detected, identified, and flagged for the step of fiducial extraction 378 wherein characteristic data (e.g., event duration, phase, etc.) may be time stamped and stored with an event identifier.

Figure 47:
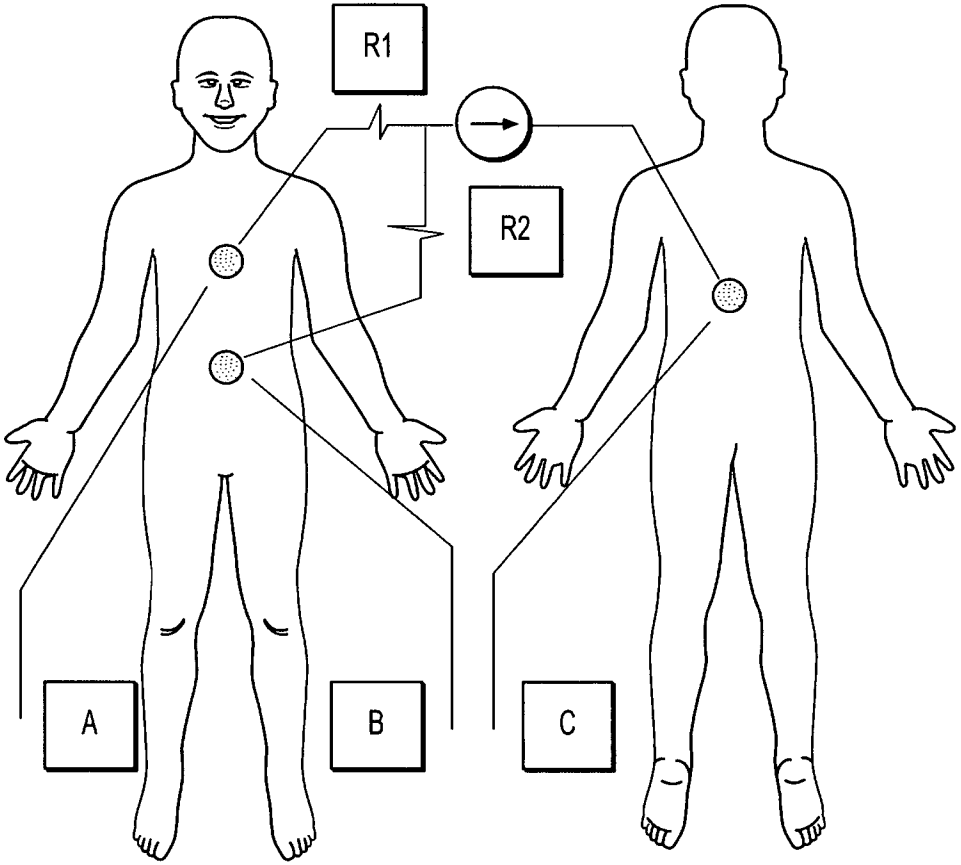
FIG. 47 schematically illustrates an alternative respiration detection technique.

An alternative method of detecting an OSA event is to make use of a split current electrode arrangement as shown in FIG. 47 which shows the positions of three electrodes on the subject. Electrode A may be above the zyphoid, electrode B may be just above the belly button, and electrode C may be on the back a couple of inches below electrode A. Electrodes A and B are connected to a common constant current source through resistors R1 and R2. The voltage measured across the current source is a measure of the bio-impedance during normal respiration. The voltage across R1 is an indicator of the paradoxical motion associated with apnea. An unbalanced current split between R1 and R2 resulting in large bio-Z voltage swings is indicative of OSA. During normal respiration or even very deep breaths there is almost no effect on the apnea detection channel. Accordingly, OSA events may be detected, identified, and flagged for the step of fiducial extraction 378 wherein characteristic data (e.g., event duration, voltage swing magnitude, etc.) may be time stamped and stored with an event identifier.

Generally, the extracted 378 waveform and event data may be used for therapy tracking, for stimulus titration, and/or for closed loop therapy control. For example, data indicative of apneas and hypopneas (or other events) may be stored by the INS 50 and/or telemetered to the patient controlled 40. The data may be subsequently transmitted or downloaded to the physician programmer 30. The data may be used to determine therapeutic efficacy (e.g., apnea hypopnea index, amount of REM sleep, etc.) and/or to titrate stimulus parameters using the physician programmer 30. The data may also be used to control stimulus in a closed loop fashion by, for example, increasing stimulus intensity during periods of increased apnea and hypopnea occurrence or decreasing stimulus intensity during periods of decreased apnea and hypopnea occurrence (which may be observed if a muscle conditioning effect is seen with chronic use). Further, the data may be used to turn stimulus on (e.g., when apnea or hypopnea events start occurring or when motion artifact is absent) or to turn stimulus off (e.g., when no apnea or hypopnea events are occurring over a present time period or when motion artifact is predominant).

Description of Stimulus Trigger Algorithms

As mentioned previously with reference to FIG. 39, the neurostimulation system described herein may operate in a closed-loop process wherein the step of delivering stimulation 390 to the targeted nerve may be a function of a sensed feedback parameter (e.g., respiration). For example, stimulation of the hypoglossal nerve may be triggered to occur during the inspiratory phase of respiration. In a health human subject, the hypoglossal nerve is triggered about 300 mS before inspiration. Accordingly, a predictive algorithm may be used to predict the inspiratory phase and deliver stimulation accordingly. FIG. 48 schematically illustrates a system 480 including devices, data and processes for implementing a self-adjusting predictive trigger algorithm.

The system components 482 involved in implementing the algorithm may include the physician programmer (or patient controller), INS and associated device memory, and the respiratory sensor(s). The sensors and device memory are the sources of real-time data and historical fiducial data which the current algorithm uses to generate a stimulation trigger signal. The data 484 utilized in implementing the algorithm may include patient specific data derived from a sleep study (i.e., PSG data), data from titrating the system post implantation, and historic and real-time respiratory data including respiratory and event fiducials. The processes 486 utilized in implementing the algorithm may include providing a default algorithm pre-programmed in the INS, patient controller or physician programmer, modifying the default algorithm, and deriving a current algorithm used to generate a trigger signal 488.

More specifically, the processes 486 utilized in implementing a predictive trigger algorithm may involve several sub-steps. First, a default algorithm may be provided to predict onset of inspiration from fiducial data. Selecting an appropriate default algorithm may depend on identifying the simplest and most robust fiducial data subsets which allow effective prediction of onset. It also may depend on a reliable means of modifying the algorithm for optimal performance. Second, modification of the default algorithm may require a reference datum. The reference datum may be the estimated onset for past respiratory cycles. It is therefore useful to precisely estimate inspiratory onset for previous respiratory cycles from historical fiducial data. This estimation of inspiratory onset for previous respiratory cycles may be specific to person, sensor location, sleep stage, sleep position, or a variety of other factors. Third, the current algorithm may be derived from real-time and historical data to yield a stimulation trigger signal 488.

Figure 47A:
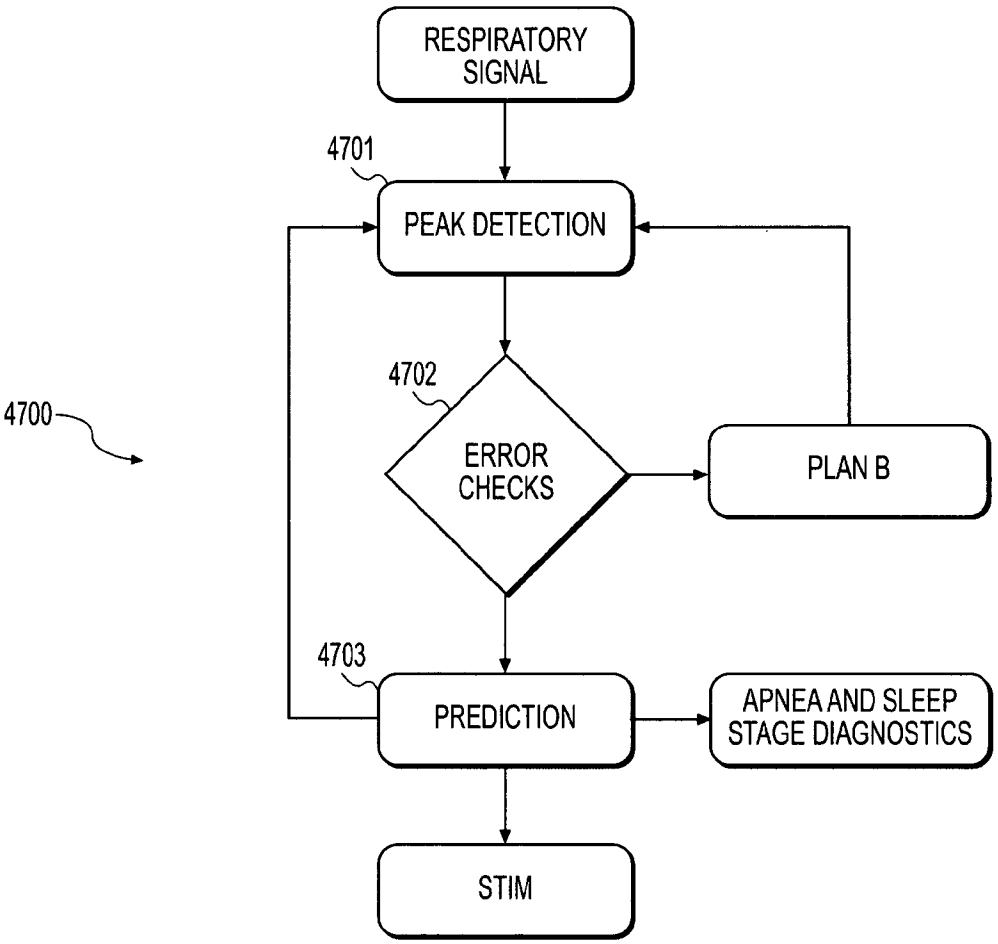
FIGS. 47A-47D illustrate an exemplary stimulation trigger algorithm.

As alluded to above, a trigger algorithm, such as, for example, trigger algorithm 4700 depicted in FIG. 47A, may be applied to a detected respiratory signal to begin and/or control delivery of the stimulation signal. As illustrated, trigger algorithm 4700 may include a plurality of sub-routines 4701-4703 for performing various analyses on a sensed respiratory signal. These sub-routines may include, but are not limited to, performing peak detection 4701, error checking 4702, and prediction 4703, on a detected respiratory signal.

Figure 47B:
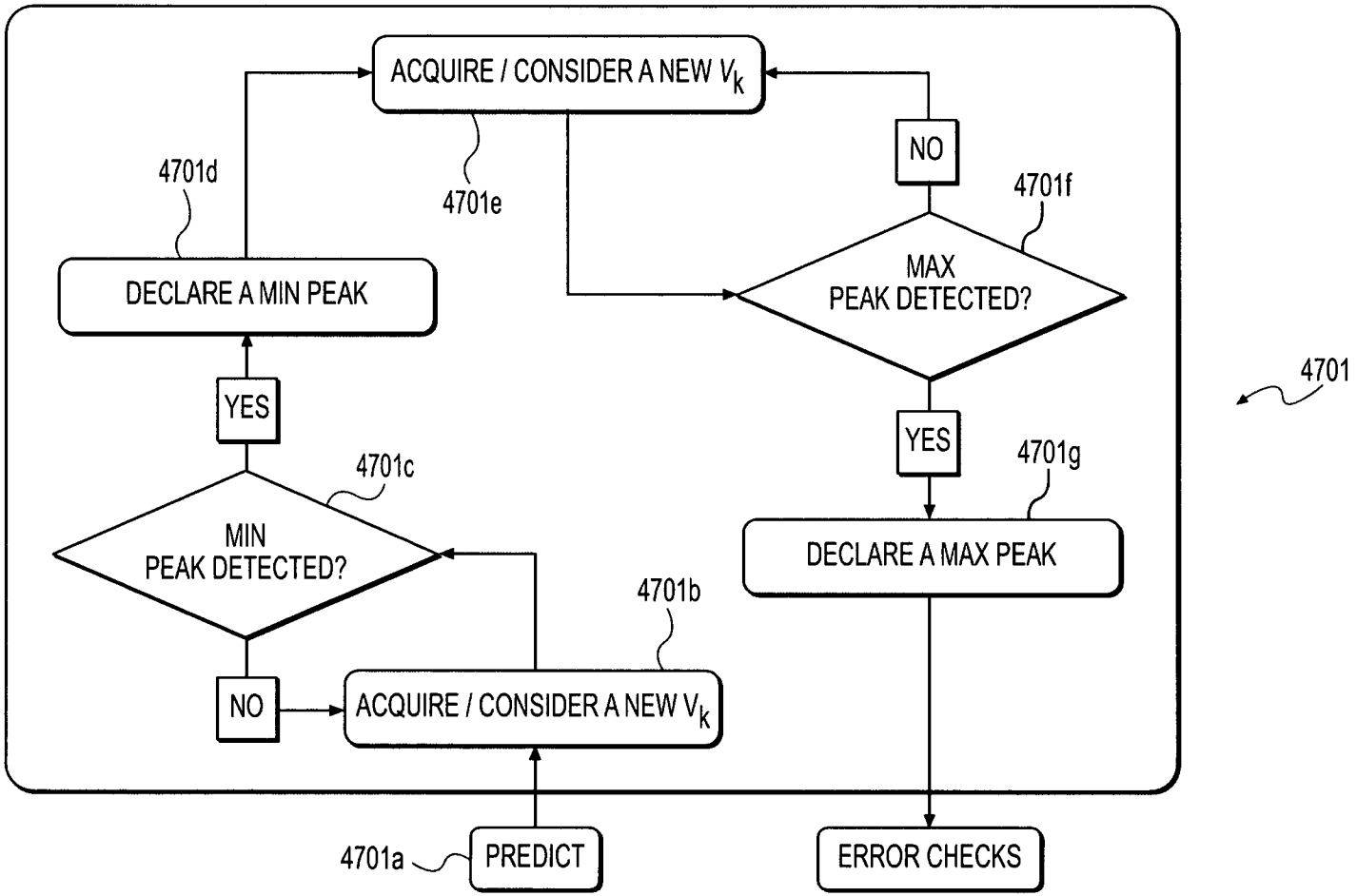
Figure 47C:
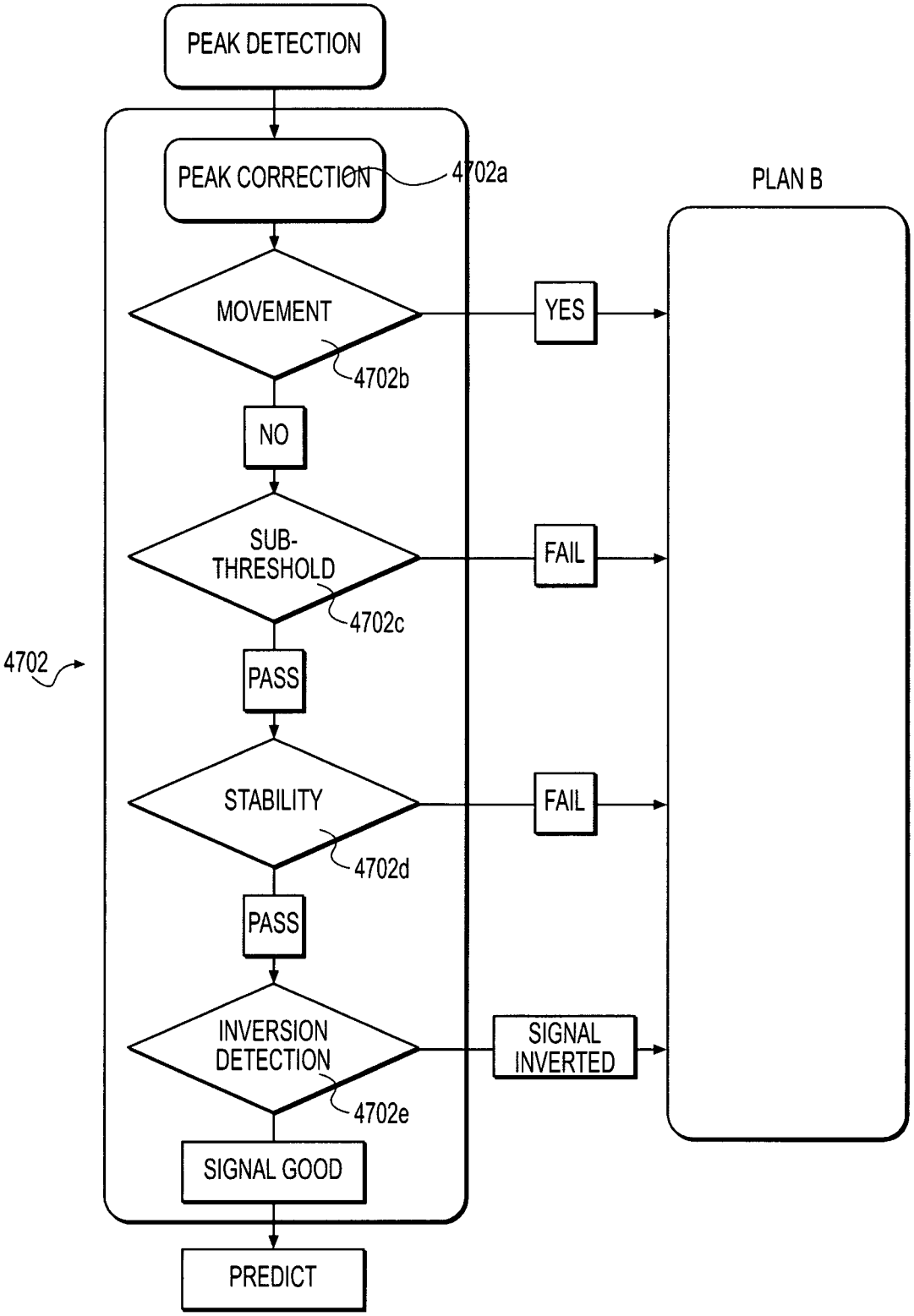
Figure 47D:
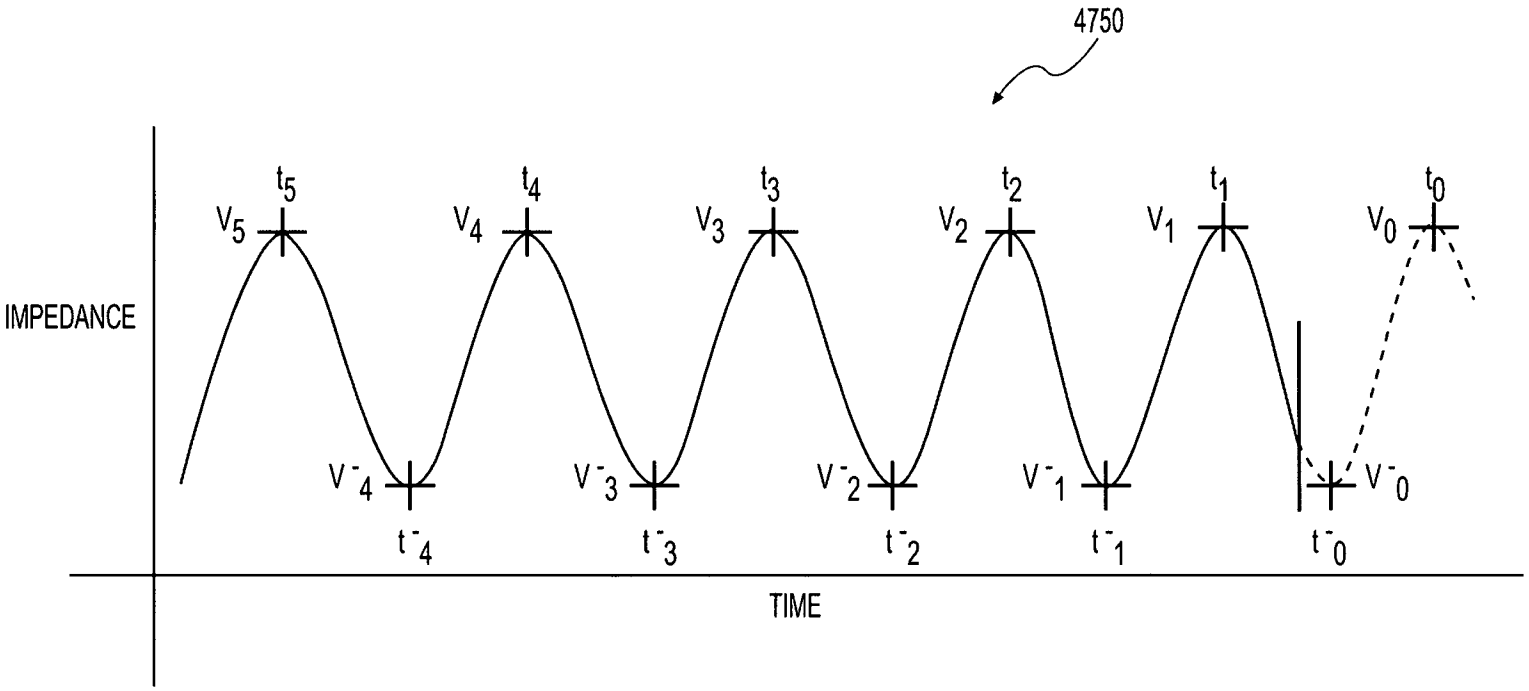

With reference now to FIG. 47D, there is depicted an exemplary sensed respiratory signal 4750. Respiratory signal 4750 may be displayed as a substantially sinusoidal waveform having a component that varies with time. As shown in FIG. 47D, respiratory signal 4750 may include a plurality of peaks, such as, for example, the peak located at $v_4t_4$, and a plurality of valleys, such as, for example, the valley located $v_4^-t_4^-$. Therefore, as will be discussed in greater detail below, peak detection sub-routine 4701 may be applied to sensed respiratory signal 4750 to detect the peaks of signal 4750. Error checking sub-routine 4702 may be applied to signal 4750 to, among other things, ensure signal 4750 is an accurate representation of a patient's respiration and free from undesirable artifacts caused by, for example, a patient's movement or cardiac activity. Prediction sub-routine 4703 may then be applied to signal 4750 to predict when future peaks will occur in accordance with the sensed signal 4750.

With reference to FIG. 47B, peak detection 4701 may include a plurality of steps 4701a-g. Step 4701a may include first detecting the peaks, such as, for example, the peak located at $v_4t_4$, of signal 4750. The detected peaks may be an indication of when onset of expiration occurs during the monitored respiratory cycles. Next, step 4701b may include acquiring and/or considering a new voltage $V_k$, where $V_k$ may be the most recently acquired data point time $T_k$ under consideration, where a number of recently acquired data points may be under consideration. Step 4701c may determine whether the data points under consideration meet the criteria to indicate that a minimum (min) peak has been detected. One example of such a criteria to indicate a minimum peak has been detected is if the oldest data point under consideration, $V_{k+m}$ is less than more recent data points under consideration, $(V_{k+m-1} \ldots V_k)$, which can be expressed mathematically as $V_{k+m} \leq \min (V_{k+m-1} \ldots V_k)$. Another example of such a criteria to indicate a minimum peak has been detected is if the most recent data point under consideration, $V_k$, is greater than all other less-recently acquired data points under consideration, $(V_{k+m} \ldots V_{k+1})$, which can be expressed mathematically as $V_k \geq \max (V_{k+m-1} \ldots V_{k+1})$. If the criteria for detecting a minimum peak is not met, step 4701b may be repeated to acquire and/or consider a new voltage $V_k$. If the criteria has been met, step 4701d may declare a minimum peak reference. Next, step 4701e may again acquire and/or consider a new voltage $V_k$. Subsequently, step 4701f may determine whether the data points under consideration meet the criteria to indicate a maximum peak has been detected. One example of such a criteria to indicate a maximum peak has been detected is if the oldest data point under consideration, $V_{k+m}$, is greater than more recent data points under consideration $(V_{k+m-1} \ldots V_k)$, which can be expressed mathematically as $V_{k+m} \geq \max (V_{k+m-1} \ldots V_k)$. Another example of such a criteria to indicate a maximum peak has been detected is if the most recent data point under consideration, $V_k$, is less than all other less-recently acquired data points under consideration, $(V_{k+m} \ldots V_{k+})$), which can be expressed mathematically as $V_k \leq \max (V_{k+m} \ldots V_{k+1})$. If the criteria for detecting a maximum peak is not met, step 4701e may be repeated to acquire and/or consider a new voltage $V_k$. If the criteria has been met, step 4701g may declare a maximum peak, and trigger algorithm 4700 may proceed to error-checking sub-routine 4702. The declared peak will depend on the criteria used for peak detection. For example, if the criteria for detecting a peak was based on comparing $V_k$ to less recently acquired data points, $(V_{k+m} \ldots V_{k+1})$, then the peak magnitude and time would be declared to be $V_{k+m/2}$, $t_{k+m/2}$. As another example, if the criteria for detecting a peak was based on comparing the oldest considered data point, $V_{k+m}$, to more recently acquired data points $(V_{k+m} \ldots V_k)$, then the peak magnitude and time would be declared to be $V_{k+m}$, $t_{k+m}$.

With reference now to FIG. 47C, error-checking sub-routine 4702 may include a plurality of steps 4702a-e to determine whether a sensed respiratory signal may be adequate for respiration detection. For example, step 4702a, peak correction, may include receiving information relating to the peaks detected in step 4701 and corrections, as necessary. Next, steps 4702b-e may include analyzing the sensed respiratory signal to determine whether the signal includes "noise" caused by a patient's movement (4702b), whether the signal is sub-threshold (e.g., has a relatively low amplitude) (4702c), whether the signal is sufficiently stable (4702d), and whether the inversion detection is possible with the sensed signal (4702e). If the sensed signal passes all of error-checking steps 4702b-e, trigger algorithm 4700 may proceed to prediction sub-routine 4703. However, if the sensed signal fails any of steps 4702b-e, the trigger algorithm may terminate and the pulse generator (e.g., INS 50) may either cease stimulation, continue stimulation with continuous pulses of predetermined duration, and/or continue to stimulate at the same or a fraction (e.g., one quarter) of the stimulation rate for the most recently measured respiratory cycle, as discussed in greater detail below.

As described above, a peak is declared for a given set of data points under consideration when a peak detection criteria is met. The declared peak itself may be used in further algorithm calculations or a more precise estimate of peak time and voltage may be calculated. The more precise estimates of peak time and voltage are referred to as the peak correction. With regard to step 4702a, peak correction may be calculated as follows:

$$\Delta V_{pk,i}=V_{pk,i}-V_{pk,i-1} \text{ for } -n\le i\le n$$

$V_{pk,0}$ is defined to be the declared peak for which a correction is being calculated. The difference in voltage between successive data points is calculated for a given number of data points, n, to either side of the declared peak.

$$\Delta V_{pk,0th} = \frac{1}{2n}\sum(\Delta V_{pk,i})$$

The peak in signal ideally occurs when the rate of change of the signal is zero. Taking successive differences in measured voltage is an approximation to the rate of change of the signal. Linear regression is used on a range of successive differences to estimate the point in time when the rate of change is zero. Due to the fact that the data points are collected at equal increments of time, calculating the statistics $\Delta V_{pk,0th}$, $\Delta V_{pk,1st}$ and DEN allows a simple calculation based on linear regression to estimate the point in time at which the rate of change of the signal is zero.

$$\Delta V_{pk,1st} = \sum(i*\Delta V_{pk,i}) \text{ for } -n\le i\le n$$

$$DEN = \sum(i^2) \text{ for } -n\le i\le n$$

$$\text{Correction} = \Delta V_{pk,0th}\left(\frac{Den}{\Delta V_{pk,1st}}\right)$$

Additionally, an estimated peak time after correction may be determined as follows:

$$t'_{pk,0}=t_{pk,0}+\text{Correction}$$

With regards to step 4702e, a peak curvature estimate for inversion detection can be obtained from one of the statistics, $\Delta V_{pk,1st}$, calculated for peak correction. Maximum peaks are sharper than minimum peaks and so typically have higher values of $\Delta V_{pk,1st}$. One means of determining if a signal is inverted would be to compare the values of $\Delta V_{pk,1st}$ for a series of maximum peaks to a series of minimum peaks.

With renewed reference to FIG. 47A, prediction subroutine 4703 may include predicting the time between sequentially identified peaks with either a parametric option or a non-parametric option. The parametric option makes a prediction of the duration of the next respiratory period based on the average duration of recent respiratory cycles and the rate of change of the duration of recent respiratory cycles. The parametric option also takes advantage of the fact that data points are collected at equal increments of time which simplifies the linear regression calculation. The parametric option may be defined as follows:

$$\Delta t_i=t_i-t_{i-1}$$

Zeroth order estimate of next peak.

$$\Delta t_{0,0th}=1/h\cdot\Sigma(\Delta t_i), \text{ for } 1\le i\le n$$

where n is the number of past respiration cycles used

First Order Estimate $$\Delta t_{0,1st} = \sum\left(i-\left(\frac{n+1}{2}\right)*\Delta t_i\right), \text{ for } 1\le i\le n$$

$$DEN1 = \sum\left(\left(i-\left(\frac{n+1}{2}\right)\right)^2\right), \text{ for } 1\le i\le n$$

Predicted Interval Length for Current Respiration Cycle $$\Delta t_{0,pred} = \Delta t_{0,0th} + \left(\frac{t_{0,1st}}{DEN1}\right)\cdot\left(\frac{n+1}{2}\right)$$

Next Predicted Offset at $$t_{0,pred}=t_1+\Delta t_{0,pred}$$

Begin therapy delivery at:

$t_{therapy}=t_1+(1-DC)*\Delta t_{0,pred}$, where DC may be the allowable duty cycle for therapy delivery.

The non-parametric option is very similar to the parametric option in that it also estimates the duration of the next respiratory period based on the nominal duration of recent respiratory cycles and the rate of change of the duration of recent respiratory periods. The method is explained in more detail in "Nonparametric Statistic Method" by Hollander and Wolfe in sections related to the Theil statistic and the Hodges-Lehman, there disclose of which is incorporated herein by reference. The non-parametric prediction method may be defined as follows:

$$\Delta t_i=t_i-t_{i-1}$$

Zeroth Order Estimate $$\Delta t_{0,oth}=\tfrac{1}{2}\text{median}\{\Delta t_i+\Delta t_j, i+\epsilon_0\le j\le 1, \ldots, n\}$$

Where $\epsilon_0$ is optimally 0, 1, 2 or 3

First Order Estimate $$S_{ij} = \frac{\Delta t_j-\Delta t_i}{j-i} 1\le i+\epsilon_1<j\le n$$

where $\epsilon_1$ is optimally 0, 1, 2, or 3

$$\Delta t_{0,1st} = \text{median}\{S_{ij}, 1\le i\le\epsilon_1<j\le n\}$$

Predicted Interval Length for Current Respiration cycle $$\Delta t_{0,pred} = \Delta t_{0,0th} + \Delta t_{0,1st} \cdot \left(\frac{n+1}{2}\right)$$

Next Predicted Offset $t_{0,pred} = t_1 + \Delta t_{0,pred}$

Begin Therapy Delivery at $t_{therapy} = t_1 + (1-DC)*\Delta t_{0,pred}$, where DC may be the allowable duty cycle for therapy delivery.

Stimulation may then commence at the calculated $t_{therapy}$.

With reference to FIG. 48, a self adjusting predictive algorithm may be implemented in the following manner.

The Programmer block illustrates means by which PSG-derived data may be uploaded into the device.

The Sensors and Device Memory block includes the sources of real-time data and historical fiducial variables which the current algorithm uses to generate a stimulation trigger signal.

The Patient PSG Titration Data block includes conventional polysomnographic (PSG) data obtained in a sleep study. A self-adjusting predictive algorithm utilizes a reference datum to which the algorithm can be adjusted. Onset may be defined as onset of inspiration as measured by airflow or pressure sensor used in a sleep study, for example. Estimated Onset may be defined as an estimate of Onset calculated solely from information available from the device sensors and memory. To enable the predictive algorithm to be self-adjusting, either Onset or Estimated Onset data is used. During actual use, the implanted device will typically not have access to Onset as that would require output from an airflow sensor. The device then may rely on an estimate of Onset or Estimated Onset. The calibration of Estimated Onset to Onset may be based on PSG data collected during a sleep study. The calibration may be unique to a person and/or sleep stage and/or sleep position and/or respiratory pattern.

The Historical Fiducial Variables block represents the Historical Fiducial Variables (or data) which have been extracted from the bio-Z waveform and stored in the device memory. This block assumes that the raw sensor data has been processed and is either clean or has been flagged for cardiac, movement, apnea or other artifacts. Note that fiducial data includes fiducials, mathematical combinations of fiducials or a function of one or more fiducials such as a fuzzy logic decision matrix.

The Real-Time Data and Historical Fiducial Variables block incorporates all the information content of the Historical Fiducial Variables block and also includes real-time bio-Z data.

The Default Algorithm block represents one or more preset trigger algorithms pre-programmed into the INS or physician programmer. The default algorithm used at a specific point in time while delivering therapy may be selected from a library of pre-set algorithms. The selection of the algorithm can be made automatically by the INS based on: patient sleep position (position sensor), heart rate (detectable through the impedance measuring system) or respiration rate. Clinical evidence supports that the algorithm used to predict the onset of inspiration may be dependant on sleep position, sleep state or other detectable conditions of the patient.

The Modify Algorithm block represents the process of modifying the Default Algorithm based on historical data to yield the Current Algorithm. Once the calibration of Estimated Onset to Onset is resident in the device memory it can be used to calculate Estimated Onset for past respiratory cycles from Fiducial Variables. The variable used to represent the Estimated Onset will be TEST or TEST(i) where the "i" indicates the cycle number. Note that Estimated Onset is calculated for past respiratory cycles. This means that sensor fiducial variables which either proceed or follow each Onset event may be used to calculate the Estimated Onset.

The Current Algorithm block represents the process of using the Modified Default Algorithm to predict the next inspiratory onset (Predicted Onset). The Predicted Onset for the next respiratory cycle may be calculated from real-time data and historical fiducial variables. The calculation may be based on the Modified Default Algorithm. Modification of the Modified Default Algorithm to derive the Current Algorithm may be dependent on the calibration of Estimated Onset to Onset which was input from the physician programmer and may be based on comparison of real-time bio-Z data to data collected during a PSG titration study. The Current Algorithm may use historic and/or real-time sensor fiducial variables to predict the next onset of inspiration. This predicted onset of inspiration may be referred to as Predicted Onset. The variable used to represent Predicted Onset may be TPRED or TPRED(i) where the "i" indicates the respiratory cycle.

The Stimulation Trigger Signal block represents the Current Algorithm generating a trigger signal which the device uses to trigger stimulation to the hypoglossal nerve.

FIG. 49 is a table of some (not all) examples of waveform fiducials which can be extracted from each respiratory cycle waveform. For each fiducial there is a magnitude value and a time of occurrence. Each waveform has a set of fiducials associated with it. As a result, fiducials may be stored in the device memory for any reasonable number of past respiratory cycles. The values from past respiratory cycles which are stored in device memory are referred to as Historical Fiducial Variables.

Figure 50:
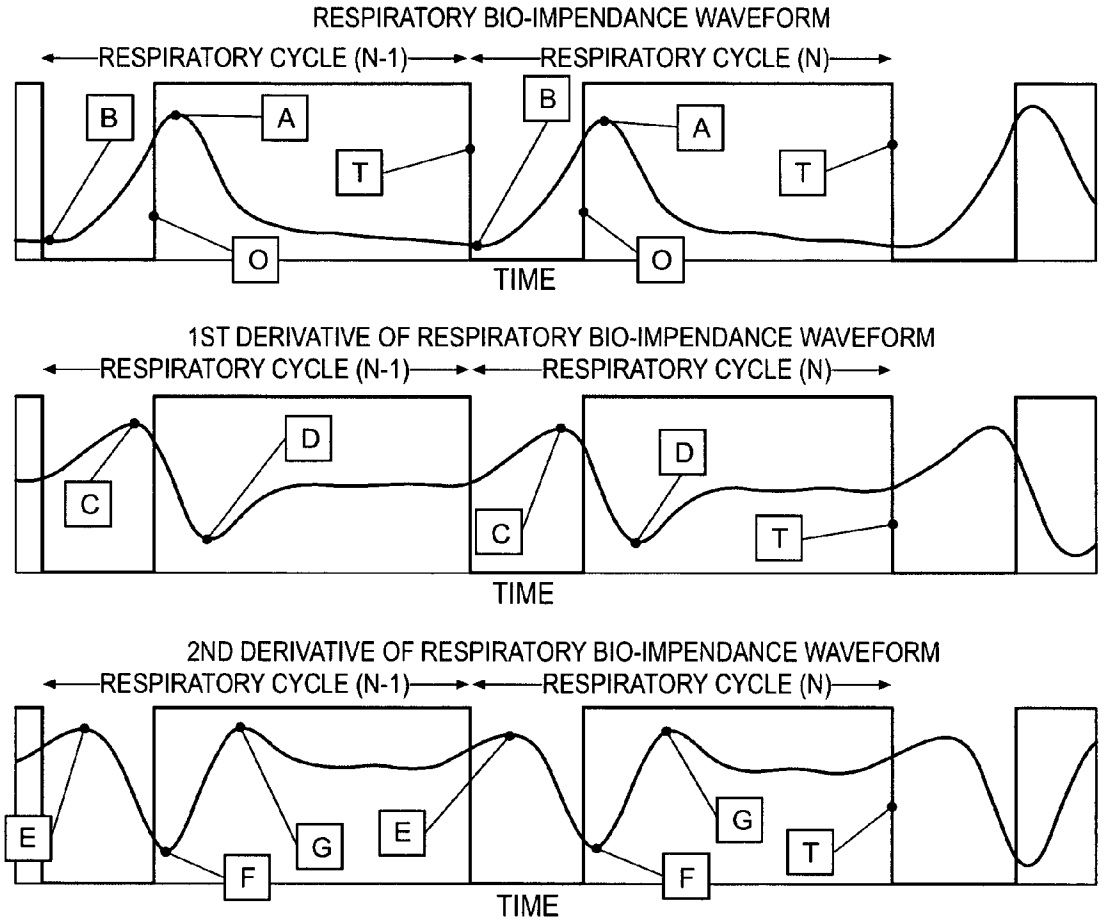

The graphs illustrated in FIG. 50 are examples of fiducials marked on bio-Z waveforms. The first of the three graphs illustrate the bio-impedance signal after it has been filtered and cleared of cardiac and motion artifacts. The first graph will be referred to as the primary signal. The second graph is the first derivative of the primary signal and the third graph is the second derivative of the primary signal. Each graph also displays a square wave signal which is derived from airflow pressure. The square wave is low during inspiration. The falling edge of the square wave is onset of inspiration.

Due to the fact that it may be difficult to identify onset of inspiration in real-time from respiratory bio-impedance, a goal is to construct an algorithm which can reliably predict onset of inspiration "T" for the next respiratory cycle from information available from the current and/or previous cycles. A reliable, distinct and known reference point occurring prior to onset of inspiration, "T", is "A", the peak of the primary signal in the current cycle. As can be seen in FIG. 50, the upper peak of the bio-Z waveform "A" approximately corresponds to the onset of expiration "O." A dependent variable $t_{T-PK}$ is created to represent the period of time between the positive peak of the primary signal for the current cycle, t.Vmax(n), indicated by "An" on the graph, and onset of inspiration for the next cycle, t.onset(n+1), indicated by "T" on the graph. The variable $t_{T-PK}$ may be defined as:

$$t_{T-PK} = t.onset(n+1) - t.Vmax(n)$$

Note that t.Vmax could be replaced by any other suitable fiducial in defining a dependent variable for predicting onset.

A general model for a predictive algorithm may be of the following form:

$t_{T-PK}$=f(fiducials extracted from current and/or previous cycles)

A less general model would be to use a function which is a linear combination of Fiducial Variables and Real-Time Data.

The following fiducials may be both highly statistically significant and practically significant in estimating T:

t.Vmax(n)=the time where positive peak occurs for the current cycle;

t.dV.in(n)=the time of most positive $1^{st}$ derivative during inspiration for the current cycle; and t.Vmax(n−1)=the time of positive peak for the previous cycle.

This model can be further simplified by combining the variables as follows:

$$\Delta t.pk(n)=t.Vmax(n)-t.Vmax(n-1)$$

$$\Delta t.in(n)=t.Vmax(n)-t.dV.in(n)$$

Either Δt.pk(n) or Δt.in(n) is a good predictor of Onset.

The following example uses Δt.pk(n). The time from a positive peak until the next inspiration onset can be estimated by:

$$T_{pred}=t.Vmax(n)+k0+k1*\Delta t.pk(n)$$

The coefficients k0 and k1 would be constantly modified by optimizing the following equation for recent historical respiratory cycles against $T_{est}$:

$$T_{est}=t.Vmax(n)+k0+k1*\Delta t.pk(n)$$

Thus, the predictive trigger time $T_{pred}$ may be determined by adding $t_{T-PK}$ to the time of the most recent peak (PK) of the bio-Z signal, where:

$$t_{T-PK}=k0+k1*\Delta t.pk(n)$$

The predictive equation we are proposing is based on the fact that the very most recent cycle times should be negatively weighted. Regression analysis supports this approach and indicates a negative weighting is appropriate for accurate prediction of onset. Thus, predicting onset is more effective if the most recent historical cycle time is incorporated into an algorithm with a negative coefficient.

As noted above, stimulation may be delivered for only a portion of the respiratory cycle, such as, for example, during inspiration. Additionally, it may be desirable to begin stimulation approximately 300 milliseconds before the onset of inspiration to more closely mimic normal activation of upper airway dilator muscles. However, predicting and/or measuring inspiration, in particular, the onset of inspiration, may be relatively challenging. Thus, since the onset of expiration may be relatively easy to measure and/or predict (as discussed in greater detail below) when an adequate measure of respiration is available, it is contemplated that stimulation may be triggered as a function of expiration onset.

Figure 50A:
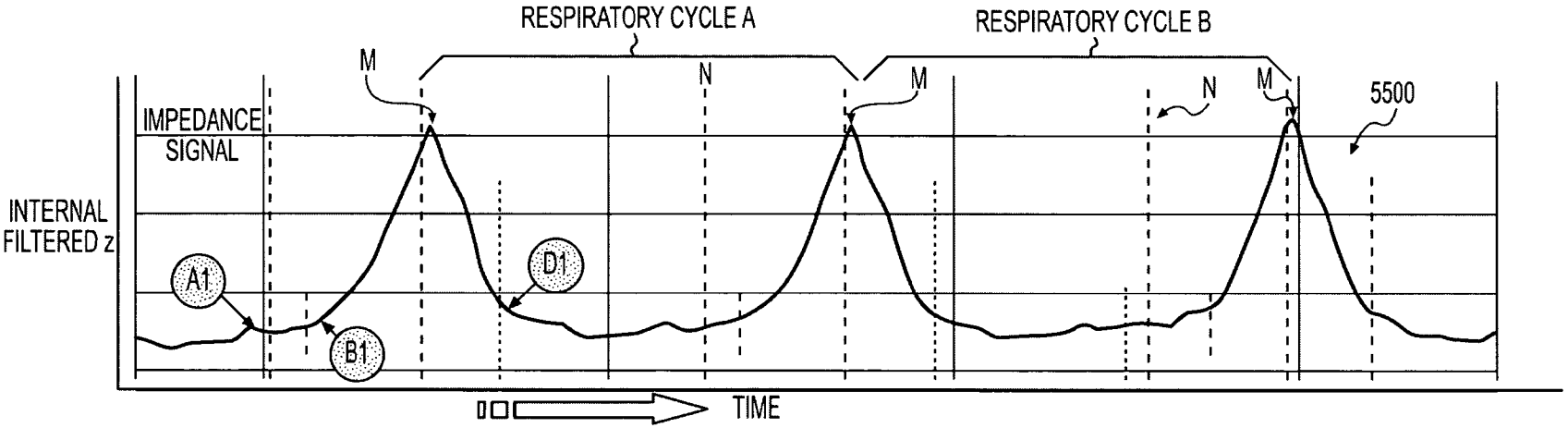
FIG. 50A illustrates an exemplary waveform of a patient's respiratory cycle.

Turning now to FIG. 50A, there is depicted an exemplary respiratory waveform 5500 for two complete respiratory cycles A and B. In analyzing exemplary waveform 5500, it may be determined that peaks M of the waveform 5500 may indicate onset of the expiratory phases of respiration cycles A and B. Furthermore, it may be discovered that peaks M occur at regular intervals of approximately 3-4 seconds. Thus, it may be relatively easy to predict the occurrence of subsequent peaks M, and consequently, the onset of expiration for future respiratory cycles.

Therefore, in order to deliver a stimulus to a patient in accordance with the principles of the present disclosure, the start of stimulation may be calculated by first predicting the time intervals between the start of expiration for subsequently occurring respiratory cycles. Next, in order to capture the entire inspiratory phase, including the brief pre-inspiratory phase of approximately 300 milliseconds, stimulation may be started at the time N that is prior to the next onset of expiration by approximately 30% to 50% of the time between subsequently occurring expiratory phases. Stimulating less than 30% or more than 50% prior to the next expiratory phase may result in an inadequate stimulation period and muscle fatigue, respectively.

In some embodiments, however, it is contemplated that an adequate measure of respiration may not be available, such as, for example, when a relied upon signal has failed. In these embodiments, it is contemplated that the implanted neurostimulator system may be configured to respond in one or more of the following three ways. First, the implanted neurostimulator may completely cease stimulation until an adequate signal is acquired. Second, the neurostimulator may deliver continuous simulation pulses of predetermined durations (e.g., up to 60 seconds) until an adequate signal is acquired; or if an adequate signal is not acquired in this time, the stimulation will be turned off. Third, the neurostimulator may continue to stimulate at the same or a fraction (e.g., one quarter) of the stimulation rate for the most recently measured respiratory cycle. That is to say, the neurostimulator may deliver stimulation pulses of relatively long durations at a frequency that is less than the frequency of stimulation utilized with an adequate measure of respiration. Alternatively, the neurostimulator may deliver stimulation pulses of relatively short durations at a frequency that is greater than the frequency used with an adequate measure of respiration.

Description of an Exemplary Stimulation Pulse

Figure 50B:
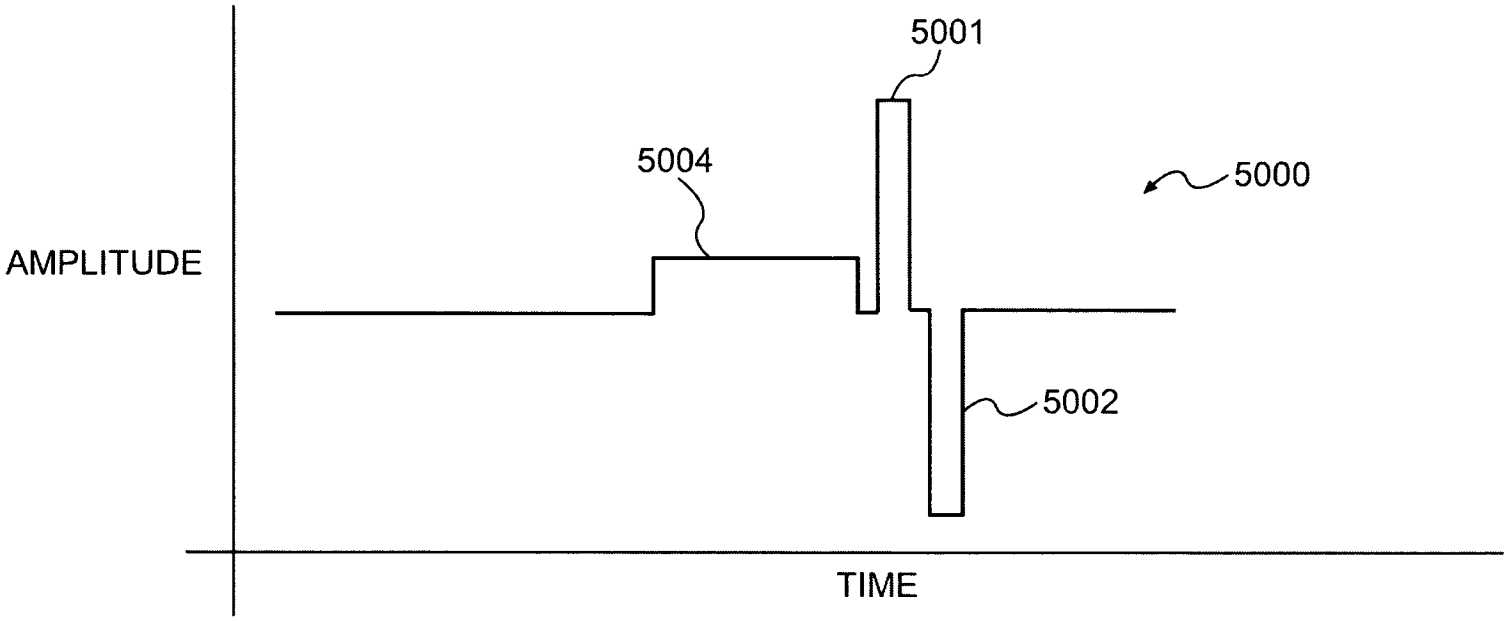
FIG. 50B illustrates an exemplary stimulation waveform.

Turning now to FIG. 50B, there is depicted an exemplary stimulation pulse waveform 5000 that may be emitted from an INS in accordance with the principles of the present disclosure. Typically, exemplary stimulation pulse waveform 5000 may include a square wave pulse train having one or more square wave pulses 5001 of approximately 1 to 3 volts in amplitude, a duration of approximately 100 ms, and a frequency of approximately 30 Hz, assuming a 1000 ohm impedance at the electrodes and a constant current or voltage.

In some embodiments, exemplary stimulation pulse waveform 5000 may include a bi-phasic charge balanced waveform square pulses 5001 and 5002, as depicted in FIG. 50B. Square pulse 5002 may be included in waveform 5000 to, among other things, promote efficient stimulation and/or mitigate electrode corrosion. However, square pulse 5002 may be excluded from waveform 5000 as desired. Furthermore, although the depicted exemplary waveform 5000 includes square pulse 5002 that exactly balances the stimulation wave pulse 5001, in certain circumstances, square pulse 5002 may not exactly balance the stimulation wave pulse 5001, and may not be a square pulse.

In some embodiments, exemplary stimulation pulse waveform 5000 may include the delivery of a low amplitude (e.g., below the stimulation threshold), long duration, pre-stimulation pulse 5004. The pre-stimulation pulse 5004 may include any suitable low amplitude, long duration pulse, and may be provided approximately 0.5 ms before the delivery of a first stimulation pulse 5001.

Pre-stimulation pulse 5004 may facilitate selectively stimulating certain fibers of a nerve, such as, for example, the hypoglossal nerve or the superior laryngeal nerve. In particular, when stimulating the hypoglossal nerve, the presence of a pre-stimulation pulse, such as, for example, pulse 5004, before a stimulation pulse (e.g., the bi-phasic stimulation pulse 5001 depicted in FIG. 50B) may serve to saturate the large diameter fibers of the nerve so as to allow the stimulation pulse 5001 to only affect (e.g., stimulate) the smaller diameter fibers of the nerve. In circumstances where a nerve (e.g., the hypoglossal nerve) may be stimulated for extended periods of time, a pre-stimulation pulse 5004 may be selectively introduced to waveform 5000, so as to permit selective switching between stimulating the large and small diameter fibers of the nerve, in order to reduce muscle fatigue. Similarly, in situations where OSA may be treated by stimulating the superior laryngeal nerve to open the upper airway through a reflex mechanism, the presence of pre-stimulation pulse 5004 may serve to saturate the larger diameter efferent fibers so as to allow the stimulation pulse 5001 to only affect the smaller diameter afferent fibers of the nerve.

Description of External (Partially Implanted) System

Figure 51B:
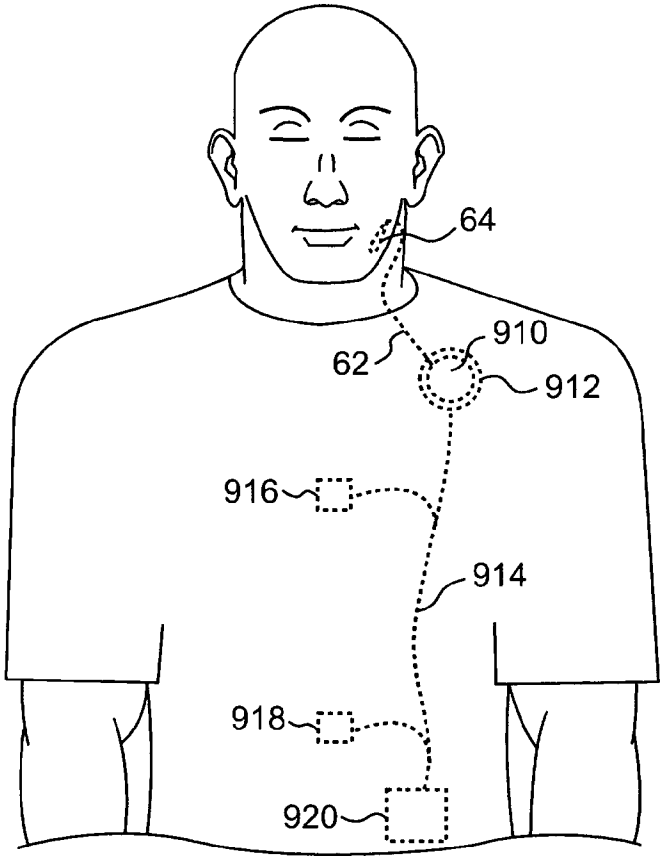
FIGS. 51A-51M are schematic illustrations of various external (partially implanted) neurostimulation systems for treating obstructive sleep apnea.
Figure 51A:
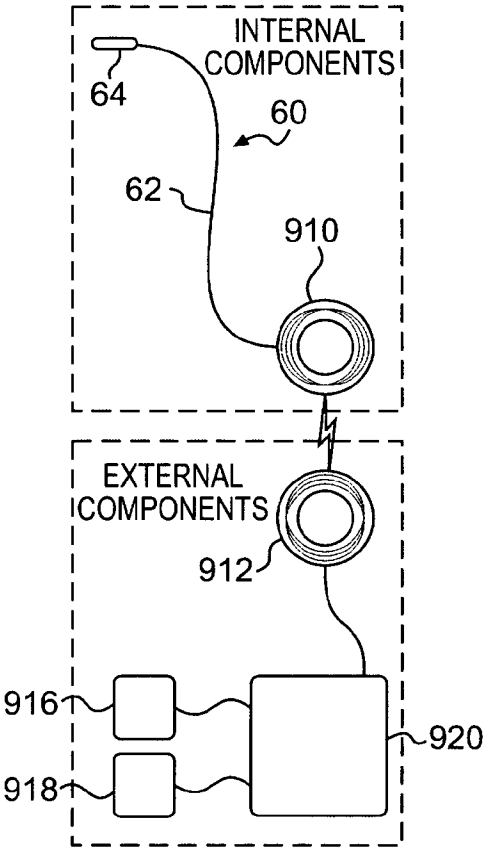

With reference to FIGS. 51A and 51B, an example of an external neurostimulator system inductively coupled to an internal/implanted receiver is shown schematically. The system includes internal/implanted components comprising a receiver coil 910, a stimulator lead 60 (including lead body 62, proximal connector and distal nerve electrode 64). Any of the stimulation lead designs and external sensor designs described in more detail herein may be employed in this generically illustrated system, with modifications to position, orientation, arrangement, integration, etc. made as dictated by the particular embodiment employed. The system also includes external components comprising a transmit coil 912 (inductively linked to receiver coil 910 when in use), an external neurostimulator or external pulse generator 920 (ENS or EPG), and one or more external respiratory sensors 916/918.

As illustrated, the receiver coil 910 is implanted in a subcutaneous pocket in the pectoral region and the stimulation lead body 62 is tunneled subcutaneously along the platysma in the neck region. The nerve electrode 64 is attached to the hypoglossal nerve in the submandibular region.

The transmitter coil 912 may be held in close proximity to the receiver coil 910 by any suitable means such as an adhesive patch, a belt or strap, or an article of clothing (e.g., shirt, vest, brazier, etc.) donned by the patient. For purposes of illustration, the transmitter coil 912 is shown carried by a t-shirt 915, which also serves to carry the ENS 920 and respiratory sensor(s) 916, 918. The ENS 920 may be positioned adjacent the waist or abdomen away from the ribs to avoid discomfort while sleeping. The respiratory sensor(s) 916, 918 may be positioned as a function of the parameter being measured, and in this embodiment, the sensors are positioned to measure abdominal and thoracic/chest expansion which are indicative of respiratory effort, a surrogate measure for respiration. The external components may be interconnected by cables 914 carried by the shirt or by wireless means. The shirt may incorporate recloseable pockets for the external components and the components may be disconnected from the cables such that the reusable components may be removed from the garment which may be disposed or washed.

The transmitting coil antenna 912 and the receiving coil antenna 910 may comprise air core wire coils with matched wind diameters, number of wire turns and wire gauge. The wire coils may be disposed in a disc-shaped hermetic enclosure comprising a material that does not attenuate the inductive link, such as a polymeric or ceramic material. The transmitting coil 912 and the receiving coil 910 may be arranged in a co-axial and parallel fashion for coupling efficiency, but are shown side-by-side for sake of illustration only.

Because power is supplied to the internal components via an inductive link, the internal components may be chronically implanted without the need for replacement of an implanted battery, which would otherwise require re-operation. Examples of inductively powered implantable stimulators are described in U.S. Pat. No. 6,609,031 to Law et al., U.S. Pat. No. 4,612,934 to Borkan, and U.S. Pat. No. 3,893,463 to Williams, the entire disclosures of which are incorporated herein by reference.

With reference to FIGS. 51C-51G, alternative embodiments of an external neurostimulator system inductively coupled to an internal/implanted receiver are schematically shown. These embodiments are similar to the external embodiment described above, with a few exceptions. In these embodiments, the receiver coil 910 is implanted in a positioned proximate the implanted stimulation lead body 62 and nerve electrode 64. The receiver coil 910 may be positioned in a subcutaneous pocket on the platysma muscle under the mandible, with the lead body 62 tunneling a short distance to the nerve electrode 64 attached to the hypoglossal nerve. Also in these embodiments, the respiratory sensor(s) 916/918 may be integrated into the ENS 920 and attached to a conventional respiratory belt 922 to measure respiratory effort about the abdomen and/or chest. An external cable 914 connects the ENS 920 to the transmitter coil 912.

Figure 51D:
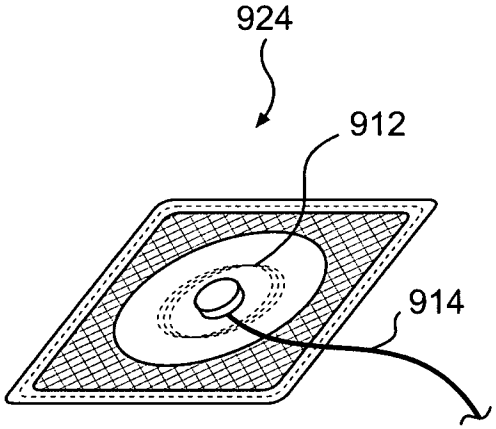
Figure 51C:
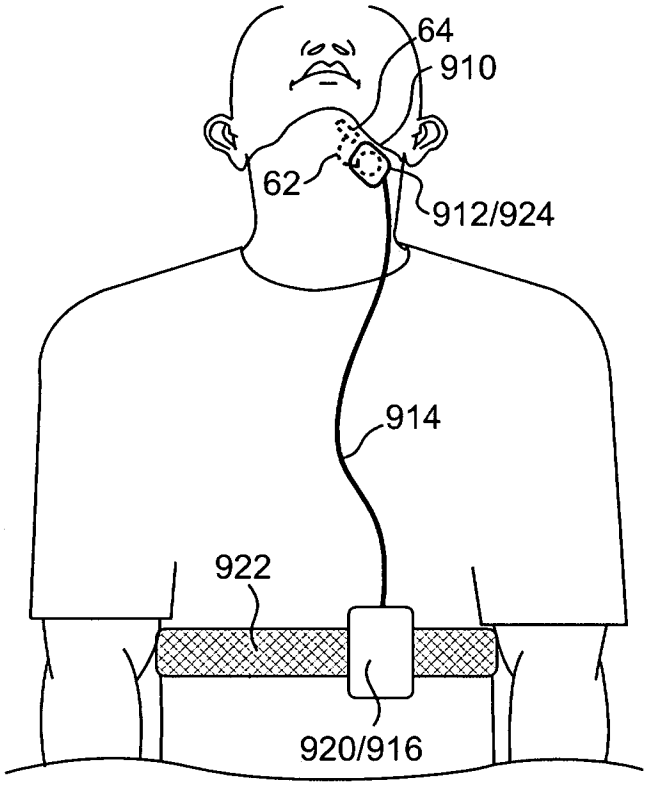
Figure 51F:
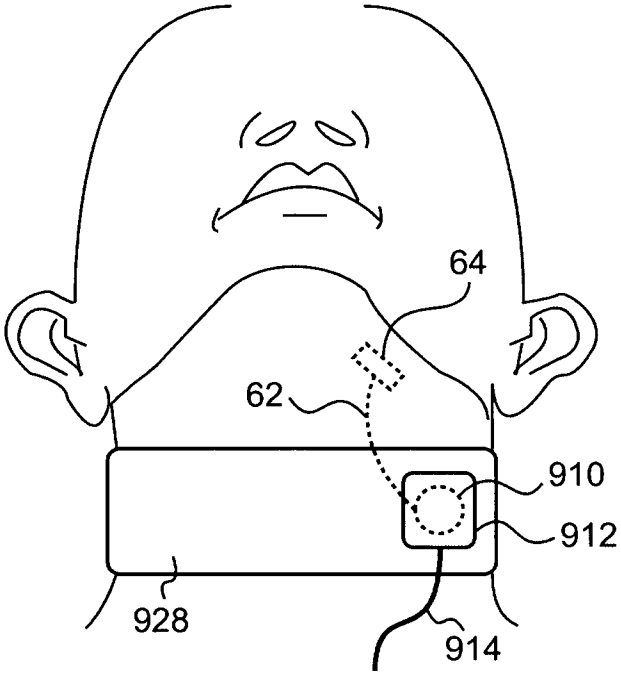
Figure 51E:
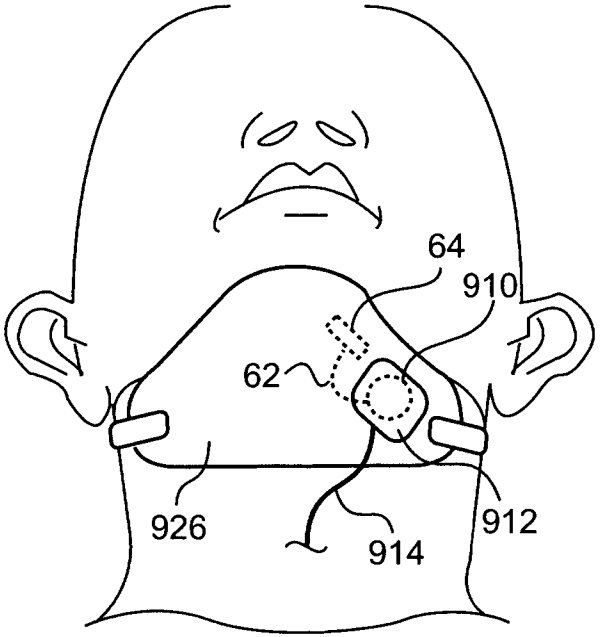
Figure 51G:
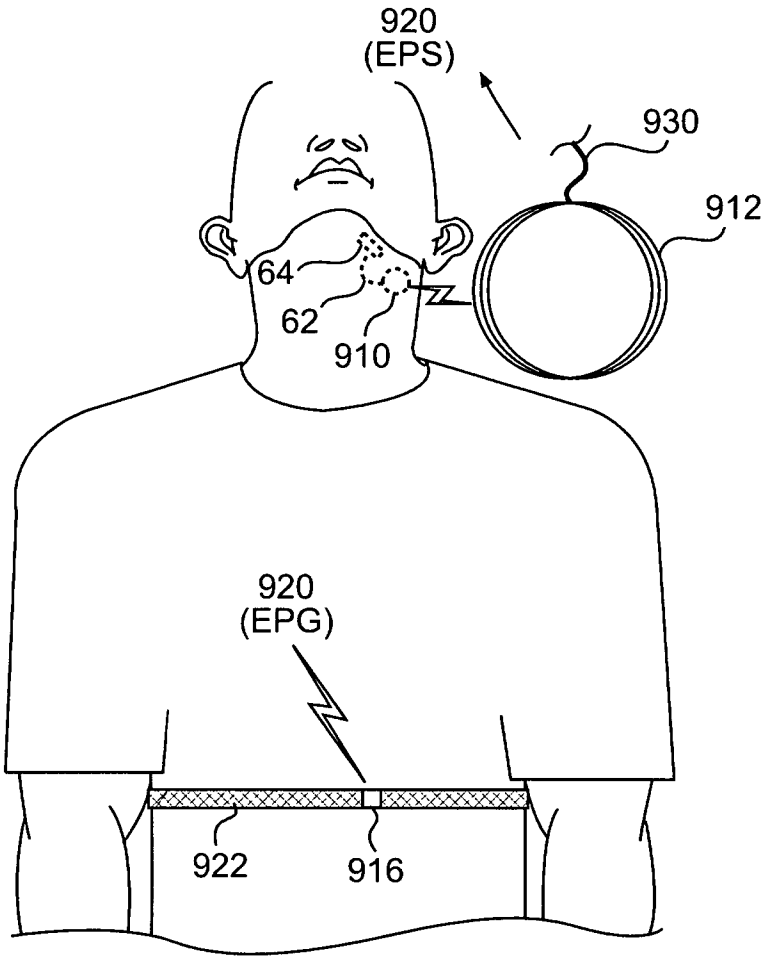

In the embodiment of FIG. 51D, the transmitter coil 912 is carried by an adhesive patch 924 that may be placed on the skin adjacent the receiver coil 910 under the mandible. In the embodiment of FIG. 51E, the transmitter coil 912 is carried by an under-chin strap 926 worn by the patient to maintain the position of the transmitter coil 912 adjacent the receiver coil 910 under the mandible. In the embodiment of FIG. 51F, the receiver coil 910 may be positioned in a subcutaneous pocket on the platysma muscle in the neck, with the lead body 122 tunneling a slightly greater distance. The transmitter coil 912 may be carried by a neck strap 928 worn by the patient to maintain the position of the transmitter coil 912 adjacent the receiver coil 910 in the neck.

With reference to FIGS. 51G-51K, additional alternative embodiments of an external neurostimulator system inductively coupled to an internal/implanted receiver are schematically shown. These embodiments are similar to the external embodiment described above, with a few exceptions. As above, the receiver coil 910 may be positioned in a subcutaneous pocket on the platysma muscle under the mandible, with the lead body 62 tunneling a short distance to the nerve electrode 64 attached to the hypoglossal nerve. However, in these embodiments, the ENS 920 (not shown) may be located remote from the patient such as on the night stand or headboard adjacent the bed. The ENS 920 may be connected via a cable 930 to a large transmitter coil 912 that is inductively coupled to the receiver coil 910. The respiratory sensor 916 may comprise a conventional respiratory belt 922 sensor to measure respiratory effort about the abdomen and/or chest, and sensor signals may be wirelessly transmitted to the remote ENS 920. As compared to other embodiments described above, the transmitter coil 912 is not carried by the patient, but rather resides in a proximate carrier such as a bed pillow, under a mattress, on a headboard, or in a neck pillow, for example. Because the transmitter coil 912 is not as proximate the receiver coil as in the embodiments described above, the transmitter coil may be driven by a high powered oscillator capable of generating large electromagnetic fields.

Figure 51I:
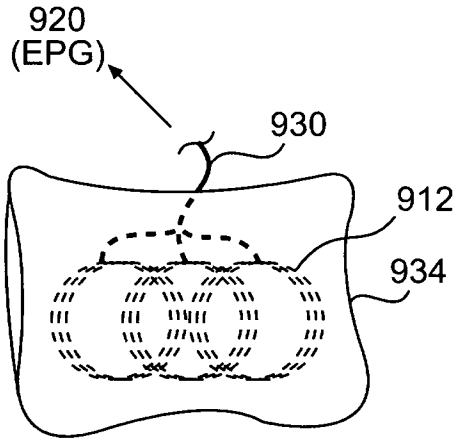
Figure 51J:
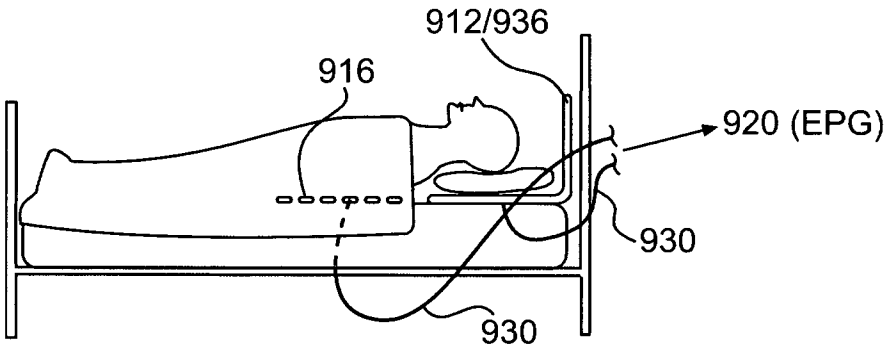
Figure 51H:
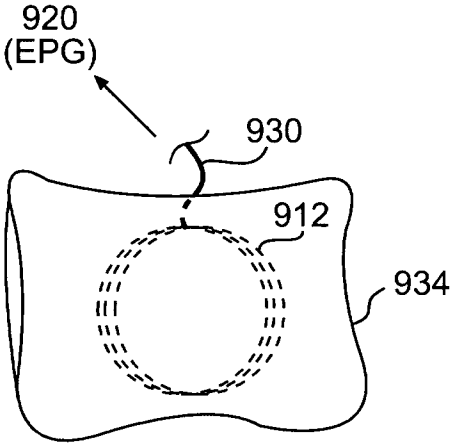
Figure 51K:
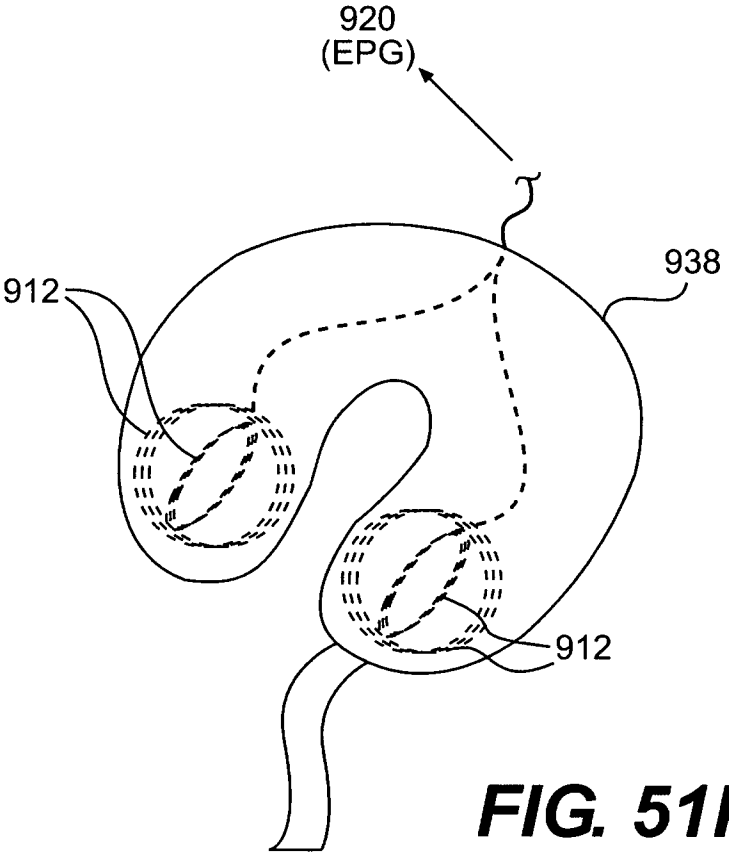
Figure 51M:
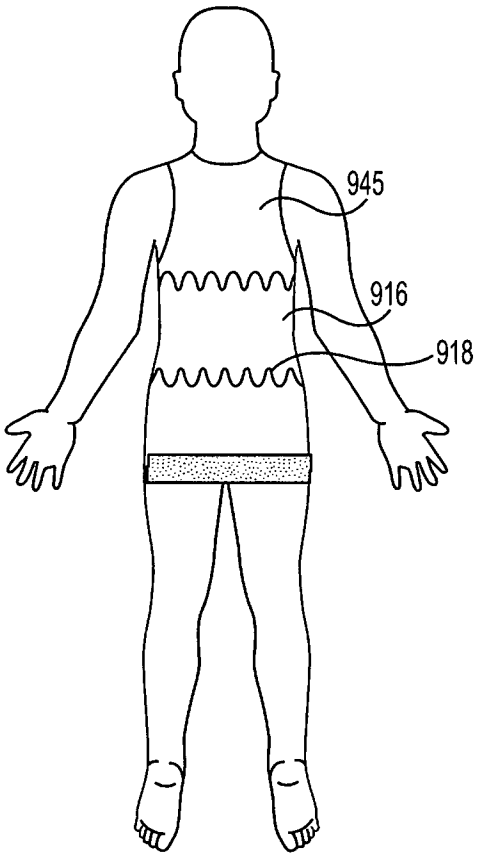

As shown in FIG. 51H, the transmitter coil 912 may be disposed in a bed pillow 934. As shown in FIG. 51I, the transmitter coil 912 may comprise a series of overlapping coils disposed in a bed pillow 934 that are simultaneously driven or selectively driven to maximize energy transfer efficiency as a function of changes in body position of the patient corresponding to changes in position of the receiver coil 910. This overlapping transmitter coil arrangement may also be applied to other embodiments such as those described previously wherein the transmitter coil is carried by an article donned by the patient. In FIG. 51J, two or more transmitter coils 912 are carried by orthogonal plates 936 arranged as shown to create orthogonal electromagnetic fields, thereby increasing energy transfer efficiency to compensate for movement of the patient corresponding to changes in position of the receiver coil 910. FIG. 51J also illustrates a non-contact respiratory sensor 916 arrangement as utilized for detecting sudden infant death syndrome (SIDS). As shown in FIG. 51K, two orthogonal transmitter coils 912 are located on each side of a neck pillow 938, which is particularly beneficial for bilateral stimulation wherein a receiver coil 910 may be located on either side of the neck.

Figure 51L:
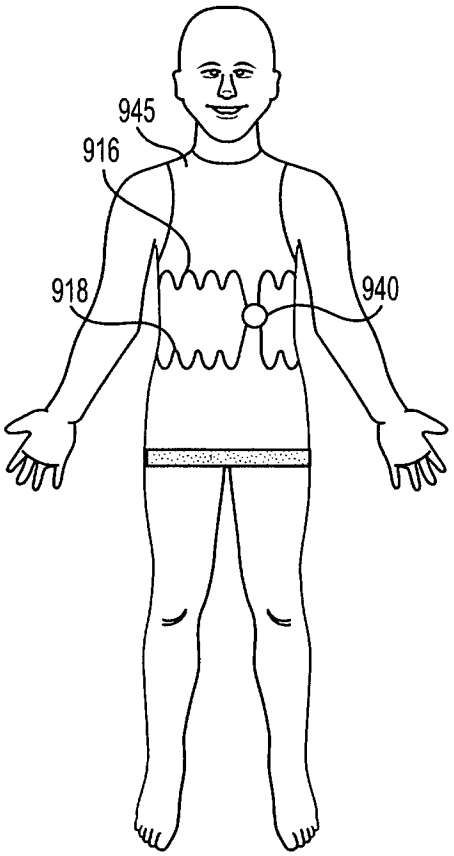

With reference to FIGS. 51L (front view) and 51M (rear view), external respiratory effort sensors 916/918 are schematically shown incorporated into a stretchable garment 945 donned by the patient. The sensors 916/918 generally include one or more inductive transducers and an electronics module 942. The inductive transducers may comprise one or more shaped (e.g., zig-zag or sinusoidal) stranded wires to accommodate stretching and may be carried by (e.g., sewn into) the garment 945 to extend around the patient's abdomen and chest, for example. As the patient breathes, the patient's chest and/or abdomen expands and contracts, thus changing the cross-sectional area of the shape (i.e., hoop) formed by the wire resulting in changes in inductance. The electronics module may include an oscillator (LC) circuit with the inductive transducer (L) comprising a part of the circuit. Changes in frequency of the oscillator correspond to changes in inductance of the shaped wires which correlate to respiratory effort. The electronics module may be integrated with an ENS (not shown) or connected to an ENS via a wired or wireless link for triggering stimulus as described previously.

The garment 945 may include features to minimize movement artifact and accommodate various body shapes. For example, the garment 945 may be form-fitting and may be sleeveless (e.g., vest) to reduce sensor artifacts due to arm movement. Further, the garment 945 may be tailored to fit over the patient's hips with a bottom elastic band which helps pull the garment down and keep the sensors 916/918 in the proper location.

Description of a Specific External (Partially Implanted) Embodiment

With reference to FIGS. 52A-52G a specific embodiment utilizing an external neurostimulator system inductively coupled to an internal/implanted receiver is schematically shown. With initial reference to FIG. 52A, the illustrated hypoglossal nerve stimulator includes several major components, namely: an implantable electronics unit that derives power from an external power source; a stimulation delivery lead that is anchored to the nerve or adjacent to the nerve and provides electrical connection between the electronics unit and the nerve, an external (non-implanted) power transmitting device that is inductively coupled with the implant to convey a powering signal and control signals; a power source for the external device that is either small and integrated into the body-worn coil and transmitter or is wired to the transmitter and transmit induction coil and can be powered by primary or secondary batteries or can be line powered; and a respiratory sensor such as those described previously.

These components may be configured to provide immediate or delayed activation of respiration controlled stimulation. Initiation of the stimulation regimen may be by means of activation of an input switch. Visual confirmation can be by an LED that shows adequate signal coupling and that the system is operating and is or will be applying stimulation. As a means of controlling gentleness of stimulation onset and removal, either pulse width ramping of a constant amplitude stimulation signal can be commanded or amplitude of a constant pulse width stimulation signal or a combination thereof can be performed.

The electrical stimulation signal is delivered by the stimulation lead that is connected to the implanted nerve stimulator and attached to or in proximity of a nerve. The implanted electronics unit receives power through a magnetically coupled inductive link. The operating carrier frequency may be high enough to ensure that several cycles (at least 10) of the carrier comprise the output pulse. The operating frequency may be in a band of frequencies approved by governmental agencies for use with medical instruments operating at high transmitted radio frequency (RF) power (at least 100 milliwatts). For example, the operating frequency may be 1.8 MHz, but 13.56 MHz is also a good candidate since it is in the ISM (Industrial/Scientific/Medical) band. The non-implanted (external) transmitter device integrates respiration interface, waveform generation logic and transmit power driver to drive an induction coil. The power driver generates an oscillating signal that drives the transmitter induction coil and is designed to directly drive a coil of coil reactance that is high enough or can be resonated in combination with a capacitor. Power can come from a high internal voltage that is used to directly drive the transmit induction coil or power can come from a low voltage source applied to a tap point on the induction coil.

With reference to FIGS. 52B-52E, the waveform generation logic may be used to modulate the carrier in such a way that narrow gaps in the carrier correspond to narrow stimulation pulses. When stimulator pulses are not needed, interruptions to the carrier are stopped but the carrier is maintained to ensure that power is immediately available within the stimulator upon demand. Presence or absence of electrical nerve stimulation is based on respiration or surrogates thereof. The transmitted signal may comprise a carrier of about 1.8 MHz. To control the implanted electronics unit to generate individual nerve stimulation pulses, the carrier signal is interrupted. The duration of the interruption is about equal to the duration of the output stimulation pulse. The stimulation pulses may be about 110 microseconds in duration and are repeated at a rate of approximately 33 per second. In addition, multiple pulses can be transmitted to logic within the implant to control stimulation pulse amplitude, pulse width, polarity, frequency and structure if needed. Further, onset and removal of stimulation can be graded to manage patient discomfort from abruptness. Grading may comprise pulse width control, signal amplitude control or a combination thereof.

An indicator (not shown) may be used to show when the transmitter is properly positioned over the implant. The indicator may be a part of the transmitter or by way of communication with the transmitter, or a part of related patient viewable equipment. Determination of proper position may be accomplished by monitoring the transmitter power output loading relative to the unloaded power level. Alternatively, the implant receive signal level transmitted back by a transmitter within the implant may be monitored to determine proper positioning. Or, the implant receive signal level that is communicated back to the transmitter by momentarily changing the loading properties presented to the transmitter, such a shorting out the receive coil may be monitored to determine proper positioning. Such communication may be by means of modulation such as pulse presence, pulse width, pulse-to-pulse interval, multi-pulse coding.

The transmitter may be powered by an internal primary power source that is used until it is exhausted, a rechargeable power source or a power source wired to a base unit. In the case of the wired base unit, power can be supplied by any combination of battery or line power.

The respiration interface may transduce sensed respiratory activity to an on-off control signal for the transmitter. Onset of stimulation may be approximately correlated slightly in advance of inspiration and lasts through the end of inspiration, or onset may be based on anticipation of the next respiration cycle from the prior respiration cycle or cycles. The respiration sensor may comprise any one or combination of devices capable of detecting inspiration. The following are examples: one or more chest straps; an impedance sensor; an electromiographical measurement of the muscles involved with respiration; a microphone that is worn or is in proximity to the patients' face; a flow sensor; a pressure sensor in combination with a mask to measure flow; and a temperature sensor to detect the difference between cool inspired air versus warmed expired air.

Figure 52A:
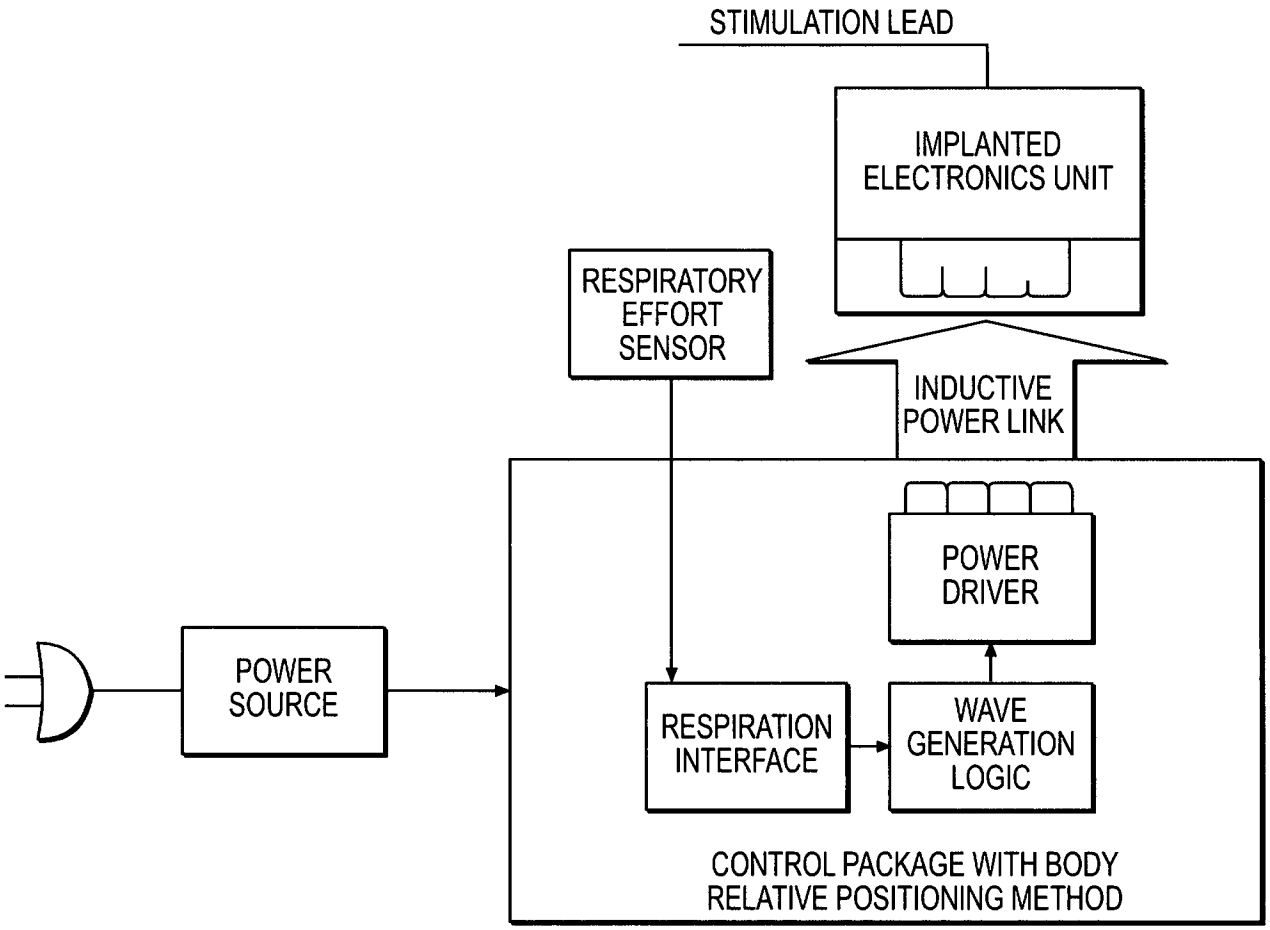
FIGS. 52A-52G are schematic illustrations of a specific embodiment of an external (partially implanted) neurostimulation system.
Figure 52B:
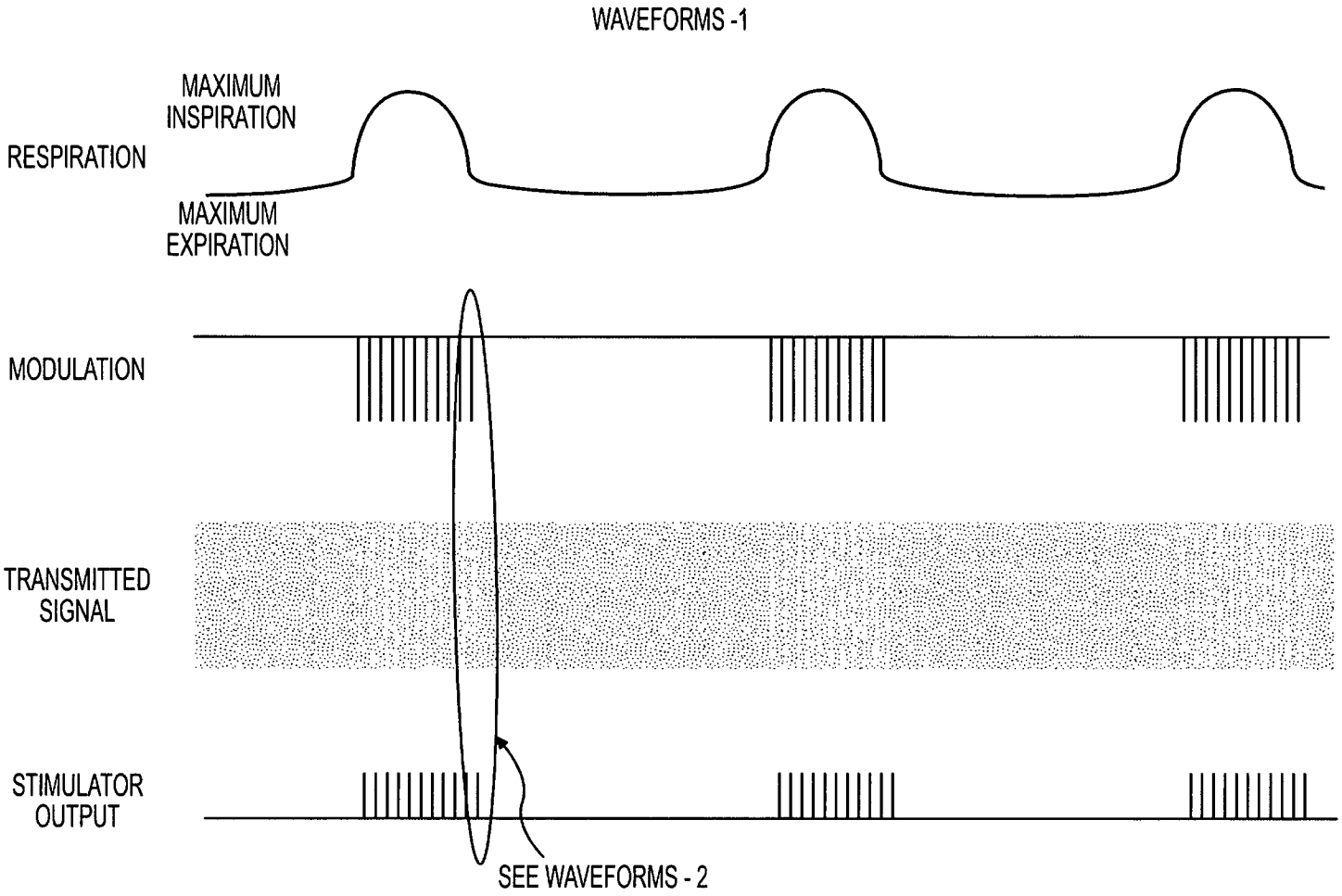
Figure 52C:
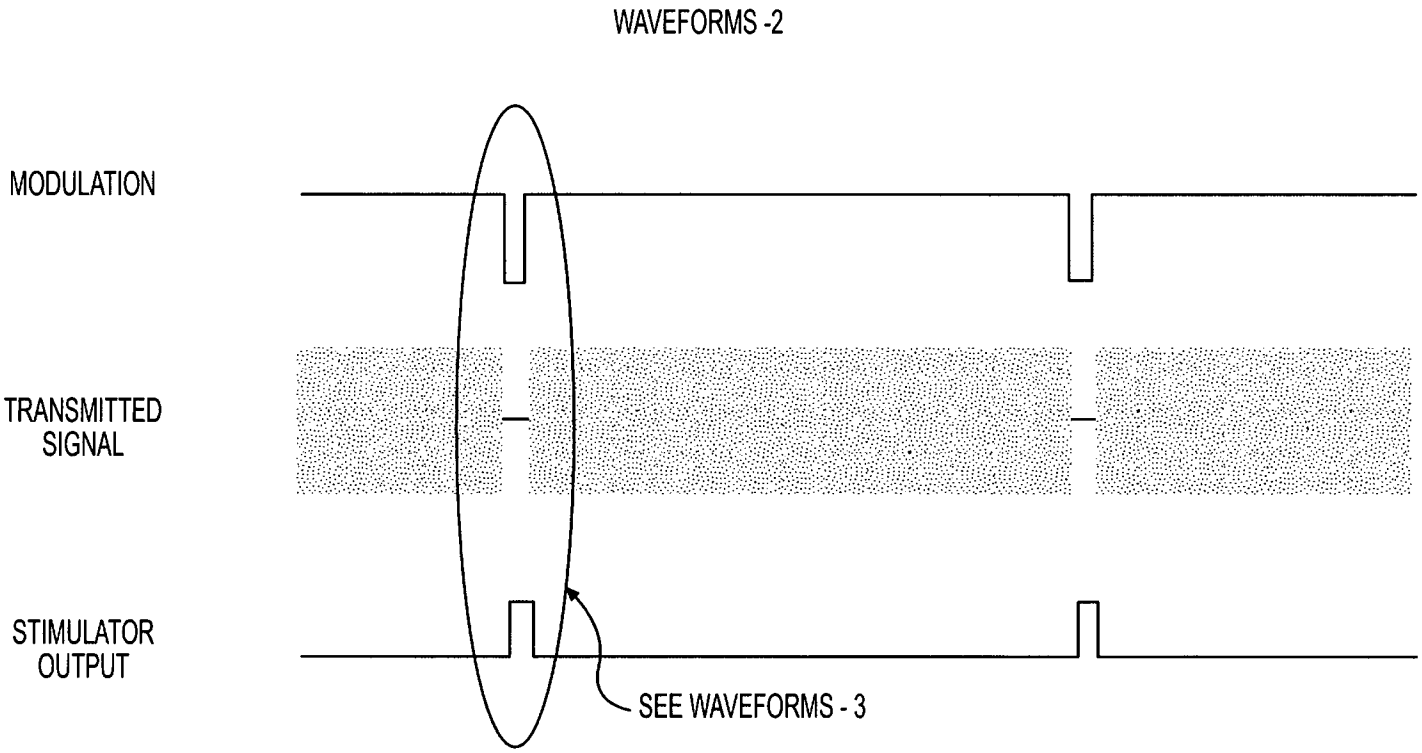
Figure 52D:
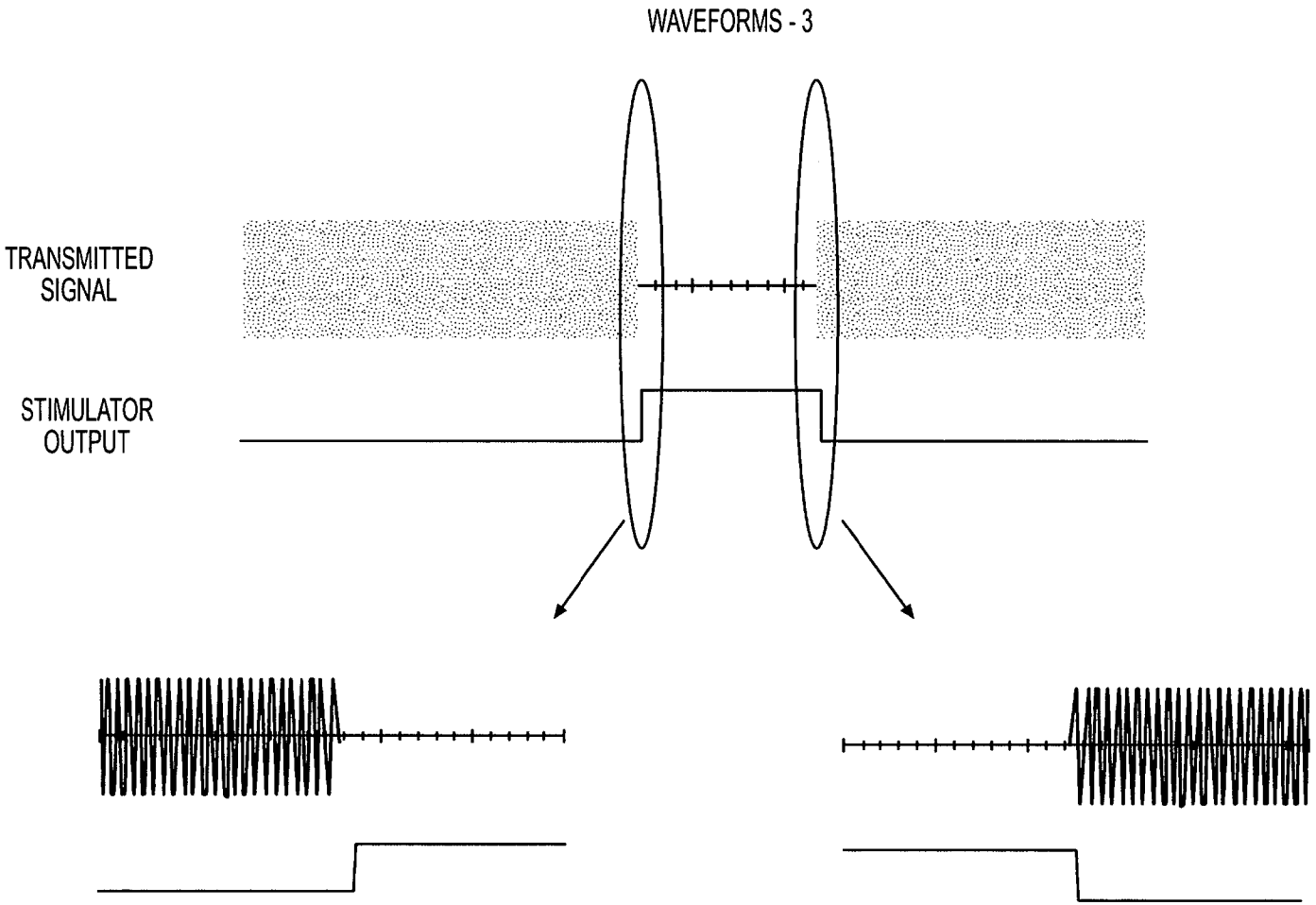
Figure 52E:
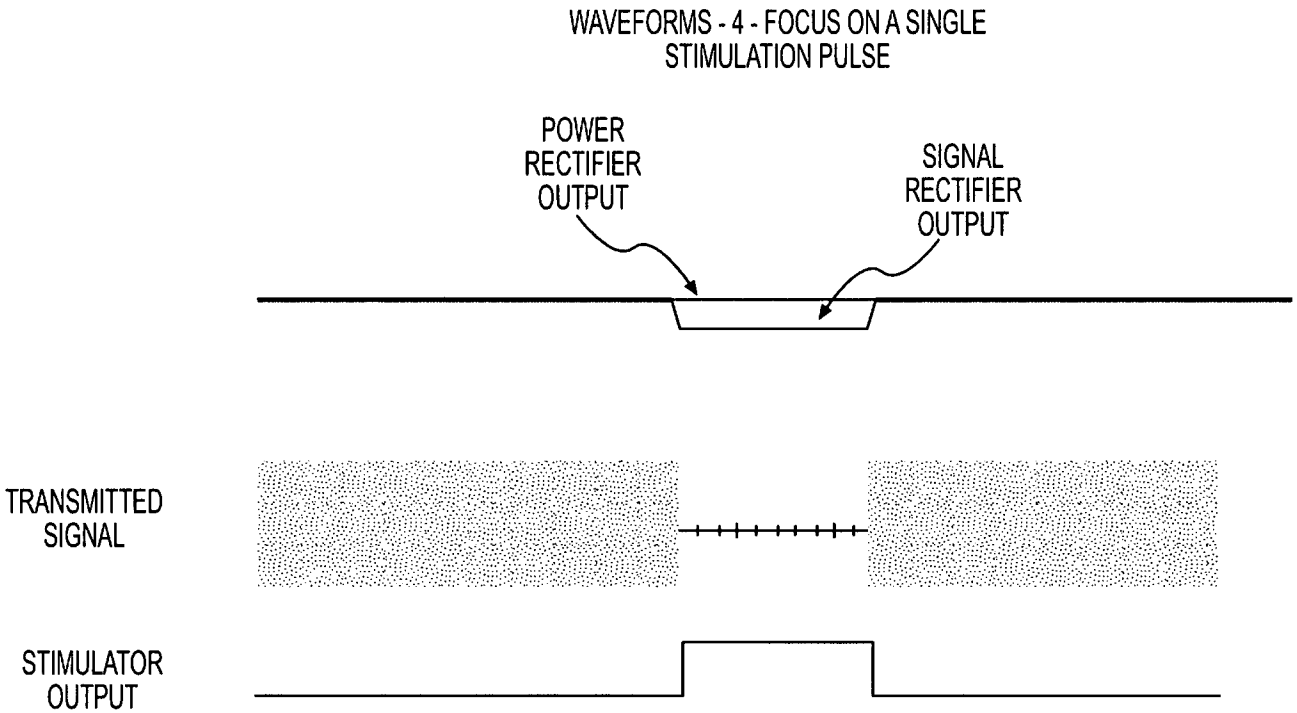
Figure 52F:
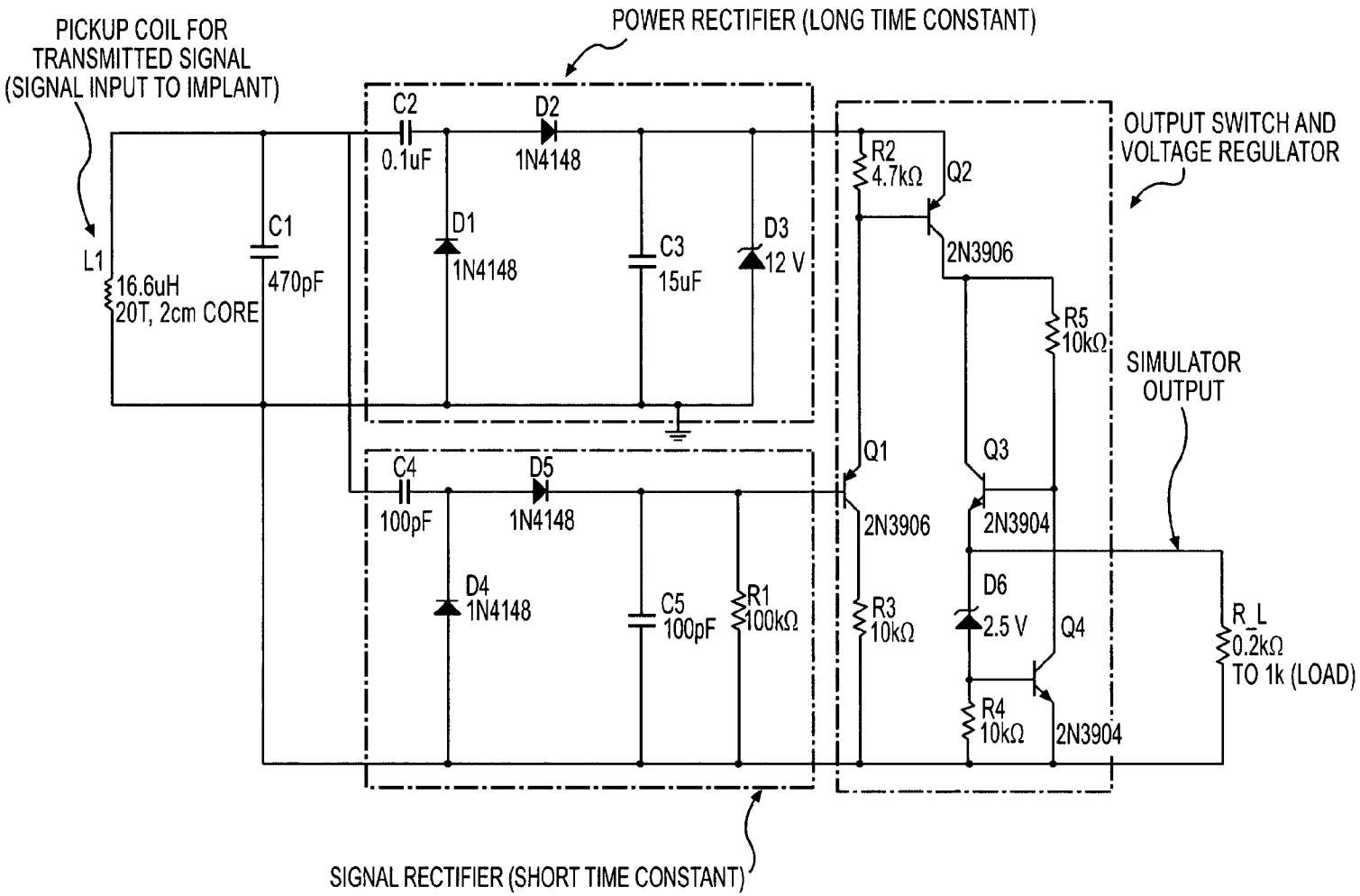

The circuit illustrated in FIG. 52F may be used for the implanted electronics unit. There are five main subsystems within the design: a receive coil, a power rectifier, a signal rectifier, an output switch and an output regulator. The signal from the inductive link is received by L1 which is resonated in combination with C1 and is delivered to both the power and signal rectifiers. Good coupling consistent with low transmitter coil drive occurs when the transmit coil diameter is equal to the receive coil diameter. When coil sizes are matched, coupling degrades quickly when the coil separation is about one coil diameter. A large transmit coil diameter will reduce the criticality of small coil spacing and coil-to-coil coaxial alignment for maximum signal transfer at the cost of requiring more input drive power.

The power rectifier may comprise a voltage doubler design to take maximum advantage of lower signal levels when the transmit to receive coil spacing is large. The voltage doubler operates with an input AC voltage that swing negative (below ground potential) causes D1 to conduct and forces C2 to the maximum negative peak potential (minus a diode drop). As the input AC voltage swings away from maximum negative, the node of C2, D1, D2 moves from a diode drop below ground to a diode drop above ground, forward biasing diode D2. Further upswing of the input AC voltage causes charge accumulated on C2 to be transferred through D2 to C3 and to "pump up" the voltage on C3 on successive AC voltage cycles. To limit the voltage developed across C3 so that an over-voltage condition will not cause damage, and Zener diode, D3 shunts C3. Voltage limiting imposed by D3 also limits the output of the signal rectifier section. The power rectifier has a long time constant, compared to the signal rectifier section, of about 10 milliseconds.

The signal rectifier section may be similar in topology to the power rectifier except that time constants are much shorter—on the order of 10 microseconds—to respond with good fidelity to drop-outs in the transmitted signal. There is an output load of 100K (R1) that imposes a controlled discharge time constant. Output of the signal rectifier is used to switch Q1, in the output switching section, on and off.

The output switching section compares the potential of C3 to that across C5 by means of the Q1, Q2 combination. When there is a gap in the transmitted signal, the voltage across C5 falls very rapidly in comparison with C3. When the voltage difference between C5 and C3 is about 1.4 volts, Q1 and Q2 turn on. Q1 and Q2 in combination form a high gain amplifier stage that provides for rapid output switching time. R3 is intended to limit the drive current supplied to Q2, and R2 aids in discharging the base of Q2 to improve the turn-off time.

In the output regulator section, the available power rectifier voltage is usually limited by Zener diode D3. When the coil separation becomes suboptimal or too large the power rectifier output voltage will be come variable as will the switched voltage available at the collector of Q2. For proper nerve stimulation, it may be necessary to regulate the (either) high or variable available voltage to an appropriate level. An acceptable level is about 3 volts peak. A switched voltage is applied to Zener diode D6 through emitter follower Q3 and bias resistor R5. When the switched voltage rises to a level where D6 conducts and develops about 0.6 volts across R4 and the base-emitter junction of Q4, Q4 conducts. o Increased conduction of Q4 is used to remove bias from Q3 through negative feedback. Since the level of conduction of Q4 is a very sensitive function of base to emitter voltage, Q4 provides substantial amplification of small variations in D6 current flow and therefore bias voltage level. The overall result is to regulate the bias voltage applied to Zener diode D6. Output is taken from the junction of the emitter of Q3 and D6 since that point is well regulated by the combination of Zener diode breakdown voltage combined with the amplification provided by Q4. In addition to good voltage regulation a the junction of the emitter of Q3 and D6, the output is very tolerant of load current demand since the conductivity of Q3 will be changed by shifts in the operating point of Q4. Due to amplification by Q3 and Q4, the circuit can drive a range of load resistances. Tolerable load resistances above 1000 ohms and less than 200 ohms. The regulator has the advantage of delivering only the current needed to operate the load while consuming only moderate bias current. Further, bias current is only drawn during delivery of the stimulation pulse which drops to zero when no stimulation is delivered. As a comparison, a simple series resistance biased Zener diode requires enough excess current to deliver a stimulation pulse and still maintain adequate Zener bias. As a further comparison, conventional integrated circuit regulators, such as three terminal regulators are not designed to well regulate and respond quickly to short input pulses. Experiment shows that three-terminal regulators exhibit significant output overshoot and ramp-up time upon application of an input pulse. This can be addressed by applying a constant bias to a regulator circuit or even moving the regulator before the output switching stage but this will be at the cost of constant current drain and subsequently reduced range.

The implanted electronics unit may be used to manage the loss of control and power signals. With this design, more than enough stimulation power is stored in C3 to supply multiple delivered stimulation pulses. This design is intended to ensure that the voltage drop is minimal on any individual pulse. One of the consequences is that when signal is lost, the circuit treats the condition as a commanded delivery of stimulation and will apply a single, extended duration, energy pulse until the full stored capacity of C3 is empty. An alternative method may be to use an indirect control modulation to command delivery of a nerve stimulation pulse through logic and provide for a time-out that limits pulse duration.

Figure 52G:
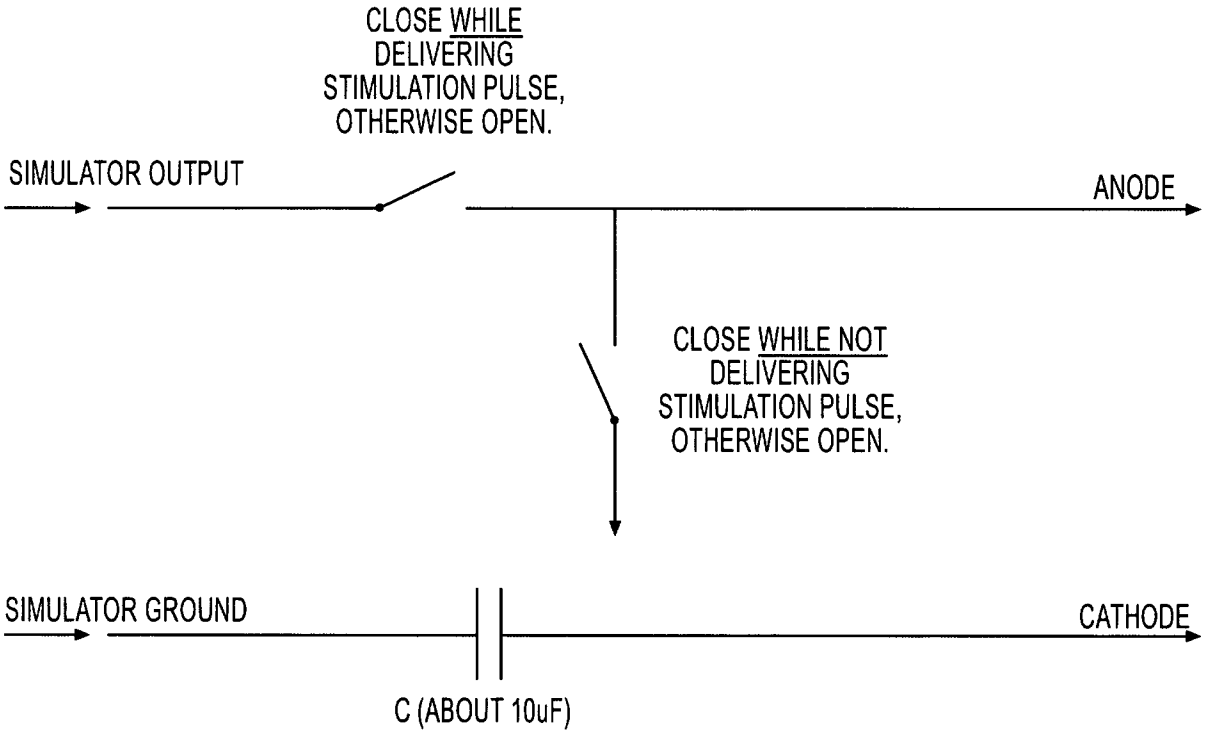

To stimulate tissue, a modified output stage may be used to mitigate electrode corrosion and establish balanced charging. The output stage is illustrated in FIG. 52G and includes a capacitive coupling between the ground side of the stimulator and tissue interface in addition to a shunt from the active electrode to circuit ground for re-zeroing the output coupling capacitor when an output pulse is not being actively delivered.

Description of Alternative Screening Methods

Screening generally refers to selecting patients that will be responsive to the therapy, namely neurostimulation of the upper airway dilator nerves and/or muscles such as the hypoglossal nerve that innervates the genioglossus. Screening may be based on a number of different factors including level of obstruction and critical collapse pressure (Pcrit) of the upper airway, for example. Because stimulation of the hypoglossal nerve affects the genioglossus (base of tongue) as well as other muscles, OSA patients with obstruction at the level of the tongue base and OSA patients with obstruction at the level of the palate and tongue base (collectively patients with tongue base involvement) may be selected. Because stimulation of the hypoglossal nerve affects upper airway collapsibility, OSA patients with airways that have a low critical collapse pressure (e.g., Pcrit of less than about 5 cm water) may be selected. Pcrit may be measured using pressure transducers in the upper airway and measuring the pressure just prior to an apnea event (airway collapse). Alternatively, a surrogate for Pcrit such as CPAP pressure may be used. In this alternative, the lowest CPAP pressure at which apnea events are mitigated may correlate to Pcrit.

The critical collapse pressure (Pcrit) may be defined as the pressure at which the upper airway collapses and limits flow to a maximal level. Thus, Pcrit is a measure of airway collapsibility and depends on the stability of the walls defining the upper airway as well as the surrounding pressure. Pcrit may be more accurately defined as the pressure inside the upper airway at the onset of flow limitation when the upper airway collapses. Pcrit may be expressed as:

$$Pcrit=Pin-Pout$$

where

Pin=pressure inside the upper airway at the moment of airway collapse; and

Pout=pressure outside the upper airway (e.g., atmospheric pressure).

Other screening methods and tools may be employed as well. For example, screening may be accomplished through acute testing of tongue protruder muscle contraction using percutaneous fine wire electrodes inserted into the genioglossus muscle, delivering stimulus and measuring one or more of several variables including the amount of change in critical opening pressure, the amount of change in airway caliber, the displacement of the tongue base, and/or the retraction force of the tongue (as measured with a displacement and/or force gauge). For example, a device similar to a CPAP machine can be used to seal against the face (mask) and control inlet pressure down to where the tongue and upper airway collapse and occlude during inspiration. This measurement can be repeated while the patient is receiving stimulation of the geneoglossus muscle (or other muscles involved with the patency of the upper airway). Patients may be indicated for the stimulation therapy if the difference in critical pressure (stimulated vs. non-stimulated) is above a threshold level.

Similarly, a flexible optical scope may be used to observe the upper airway, having been inserted through the mask and nasal passage. The difference in upper airway caliber between stimulation and non-stimulation may be used as an inclusion criterion for the therapy. The measurement may be taken with the inlet air pressure to the patient established at a pre-determined level below atmospheric pressure to better assess the effectiveness of the stimulation therapy.

Another screening technique involves assessing the protrusion force of the tongue upon anterior displacement or movement of the tongue with and without stimulation while the patient is supine and (possibly) sedated or asleep. A minimum increase in protrusion force while under stimulation may be a basis for patient selection.

Figure 53:
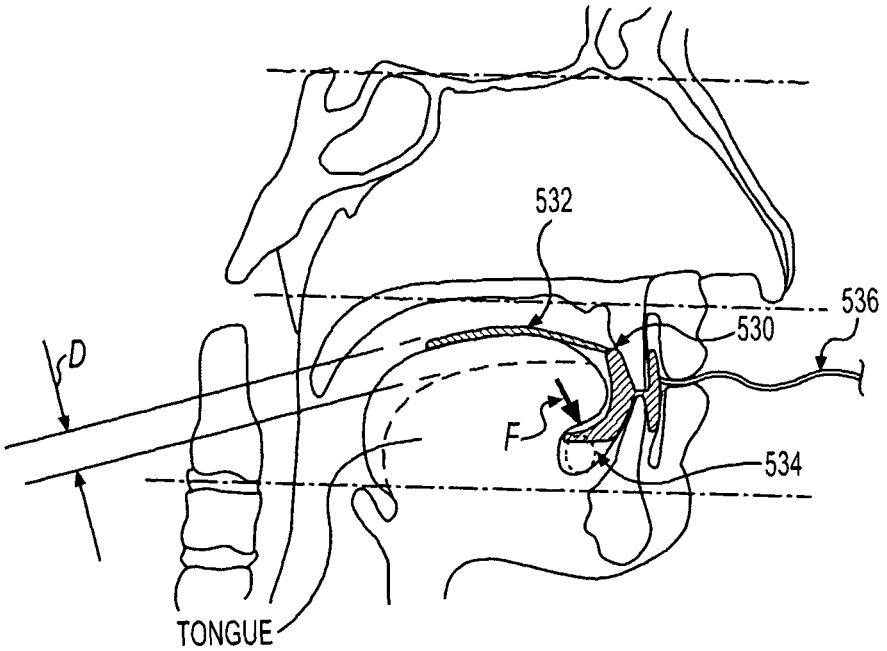
FIGS. 53-56 schematically illustrate alternative screening tools.

For example, with reference to FIG. 53, a non-invasive oral appliance 530 may be worn by the patient during a sleep study that can directly measure the protrusion force of the tongue as a basis for patient selection. The oral appliance 530 may include a displacement probe 532 for measuring tongue movement protrusion force by deflection (D). The oral appliance 530 may also include a force sensor 534 for measuring the force (F) applied by protrusion of the tongue. The sensors in the displacement probe 532 and the force sensor 534 may be connected to measurement apparatus by wires 536.

Figure 54:
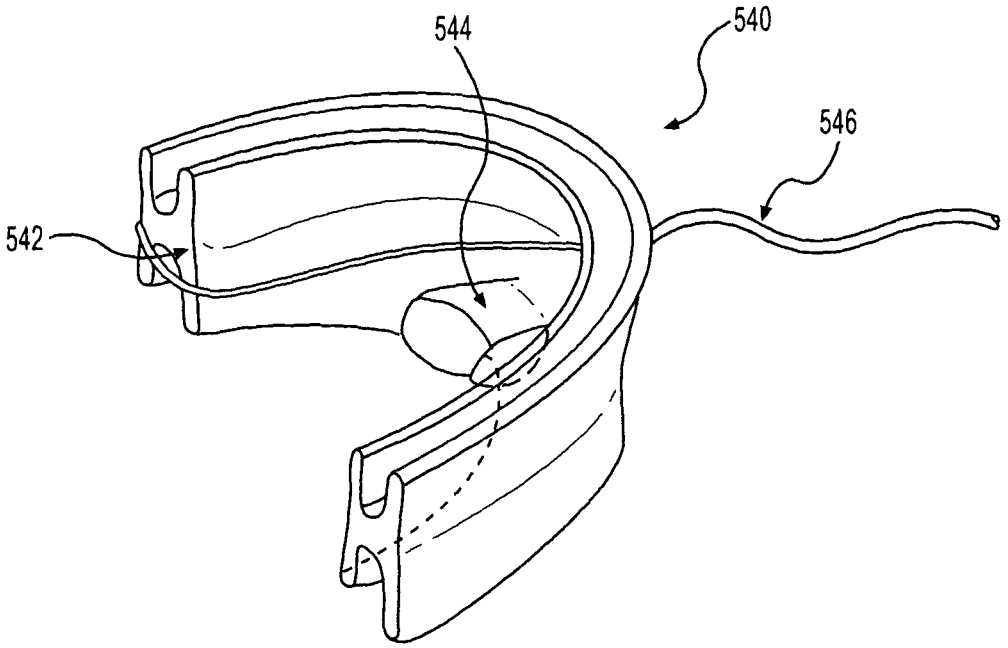

FIG. 54 illustrates another example of a non-invasive oral appliance 540 that may be worn by the patient during a sleep study to directly measure the protrusion force of the tongue as a basis for patient selection. The oral appliance 540 includes a displacement sensor 542 for measuring tongue movement and a force sensor for measuring tongue protrusion force. The displacement sensor and the force sensor may be connected to measurement apparatus by wires 546.

Oral appliances 530 and 540 could be worn during a sleep study and would measure the tongue protrusion force during (and just prior to) an apnea event when the protruder muscle tone is presumed to be inadequate to maintain upper airway patency. The protrusion force measured as the apnea is resolved by the patient will increase as the patient changes sleep state and the airway again becomes patent. The force difference may be used as a basis for patient selection.

Another screening technique involves the use of an oral appliance with sub-lingual surface electrodes contacting the base of the tongue or fine wire electrodes inserted into the genioglossus muscle to stimulate the tongue protruder muscle(s) synchronous with respiration during a sleep study. The oral appliance may be fitted with a drug delivery system (e.g., drug eluting coating, elastomeric pump, electronically controlled pump) for topical anesthesia to relieve the discomfort of the electrodes.

Figure 55:
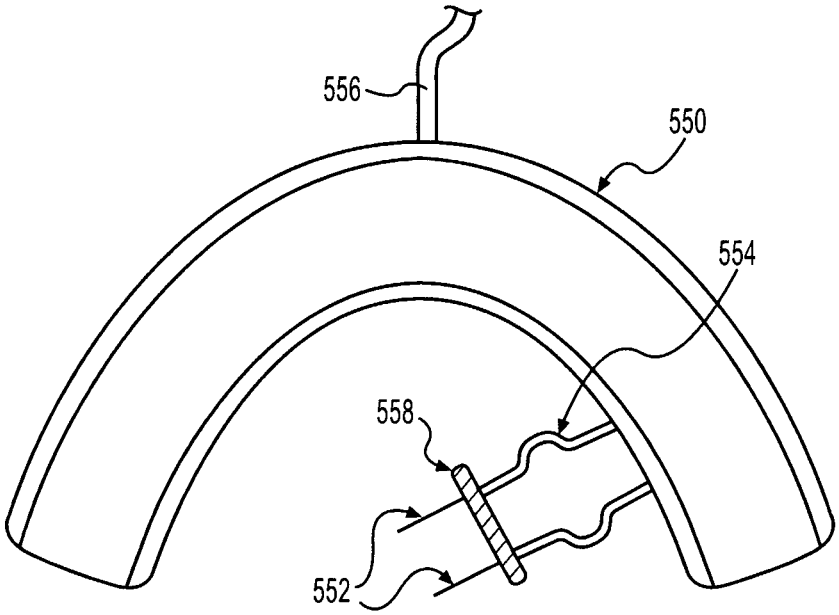

For example, with reference to FIG. 55, an oral appliance 550 includes a pair of small needle intramuscular electrodes 552 that extend into the genioglossus. The electrodes 552 are carried by flexible wires 554 and may be coupled to an external pulse generator (not shown) by wires 556. The electrodes 552 may be supported by a drug (e.g., anesthetic) eluting polymeric member 558.

Figure 56:
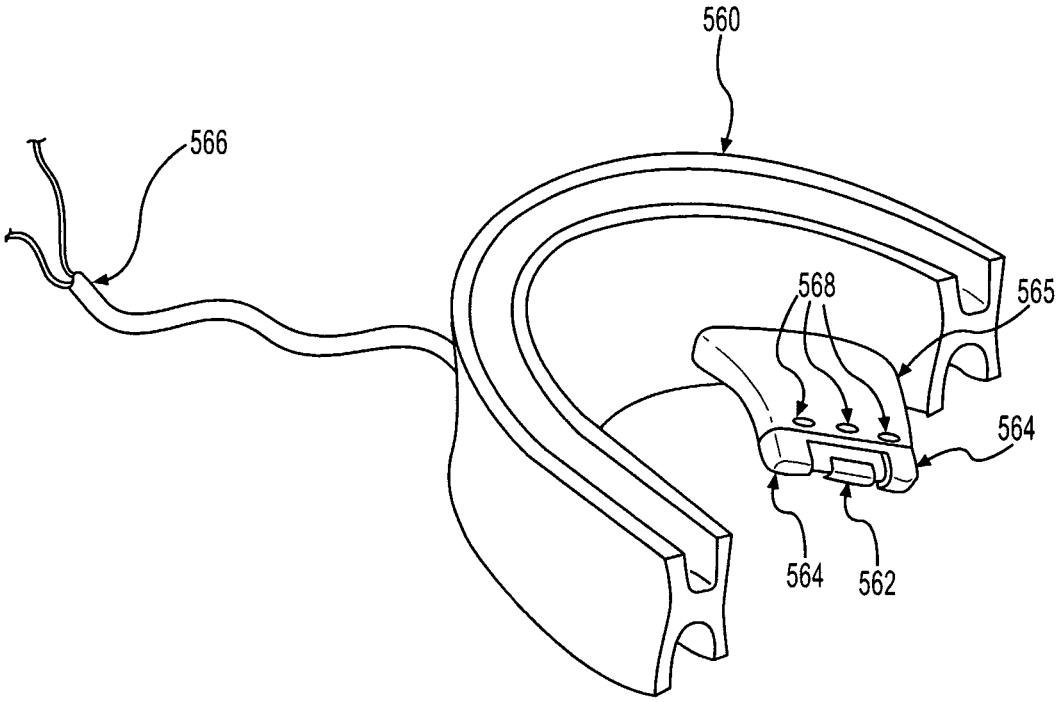

Alternatively, with reference to FIG. 56, an oral appliance 560 includes a cathode electrode 562 guarded by two anode electrodes 564 carried by a soft extension 565 that extends under the tongue. The surface electrodes 562 and 564 contact the floor of the mouth under the tongue to indirectly stimulate the genioglossus. The electrodes 562 and 564 may be coupled to an external pulse generator (not shown) by wires 566. The extension 565 may incorporate holes 568 through which a drug (e.g., anesthetic) may be eluted.

Oral appliances 550 and 560 may be used during a sleep study and stimulation of the target tissue can be performed synchronous with respiration and while inlet airflow pressure can be modulated. The ability to prevent apneas/hypopneas can be directly determined. Also the critical opening pressure with and without stimulation can be determined. Alternatively or in addition, the intramuscular or surface electrodes may be used to measure genioglossus EMG activity, either with or without stimulation. On any of theses bases, patient selection may be made.

Patient selection may also be applied to the respiratory sensors to determine if the respiratory sensors will adequately detect respiration for triggering stimulation. For example, in the embodiment wherein bio-Z is used to detect respiration using an implanted lead 70, skin surface or shallow needle electrodes may be used prior to implantation to determine if the signal will be adequate. This method may also be sued to determine the preferred position of the electrodes (i.e., optimal bio-Z vector). This may be done while the patient is sleeping (i.e., during a sleep study) or while the patient is awake.

Description of Alternative Intra-operative Tools

Intra-operatively, it may be desirable to determine the correct portion of the nerve to stimulate in order to activate the correct muscle(s) and implant the nerve cuff electrode accordingly. Determining the correct position may involve stimulating at different locations along the length or circumference of the nerve and observing the effect (e.g., tongue protrusion). In addition or in the alternative, and particularly in the case of field steering where multiple combinations of electrode contacts are possible, it may be desirable to determine optimal electrode or filed shape combinations.

Figure 57A:
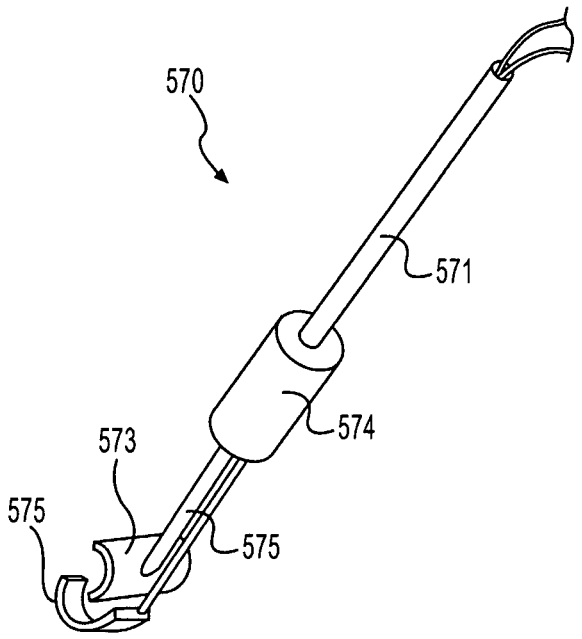
FIGS. 57A-58B schematically illustrate alternative intraoperative tools.
Figure 57B:
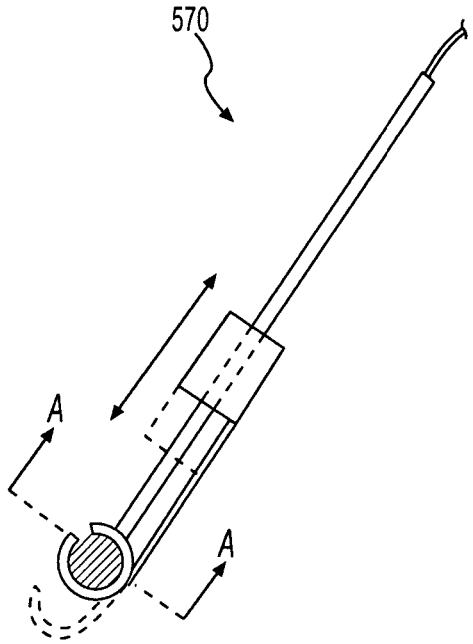
Figure 57C:
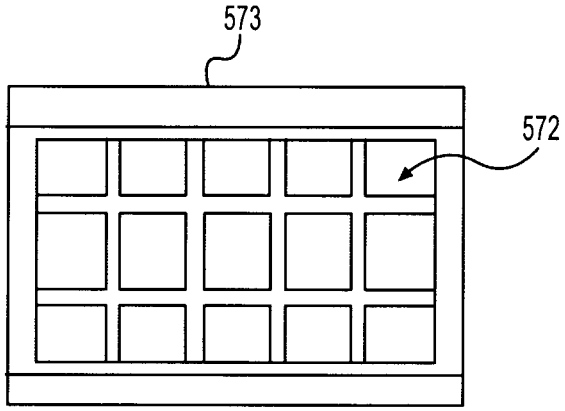

An example of an intra-operative stimulating tool 570 is shown in FIGS. 57A and 57B. In this embodiment, the tool 570 includes a first shaft 571 with a distal half-cuff 573. Tool 570 further includes a second shaft 575 with a proximal movable collar 574 and a distal half-cuff 575. Stimulating tool 570 includes multiple electrodes 572 on half-cuff 573 and/or half-cuff 575 that may be arranged in an array or matrix as shown in FIG. 57C, which is a view taken along line A-A in FIG. 57B. The half-cuffs 573 and 575 may be longitudinally separated for placement about a nerve and subsequently closed such that the half-cuffs 573 and 575 gently grasp the nerve. The electrodes 575 may be sequenced through a series of electrode/field shape combinations to optimize (lower) the critical opening pressure, airway caliber, tongue protrusion force or other acute indicia of therapeutic efficacy.

The tool 570 may be part of an intra-operative system including: (1) tool 570 or other tool with one or more stimulating electrodes that are designed to be easily handled by the surgeon during implant surgery; (2) an external pulse generator which triggers off of a respiration signal; (3) a feedback diagnostic device that can measure critical closing pressure intra-operatively; and (4) an algorithm (e.g., firmware or software in the programmer) that is design to automatically or manually sequence through a series of electrode configurations that will identify the best placement of electrode cuffs on the nerves and configuration of electrode polarity and amplitude settings. Information from the intra-operative system may greatly speed the process of identifying where to place the electrode cuff(s) on the hypoglossal nerve and what field steering may be optimal or necessary to provide efficacy.

Figure 58A:
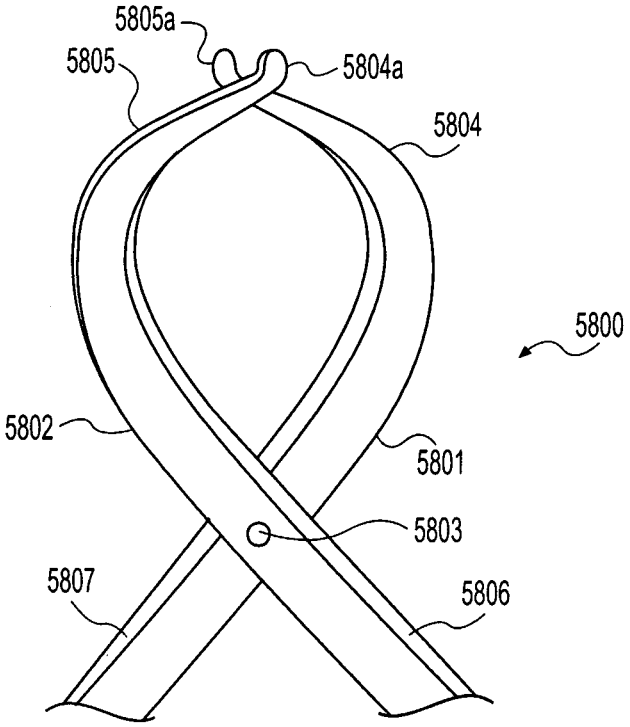
Figure 58B:
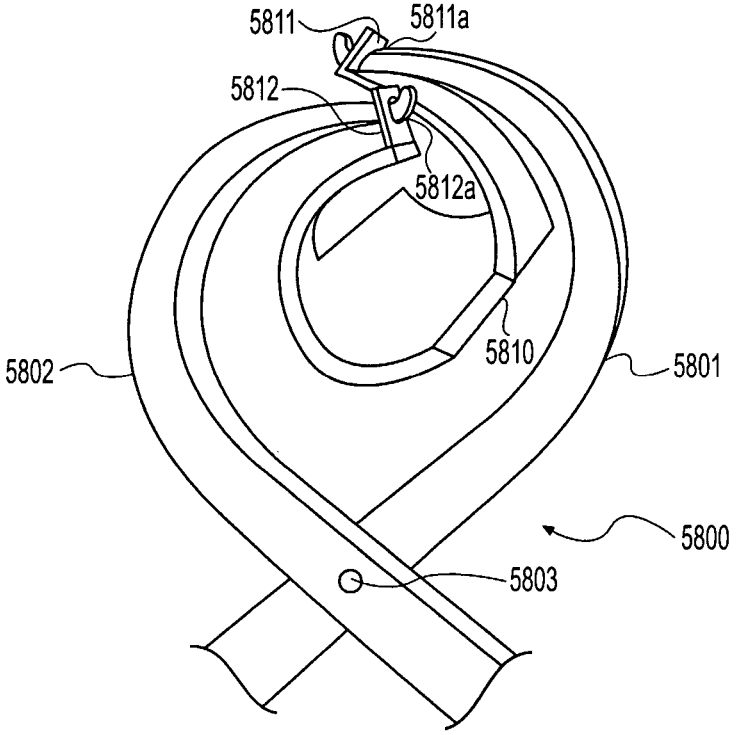

In certain circumstances, such as, when treating a child or a small adult, it may be difficult to implant a nerve cuff electrode of the present disclosure about a nerve in a patient's body. Accordingly, it may be desirable to provide a tool capable of facilitating temporary expansion of a nerve cuff electrode of the present disclosure, so as to slip the nerve cuff electrode around a patient's nerve. Turning now to FIGS. 58A-58B, there is depicted a tool 5800 for temporarily expanding a nerve cuff electrode in accordance with the principles of the present disclosure. Tool 5800 may include a substantially scissor-like configuration having a first element 5801 and a second element 5802 pivotably secured together by a suitable fastener, such as, for example, pivot pin 5803, acting as a fulcrum. Elements 5801 and 5802 may be substantially similar to each other or may differ as necessary. In the depicted embodiment, elements 5801 and 5802 may include levers having distal effecting portions 5804, 5805 and proximal actuating portions 5806, 5807.

Proximal actuating portions 5806, 5807 may be of any suitable length and may be connected to respective handles (not shown), which may be used to operate tool 5800. Alternatively, proximal actuating portions 5806, 5807 themselves may be used to operate tool 5800. Distal effecting portions 5804, 5805 may include any suitable configuration to achieve the desired effect. For example, each portion 5804, 5805 may include a substantially curved configuration. Additionally, a distal end of each portion 5804, 5805 may be provided with a fastening mechanism, such as, for example, hook-like projection 5804a, 5805a, for facilitating connection of tool 5800 to a nerve cuff electrode. As shown in FIGS. 58A-58B, hook-like projections 5804a, 5805a may be configured to be disposed in differing parallel planes, such that projections 5804a, 5805a may be spaced (offset) horizontally from one another. In use, distal effecting portions 5804, 5805 may be opened and closed as proximal actuating portions 5806, 5807 may be rotated about pivot pin 5803.

In embodiments where tool 5800 may be used to temporarily expand a nerve cuff electrode for implantation purposes, the nerve cuff electrode, e.g., nerve cuff electrode 5810, may be provided with one more geometric configurations for facilitation connection with tool 5800. In the depicted embodiment, nerve cuff electrode 5810 may be provided with extensions 5811, 5812 for facilitating connection with tool 5800. Each extension 5811, 5812 may be provided with openings 5811a, 5812a, respectively, for receiving hook-like projections 5804a, 5805a, so as to operably couple nerve cuff electrode 5811 with tool 5800.

Description of Miscellaneous Alternatives

The implanted neurostimulation system may be configured so that stimulation of the nerve is set at a relatively low level (i.e., low voltage amplitude, narrow pulse width, lower frequency) so as to maximize battery life of the INS and to minimize the chances that the electrical stimulation will cause arousal from sleep. If apneas/hypopneas are detected, then the electrical stimulation can be increased progressively until the apneas/hypopneas are no longer detected, up to a maximum pre-set stimulation level. This auto titration may automatically be reset to the low level after the patient is awakened and sits up (position detector) or manually reset using the patient controller. The stimulation level may be automatically reduced after a period of time has elapsed with no (or few) apneas/hypopneas detected.

The stimulation level (i.e., voltage amplitude, pulse width, frequency) may be adjusted based on changes in respiration rate. Respiration rate or patterns of rate change may be indicative of sleep state. A different power level based on sleep state may be used for minimal power consumption, minimal unwanted stimulation (sensory response), etc., while providing adequate efficacy.

The electrical field shape used to stimulate the target nerve can be changed while the system is proving therapy based on feedback indicating the presence (or lack) of apneas/hypopneas. The electrical field shape for an implanted system can be changed by adjusting the polarity, amplitude and other stimulation intensity parameters for each of the electrodes within the nerve stimulating cuff. An algorithm within the INS may change the currently operating electrical field shape if the presence of apneas/hypopneas is detected, and then wait a set period of time to determine if the new configuration was successful in mitigating the apneas/hypopneas before adjusting the field shape again. Additionally, the system may be designed to keep a log of the most successful stimulation patterns and when they were most likely to be effective. This may allow the system to "learn" which settings to be used during what part of the night, for example, or with specific breathing patterns or cardiac signal patterns or combinations thereof.

The proportion of stimulation intensity of two electrode cuffs used to stimulate a nerve can be modulated while the system is providing therapy based on feedback indicating the presence (or lack) of apneas/hypopneas. For example, one nerve stimulating electrode cuff may be place on the more proximal section of the hypoglossal nerve, while a second is placed more distally. The proximal cuff will be more likely to stimulate branches of the hypoglossal nerve going to muscles in the upper airway involved with tongue or hyoid retrusion while the more distal electrode cuff will more likely stimulate only the muscles involved with tongue/hyoid protrusion. Research suggests that to best maintain upper airway patency, stimulating both protrudes and retruders (in the right proportion) may be more effective that stimulating protruders alone. Software within the INS may change the currently operating proportion of electrical stimulation going to the distal electrode cuff in proportion to that going to the proximal cuff based on the presence of apneas/hypopneas detected. The system may then wait a set period of time to determine if the new configuration was successful in mitigating the apneas/hypopneas before adjusting the system again. Additionally, the system software may be designed to keep a log of the most successful stimulation proportion and when they were most likely to be effective. This may allow the system to "learn" which settings to be used during what part of the night, for example, or with specific breathing patterns or cardiac signal patterns or combinations thereof.

The system described above may modulate electrical stimulation intensity proportion based on electromyogram (EMG) feedback from the muscles in the upper airway being stimulated or others in the area. This feedback may be used to determine the correct proportion of stimulation between protruders and retruders. The correct ratio of EMG activity between retruders and protruders may be determined during a sleep study for an individual, may be determined to be a constant for a class of patients or may be "learned" my the implanted system by using the detection of apneas/hypopneas as feedback.

A library of electrical stimulation parameter settings can be programmed into the INS. These settings listed in the library may be selected by the patient manually using the patient programmer based on, for example: (1) direct patient perception of comfort during stimulation; (2) a log of the most successful settings compiled by the software in the INS (assumes apnea/hypopnea detection capability); (3) a sleep physician's or technician's assessment of the most effective stimulation as determined during a sleep study; and/or (4) a list of the most effective parameters produced for a particular class of patient or other.

The electrical stimulation parameters described above may be adjusted based on patient position as detected by a position sensor within the INS. The best setting for a given position may be determined by, for example: (1) a log of the most successful settings compiled or learned by the software in the INS (assumes apnea/hypopnea detection capability); (2) a sleep physician's or technician's assessment of the most effective stimulation as determined during a sleep study; and/or (3) a list of the most effective parameters produced for a particular class of patient or other.

To avoid fatigue using a normal duty cycle or to extend the time that the upper airway is opened through neurostimulation, different parts of the genioglossus muscle and/or different muscles involved with establishing patency of the upper airway can be alternately stimulated. For example, using two or more nerve or muscle electrode cuffs, the left and right side genioglossus muscles can be alternately stimulated, cutting the effective duty cycle on each muscle in half. In addition, different protruder muscles on the ipsilateral side such as the geniohyoid and the genioglossus muscle can be alternately stimulated to the same effect. This may also be accomplished through one electrode cuff using field steering methods that selectively stimulated the fascicles of the hypoglossal nerve going to one group of protruders alternating with stimulating the fascicles leading to a different protruder muscle group. This method may also be used to alternately stimulate one group of muscle fibers within the genioglossus muscle with the compliment of muscle fibers in the same muscle group.

To increase the ability of the upper airway to open during a (sensed) apnea/hypopnea through neurostimulation, different parts of the genioglossus muscle and/or different muscles involved with establishing patency of the upper airway can be simultaneously stimulated. For example, using two or more nerve or muscle electrode cuffs, the left and right side genioglossus muscles can be simultaneously stimulated, greatly increasing the protrusion forces. In addition, different protruder muscles on the ipsilateral side such as the geneohyoid and the genioglossus muscle can be simultaneously stimulated to the same effect. This may also be accomplished through one electrode cuff using field steering methods that selectively stimulated the fascicles of the hypoglossal nerve going to one group of protruders simultaneously with stimulating the fascicles leading to a different protruder muscle group. This may be achieved with one electrode cuff using field steering on a more proximal location on the hypoglossal nerve or two or more electrode cuffs, one on each branch going to a muscle involved with maintaining muscle patency.

A sensor inside the INS (or elsewhere in system implanted) may detect body position and automatically shut off stimulation when patient sits up or stands up. This will prevent unwanted stimulation when patient is no longer sleeping. The device may automatically restart the stimulation after the sensor indicates the patient is again horizontal, with or without a delay. The system may also be configured so that the stimulation can only be restarted using the patient controller, with, or without a delay.

The respiration signal using impedance and/or EMG/ENG are easily capable of determining heart rate. The stimulation may be interrupted or turned off when the heart rate falls outside out a pre-determined acceptable range. This may be an effective safety measure that will decrease the chance that hypoglossal nerve stimulation will interfere with mitigating physiological processes or interventional emergent medical procedures.

Respiration waveforms indicating apneas/hypopneas or of other clinical interest may be recorded and automatically telemetered to a bed-side receiver unit or patient programmer. Respiration waveforms indicating frequent apneas/hypopneas, abnormal breathing patterns, irregular heart rate/rhythm may be recorded and automatically telemetered to a bed-side deceiver unit or patient programmer causing an alarm to be issued (audible/visible). The INS status such as low battery or system malfunction may also trigger an alarm.

Electrical stimulation intensity could be ramped up for each respiration cycle by increasing amplitude or pulse width from 0 to a set point to prevent sudden tongue protrusion or sudden airway opening causing the patient to wake up. During inspiration, the system may deliver approximately 30 pulses per second for a length of time of one to one and one half seconds, totaling between about 30 and 45 pulses per respiration cycle. Prior to delivery of these 30 to 45 pulses, amplitude of each individual therapy pulse (in an added group of pulses) could be ramped up from 0 to a set point at a rate of <10% of the amplitude intended for the active duty cycle or 200 mS, whichever is less. The pulse width of each individual therapy pulse could be ramped up from 0 to a set point at a rate of <10% of the active duty cycle or 200 mS, whichever is less. Each of these ramp methods would require a predictive algorithm that would stimulate based on the previous inspiration cycle.

Nerves innervating muscles that are involved with inspiration, such as the hypoglossal nerve, have been shown to have greater electrical activity during apnea or hypopnea. This signal cannot be easily measured while simultaneously stimulating the same nerve. One method of stimulating and sensing using the same lead is to interleave a sensing period within the stimulation pulse bursts during the duty cycle. In other words, the sensing period may occur between pulses within the stimulation pulse train. This approach may be used with electrodes/leads that directly stimulate and alternately sense on a nerve involved with inspiration or on a muscle involved with inspiration or a combination of the two. The approach may allow sensing of apnea/hypopnea, as well as therapeutic stimulation.

From the foregoing, it will be apparent to those skilled in the art that the present invention provides, in exemplary non-limiting embodiments, devices and methods for nerve stimulation for OSA therapy. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of treating obstructive sleep apnea, the method comprising:

chronically implanting an electrode on a nerve innervating an upper airway dilator muscle;

sensing a measure of respiration;

analyzing the measure of respiration to identify onsets of expiration;

calculating a respiratory period from the onsets of expiration;

predicting the onset of a future expiratory phase; and beginning stimulation of the nerve a fraction of the calculated respiratory period before the onset of the future expiratory phase, and continuing stimulation of the nerve during an entire inspiratory phase, wherein the method is performed without identifying an onset of the inspiratory phase.

2. The method of claim 1, wherein the fraction ranges between $^{30}/_{100}$ and $^{50}/_{100}$.

3. The method of claim 1, wherein the fraction is selectively adjustable.

4. The method of claim 1, wherein the measure of respiration is bio-impedance.

5. The method of claim 1, wherein the electrode is disposed on a nerve cuff operably connected to a first end of a stimulation lead.

6. The method of claim 5, wherein a second end of the stimulation lead is operably connected to a neurostimulator.

7. The method of claim 6, wherein the neurostimulator is operably connected to a respiration sensing lead having a proximal end and a distal portion, wherein the distal portion is connected to a respiration sensor.

8. The method of claim 6, wherein the neurostimulator includes electronics containing an algorithm.

9. The method of claim 8, wherein the algorithm triggers the delivery of the stimulation via the stimulation lead.

10. The method of claim 5, wherein the stimulation lead includes a sigmoid-shaped section.

11. The method of claim 5, wherein the nerve cuff is cylindrical and includes a first semi-cylindrical portion connected to a second semi-cylindrical portion.

12. The method of claim 11, wherein the first semi-cylindrical portion is shorter in length than the second semi-cylindrical portion.

13. The method of claim 5, wherein the nerve cuff is cylindrical and includes a semi-cylindrical portion having a plurality of extending semi-cylindrical arms having free ends.

14. The method of claim 5, wherein the nerve cuff includes a plurality of electrodes configured to steer an electrical field.

15. A method of treating obstructive sleep apnea, the method comprising:

obtaining a respiration waveform;

analyzing the respiration waveform to identify onsets of expiration;

calculating a respiratory period from the onsets of expiration;

predicting the onset of a future expiratory phase; and stimulating a nerve to cause dilation of a patient's upper airway, wherein stimulation of the nerve begins a fraction of the calculated respiratory period before the onset of the future expiratory phase, and continuing stimulation of the nerve during an entire inspiratory phase, wherein the method is performed without identifying an onset of the inspiratory phase.

16. The method of claim 15, wherein the fraction is selectively adjustable.

17. The method of claim 15, wherein analyzing the respiration waveform to identify onsets of expiration includes identifying a peak of the respiration waveform.

*18. A method of treating obstructive sleep apnea with an electrode implanted on a nerve innervating an upper airway dilator muscle, the method comprising:*

*sensing a measure of respiration to generate a respiration waveform;*

*analyzing the respiration waveform to identify onsets of expiration;*

*calculating a respiratory period from the onsets of expiration identified in the respiration waveform; and*

*beginning stimulation of the nerve a fraction of the calculated respiratory period before an onset of a subsequent expiratory phase, and continuing stimulation of the nerve during an entire inspiratory phase, wherein the method is performed without identifying an onset of the inspiratory phase.*

*19. The method of claim 18, wherein the fraction ranges between 30/100 and 50/100.*

*20. The method of claim 18, wherein the fraction is selectively adjustable.*

*21. The method of claim 18, wherein the fraction of the calculated respiratory period is a predetermined amount of time.*

*22. The method of claim 18, wherein the measure of respiration is bio-impedance.*

*23. The method of claim 18, wherein the electrode is disposed on a nerve cuff operably connected to a first end of a stimulation lead including a first sigmoid section.*

*24. The method of claim 23, wherein the stimulation lead includes an anchor device disposed between the first sigmoid section and a second sigmoid section.*

*25. The method of claim 23, wherein a second end of the stimulation lead is operably connected to a neurostimulator.*

*26. The method of claim 25, wherein the neurostimulator is operably connected to a respiration sensing lead having a proximal end and a distal portion, wherein the distal portion is connected to a respiration sensor.*

*27. The method of claim 23, wherein the nerve cuff is cylindrical and includes a first semi-cylindrical portion connected to a second semi-cylindrical portion.*

*28. The method of claim 27, wherein the first semi-cylindrical portion is shorter in length than the second semi-cylindrical portion.*

*29. The method of claim 23, wherein the nerve cuff is cylindrical and includes a semi-cylindrical portion having a plurality of semi-cylindrical arms extending therefrom, the plurality of semi-cylindrical arms having free ends.*

*30. The method of claim 23, wherein the nerve cuff includes a plurality of electrodes configured to steer an electrical field.*

*31. The method of claim 18, wherein the onsets of expiration are identified without identifying an onset of an inspiratory phase.*

*32. A method of treating obstructive sleep apnea the method comprising:*

*obtaining a respiration waveform;*

*analyzing the respiration waveform to identify onsets of expiration;*

*calculating a respiratory period from the identified onsets of expiration;*

*stimulating a nerve to cause dilation of a patient's upper airway, wherein stimulation of the nerve begins a fraction of the calculated respiratory period before an onset of an expiratory phase; and*

*continuing stimulation of the nerve during an entire inspiratory phase, wherein the step of stimulating the nerve is performed without identifying an onset of the inspiratory phase, and*

*wherein the stimulation is delivered to the nerve via an electrode cuff positioned on the nerve and disposed on a distal end of a stimulation lead having a sigmoid section.*

*33. The method of claim 32, wherein analyzing the respiration waveform to identify onsets of expiration includes identifying a peak of the respiration waveform.*

*34. The method of claim 32, wherein the onsets of expiration are identified without identifying an onset of an inspiratory phase.*

*35. A method of treating obstructive sleep apnea using an electrode implanted on a nerve innervating an upper airway dilator muscle, the method comprising:*

*sensing a biological parameter to generate a respiration waveform;*

*analyzing the respiration waveform to identify at least a first onset of expiration and a second onset of expiration;*

*calculating a respiratory period from the identified first and second onsets of expiration; and*

*beginning stimulation of the nerve a fraction of the calculated respiratory period after the identified second onset of expiration, and continuing stimulation of the nerve during an entire inspiratory phase subsequent to the identified second onset of expiration, wherein the step of beginning stimulation is performed without identifying an onset of the subsequent inspiratory phase.*

*36. The method of claim 35, wherein the fraction ranges between 50/100 to 70/100.*

*37. The method of claim 35, wherein the electrode is disposed on a nerve cuff operably connected to a first end of a stimulation lead including a first sigmoid section.*

*38. The method of claim 37, wherein the stimulation lead includes an anchor disposed between the first sigmoid section and a second sigmoid section.*

*39. The method of claim 35, wherein the first and second onsets of expiration are identified without identifying an onset of an inspiratory phase.*

*40. A method of treating obstructive sleep apnea with an electrode implanted on a nerve innervating an upper airway dilator muscle, the method comprising:*

*sensing a measure of respiration;*

*analyzing the measure of respiration to identify onsets of expiration;*

*calculating a respiratory period from the onsets of expiration; and*

*beginning stimulation of the nerve a fraction of the calculated respiratory period before an onset of an expiratory phase, and continuing stimulation of the nerve during an entire inspiratory phase, wherein the method is performed without identifying an onset of the inspiratory phase.*

*41. The method of claim 40, wherein the electrode is disposed on a nerve cuff operably connected to a first end of a stimulation lead including a first sigmoid section.*

*42. The method of claim 41, wherein the stimulation lead includes an anchor disposed between the first sigmoid section and a second sigmoid section.*

*43. A method of treating obstructive sleep apnea using an electrode implanted on a nerve innervating an upper airway dilator muscle, the method comprising:*

*sensing a measure of respiration;*

*analyzing the measure of respiration to identify onsets of expiration;*

*calculating a respiratory period from the onsets of expiration; and*

*beginning stimulation of the nerve a predetermined amount of time after the onset of an expiratory phase, and continuing stimulation of the nerve during an entire subsequent inspiratory phase, wherein the method is performed without identifying an onset of the subsequent inspiratory phase.*

*44. The method of claim 43, wherein the electrode is disposed on a nerve cuff operably connected to a first end of a stimulation lead including a first sigmoid section.*

*45. The method of claim 44, wherein the stimulation lead includes an anchor disposed between the first sigmoid section and a second sigmoid section.*

*46. A method of treating obstructive sleep apnea with an electrode implanted on a nerve innervating an upper airway dilator muscle, the method comprising:*

*sensing a measure of respiration;*

*analyzing the measure of respiration to identify onsets of expiration;*

*calculating a respiratory period from the identified onsets of expiration; and*

*beginning stimulation of the nerve a fraction of the calculated respiratory period before an onset of a subsequent expiratory phase, and continuing stimulation of the nerve during an entire inspiratory phase prior to the subsequent expiratory phase, wherein the step of beginning stimulation is performed without identifying an onset of the inspiratory phase.*

*47. The method of claim 46, wherein the fraction ranges between 30/100 and 50/100.*

*48. The method of claim 46, wherein the onsets of expiration are identified without identifying an onset of an inspiratory phase.*

*49. A method of treating obstructive sleep apnea with an electrode implanted on a nerve innervating an upper airway dilator muscle of a subject having a breathing pattern, the method comprising:*

*identifying onsets of expiration by analyzing portions of the breathing pattern;*

*calculating a respiratory period from the identified onsets of expiration; and*

*beginning stimulation of the nerve a fraction of the calculated respiratory period before an onset of a subsequent expiratory phase, and continuing stimulation of the nerve during an entire inspiratory phase prior to the subsequent expiratory phase, wherein the step of beginning stimulation is performed without identifying an onset of the inspiratory phase.*

*50. The method of claim 49, wherein the fraction ranges between 30/100 and 50/100.*

*51. The method of claim 49, wherein the onsets of expiration are identified without identifying an onset of an inspiratory phase.*

* * * * *